US008629250B2

(12) United States Patent
Sasu et al.

(10) Patent No.: US 8,629,250 B2
(45) Date of Patent: Jan. 14, 2014

(54) HEPCIDIN, HEPCIDIN ANTAGONISTS AND METHODS OF USE

(75) Inventors: Barbra Sasu, San Bruno, CA (US); Mitsuru Haniu, Thousand Oaks, CA (US); Thomas Charles Boone, Newbury Park, CA (US); Xiao-juan Bi, Newbury Park, CA (US); Grace Ki Jeong Lee, Simi Valley, CA (US); Tara Arvedson, Simi Valley, CA (US); Aaron George Winters, Ventura, CA (US); Keegan Cooke, Ventura, CA (US); Jackie Z. Sheng, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 580 days.

(21) Appl. No.: 12/022,515

(22) Filed: Jan. 30, 2008

(65) Prior Publication Data

US 2008/0213277 A1 Sep. 4, 2008

Related U.S. Application Data

(60) Provisional application No. 60/888,059, filed on Feb. 2, 2007, provisional application No. 61/015,138, filed on Dec. 19, 2007.

(51) Int. Cl.
*C07K 16/00* (2006.01)
*A61K 39/395* (2006.01)
*C07K 16/28* (2006.01)

(52) U.S. Cl.
USPC .................................. 530/388.15; 424/130.1

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,850,752 A | 11/1974 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,179,337 A | 12/1979 | Davis et al. |
| 4,301,144 A | 11/1981 | Iwashita et al. |
| RE30,985 E | 6/1982 | Cartaya |
| 4,376,110 A | 3/1983 | David et al. |
| 4,452,901 A | 6/1984 | Gordon et al. |
| 4,495,285 A | 1/1985 | Shimizu et al. |
| 4,496,689 A | 1/1985 | Mitra |
| 4,560,655 A | 12/1985 | Baker |
| 4,609,546 A | 9/1986 | Hiratani |
| 4,640,835 A | 2/1987 | Shimizu et al. |
| 4,657,866 A | 4/1987 | Kumar |
| 4,667,016 A | 5/1987 | Lai et al. |
| 4,670,417 A | 6/1987 | Iwasaki et al. |
| 4,676,980 A | 6/1987 | Segal et al. |
| 4,703,008 A | 10/1987 | Lin |
| 4,766,106 A | 8/1988 | Katre et al. |
| 4,767,704 A | 8/1988 | Cleveland et al. |
| 4,791,192 A | 12/1988 | Nakagawa et al. |
| 4,892,538 A | 1/1990 | Aebischer et al. |
| 4,927,762 A | 5/1990 | Darfler |
| 5,093,246 A | 3/1992 | Cech et al. |
| 5,122,469 A | 6/1992 | Mather et al. |
| 5,223,409 A | 6/1993 | Ladner et al. |
| 5,229,275 A | 7/1993 | Goroff |
| 5,244,805 A | 9/1993 | Miller |
| 5,283,187 A | 2/1994 | Aebischer et al. |
| 5,338,665 A | 8/1994 | Schatz et al. |
| 5,359,681 A | 10/1994 | Jorgenson et al. |
| 5,432,018 A | 7/1995 | Dower et al. |
| 5,441,868 A | 8/1995 | Lin |
| 5,498,530 A | 3/1996 | Schatz et al. |
| 5,530,101 A | 6/1996 | Queen et al. |
| 5,545,807 A | 8/1996 | Surani et al. |
| 5,547,933 A | 8/1996 | Lin |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,591,828 A | 1/1997 | Bosslet et al. |
| 5,618,698 A | 4/1997 | Lin |
| 5,621,080 A | 4/1997 | Lin |
| 5,693,762 A | 12/1997 | Queen et al. |
| 5,723,750 A | 3/1998 | Stubbs et al. |
| 5,733,731 A | 3/1998 | Schatz et al. |
| 5,756,349 A | 5/1998 | Lin |
| 5,766,866 A | 6/1998 | Center et al. |
| 5,767,078 A | 6/1998 | Johnson et al. |
| 5,773,569 A | 6/1998 | Wrighton et al. |
| 5,830,851 A | 11/1998 | Wrighton et al. |
| 5,856,298 A | 1/1999 | Strickland |
| 5,877,293 A | 3/1999 | Adair et al. |
| 5,922,545 A | 7/1999 | Mattheakis et al. |
| 5,939,598 A | 8/1999 | Kucherlapati et al. |

(Continued)

FOREIGN PATENT DOCUMENTS

| | | |
|---|---|---|
| AU | 2003254950 A1 | 3/2004 |
| CN | 1403154 A | 3/2003 |

(Continued)

OTHER PUBLICATIONS

Kipryannov et al. Moleuclar Biotechnology, vol. 12, 1999, p. 173-201.*

(Continued)

*Primary Examiner* — Yunsoo Kim
(74) *Attorney, Agent, or Firm* — Lawrence B. Bugaisky

(57) ABSTRACT

The invention relates to purified, correctly folded hepcidin, antibodies that bind hepcidin, and methods of making and using such materials. Also provide are methods of treated hepcidin-related disorders.

15 Claims, 35 Drawing Sheets

(56) References Cited

U.S. PATENT DOCUMENTS

| | | |
|---|---|---|
| 5,955,422 A | 9/1999 | Lin |
| 5,986,047 A | 11/1999 | Wrighton et al. |
| 5,989,830 A | 11/1999 | Davis et al. |
| 6,019,944 A | 2/2000 | Buechler |
| 6,054,287 A | 4/2000 | Gao et al. |
| 6,110,462 A | 8/2000 | Barbas et al. |
| 6,171,586 B1 | 1/2001 | Lam et al. |
| 6,210,924 B1 | 4/2001 | Hu et al. |
| 6,251,588 B1 | 6/2001 | Shannon et al. |
| 6,262,247 B1 | 7/2001 | Kaser et al. |
| 6,278,039 B1 | 8/2001 | Johnson et al. |
| 6,306,393 B1 | 10/2001 | Goldenberg |
| 6,310,078 B1 | 10/2001 | Connolly et al. |
| 6,391,633 B1 | 5/2002 | Stern et al. |
| 6,583,272 B1 | 6/2003 | Bailon |
| 6,586,398 B1 | 7/2003 | Kinstler et al. |
| 6,750,369 B2 | 6/2004 | Connolly et al. |
| 6,900,292 B2 | 5/2005 | Sun et al. |
| 7,030,226 B2 | 4/2006 | Sun et al. |
| 7,084,245 B2 | 8/2006 | Holmes et al. |
| 7,217,689 B1 | 5/2007 | Elliott et al. |
| 7,232,892 B2 | 6/2007 | Goddard et al. |
| 7,294,690 B2 | 11/2007 | Goddard et al. |
| 7,723,063 B2 * | 5/2010 | Lauth et al. .............. 435/7.93 |
| 7,820,163 B2 | 10/2010 | Leung et al. |
| 2002/0004215 A1 | 1/2002 | Osbourn et al. |
| 2002/0091240 A1 | 7/2002 | Vasquez et al. |
| 2002/0155998 A1 | 10/2002 | Young et al. |
| 2002/0199213 A1 | 12/2002 | Tomizuka et al. |
| 2003/0031667 A1 | 2/2003 | Deo et al. |
| 2003/0044772 A1 | 3/2003 | Watkins et al. |
| 2003/0077753 A1 | 4/2003 | Tischer |
| 2003/0082749 A1 | 5/2003 | Sun et al. |
| 2003/0092125 A1 | 5/2003 | Davis et al. |
| 2003/0113316 A1 | 6/2003 | Kaisheva et al. |
| 2003/0118592 A1 | 6/2003 | Ledbetter et al. |
| 2003/0133939 A1 | 7/2003 | Ledbetter et al. |
| 2003/0143202 A1 | 7/2003 | Binley et al. |
| 2003/0187228 A1 | 10/2003 | Eaton et al. |
| 2003/0190317 A1 | 10/2003 | Baca et al. |
| 2003/0194404 A1 | 10/2003 | Greenfeder et al. |
| 2003/0198637 A1 | 10/2003 | Zhou et al. |
| 2003/0215444 A1 | 11/2003 | Elliott |
| 2004/0009902 A1 | 1/2004 | Boime et al. |
| 2004/0071694 A1 | 4/2004 | DeVries et al. |
| 2004/0091961 A1 | 5/2004 | Evans et al. |
| 2004/0096987 A1 | 5/2004 | Geacintov et al. |
| 2004/0096990 A1 | 5/2004 | Geacintov et al. |
| 2004/0143857 A1 | 7/2004 | Young et al. |
| 2004/0157293 A1 | 8/2004 | Evans et al. |
| 2004/0175379 A1 | 9/2004 | DeVries et al. |
| 2004/0175824 A1 | 9/2004 | Sun et al. |
| 2004/0229318 A1 | 11/2004 | Heavner |
| 2004/0248815 A1 | 12/2004 | Connolly et al. |
| 2004/0266690 A1 | 12/2004 | Pool |
| 2005/0019914 A1 | 1/2005 | Staerk et al. |
| 2005/0020487 A1 | 1/2005 | Klaus et al. |
| 2005/0026834 A1 | 2/2005 | Cox, III et al. |
| 2005/0037421 A1 | 2/2005 | Honda et al. |
| 2005/0037971 A1 | 2/2005 | Nicolas et al. |
| 2005/0096461 A1 | 5/2005 | Cox, III |
| 2005/0107297 A1 | 5/2005 | Holmes et al. |
| 2005/0107591 A1 | 5/2005 | Cox, III |
| 2005/0124045 A1 | 6/2005 | Sun et al. |
| 2005/0124564 A1 | 6/2005 | Binley et al. |
| 2005/0136049 A1 | 6/2005 | Ledbetter et al. |
| 2005/0137329 A1 | 6/2005 | Holmes et al. |
| 2005/0142642 A1 | 6/2005 | Sun et al. |
| 2005/0143292 A1 | 6/2005 | DeFrees et al. |
| 2005/0148025 A1 | 7/2005 | Lehmann et al. |
| 2005/0153879 A1 | 7/2005 | Svetina et al. |
| 2005/0158822 A1 | 7/2005 | Pecker |
| 2005/0158832 A1 | 7/2005 | Young et al. |
| 2005/0170457 A1 | 8/2005 | Pool et al. |
| 2005/0181359 A1 | 8/2005 | Optelten et al. |
| 2005/0181482 A1 | 8/2005 | Meade et al. |
| 2005/0192211 A1 | 9/2005 | Gillies et al. |
| 2005/0202538 A1 | 9/2005 | Gillies et al. |
| 2005/0223427 A1 | 10/2005 | Leake et al. |
| 2005/0227289 A1 | 10/2005 | Reilly et al. |
| 2005/0244409 A1 | 11/2005 | Erickson-Miller et al. |
| 2005/0255487 A1 | 11/2005 | Khvorova et al. |
| 2006/0019339 A1 | 1/2006 | Lauth et al. |
| 2006/0040858 A1 | 2/2006 | Holmes et al. |
| 2006/0073497 A1 | 4/2006 | Goldberg et al. |
| 2006/0088906 A1 | 4/2006 | DeFrees et al. |
| 2006/0111279 A1 | 5/2006 | DeFrees et al. |
| 2006/0223114 A1 | 10/2006 | Stemmer et al. |
| 2006/0286603 A1 | 12/2006 | Kolkman et al. |
| 2007/0224186 A1 | 9/2007 | Kulaksiz et al. |
| 2009/0173876 A1 | 7/2009 | Li et al. |

FOREIGN PATENT DOCUMENTS

| | | |
|---|---|---|
| EP | 315 456 | 5/1989 |
| EP | 404 097 | 12/1990 |
| WO | WO 87/00195 | 1/1987 |
| WO | WO 87/05330 | 9/1987 |
| WO | WO 88/04300 | 6/1988 |
| WO | WO 89/05852 | 6/1989 |
| WO | WO 90/03430 | 4/1990 |
| WO | WO 91/00741 | 1/1991 |
| WO | WO 91/05867 | 5/1991 |
| WO | WO 91/10741 | 7/1991 |
| WO | WO 91/17271 | 11/1991 |
| WO | WO 92/01047 | 1/1992 |
| WO | WO 92/11018 | 7/1992 |
| WO | WO 93/11161 | 6/1993 |
| WO | WO 93/11236 | 6/1993 |
| WO | WO 93/19172 | 9/1993 |
| WO | WO 93/25673 | 12/1993 |
| WO | WO 94/02602 | 2/1994 |
| WO | WO 94/13806 | 6/1994 |
| WO | WO 95/05465 | 2/1995 |
| WO | WO 95/15388 | 6/1995 |
| WO | WO 96/27011 | 9/1996 |
| WO | WO 96/30498 | 10/1996 |
| WO | WO 96/33735 | 10/1996 |
| WO | WO 96/34096 | 10/1996 |
| WO | WO 96/40987 | 12/1996 |
| WO | WO 98/15833 | 4/1998 |
| WO | WO 98/24893 | 6/1998 |
| WO | WO 98/25965 | 6/1998 |
| WO | WO 99/66054 | 12/1999 |
| WO | WO 00/24782 | 5/2000 |
| WO | WO 00/24893 | 5/2000 |
| WO | WO 00/61637 | 10/2000 |
| WO | WO 01/36489 | 5/2001 |
| WO | WO 01/81405 | 11/2001 |
| WO | WO 02/14356 | 2/2002 |
| WO | WO 02/19963 | 3/2002 |
| WO | WO 02/20034 | 3/2002 |
| WO | WO 02/49673 | 6/2002 |
| WO | WO 02/085940 | 10/2002 |
| WO | WO 02/098444 | 12/2002 |
| WO | WO 03/029291 | 4/2003 |
| WO | WO 03/055526 | 7/2003 |
| WO | WO 03/084477 | 10/2003 |
| WO | WO 03/094858 | 11/2003 |
| WO | WO 2004/002417 | 1/2004 |
| WO | WO 2004/002424 | 1/2004 |
| WO | WO 2004/009627 | 1/2004 |
| WO | WO 2004/018667 | 3/2004 |
| WO | WO 2004/024761 | 3/2004 |
| WO | WO 2004/033651 | 4/2004 |
| WO | WO 2004/035603 | 4/2004 |
| WO | WO 2004/043382 | 5/2004 |
| WO | WO 2004/045543 | 6/2004 |
| WO | WO 2004/058044 | 7/2004 |
| WO | WO 2004/090105 | 10/2004 |
| WO | WO 2004/101600 | 11/2004 |
| WO | WO 2004/101606 | 11/2004 |
| WO | WO 2004/101611 | 11/2004 |
| WO | WO 2004/106362 | 12/2004 |

(56) References Cited

FOREIGN PATENT DOCUMENTS

| | | |
|---|---|---|
| WO | WO 2004/106373 | 12/2004 |
| WO | WO 2005/001025 | 1/2005 |
| WO | WO 2005/001136 | 1/2005 |
| WO | WO 2005/021579 | 3/2005 |
| WO | WO 2005/025606 | 3/2005 |
| WO | WO 2005/032460 | 4/2005 |
| WO | WO 2005/051327 | 6/2005 |
| WO | WO 2005/063808 | 7/2005 |
| WO | WO 2005/063809 | 7/2005 |
| WO | WO 2005/070451 | 8/2005 |
| WO | WO 2005/078094 | 8/2005 |
| WO | WO 2005/081687 | 9/2005 |
| WO | WO 2005/084711 | 9/2005 |
| WO | WO 2005/092369 | 10/2005 |
| WO | WO 2005/100403 | 10/2005 |
| WO | WO 2005/103076 | 11/2005 |
| WO | WO 2006/002646 | 1/2006 |
| WO | WO 2006/029094 | 3/2006 |
| WO | WO 2006/050959 | 5/2006 |
| WO | WO 2006/099126 | 9/2006 |
| WO | WO 2007/120883 | 10/2007 |
| WO | WO 2008/011158 | 1/2008 |
| WO | WO 2008/089795 | 7/2008 |

OTHER PUBLICATIONS

Fundamental Immunology, William E. Paul, 3$^{rd}$ ed. 1993, p. 242.*
Portolano et al., J. Immunology, 1993, vol. 150, p. 880-887.*
Janeway, Immunobiology, 3$^{rd}$ ed., Garland Press, 1997, p. 3:7-3:11.*
Alexander et al., "Efficacy and Safety of Edifoligide, an E2F Transcription Factor Decoy, for Prevention of Vein Graft Failure Following Coronary Artery Bypass Graft Surgery PREVENT IV: A Randomized Controlled Trial," *J. Am. Med. Assoc.*, 294: 2446-2454 (2005).
Al-Obeidi et al., "Peptide and Peptidomimetic Libraries: Molecular Diversity and Drug Design," *Mol. Biotechnol.*, 9(3):205-223 (1998).
Anderson, "Human gene therapy," *Nature*, 392(Supp: No. 6679):25-30 (1998).
Anderson, "Human Gene Therapy," *Science*, 256:808-813 (1992).
Andrews, "Iron Metabolism: Iron Deficiency and Iron Overload," *Annu. Rev. Genomics Hum. Genet.*, 1:75-98 (2000).
Aplin and Wriston, "Preparation, Properties, and Applications of Carbohydrate Conjugates of Proteins and Lipids," *CRC Crit. Rev. Biochem.*, pp. 259-306 (1981).
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells," *J. Biol. Chem.*, 272(18): 11994-12000 (1997).
Ballas et al., "Liposomes bearing a quaternary ammonium detergent as an efficient vehicle for functional transfer of TMV-RNA into plant protoplast," *Biochim. Biophys. Acta*, 939:8-18 (1988).
Barnes et al., "Methods for Growth of Cultured Cells in Serum-free Medium," *Anal. Biochem.*, 102(2):255-270 (1980).
Bass, "RNA interference: The short answer," *Nature*, 411:428-429 (2001).
Been et al., "One Binding Site Determines Sequence Specificity of *Tetrahymena* Pre-rRNA Self-Splicing, *Trans*-Splicing, and RNA Enzyme Activity," *Cell*, 47:207-216 (1986).
Behr et al., "Efficient gene transfer into mammalian primary endocrine cells with lipopolyamine-coated DNA," *Proc. Natl. Acad. Sci. USA*, 86:6982-6986 (1989).
Behr, "DNA strongly binds to micelles and vesicles containing lipopolyamines or lipointercalants," *Tetrahedron Lett.*, 27, 5861-5864 (1986).
Behr, "Gene Transfer with Synthetic Cationic Amphiphiles: Prospects for Gene Therapy," *Bioconjugate Chem.*, 5:382-389 (1994).
Bernstein et al., "Role for a bidentate ribonuclease in the initiation step of RNA interference," *Nature*, 409: 363-366 (2001).
Better et al., "*Escherichia coli* Secretion of an Active Chimeric Antibody Fragment," *Science*, 240: 1041-1043 (1988).

Beutler et al., "Genetics of Iron Storage and Hemochromatosis," *Drug-Metabolism Disposition*, 29:495-499 (2001).
Bhatnagar et al., "Structure-Activity Relationships of Novel Hematoregulatory Peptides," *J. Med. Chem.*, 39:3814-3819 (1996).
Biocca, et al., "Expression and targeting of intracellular antibodies in mammalian cells," *EMBO J.* 9(1):101-108,( 1990).
Bird et al., "Single-Chain Antigen-Binding Proteins," *Science*, 242:423-426, (1988).
Boulianne et al., Production of functional chimaeric mouse/human antibody, *Nature*, 312:643-646 (1984).
Breaker and Joyce, "A DNA enzyme that cleaves RNA," *Chem. Biol.*, 1(4): 223-229 (1994).
Brennan et al., "Preparation of Bispecific Antibodies by Chemical Recombination of Monoclonal Immunoglobulin $G_1$ Fragments," *Science*, 229:81-83 (1985).
Brooks et al., "Human lymphocyte markers defined by antibodies derived from somatic cell hybrids: I. A hybridoma secreting antibody against a marker specific for human B lymphocytes," *Clin. Exp. Immunol.*, 39: 477, 1980.
Brown et al., "Protein Antigens of Normal and Malignant Human Cells Identified by Immunoprecipitation with Monoclonal Antibodies," J. Biol. Chem., 255(10):4980-4983l(1980).
Brüggemann et al., "Designer Mice: The Production of Human Antibody Repertoires in Transgenic Animals," *Year in Immunol.*, 7:33-40 (1993).
Brummelkamp et al., "A System for Stable Expression of Short Interfering RNAs in Mammalian Cells," *Science*, 296:550-553 (2000).
Brummelkamp et al., "Stable suppression of tumorigenicity by virus-mediated RNA interference," *Cancer Cell*, 2:243-247 (2002).
Burton and Barbas III, Human Antibodies from Combinatorial Libraries, *Adv. Immunol.*, 57:191-280 (1994).
Cane et al., "Harnessing the Biosynthetic Code: Combinations, Permutations, and Mutations," *Science*, 282:63-68 (1998).
Caron et al., "Engineered Humanized Dimeric Forms of IgG Are More Effective Antibodies," *J. Exp. Med.*, 176: 1191-1195 (1992).
Carpenter et al., "Interactions of stabilizing additives with proteins during freeze-thawing and freeze-drying," *Developments in Biological Standardization*, vol. 74, (Karger, Basel (1991)) pp. 225-239.
Carter et al., "High Level *Escherichia coli* Expression and Production of a Bivalent Humanized Antibody Fragment," *Bio/Technology*, 10:163-167 (1992).
Caton et al, "Influenza virus hemagglutinin-specific antibodies isolated from a combinatorial expression library are closely related to the immune response of the donor," *Proc. Natl. Acad. Sci. USA*, 87:6450-6454 (1990).
Champe et al., "Monoclonal Antibodies That Block the Activity of Leukocyte Function-associated Antigen 1 Recognize Three Discrete Epitopes in the Inserted Domain of CD11a," *J. Biol. Chem.*, 270(3):1388-1394 (1995).
Chen, "Formulation Concerns of Protein Drugs," *Drug Development and Industrial Pharmacy*, 18:1311-1354 (1992).
Chothia et al., "Canonical Structures for the Hypervariable Regions of Immunoglobulins," *J. Mol.Biol.*, 196: 901-917 (1987).
Chowdhury, "Targeting Random Mutations to Hotspots in Antibody Variable Domains for Affinity Improvement," *Methods Mol. Biol., Antibody Phage Display: Methods and Protocols*, vol. 178, Ch. 24, Eds. O'Brien and Aiken, (Humana Press Inc., Totowa, NJ (2001)) pp. 269-285.
Clackson and Wells, "In vitro selection from protein and peptide libraries," *Trends Biotechnol.*, 12:173-184 (1994).
Clackson et al., "A Hot Spot of Binding Energy in a Hormone-Receptor Interface," *Science*, 267: 383-386 (1995).
Co et al., "A Humanized Antibody Specific for the Platelet Integrin gpIIb/IIIa," *J. Immunol.*, 152:2968-2976, (1994).
Cochran et al., "The Relationship of MHC-Peptide Binding and T Cell Activation Probed Using Chemically Defined MHC Class II Oligomers," *Immunity*, 12(3): 241-250 (2000).
Colby et al., "Potent inhibition of huntingtin aggregation and cytotoxicity by a disulfide bond-free single-domain intracellular antibody," *Proc. Natl. Acad. Sci. USA*, 101(51):17616-17621 (2004).

(56) References Cited

OTHER PUBLICATIONS

Conrath et al., "β-Lactamase Inhibitors Derived from Single-Domain Antibody Fragments Elicited in the *Camelidae*," *Antimicrob. Agents Chemother.*, 45: 2807-2812 (2001).
Cortese et al., "Selection of biologically active peptides by phage display of random peptide libraries," *Curr. Opin. Biotechnol.*, 7: 616-621 (1996).
Cortez-Retamozo et al., "Efficient Cancer Therapy with a Nanobody-Based Conjugate," *Cancer Research*, 64:2853-2857, 2004.
Cotes and Bangham, "Bio-Assay of Erythropoietin in Mice Made Polycythaemic by Exposure to Air at a Reduced Pressure," *Nature*, 191:1065-1067 (1961).
Creighton, "Proteins: Structures and Molecular Principles," (W.H. Freeman & Co., (1983)) pp. 79-86.
Crooke, "Progress in Antisense Technology: The End of the Beginning," *Methods Enzymol.*, 313: 3-45 (2000).
Crosby et al., "Targeting Hepcidin with Antisense Oligonucleotides Improves Anemia Endpoints in Mice," Abstract 269, *Blood*, 108(11):83a-84a, (2006).
Cullen, "RNA interference: antiviral defense and genetic tool," *Nature Immunol*, 3(7):597-599 (2002).
Cunningham et al., "High-Resolution Epitope Mapping of hGH-Receptor Interactions by Alanine-Scanning Mutagenesis," *Science*, 244:1081-1085 (1989).
Cuthbertson et al., "Design of Low Molecular Weight Hematoregutatory Agents from the Structure-Activity Relationship of a Dimeric Pentapeptide," *J. Med. Chem.*, 40: 2876-2882 (1997).
Cwirla et al., "Peptide Agonist of the Thrombopoietin Receptor as Potent as the Natural Cytokine," *Science*, 276: 1696-1699 (1997).
Dall'Acqua et al., "Antibody engineering," *Curr. Opin. Struct. Biol.*, 8:443-450 (1998).
Daugherty et al., "Quantitative analysis of the effect of the mutation frequency on the affinity maturation of single chain Fv antibodies," *Proc. Natl. Acad. Sci. USA*, 97(5):2029-2034 (2000).
De Domenico, et al., "The Molecular Mechanism of Hepcidin-mediated Ferroportin Down-Regulation," *Mol. Biol. Cell.*, 18:2569-2578, (2007).
De Feyter and Gaudron, "Expressing Ribozymes in Plants," *Methods in Molecular Biolog: Ribozyme Protocols*, vol. 74, Ch. 43, Edited by Turner, P. C, (Humana Press Inc., Totowa, N.J. (1997)).
DRG International Inc., USA, "New ELISA Hepcidin Prohormone: Enzymeimmunoassay for the quantitative measurement of Pro-Hepcidin in human serum," *Product Brochure*, 1997.
Elbashir et al., "RNA interference is mediated by 21- and 22-nucleotide RNAs," *Genes Dev.*, 15:188-200 (2001).
Ferrara et al., "The Carbohydrate at FcγRIIIa Asn-162. An Element Required for High Affinity Binding to Non-fucosylated IgG Glycoforms," *J. Biol. Chem.*, 281(8):5032-5036 (2006).
Fire et al., "Potent and specific genetic interference by double-stranded RNA in *Caenorhabditis elegans*," *Nature*, 391: 806-811 (1998).
François et al., "Sequence-specific recognition of the major groove of DNA by oligodeoxynucleotides via triple helix formation," *Nucleic Acids Res.*, 16: 11431-11440 (1988).
Fredericks et al., "Identification of potent human anti-IL-1$R_1$ antagonist antibodies," *Protein Engineering, Design & Selection*, 17(1):95-106 (2004).
Friedmann, "Progress Toward Human Gene Therapy," *Science*, 244:1275-1281 (1989).
Gaarde et al., "Antisense Oligonucletides Targeting Hepcidin Improve Iron Availability in Mouse Models of Iron Sequestration," Poster Presented at *American Society of Hematology Meeting*, (2006).
Gao et al., "A Novel Cationic Liposome Reagent for Efficient Transfection of Mammalian Cells," *Biochemical and Biophysical Research Communications*, 179(1):280-285 (1991).
Gilmore et al., "The Design and Exogenous Delivery of siRNA for Post-transcriptional Gene Silencing,"*J. Drug Target.*, 12(6): 315-340 (2004).

Gleave and Monia, "Antisense Therapy for Cancer," *Nature Rev. Cancer*, 5: 468-479 (2005).
Gragoudas et al., "Pegaptanib for Neovascular Age-Related Macular Degeneration," *N. Engl. J. Med.*, 351: 2805-2816 (2004).
Graham et al., "Characteristics of a Human Cell Line Transformed by DNA from Human Adenovirus Type 5," *J. Gen. Virol.*, 36: 59-72 (1977.).
Grant et al., "Edman Sequencing as Tool for Characterization of Synthetic Peptides," *Meth. Enzymol.*, 289:395-419, (1997).
Gruber et al., "Efficient tumor cell lysis mediated by a bispecific single chain antibody expressed in *Escherichia coli*," *J. Immunology*, 152: 5368-5374 (1994).
Guggenbuhl et al., "Bone mineral density in men with genetic hemochromatosis and HFE gene mutation," *Osteoporos. Int.*, 16:1809-1814 (2005).
Güntert, "Automated NMR Structure Calculation with CYANA," *Meth. Mol. Biol.: Protein NMR Techniques*, 278, Ed., Downing (Humana Press Totoma, NJ, (2004)) pp. 353-378.
Guss et al., "Structure of the IgG-binding regions of streptococcal protein G," *EMBO J.*, 5(7):1567-1575, 1986.
Guvakova et al., "Phosphorothioate Oligodeoxynucleotides Bind to Basic Fibroblast Growth Factor, Inhibit Its Binding to Cell Surface Receptors, and Remove It from Low Affinity Binding Sites on Extracellular Matrix," *J. Biol. Chem.*, 270(6): 2620-2627 (1995).
Ham et al., "Media and Growth Requirements," *Meth. Enzymol.*, 58: 44-93 (1979).
Hannon et al., "Unlocking the potential of the human genome with RNA interference," *Nature*, 431:371-378 (2004).
Hannon, "RNA interference," *Nature*, 418: 244-251 (2002).
Hansen, "Assignment of the Natural Abundance $^{13}$C Spectrum Of Proteins using $^{13}$C $^{1}$H-Detected Heteronuclear Multiple-Bond Correlation NMR Spectroscopy: Structural Information and Stereospecific Assignments from Two- and Three-Bond Carbon-Hydrogen Coupling Constants," *Biochemistry*, 30:10457-10466 (1991).
Haseloff and Gerlach, "Simple RNA enzymes with new and highly specific endoribonuclease activities," *Nature 334*:585-591 (1988).
Hawkins et al., "Selection of Phage Antibodies by Binding Affinity: Mimicking Affinity Maturation," *J. Mol. Biol.*, 226:889-896 (1992).
Hélène, "The anti-gene strategy: control of gene expression by triplex-forming-oligonucleotides," *Anti-Cancer Drug Des.*, 6:569-584 (1991).
Hélène, et al., "Control of Gene Expression by Triple Helix-Forming Oligonucleotides: The Antigene Strategy," *Ann. N.Y. Acad. Sci.*, 660:27-36 (1992).
Heng et al., "Making cell-permeable antibodies (Transbody) through fusion of protein transduction domains (PTD) with single chain variable fragment (scFv) antibodies: Potential advantages over antibodies expressed within the intracellular environment (Intrabody)," *Medical Hypotheses*, 64:1105-1108 (2005).
Hey, "Artificial, non-antibody binding proteins for pharmaceutical and industrial applications," *Trends in Biotechnol.*, 23(10):514-522 (2005).
Holliger et al., "'Diabodies': small bivalent and bispecific antibody fragments," *Proc. Natl. Acad. Sci. USA*, 90:6444-6448 (1993).
Hoogenboom et al., "By-passing Immunisation: Human Antibodies from Synthetic Repertoires of Germline $V_H$ Gene Segments Rearranged in Vitro," *J. Mol. Biol.*, 227:381-388 (1992).
Hruby et al., "Synthesis of oligopeptide and peptidomimetic libraries," *Curr Opin. Chem. Biol.*, 1(1):114-119 (1997).
Hsu et al., "Plasma Prohepcidin Positively Correlates with Hematocrit in Chronic Hemodialysis Patients," *Blood Purification*, 24:311-316 (2006).
Huls et al., "Tumor cell killing by in vitro affinity-matured recombinant human monoclonal antibodies," *Cancer Immunol. Immunother.*, 50:163-171 (2001).
Hunter et al., "The Characteristics of Inhibition of Protein Synthesis by Double-Stranded Ribonucleic Acid in Reticulocyte Lysates," *J. Biol. Chem.*, 250:409-417 (1975).
Hunter et al., "The Solution Structure of Human Hepcidin, a Peptide Hormone with Antimicrobial Activity That Is Involved in Iron Uptake and Hereditary Hemochromatosis,"*J. Biol. Chem.*, 277(40):37597-37603 (2002).

(56) References Cited

OTHER PUBLICATIONS

Huston et al., "Protein engineering of antibody binding sites: Recovery of specific activity in an anti-digoxin single-chain Fv analogue produced in *Escherichia coli,*" *Proc. Natl. Acad. Sci. USA*, 85:5879-5883 (1988).
Ito et al. "Synthetic Cationic Amphiphiles for Liposome-mediated DNA Transfection," *Biochem. Inter.*, 22(2):235-241 (1990).
Jaeger et al., "Improved Predictions of Secondary Structures for RNA," *Proc. Natl. Acad. Sci. USA*, 86:7706-7710 (1989).
Jakobovits et al., "Analysis of homozygous mutant chimeric mice: Deletion of the immunoglobulin heavy-chain joining region blocks B-cell development and antibody production," *Proc. Natl. Acad. Sci. USA*, 90:2551-2555 (1993).
Jakobovits et al., "Germ-line transmission and expression of a human-derived yeast artificial chromosome," *Nature*, 362:255-258 (1993).
Jermutus et al., "Tailoring in vitro evolution for protein affinity or stability," *Proc. Natl. Acad. Sci. USA*, 98(1):75-80 (2001).
Jespers et al., "Guiding the Selection of Human Antibodies from Phage Display Repertoires to a Single Epitope of an Antigen," *Bio/Technology*, 12:899-903 (1994).
Jones et al., "Replacing the complementarity-determining regions in a human antibody with those from a mouse," *Nature*, 321:522-525 (1986).
Kaur et al., "Does cellular iron dysregulation play a causative role in Parkinson's disease?" *Ageing Res. Rev.*, 3:327-343 (2004).
Kawasaki et al., "Distinct roles of the co-activators p300 and CBP in retinoic-acid-induced F9-cell differentiation," *Nature*, 393:284-289 (1998).
Kehlenbach et al., "Nucleocytoplasmic Shuttling Factors Including Ran and CRM1 Mediate Nuclear Export of NFAT In Vitro," *J. Cell Biol.*, 141(4):863-874 (1998).
Kemna et al., "Time-course analysis of hepcidin, serum iron, and plasma cytokine levels in humans injected with LPS," *Blood*, 106(5):1864-1866 (2005).
Kessler et al., "Noesy-Tocsy, an Advantageous 2D NMR Technique for the Analysis of Peptide Sequences," *Angew. Chem. Int. Ed. Engl.*, 27:564-566 (1988).
Kettleborough et al., Humanization of a mouse monoclonal antibody by CDR—grafting: the importance of framework residues on loop conformation, *Protein Enineering*, 4(7):773-783 (1991).
Khachigian, "Deoxyribozymes as Inhibitors of Vascular Smooth Muscle Cell Growth," *Curr. Pharm. Biotechnol.*, 5: 337-339 (2004).
Khachigian, "DNAzymes as molecular agents that manipulate Egr-1 gene expression," *Biochem. Pharmacol.*, 68: 1023-1025 (2004).
Khan et al., "Simultaneous Detection of Antibodies to Six Nonhuman-Primate Viruses by Multiplex Microbead Immunoassay," *Clin. Vaccine Immunol.*, 13(1): 45-52 (2006).
Khvorova et al., "Functional siRNAs and miRNAs Exhibit Strand Bias," *Cell*, 115:209-216 (2003).
Kipriyanov et al., "Single-chain antibody streptavidin fusions: Tetrameric bifunctional scFv-complexes with biotin binding activity and enhanced affinity to antigen," *Hum. Antibodies Hybridomas*, 6(3): 93-101 (1995).
Koseki et al., "Factors Governing the Activity In Vivo of Ribozymes Transcribed by RNA Polymerase III," *J. Virol* 73(3):1868-1877 (1999).
Kostelny et al., "Formation of a Bispecific Antibody by the Use of Leucine Zippers," *J. Immunol.*, 148(5):1547-1553 (1992).
Kourlas and Schiller et al., "Pegaptanib Sodium for the Treatment of Neovascular Age-Related Macular Degeneration: A Review," *Clin. Ther.*, 28(1):36-44 (2006).
Krause et al., "LEAP-1, a novel highly disulfide-bonded human peptide, exhibits antimicrobial activity," *FEBS Lett.*, 480:147-150 (2000).
Kreeger, "Immunological Applications: Top List of Peptide Synthesis Services," *The Scientist*, 10(13):18-19 (1996).
Kruger et al., "Self-splicing RNA: Autoexcision and Autocyclization of the Ribosomal RNA Intervening Sequence Of Tetrahymena," *Cell*, 31: 147-157 (1982).
Kulaksiz et al., "Pro-hepcidin: expression and cell specific localisation in the liver and its regulation in hereditary haemochromatosis, chronic renal insufficiency, and renal anaemia," *Gut*, 53:735-743, (2004).
Kumar et al., "Gene targeting by ribozyme against TNF-α mRNA inhibits autoimmune arthritis," *Gene Ther.*, 12: 1486-1493 (2005).
Kuragano et al., "Plasma Hepcidin was Significant Predictor for Iron Storage but Independent of Inflammation and Cytokines in Hemodialysis Patients (HD)," Abstract SC-FU068, *American Society of Nephrology Meeting, J. Am. Soc. Nephrol.*, 18(Abstracts Issue):82A (2007).
Kurreck, "Antisense technologies: Improvement through novel chemical modifications," *Eur. J. Biochem.*, 270: 1628-1644 (2003).
Kuwabara et al., "A Novel Allosterically trans-Activated Ribozyme, the Maxizyme, with Exceptional Specificity In Vitro and In Vivo," *Mol. Cell* 2:617-627 (1998).
Kuwabara et al., "Formation of a catalytically active dimer by $tRNA^{Val}$-driven short ribozymes," *Nature Biotechnol.* 16:961-965 (1998).
Kuwabara et al., "$tRNA^{Val}$-heterodimeric maxizymes with high potential as gene-inactivating agents: Simultaneous cleavage at two sites in HIV-1 tat mRNA in cultured cells," *Proc. Natl. Acad. Sci. USA*, 96:1886-1891 (1999).
Lauth et al., "Bass Hepcidin Synthesis, Solution Structure, Antimicrobial Activities and Synergism, and in Vivo Hepatic Response to Bacterial Infections," *J. Biol. Chem.*, 280(10):9272-9282 (2005).
Letsinger et al., "Cholesteryl-conjugated oligonucleotides: Synthesis, properties, and activity as inhibitors of replication of human immunodeficiency virus in cell culture," *Proc. Natl. Acad. Sci. USA*, 86(17):6553-6556 (1989).
Leventis et al., "Interactions of mammalian cells with lipid dispersions containing novel metabolizable cationic amphiphiles," *Biochim. Biophys. Acta*, 1023:124-132 (1990).
Lewis et al., "Identification of viral mutants by mass spectrometry," *Proc. Natl. Acad. Sci. USA*, 95:8596-8601 (1998).
Li et al., "High-Accuracy Molecular Mass Determination for Peptides and Proteins by Fourier Transform Mass Spectrometry," *Anal. Chem.*, 66(13):2077-2083 (1994).
Lin et al., "Modulation of Bone Morphogenetic Protein Signaling In Vivo Regulates Systemic Iron Balance," Abstract F-PO157, *American Society of Nephrology Meeting, J. Am. Soc. Nephrol.*, 18(Abstracts Issue):140A (2007).
Lindmark et al., "Binding of Immunoglobulins to Protein A and Immunoglobulin Levels in Mammalian Sera," *J. Immunol. Meth.*, 62: 1-13 (1983).
Low et al., "Mimicking Somatic Hypermutation: Affinity Maturation of Antibodies Displayed on Bacteriophage Using a Bacterial Mutator Strain," *J. Mol. Biol.*, 260:359-368, 1996.).
Lowman, "Bacteriophage Display and Discovery of Peptide Leads for Drug Development," *Annu. Rev. Biophys. Biomol. Struct.* 26: 401-424 (1997).
Maher, "DNA Triple-Helix Formation: An Approach to Artificial Gene Repressors?" *BioEssays*, 14(12):807-815 (1992).
Mallender and Voss, "Construction, Expression, and Activity of a Bivalent Bispecific Single-chain Antibody," *J. Biol. Chem.*, 269:199-206 (1994).
Malone et al., "Cationic liposome-mediated RNA transfection," *Proc. Nati Acad. Sci. USA*, 86:6077-6081 (1989).
Malyszko et al., "Erythropoiesis Stimulating Agents (ESA) Therapy in Dialyzed Patients; Could Hepcidin Be a Possible Link to Hyporesponsiveness?" Abstract F-PO838, *American Society of Nephrology Meeting, J. Am. Soc. Nephrol.*, 18(Abstracts Issue):286A (2007).
Manche et al., "Interactions between Double-Stranded RNA Regulators and the Protein Kinase DAI," *Mol. Cell. Biol.*, 12(11):5238-5248 (1992).
Mann and Dzau, "Therapeutic applications of transcription factor decoy oligonucleotides," *J. Clin. Invest.*, 106(9): 1071-1075 (2000).
Manoharan, "2'-Carbohydrate modifications in antisense oligonucleotide therapy: importance of conformation, configuration and conjugation," *Biochim. Biophys. Acta*, 1489:117-130 (1999).

(56) References Cited

OTHER PUBLICATIONS

Marks et al., "By-passing Immunization: Human Antibodies from V-gene Libraries Displayed on Phage," *J. Mol. Biol.*, 222:581-597 (1991).

Marshall et al., "Fourier Transform Ion Cyclotron Resonance Mass Spectrometry: A Primer," *Mass Spectrometry Reviews*, 17:1-35 (1998).

Marwick; "First "Antisense" Drug Will Treat CMV Retinitis," *J. Am. Med. Assoc.*, 280(10): 871 (1998).

Mast et al., "Superdonors Have Decreased Iron Stores but Can Repeatedly Donate Whole Blood through Use of Iron Supplements and Decreased Serum Hepcidin Concentration," Abstract 2887, 2007 American Society of Haematology Meeting Abstracts, *Blood*, 110(11):849A-850A, (2007).

Mather, "Establishment and Characterization of Two Distinct Mouse Testicular Epithelial Cell Lines," *Biol. Reprod.*, 23: 243-252 (1980).

Mhashilkar et al., "Inhibition of HIV-1 Tat-mediated LTR transactivation and HIV-1 infection by anti-Tat single chain intrabodies," *EMBO J.* 14(7):1542-1551 (1995).

Michiels et al., "Arrayed adenoviral expression libraries for functional screening," *Nature Biotechnol,*. 20:1154-1157 (2002).

Miller et al., "Targeting Alzheimer's disease genes with RNA interference: an efficient strategy for silencing mutant alleles," *Nucleic Acids Res.*, 32(2): 661-668 (2004.).

Miller, "Human gene therapy comes of age," *Nature*, 357: 455-460 (1992).

Minks et al., "Structural Requirements of Double-stranded RNA for the Activation of 2',5'-Oligo(A) Polymerase and Protein Kinase of Interferon-treated HeLa Cells," *J. Biol. Chem.*, 254(20):10180-10183 (1979).

Montgomery et al., "RNA as a target of double-stranded RNA-mediated genetic interference in *Caenorhabditis elegans*," *Proc. Natl. Acad. Sci. USA*, 95:15502-15507 (1998).

Morishita et al., "A gene therapy strategy using a transcription factor decoy of the E2F binding site inhibits smooth muscle proliferation in vivo," *Proc. Natl. Acad. Sci. USA*, 92: 5855-5859 (1995).

Morita et al., "A wheat germ cell-free system is a novel way to screen protein folding and function," *Protein Science*, 12(6), 1216-1221 (2003).

Morrison and Oi, "Genetically Engineered Antibody Molecules," *Adv. Immunol.*, 44:65-92 (1989).

Morrison et al., "Chimeric human antibody molecules: Mouse antigen binding domains with human constant region domains," *Proc. Natl. Acad. Sci. USA*, 81:6851-6855 (1984).

Moser and Dervan, "Sequence-Specific Cleavage of Double Helical DNA by Triple Helix Formation," *Science*, 238: 645-650 (1987).

Myers, "Will combinatorial chemistry deliver real medicines?" *Curr. Opin. Biotechnol.*, 8:701-707 (1997).

Nemeth et al., "Hepcidin Regulates Cellular Iron Efflux by Binding to Ferroportin and Inducing Its Internalization," *Science*, 306:2090-2093, 2004; (Epub Oct. 28, 2004).

Nemeth et al., "Hepcidin, a putative mediator of anemia of inflammation, is a type II acute-phase protein," *Blood*, 101:2461-2463, (2003).

Nemeth et al., "IL-6 mediates hypoferremia of inflammation by inducing the synthesis of the iron regulatory hormone hepcidin," *J. Clin. Invest.*, 113(9):1271-1276 (2004).

Nemeth et al., "The N-terminus of hepcidin is essential for its interaction with ferroportin: structure-function study," *Blood*, 107(1):328-333 (2006).

Neri et al., "High-affinity Antigen Binding by Chelating Recombinant Antibodies (CRAbs)," *J Mol Biol.*, 246:367-373 (1995).

Ng and Ilag, "Biomedical applications of protein chips," *J. Cell Mol. Med.*, 6(3): 329-340 (2002).

Nicolas et al., "Constitutive hepcidin expression prevents iron overload in a mouse model of hemochromatosis," *Nature Genetics*, 34:97-101 (2003).

Nicolas et al., "Lack of hepcidin gene expression and severe tissue iron overload in upstream stimulatory factor 2 (USF2) knockout mice,". *Proc. Natl. Acad. Sci. USA*, 98(15):8780-8785 (2001).

Nicolas et al., "Severe iron deficiency anemia in transgenic mice expressing liver hepcidin," *Proc. Natl. Acad. Sci. USA*, 99(7):4596-4601 (2002).

Nicolas et al., "The gene encoding the iron regulatory peptide hepcidin is regulated by anemia, hypoxia, and inflammation," *J Clin. Invest.*, 110(7):1037-1044 (2002).

Nimjee et al., "A Novel Antidote-Controlled Anticoagulant Reduces Thrombin Generation and Inflammation and Improves Cardiac Function in Cardiopulmonary Bypass Surgery," *Mol. Ther.*, 14(3): 408-415 (2006).

Nimjee et al., "Aptamers: An Emerging Class of Therapeutics," *Ann. Rev. Med.*, 56: 555-583 (2005).

Nishimiya et al., "Thermodynamic Consequences of Grafting Enhanced Affinity toward the Mutated Antigen onto an Antibody: The Case of Anti-lysozyme Antibody, HyHEL-10," *J. Biol. Chem.*, 275(17):12813-12820 (2000).

Nykänen et al., "ATP Requirements and Small Interfering RNA Structure in the RNA Interference Pathway," *Cell*, 107: 309-321 (2001).

Oğuz et al., "Hepcidin is not a marker of chronic inflammation in atherosclerosis," *Anadolu Kardiyoloji Dergisi*, 6:239-242 (2006).

Ohmori et al., "The Enhancing Effect of Anionic α-Helical Peptide on Cationic Peptide-Mediating Transfection Systems," *Biochem. Biophys. Res. Commun.*, 235(3):726-729(1997).

Olafsen et al., "Characterization of engineered anti-p185$^{HER-2}$ (scFv-$C_H3)_2$ antibody fragments (minibodies) for tumor targeting," *Protein Eng: Des. Sel.*, 17(4):315-323 (2004).

Ouwehand et al., "Novel Diagnostic and Therapeutic Strategies with Genetically Engineered Human Antibodies," *Vox Sang.*, 74(Suppl 2):223-232 (1998).

Paddison et al., "Short Hairpin Activated Gene Silencing in Mammalian Cells," *Methods Mol. Biol.: RNA Interference, Editing, and Modification*, 265:85-100 (2004).

Paddison et al., "Short hairpin RNAs (shRNAs) induce sequence-specific silencing in mammalian cells," *Genes Dev.*, 16:948-958 (2002).

Padlan, "A possible procedure for reducing the immunogenicity of antibody variable domains while preserving their ligand-binding properties," *Molecular Immunol.*, 28(4/5):489-498 (1991).

Padlan, "Anatomy of the Antibody Molecule," *Molecular Immunol.*, 31(3):169-217 (1994).

Papanikolaou et al., "Hepcidin in iron overload disorders," *Blood*, 105(10):4103-4105 (2005).

Park et al., "Hepcidin, a Urinary Antimicrobial Peptide Synthesized in the Liver," *J. Biol. Chem.*, 276(1 1):7806-7810 (2001).

Patil, "DNA-based Therapeutics and DNA Delivery Systems: A Comprehensive Review," *AAPS J.*, 7: E61-E77 (2005).

Perriman et al., "Effective ribozyme delivery in plant cells," *Proc. Natl. Acad. Sci. USA*, 92:6175-6179 (1995).

Philpott, "Molecular Aspects of Iron Absorption: Insights Into the Role of HFE in Hemochromatosis," *Hepatology*, 35(5):993-1001 (2002).

Pigeon et al., "A New Mouse Liver-specific Gene, Encoding a Protein Homologous to Human Antimicrobial Peptide Hepcidin, Is Overexpressed during Iron Overload," *J. Biol. Chem.*, 276(11):7811-7819 (2001).

Pinnaduwage et al., "Use of a quaternary ammonium detergent in liposome mediated DNA transfection of mouse L-cells," *Biochim. Biophys. Acta*, 985:33-37 (1989).

Pollard et al., "Polyethylenimine but Not Cationic Lipids Promotes Transgene Delivery to the Nucleus in Mammalian Cells," *J. Biol. Chem.*, 273(13):7507-7511 (1998).

Powers et al., "Expression of single-chain Fv-Fc fusions in *Pichia pastoris*," *Journal of Immunological Methods*, 251:123-135 (2001).

Punnonen et al., "Serum Transferrin Receptor and Its Ratio to Serum Ferritin in the Diagnosis of Iron Deficiency," *Blood*, 89(3):1052-1057 (1997).

Rader et al., "A phage display approach for rapid antibody humanization: Designed combinatorial V gene libraries," *Proc. Natl. Acad. Sci. USA*, 95:8910-8915 (1998).

Raines and Ross, "Platelet-derived Growth Factor: I. High Yield Purification and Evidence for Multiple Forms," *J. Biol. Chem.*, 257:5154-5160, 1982.

(56) References Cited

OTHER PUBLICATIONS

Rajpal et al., "A general method for greatly improving the affinity of antibodies by using combinatorial libraries," *Proc. Natl. Acad. Sci. USA*, 102(24):8466-8471 (2005).
Ralph et al., "Silencing mutant SOD1 using RNAi protects against neurodegeneration and extends survival in an ALS model," *Nature Med.*, 11(4):429-433 (2005).
Reynolds et al., "Rational siRNA design for RNA interference," *Naure, Biotechnol.*, 22(3): 326-330 (2004).
Riechmann, et al., "Single domain antibodies: comparison of camel VH and camelised human VH domains," *J. Immunol. Methods*, 231:25-38 (1999).
Rivera et al., "Hepcidin excess induces the sequestration of iron and exacerbates tumor-associated anemia," *Blood*, 105:1797-1802 (2005).
Rivera et al., "Synthetic hepcidin causes rapid dose-dependent hypoferremia and is concentrated in ferroportin-containing organs," *Blood*, 106(6):2196-2199, (2005).
Roberts and Szostak, "RNA-peptide fusions for the in vitro selection of peptides and proteins," *Proc. Natl. Acad. Sci. USA*, 94: 12297-12303 (1997).
Roetto et al., "Mutant antimicrobial peptide hepcidin is associated with severe juvenile hemochromatosis," *Nature Genetics*, 33:21-22 (2003).
Rose et al., "A New Cationic Liposome Reagent Mediating Nearly Quantitative Transfection of Animal Cells," *BioTechniques*, 10(4):520-525 (1991).
Rossi, "Practical Ribozymes: Making ribozymes work in cells," *Current Biology*, 4(5):469-471 (1994).
Roth and Craig, "VDJ Recombination: A Transposase Goes to Work," *Cell*, 94:411-414 (1998).
Rothman et al., "Antibody-Dependent Cytotoxicity Mediated by Natural Killer Cells is Enhanced by Castanospermine-Induced Alterations of IgG Glycosylation," *Mol. Immunol.*, 26(12):1113-1123 (1989).
Rusconi et al., "RNA aptamers as reversible antagonists of coagulation factor IXa," *Nature*, 419: 90-94 (2002).
Sanger et al., "DNA Sequencing with Chain-Terminating Inhibitors," *Proc. Natl. Acad. Sci. USA*, 74(12): 5463-5467 (1977).
Schoonjans et al., "Fab Chains As an Efficient Heterodimerization Scaffold for the Production of Recombinant Bispecific and Trispecific Antibody Derivatives," *J Immunol.* 165:7050-7057 (2000).
Scott et al., "Searching for Peptide Ligands with an Epitope Library," *Science*, 249: 386-390 (1990).
Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).
Shields et al., "High Resolution Mapping of the Binding Site on Human IgG1 for Fcγ RI, FcγRII, FcγRIII, and FcRn and Design of IgG1 Variants with Improved Binding to the FcγR," *J. Biol. Chem.*, 276(9):6591-6604 (2001).
Shields et al., "Lack of Fucose on Human IgG1 N-Linked Oligosaccharide Improves Binding to Human FcγRIII and Antibody-dependent Cellular Toxicity," *J. Biol. Chem.*, 277(30):26733-26740 (2002).
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J Biol Chem.*, 278(5):3466-3473 (2003).
Shopes, "A genetically engineered human IgG mutant with enhanced cytolytic activity," *J. Immunol.*, 148(9): 2918-2922 (1992).
Sierakowska et al., "Repair of thalassemic human β-globin mRNA in mammalian cells by antisense oligonucleotides," *Proc. Natl. Acad. Sci. USA*, 93:12840-12844 (1996).
Sigurdsson and Eckstein, "Structure-function relationships of hammerhead ribozymes: from understanding to applications," *Trends Biotechnol.*, 13:286-289 (1995).

Skerra et al., "Assembly of a Functional Immunoglobulin $F_v$ Fragment in *Escherichia coli*," *Science*, 240: 1038-1041 (1988).
Sojar et al., "A Chemical Method for the Deglycosylation of Proteins," *Arch. Biochem. Biophys.*, 259(1): 52-57 (1987).
Soutschek et al., "Therapeutic silencing of an endogenous gene by systemic administration of modified siRNAs," *Nature*, 432:173-178 (2004).
Stegmeier et al., "A lentiviral microRNA-based system for single-copy polymerase II-regulated RNA interference in mammalian cells," *Proc. Natl. Acad. Sci. USA*, 102(37):13212-13217 (2005).
Stevenson et al., "A chimeric antibody with dual Fc regions (*bis*FabFc) prepared by manipulations at the IgG hinge," *Anti-Cancer Drug Design*, 3: 219-230 (1989).
Studnicka et al., Human-engineered monoclonal antibodies retain full specific binding activity by preserving non-CDR complementarity-modulating residues, *Protein Engineering*, 7(6): 805-814 (1994).
Swenkels et al., "Heriditary Hemochromatosis: Genetic Complexity and New Diagnostic Approaches," *Clin. Chem.*, 52(6):950-968, (2006).
Taes et al., "Prohepcidin accumulates in renal insufficiency," *Clinical Chemistry & Laboratory Medicine*, 42(4):387-389 (2004).
Takasaki et al., "Structure-based design and characterization of exocyclic peptidomimetics that inhibit TNFα binding to its receptor," *Nature Biotech.*, 15:1266-7120 (1997).
Tanabe et al., "Oncogene inactivation in a mouse model," *Nature*, 406:473-474 (2000).
Theurl et al., "Dysregulated monocyte iron homeostasis and erythropoietin formation in patients with anemia of chronic disease," *Blood*, 107(10):4142-4148 (2006).
Thotakura et al., "Enzymatic deglycosylation of glycoproteins," *Meth. Enzymol.*, 138: 350-359 (1987).
Tomita and Morishita, "Antisense Oligonucleotides as a Powerful Molecular Strategy for Gene Therapy in Cardiovascular Diseases," *Curr. Pharm. Des.*, 10: 797-803 (2004).
Tomosugi et al., "Detection of serum hepcidin in renal failure and inflammation by using ProteinChip System," *Blood*, 108:1381-1387, (2006); (Epub. Apr. 18, 2006, pp. 1-20).
Trülzsch and Wood, "Applications of nucleic acid technology in the CNS," *J. Neurochem.*, 88: 257-265 (2004).
Tsuchiya et al., "Measurement of Serum Hepcidin Levels by ProteinChip System and Assessment of Iron Regulatory Protein in Mice in Various Acute and Chronic Experiments," Abstract SA-PO632, *American Society of Nephrology Meeting, J. Am. Soc. Nephrol.*, 18(Abstracts Issue):480A (2007).
Tuerk and Gold, "Systematic Evolution of Ligands by Exponential Enrichment: RNA Ligands to Bacteriophage T4 DNA Polymerase," *Science*, 249: 505-510 (1990).
Turner et al. "RNAa Structure Prediction," *Annu. Rev. Biophys. Biophys. Chem.* 17:167-192 (1988).
Tutu et al., "Trispecific F(ab')₃ derivatives that use cooperative signaling via the TCR/CD3 complex and CD2 to activate and redirect resting cytotoxic T cells," *J. Immunol.*, 147:60-69 (1991).
Uehata et al., "Quantitation of Serum Hepcidin-25 in Chronic Kidney Disease Using Mass Spectrometry," Abstract PUB489, *American Society of Nephrology Meeting, J. Am. Soc. Nephrol.*, 18(Abstracts Issue):938A (2007).
Uhlenbeck, "A small catalytic oligoribonucleotide," *Nature*, 328: 596-600 (1987).
Umaña et al., "Engineered glycoforms of an antineuroblastoma IgG1 with optimized antibody-dependent cellular cytotoxic activity," *Nature Biotechnol.* 17(2):176-180 (1999).
Verhoeyen et al., "Reshaping Human Antibodies: Grafting an Antilysozyme Activity," *Science*, 239:1534-1536 (1988).
Verma, "Gene Therapy," *Scientific American*, 68-84 (1990).
Vinores, "Technology evaluation: Pegaptanib, Eyetech/Pfizer," *Curr. Opin. Mol. Ther.*, 5:673-679 (2003).
Wagner et al., "Transferin-polycation conjugates as carriers for DNA uptake into cells," *Proc. Natl. Acad. Sci. USA*, 87:3410-3414 (1990).
Ward et al., "Binding activities of a repertoire of single immunoglobulin variable domains secreted from *Escherichia coli*," *Nature*, 341:544-546 (1989).
Watkins, "Screening of Phage-Expressed Antibody Libraries by Capture Lift," *Methods in Molecular Biology, Antibody Phage Display:*

(56) References Cited

OTHER PUBLICATIONS

*Methods and Protocols*, vol. 178, Eds. O'Brien and Aitken, (Humana Press, Totawa, NJ (2001)) pp. 187-193.

Weinstein et al., "Inappropriate expression of hepcidin is associated with iron refractory anemia: implications for the anemia of chronic disease," *Blood*, 100(10):3776-3781 (2002).

Wells and Lowman, "Rapid evolution of peptide and protein binding properties in vitro," *Curr. Opin. Biotechnol.*, 3: 355-362 (1992).

Wheeler et al., "Intrabody-based strategies for inhibition of vascular endothelial growth factor receptor-2: effects on apoptosis, cell growth, and angiogenesis," *FASEB J.*, 17:1733-1735(2003).

White et al., "Generation of Species Cross-reactive Aptamers Using "Toggle" SELEX," *Mol. Ther.*, 4(6): 567-573 (2001).

Wide, L., "Solid Phase Antigen-Antibody Systems," *Radioimmunoassay Methods: European Workshop Sep. 15-17, 1970 Edinburgh*, Eds., Kirkham and Hunter, (Churchill Livingston, Edenburgh, (1971)) pp. 405-412.

Willems et al., "Optimizing expression and purification from cell culture medium of trispecific recombinant antibody derivatives," *J Chromatogr B Analyt. Technol. Biomed. Life Sci.* 786:161-176 (2003).

Williams and Polli, "The Lyophilization of Pharmaceuticals: A Literature Review," *Journal of Parenteral Science and Technology*, 38: 48-59 (1984).

Winter et al., "Making Antibodies by Phage Display Technology," *Annu. Rev. Immunol.*, 12:433-455 (1994).

Wolff et al., "Monoclonal Antibody Homodimers: Enhanced Antitumor Activity in Nude Mice," *Cancer Research*, 53: 2560-2565 (1993).

Wu et al., "Receptor-mediated in Vitro Gene Transformation by a Soluble DNA Carrier System", *J. Biol. Chem.*, 262(10):4429-4432 (1987).

Xia et al., "RNAi suppresses polyglutamine-induced neurodegeneration in a model of spinocerebellar ataxia," *Nature Med.*, 10:816-820 (2004).

Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity," *Biotechnol Bioeng.*, 87(5):614-622 (2004).

Young et al., "Hepcidin—A Novel Biomarker of Functional Iron Status in Chronic Kidney Disease That Is Independent of Renal Function," Abstract PUB479, *American Society of Nephrology Meeting, J. Am. Soc. Nephrol.*, 18(Abstracts Issue):935A (2007).

Zaccolo et al., "The Effect of High-Frequency Random Mutagenesis on in Vitro Protein Evolution: A Study on TEM-1 β-Lactamase," *J. Mol. Biol.*, 285:775-783 (1999).

Zapata et al., "Engineering linear F(ab')$_2$ fragments for efficient production in *Escherichia coli* and enhanced antiproliferative activity," *Protein Eng.*, 8(10):1057-1062 (1995).

Zaug, et al., "A Labile Phosphodiester Bond at the Ligation Junction in a Circular Intervening Sequence RNA," *Science*, 224:574-578 (1984).

Zaug, et al., "The Intervening Sequence RNA of *Tetrahymena* Is an Enzyme," *Science*, 231:470-475 (1986).

Zaug, et al., "The *Tetrahymena* ribozyme acts like an RNA restriction endonuclease," *Nature*, 324:429-433 (1986).

Zhou et al., "Lipophilic polylysines mediate efficient DNA transfection in mammalian cells," *Biochim. Biophys. Acta*, 1065:8-14 (1991).

Zola, "Monoclonal Antibodies: *A Manual of Techniques*," (CRC Press, Inc., Boca Raton, FL (1987)) pp. 147-158.

Rudikoff, et al., "Single amino acid substitution altering antigen-binding specificity," 1982, Proc. Nat. Acad. Sci. USA, vol. 79, pp. 1979-1983.

Bates, et al., "Genetic immunization for antibody generation in research animals by intravenous delivery of plasmid DNA," BioTechniques, 2006, 40(2):199-208.

Desmyter et al., "Antigen Specificity and High Affinity Binding Provided by One Single Loop of a Camel Single-domain Antibody," *J. Biol. Chem.*, 276(28):26285-26290 (2001).

Devlin et al., "Random Peptide Libraries: A Source of Specific Protein Binding Molecules," *Science*, 249: 404-406 (1990).

Dirac et al., "Reversal of Senescence in Mouse Fibroblasts through Lentiviral Suppression of p53," *J. Biol. Chem,*. 278(14):11731-11734 (2003).

Dörner et al., "The Synthesis of Peptidomimetic Combinatorial Libraries Through Successive Amide Alkylations," *Bioorganic Medicinal Chem.*, 4(5):709-715 (1996).

Doudna et al., "Selection of an RNA molecule that mimics a major autoantigenic epitope of human insulin receptor," *Proc. Natl. Acad. Sci. USA*, 92: 2355-2359 (1995).

DRG International Inc., USA, "New ELISA Hepcidin Prohormone: Enzymeimmunoassay for the quantitative measurement of Pro-Hepcidin in human serum," *Product Brochure*.

Du Pasquier, L., "Evolution of the Immune System", Ch. 7, *Fundamental Immunology*, (Paul, W., ed., 2nd ed. Raven Press, N.Y. (1989)).

Eckstein, "Phosphorothioate Oligodeoxynucleotides: What Is Their Origin and What Is Unique About Them?" *Antisense Nucleic Acid Drug Dev.*, 10: 117-121 (2000).

Edge et al., "Deglycosylation of Glycoproteins by Trifluoromethanesulfonic Acid," *Anal. Biochem.*, 118: 131-137 (1981).

Elbashir et al., "Duplexes of 21-nucleotide RNAs mediate RNA interference in cultured mammalian cells," *Nature*, 411:494-498 (2001).

Elbashir et al., "RNA interference is mediated by 21-and 22-nucleotide RNAs," *Genes Dev.*, 15:188-200 (2001).

Ellington and Szostak, "In vitro selection of RNA molecules that bind specific ligands," *Nature*, 346: 818-822 (1990).

Ewert et al., "Biophysical Properties of Camelid $V_{HH}$ Domains Compared to Those of Human $V_H 3$ Domains," *Biochemistry*, 41:3628-3636 (2002).

Ezeh et al., "Hepcidin, haemoglobin and ferritin levels in sickle cell anaemia," *Eur. J. Haematol.*, 74:86-88, (2005).

Fasano et al., "Modifications of the iron—neuromelanin system in Parkinson's disease," *J. Neurochem.*, 96:909-916 (2006).

Felgner et al., "Lipofection: A highly efficient, lipid-mediated DNA-transfection procedure," *Proc. Natl. Acad. Sci. USA*, 84:7413-7417 (1987).

Fermér et al., "Specificity Rescue and Affinity Maturation of a Low-Affinity IgM Antibody against Pro-Gastrin-Releasing Peptide using Phage Display and DNA Shuffling," *Tumor Biol.*, 25(1-2):7-13 (2004).

Ferrara et al., "The Carbohydrate at FcγRIIIa Asn-162. An Element Required for High Affinity Binding to Non-fucosylated IgG Glycoforms," *J. Biol. Chem.*, 281(8):5032-5036 (2006).

* cited by examiner

* = ammonium salt

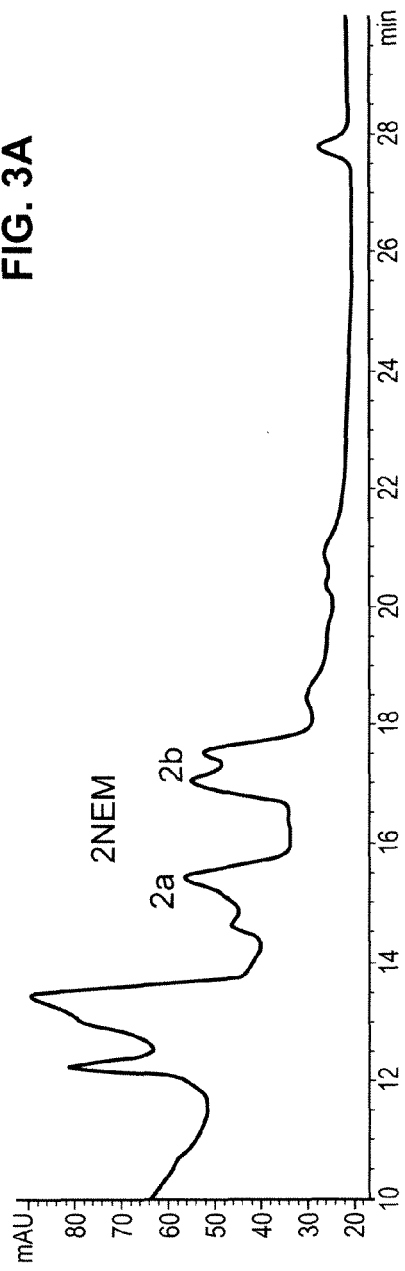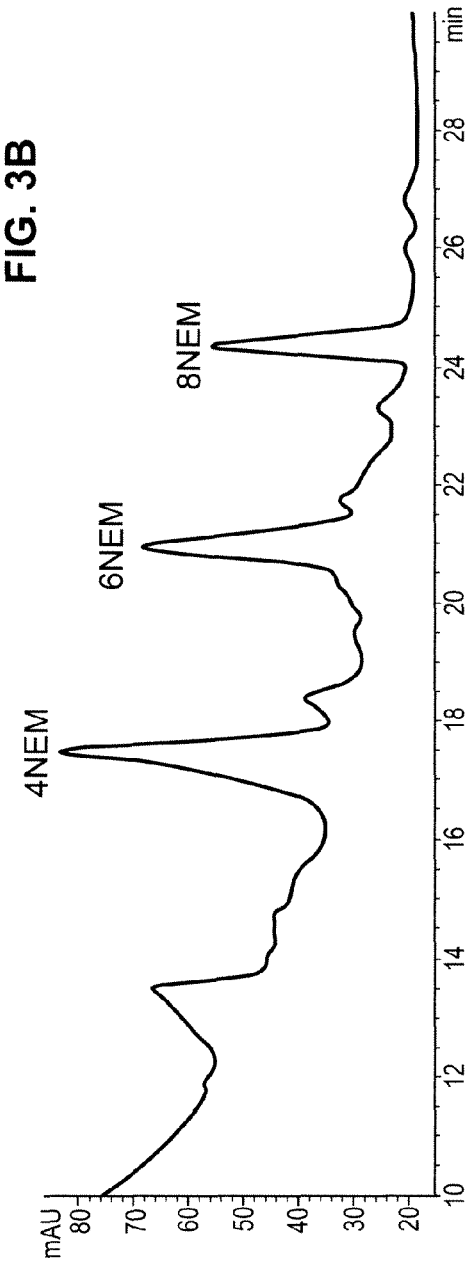

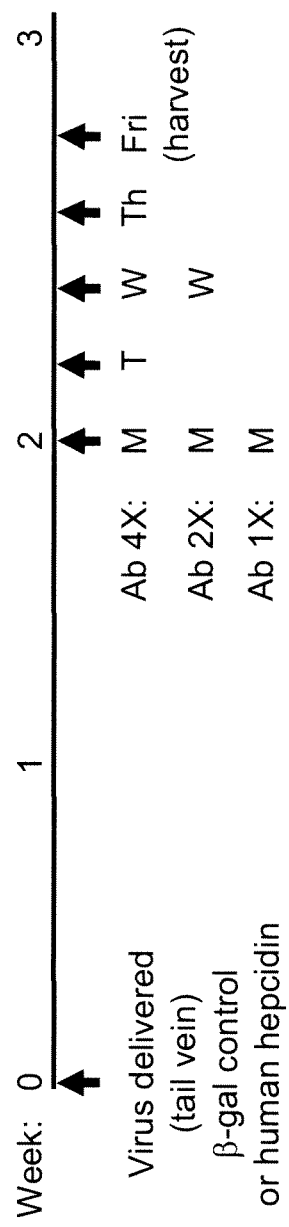

FIG. 16A

```
                      pre-bleed      Aranesp®
                         ↓              ↓
Week:  0                 6       7      8      9            13
       ↑                 ↑       ↑      ↑      ↑
   Brucella abortus      Ab      Ab     Ab     Ab        (harvest)
```

— ▲ — control Ab + saline
— ◆ — Ab 2.7 + saline
--- ● --- control Ab + Aranesp®
— □ — Ab 2.7 + Aranesp®

Current Stratification Scheme

Proposed Stratification Scheme

Breakdown of AoC diagnoses

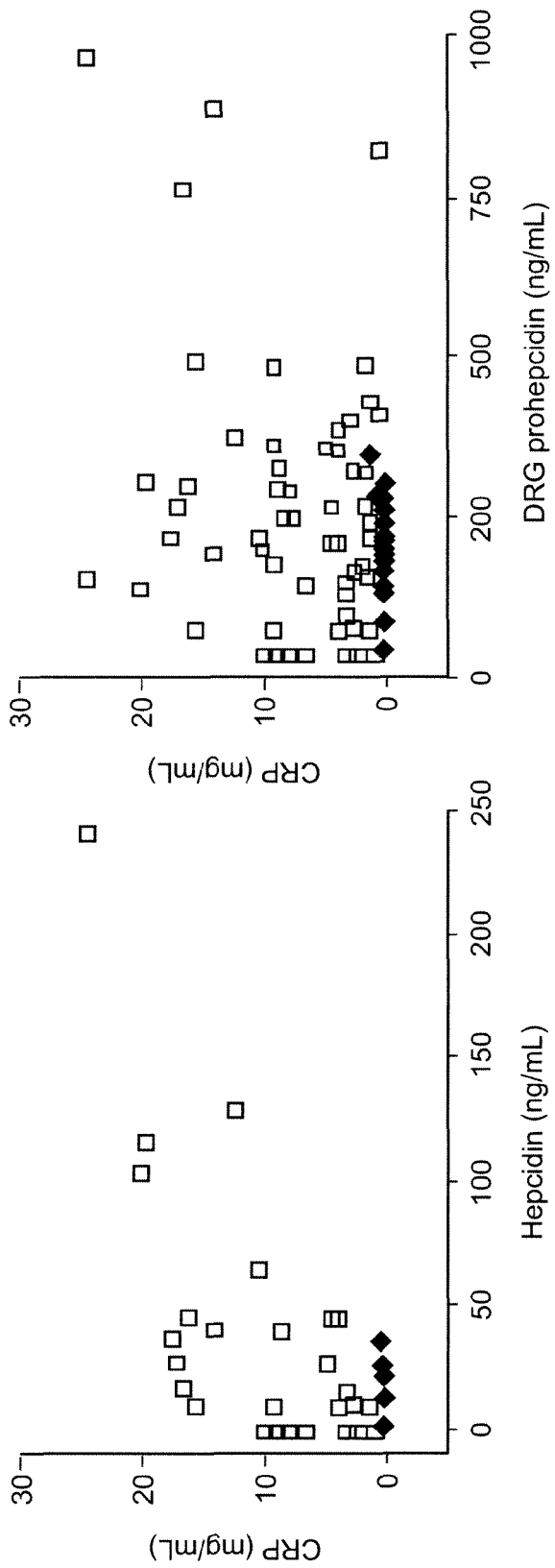

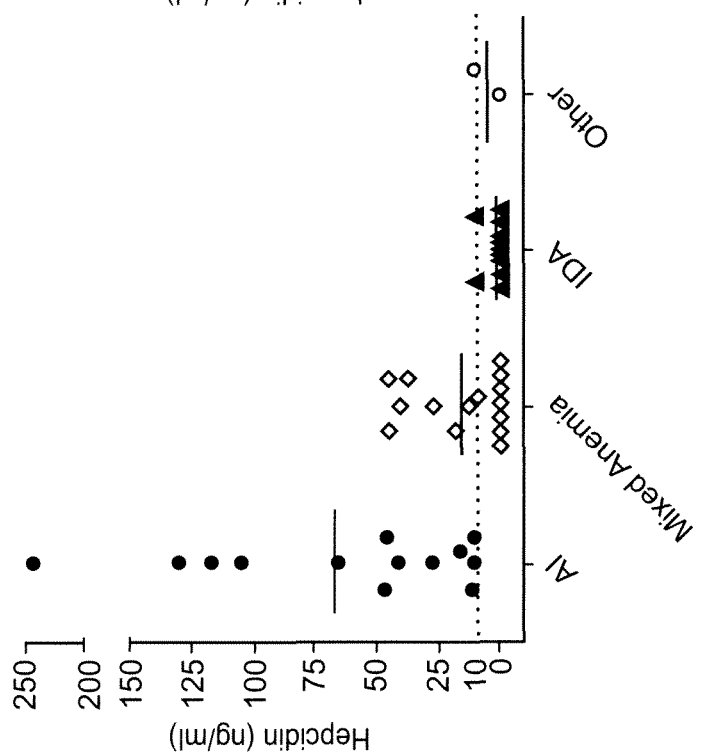
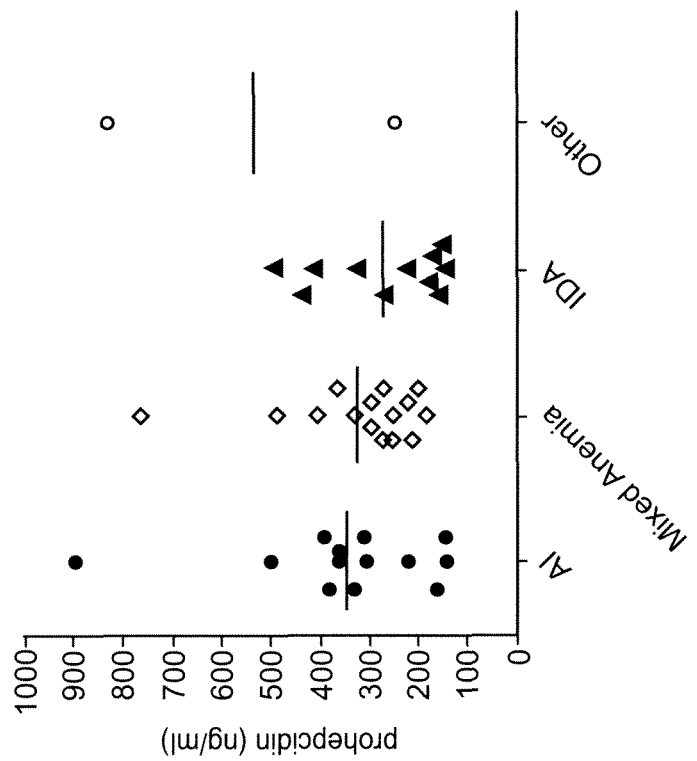
FIG. 26B
FIG. 26A

Hepcidin Assay; Hu Sera

Hepcidin level in 24 unknown Human Sera samples tested in this Competitive assay.

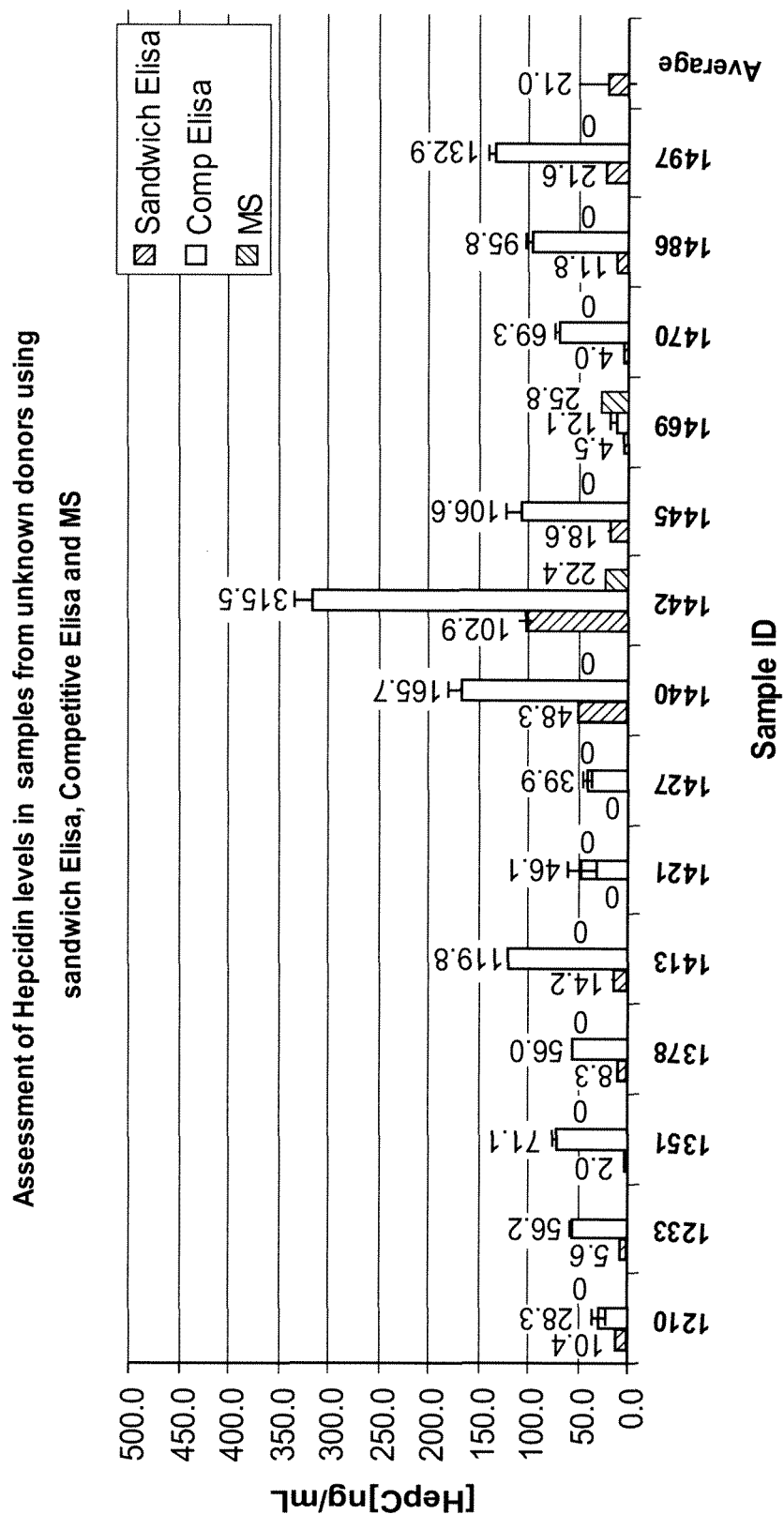

SEQUENCE LISTING

<160> NUMBER OF SEQ ID NOS: 329

<210> SEQ ID NO 1
<211> LENGTH: 249
<212> TYPE: DNA
<213> ORGANISM: Mus musculus

<400> SEQUENCE: 1

```
atggcactca gcactcggac ccaggctgcc tgtctcctgc ttctcctcct tgccagcctg      60
agcagcacca cctatctcca tcaacagatg agacagacta cagagctgca gcctttgcac     120
ggggaagaaa gcagggcaga cattgcgata ccaatgcaga agagaaggaa gagagacacc     180
aacttcccca tctgcatctt ctgctgtaaa tgctgtaaca attcccagtg tggtatctgt     240
tgcaaaaca                                                             249
```

<210> SEQ ID NO 2
<211> LENGTH: 83
<212> TYPE: PRT
<213> ORGANISM: Mus musculus

<400> SEQUENCE: 2

```
Met Ala Leu Ser Thr Arg Thr Gln Ala Ala Cys Leu Leu Leu Leu Leu
1               5                   10                  15

Leu Ala Ser Leu Ser Ser Thr Thr Tyr Leu His Gln Gln Met Arg Gln
                20                  25                  30

Thr Thr Glu Leu Gln Pro Leu His Gly Glu Glu Ser Arg Ala Asp Ile
            35                  40                  45

Ala Ile Pro Met Gln Lys Arg Arg Lys Arg Asp Thr Asn Phe Pro Ile
        50                  55                  60

Cys Ile Phe Cys Cys Lys Cys Cys Asn Asn Ser Gln Cys Gly Ile Cys
65                  70                  75                  80

Cys Lys Thr
```

<210> SEQ ID NO 3
<211> LENGTH: 252
<212> TYPE: DNA
<213> ORGANISM: Rattus norvegicus

<400> SEQUENCE: 3

```
atggcactaa gcactcggat ccaggctgcc tgtctcctgc ttctcctcct ggccagcctg      60
agcagcggtg cctatctccg gcaacagacg agacagacta cggctctgca gccttggcat     120
ggggcagaaa gcaagactga tgacagtgcg ctgctgatgc tgaagcgaag gaagcgagac     180
accaacttcc ccatatgcct cttctgctgt aaatgctgta agaattcctc ctgtggtctc     240
```
tgttgcataa ca                                                       252

<210> SEQ ID NO 4
<211> LENGTH: 84
<212> TYPE: PRT
<213> ORGANISM: Rattus norvegicus

<400> SEQUENCE: 4

Met Ala Leu Ser Thr Arg Ile Gln Ala Ala Cys Leu Leu Leu Leu
1               5                   10                  15

Leu Ala Ser Leu Ser Ser Gly Ala Tyr Leu Arg Gln Gln Thr Arg Gln
            20                  25                  30

Thr Thr Ala Leu Gln Pro Trp His Gly Ala Glu Ser Lys Thr Asp Asp
        35                  40                  45

Ser Ala Leu Leu Met Leu Lys Arg Arg Lys Arg Asp Thr Asn Phe Pro
    50                  55                  60

Ile Cys Leu Phe Cys Cys Lys Cys Cys Lys Asn Ser Ser Cys Gly Leu
65                  70                  75                  80

Cys Cys Ile Thr

<210> SEQ ID NO 5
<211> LENGTH: 78
<212> TYPE: DNA
<213> ORGANISM: Macaca fascicularis

<400> SEQUENCE: 5
gacacccact tccccatctg cattttctgc tgcggctgct gtcatcgatc aaagtgtggg    60
atgtgctgca ggacgtag                                                  78

<210> SEQ ID NO 6
<211> LENGTH: 25
<212> TYPE: PRT
<213> ORGANISM: Macaca fascicularis

<400> SEQUENCE: 6

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 7
<211> LENGTH: 252
<212> TYPE: DNA
<213> ORGANISM: Homo sapiens

<400> SEQUENCE: 7
atggcactga gctcccagat ctgggccgct tgcctcctgc tcctcctcct cctcgccagc    60
ctgaccagtg gctctgtttt cccacaacag acgggacaac ttgcagagct gcaaccccag   120
gacagagctg agccagggc cagctggatg cccatgttcc agaggcgaag gaggcgagac   180
acccacttcc ccatctgcat tttctgctgc ggctgctgtc atcgatcaaa gtgtgggatg   240
tgctgcaaga cg                                                      252

<210> SEQ ID NO 8
<211> LENGTH: 84
<212> TYPE: PRT
<213> ORGANISM: Homo sapiens

<400> SEQUENCE: 8

```
Met Ala Leu Ser Ser Gln Ile Trp Ala Ala Cys Leu Leu Leu Leu
1               5                   10                  15

Leu Leu Ala Ser Leu Thr Ser Gly Ser Val Phe Pro Gln Thr Gly
            20                  25                  30

Gln Leu Ala Glu Leu Gln Pro Gln Asp Arg Ala Gly Ala Arg Ala Ser
        35                  40                  45

Trp Met Pro Met Phe Gln Arg Arg Arg Arg Asp Thr His Phe Pro
    50                  55                  60

Ile Cys Ile Phe Cys Cys Gly Cys Cys His Arg Ser Lys Cys Gly Met
65                  70                  75                  80

Cys Cys Lys Thr

<210> SEQ ID NO 9
<211> LENGTH: 25
<212> TYPE: PRT
<213> ORGANISM: Homo sapiens

<400> SEQUENCE: 9

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 10

<400> SEQUENCE: 10

000

<210> SEQ ID NO 11

<400> SEQUENCE: 11

000

<210> SEQ ID NO 12
<211> LENGTH: 330
<212> TYPE: DNA
<213> ORGANISM: Homo sapiens

<400> SEQUENCE: 12
aacatcgtgc tgacccaatc tccagcttct ttggctgtgt ctctagggca gagggccacc      60
atatcctgca gagccagtga aagtgttgat agttatggca atagttttat gcactggtac     120
cagcagaaac caggacagcc acccaaactc ctcatctatc ttgcatccaa cctagaatct     180
ggggtccctg ccaggttcag tggcagtggg tctaggacag acttcaccct caccattgat     240
cctgtggagg ctgatgatgc tgcaacctat tactgtcagc aaaataatga ggatcggacg     300
ttcggtggag gcaccaagct ggaaatcaaa                                     330

<210> SEQ ID NO 13
<211> LENGTH: 110
<212> TYPE: PRT
<213> ORGANISM: Homo sapiens

<400> SEQUENCE: 13

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
```

```
                35                  40                  45
Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Arg Thr Phe Gly Gly Gly Thr Lys Leu Glu Ile Lys
                100                 105                 110

<210> SEQ ID NO 14
<211> LENGTH: 357
<212> TYPE: DNA
<213> ORGANISM: Homo sapiens

<400> SEQUENCE: 14
cagatccagt tggtacagtc tggacctgag ctgaagaagc ctggagagac agtcaagatc        60
tcctgcaagg cttctgggta taccttcaca acctatggaa tgagctgggt gaaacaggct       120
ccaggaaagg gtttaaagtg gatgggctgg ataaacacct actctggagt gccaacatat       180
gctgatgact tcaagggacg gtttgccttc tctttggaaa cctctgccag cactgcctat       240
ttgcagatca caaacctcaa aaatgaggac acggctacat atttctgtgc aagcttatgg       300
tactacggta gggcctttga ctactggggc caaggcacca ctctcacagt ctcctca          357

<210> SEQ ID NO 15
<211> LENGTH: 119
<212> TYPE: PRT
<213> ORGANISM: Homo sapiens

<400> SEQUENCE: 15

Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Thr Tyr
                 20                  25                  30

Gly Met Ser Trp Val Lys Gln Ala Pro Gly Lys Gly Leu Lys Trp Met
             35                  40                  45

Gly Trp Ile Asn Thr Tyr Ser Gly Val Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Ser Leu Trp Tyr Tyr Gly Arg Ala Phe Asp Tyr Trp Gly Gln Gly
                100                 105                 110

Thr Thr Leu Thr Val Ser Ser
        115

<210> SEQ ID NO 16
<211> LENGTH: 15
<212> TYPE: PRT
<213> ORGANISM: Homo sapiens

<400> SEQUENCE: 16

Arg Ala Ser Glu Ser Val Asp Ser Tyr Gly Asn Ser Phe Met His
  1               5                  10                  15

<210> SEQ ID NO 17
<211> LENGTH: 7
```

```
<212> TYPE: PRT
<213> ORGANISM: Homo sapiens

<400> SEQUENCE: 17

Leu Ala Ser Asn Leu Glu Ser
1               5

<210> SEQ ID NO 18
<211> LENGTH: 8
<212> TYPE: PRT
<213> ORGANISM: Homo sapiens

<400> SEQUENCE: 18

Gln Gln Asn Asn Glu Asp Arg Thr
1               5

<210> SEQ ID NO 19
<211> LENGTH: 5
<212> TYPE: PRT
<213> ORGANISM: Homo sapiens

<400> SEQUENCE: 19

Thr Tyr Gly Met Ser
1               5

<210> SEQ ID NO 20
<211> LENGTH: 17
<212> TYPE: PRT
<213> ORGANISM: Homo sapiens

<400> SEQUENCE: 20

Trp Ile Asn Thr Tyr Ser Gly Val Pro Thr Tyr Ala Asp Asp Phe Lys
1               5                   10                  15

Gly

<210> SEQ ID NO 21
<211> LENGTH: 10
<212> TYPE: PRT
<213> ORGANISM: Homo sapiens

<400> SEQUENCE: 21

Leu Trp Tyr Tyr Gly Arg Ala Phe Asp Tyr
1               5                   10

<210> SEQ ID NO 22

<400> SEQUENCE: 22

000

<210> SEQ ID NO 23

<400> SEQUENCE: 23

000

<210> SEQ ID NO 24
<211> LENGTH: 330
<212> TYPE: DNA
<213> ORGANISM: Homo sapiens

<400> SEQUENCE: 24
gacattgtgc tgacccaatc tccagcttct ttggctgtgt ctctagggca gagggccacc      60
atatcctgca gagccagtga aagtgttgat agttatggca atagttttat gcactggtac     120
```

```
cagcagaaac caggacagcc acccaaactc ctcatctatc gtgcatccaa cctagaatct    180
gggatccctg ccaggttcag tggcagtggg tctaggacag acttcaccct caccattaat    240
cctgtggagg ctgatgatgt tgcaacctat tactgtcacc aaagtaatga ggagtacacg    300
ttcggagggg ggaccaagct ggaaataaaa                                     330
```

<210> SEQ ID NO 25
<211> LENGTH: 110
<212> TYPE: PRT
<213> ORGANISM: Homo sapiens

<400> SEQUENCE: 25

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys His Gln Ser Asn
                85                  90                  95

Glu Glu Tyr Thr Phe Gly Gly Gly Thr Lys Leu Glu Ile Lys
            100                 105                 110
```

<210> SEQ ID NO 26
<211> LENGTH: 354
<212> TYPE: DNA
<213> ORGANISM: Homo sapiens

<400> SEQUENCE: 26

```
cagatccagt tggtacagtc tggacctgag ctgaagaagc ctggagagac agtcaagatc     60
tcctgcaagg cttctgggta taccttcaca acctatggaa tgagctgggt gaaacaggct    120
ccaggaaagg gtttaaagtg gatgggctgg ataaatacct actctggagt gccaacatat    180
gctgatgact caagggacg gtttgccttc tctttggaaa cctctgccag cactgcctat    240
ttgcagatca caacctcaa aaatgaggac acggctacat atttctgtgg aagagaccac    300
tactacgggg aggttgctta ctggggccaa gggactctgg tcactgtctc tgca           354
```

<210> SEQ ID NO 27
<211> LENGTH: 118
<212> TYPE: PRT
<213> ORGANISM: Homo sapiens

<400> SEQUENCE: 27

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
                20                  25                  30

Gly Met Ser Trp Val Lys Gln Ala Pro Gly Lys Gly Leu Lys Trp Met
            35                  40                  45

Gly Trp Ile Asn Thr Tyr Ser Gly Val Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80
```

```
Leu Gln Ile Asn Asn Leu Lys Asn Glu Asp Thr Ala Thr Tyr Phe Cys
                85                  90                  95

Gly Arg Asp His Tyr Tyr Gly Glu Val Ala Tyr Trp Gly Gln Gly Thr
            100                 105                 110

Leu Val Thr Val Ser Ala
        115
```

<210> SEQ ID NO 28
<211> LENGTH: 15
<212> TYPE: PRT
<213> ORGANISM: Homo sapiens

<400> SEQUENCE: 28

```
Arg Ala Ser Glu Ser Val Asp Ser Tyr Gly Asn Ser Phe Met His
1               5                   10                  15
```

<210> SEQ ID NO 29
<211> LENGTH: 7
<212> TYPE: PRT
<213> ORGANISM: Homo sapiens

<400> SEQUENCE: 29

```
Arg Ala Ser Asn Leu Glu Ser
1               5
```

<210> SEQ ID NO 30
<211> LENGTH: 8
<212> TYPE: PRT
<213> ORGANISM: Homo sapiens

<400> SEQUENCE: 30

```
His Gln Ser Asn Glu Glu Tyr Thr
1               5
```

<210> SEQ ID NO 31
<211> LENGTH: 5
<212> TYPE: PRT
<213> ORGANISM: Homo sapiens

<400> SEQUENCE: 31

```
Thr Tyr Gly Met Ser
1               5
```

<210> SEQ ID NO 32
<211> LENGTH: 17
<212> TYPE: PRT
<213> ORGANISM: Homo sapiens

<400> SEQUENCE: 32

```
Trp Ile Asn Thr Tyr Ser Gly Val Pro Thr Tyr Ala Asp Asp Phe Lys
1               5                   10                  15

Gly
```

<210> SEQ ID NO 33
<211> LENGTH: 9
<212> TYPE: PRT
<213> ORGANISM: Homo sapiens

<400> SEQUENCE: 33

```
Asp His Tyr Tyr Gly Glu Val Ala Tyr
1               5
```

<210> SEQ ID NO 34

```
<400> SEQUENCE: 34

000

<210> SEQ ID NO 35

<400> SEQUENCE: 35

000

<210> SEQ ID NO 36
<211> LENGTH: 330
<212> TYPE: DNA
<213> ORGANISM: Homo sapiens

<400> SEQUENCE: 36
gacattgtgc tgacccaatc tccagcttct ttggctgtgt ctctagggca gagggccacc    60
atatcctgca gagccagtga aagtgttgat agttttggca atagtttttat gcactggtac   120 cagctgaaac caggacagcc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaatttat tactgtcagc aaagtaatga ggagtacacg   300
ttcggagggg ggaccaagct ggaaataaaa                                     330

<210> SEQ ID NO 37
<211> LENGTH: 110
<212> TYPE: PRT
<213> ORGANISM: Homo sapiens

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Phe
            20                  25                  30

Gly Asn Ser Phe Met His Trp Tyr Gln Leu Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Ile Tyr Tyr Cys Gln Gln Ser Asn
                85                  90                  95

Glu Glu Tyr Thr Phe Gly Gly Gly Thr Lys Leu Glu Ile Lys
            100                 105                 110

<210> SEQ ID NO 38
<211> LENGTH: 354
<212> TYPE: DNA
<213> ORGANISM: Homo sapiens

<400> SEQUENCE: 38
cagatccagt tggtacagtc tggacctgag ctgaagaagc ctggagagac agtcaagatc    60
tcctgcaagg cttctgggta taccttcaca acctatggaa tgagctgggt gaaacaggct   120
ccaggaaagg gtttaaagtg gatgggctgg ataaacacct cctctggagt gccaacatat   180
gctgatgact tcatgggacg gtttgccttc tctttggaaa cctctgccag cactgcctat   240
ttgcagatca acaacctcaa aaatgaggac acggctacga tttctgtgc aagagaccgc    300 tactacgggg aggttgctta ctggggccaa gggactctgg tcaccgtctc tgca          354
```

<210> SEQ ID NO 39
<211> LENGTH: 118
<212> TYPE: PRT
<213> ORGANISM: Homo sapiens

<400> SEQUENCE: 39

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Ser Ser Gly Val Pro Thr Tyr Ala Asp Asp Phe
    50                  55                  60

Met Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Arg Tyr Tyr Gly Glu Val Ala Tyr Trp Gly Gln Gly Thr
            100                 105                 110

Leu Val Thr Val Ser Ala
        115

<210> SEQ ID NO 40
<211> LENGTH: 15
<212> TYPE: PRT
<213> ORGANISM: Homo sapiens

<400> SEQUENCE: 40

Arg Ala Ser Glu Ser Val Asp Ser Phe Gly Asn Ser Phe Met His
1               5                   10                  15

<210> SEQ ID NO 41
<211> LENGTH: 7
<212> TYPE: PRT
<213> ORGANISM: Homo sapiens

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Homo sapiens

<400> SEQUENCE: 42

Gln Gln Ser Asn Glu Glu Tyr Thr
1               5

<210> SEQ ID NO 43
<211> LENGTH: 5
<212> TYPE: PRT
<213> ORGANISM: Homo sapiens

<400> SEQUENCE: 43

Thr Tyr Gly Met Ser
1               5

<210> SEQ ID NO 44
<211> LENGTH: 17
<212> TYPE: PRT

<213> ORGANISM: Homo sapiens

<400> SEQUENCE: 44

Trp Ile Asn Thr Ser Ser Gly Val Pro Thr Tyr Ala Asp Asp Phe Met
1               5                   10                  15
Gly

<210> SEQ ID NO 45
<211> LENGTH: 9
<212> TYPE: PRT
<213> ORGANISM: Homo sapiens

<400> SEQUENCE: 45

Asp Arg Tyr Tyr Gly Glu Val Ala Tyr
1               5

<210> SEQ ID NO 46

<400> SEQUENCE: 46

000

<210> SEQ ID NO 47

<400> SEQUENCE: 47

000

<210> SEQ ID NO 48
<211> LENGTH: 317
<212> TYPE: DNA
<213> ORGANISM: Homo sapiens

<400> SEQUENCE: 48
acatccagat gacccagtct ccttcactcc tgtcagcatc tgtgggagac agagtcactc     60
tcagctgcaa agcaagtcag aatatttaca agtacttaaa ctggtatcag caaaagcttg    120
gagaagctcc caaactcctg atatattata caaacagttt gcaaacgggc atcccatcaa    180
ggttcagtgg cagtggatct ggtacagatt tcacacttac catcagcagc ctgcagcctg    240
aagatgttgc cacatattac tgctatcagt ataacagtgg gcccacgttt ggagctggga    300
ccaagctgga actgaaa                                                   317

<210> SEQ ID NO 49
<211> LENGTH: 106
<212> TYPE: PRT
<213> ORGANISM: Homo sapiens

<400> SEQUENCE: 49

Asp Ile Gln Met Thr Gln Ser Pro Ser Leu Leu Ser Ala Ser Val Gly
1               5                   10                  15

Asp Arg Val Thr Leu Ser Cys Lys Ala Ser Gln Asn Ile Tyr Lys Tyr
                20                  25                  30

Leu Asn Trp Tyr Gln Gln Lys Leu Gly Glu Ala Pro Lys Leu Leu Ile
            35                  40                  45

Tyr Tyr Thr Asn Ser Leu Gln Thr Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Asn Ser Gly Pro Thr
                85                  90                  95

```
Phe Gly Ala Gly Thr Lys Leu Glu Leu Lys
            100                 105
```

```
<210> SEQ ID NO 50
<211> LENGTH: 372
<212> TYPE: DNA
<213> ORGANISM: Homo sapiens

<400> SEQUENCE: 50
caggttactc tgaaagagtc tggccctggg atattgcagc cttcccagac cctcagtctg      60
acttgctctt tctctgggtt ttcactgagc acttctggta tatgtgtgag ctggattcgt     120
cagccttcag ggaagggtct ggagtggctg gcaactattt gttgggagga tagtaagggc     180
tacaacccct tctctgaagaa ccggctcaca atctccaagg acacctccaa caaccaagca    240
ttcctcaaga tcaccagtgt ggacactgca gataccgcca tatactactg tgctcggccc     300
cttaactacg gagggtatag tgagctagaa ttggattact ggggccaagg agtcatggtc     360
acagtctcct ca                                                         372
```

```
<210> SEQ ID NO 51
<211> LENGTH: 124
<212> TYPE: PRT
<213> ORGANISM: Homo sapiens

<400> SEQUENCE: 51

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Ile Cys Val Ser Trp Ile Arg Gln Pro Ser Gly Lys Gly Leu Glu
        35                  40                  45

Trp Leu Ala Thr Ile Cys Trp Glu Asp Ser Lys Gly Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Ser Val Asp Thr Ala Asp Thr Ala Ile Tyr Tyr
                85                  90                  95

Cys Ala Arg Pro Leu Asn Tyr Gly Gly Tyr Ser Glu Leu Glu Leu Asp
            100                 105                 110

Tyr Trp Gly Gln Gly Val Met Val Thr Val Ser Ser
        115                 120
```

```
<210> SEQ ID NO 52
<211> LENGTH: 11
<212> TYPE: PRT
<213> ORGANISM: Homo sapiens

<400> SEQUENCE: 52

Lys Ala Ser Gln Asn Ile Tyr Lys Tyr Leu Asn
1               5                   10
```

```
<210> SEQ ID NO 53
<211> LENGTH: 7
<212> TYPE: PRT
<213> ORGANISM: Homo sapiens

<400> SEQUENCE: 53

Tyr Thr Asn Ser Leu Gln Thr
1               5
```

```
<210> SEQ ID NO 54
<211> LENGTH: 8
<212> TYPE: PRT
<213> ORGANISM: Homo sapiens

<400> SEQUENCE: 54

Tyr Gln Tyr Asn Ser Gly Pro Thr
1               5

<210> SEQ ID NO 55
<211> LENGTH: 7
<212> TYPE: PRT
<213> ORGANISM: Homo sapiens

<400> SEQUENCE: 55

Thr Ser Gly Ile Cys Val Ser
1               5

<210> SEQ ID NO 56
<211> LENGTH: 16
<212> TYPE: PRT
<213> ORGANISM: Homo sapiens

<400> SEQUENCE: 56

Thr Ile Cys Trp Glu Asp Ser Lys Gly Tyr Asn Pro Ser Leu Lys Asn
1               5                   10                  15

<210> SEQ ID NO 57
<211> LENGTH: 14
<212> TYPE: PRT
<213> ORGANISM: Homo sapiens

<400> SEQUENCE: 57

Pro Leu Asn Tyr Gly Gly Tyr Ser Glu Leu Glu Leu Asp Tyr
1               5                   10

<210> SEQ ID NO 58
<211> LENGTH: 19
<212> TYPE: RNA
<213> ORGANISM: Homo sapiens

<400> SEQUENCE: 58
uguaaaugcu guaacaauu                                                19

<210> SEQ ID NO 59
<211> LENGTH: 19
<212> TYPE: RNA
<213> ORGANISM: Homo sapiens

<400> SEQUENCE: 59
gcuguaaaug cuguaacaa                                                19

<210> SEQ ID NO 60
<211> LENGTH: 19
<212> TYPE: RNA
<213> ORGANISM: Homo sapiens

<400> SEQUENCE: 60 guguggauc uguugcaaa                                                 19

<210> SEQ ID NO 61
<211> LENGTH: 19
<212> TYPE: RNA
<213> ORGANISM: Homo sapiens

<400> SEQUENCE: 61
```
gcagacauug cgauaccaa                                                19

<210> SEQ ID NO 62
<211> LENGTH: 19
<212> TYPE: RNA
<213> ORGANISM: Homo sapiens

<400> SEQUENCE: 62
auaccaaugc agaagagaa                                                19

<210> SEQ ID NO 63
<211> LENGTH: 19
<212> TYPE: RNA
<213> ORGANISM: Homo sapiens

<400> SEQUENCE: 63
cuacagagcu gcagccuuu                                                19

<210> SEQ ID NO 64
<211> LENGTH: 19
<212> TYPE: RNA
<213> ORGANISM: Homo sapiens

<400> SEQUENCE: 64
gaagagagac accaacuuc                                                19

<210> SEQ ID NO 65
<211> LENGTH: 19
<212> TYPE: RNA
<213> ORGANISM: Homo sapiens

<400> SEQUENCE: 65 acuucccau cugcaucuu                                                 19

<210> SEQ ID NO 66
<211> LENGTH: 19
<212> TYPE: RNA
<213> ORGANISM: Homo sapiens

<400> SEQUENCE: 66
cugagcagca ccaccuauc                                                19

<210> SEQ ID NO 67
<211> LENGTH: 19
<212> TYPE: RNA
<213> ORGANISM: Homo sapiens

<400> SEQUENCE: 67
acagaugaga cagacuaca                                                19

<210> SEQ ID NO 68
<211> LENGTH: 19
<212> TYPE: RNA
<213> ORGANISM: Homo sapiens

<400> SEQUENCE: 68
caaugcagaa gagaaggaa                                                19

<210> SEQ ID NO 69
<211> LENGTH: 19
<212> TYPE: RNA
<213> ORGANISM: Homo sapiens

<400> SEQUENCE: 69
aauucccagu gugguaucu 19

<210> SEQ ID NO 70

<400> SEQUENCE: 70

000

<210> SEQ ID NO 71

<400> SEQUENCE: 71

000

<210> SEQ ID NO 72
<211> LENGTH: 193
<212> TYPE: PRT
<213> ORGANISM: Homo sapiens

<400> SEQUENCE: 72

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg
```

<210> SEQ ID NO 73
<211> LENGTH: 193
<212> TYPE: PRT
<213> ORGANISM: Homo sapiens

<400> SEQUENCE: 73

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45
```

```
Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 74
<211> LENGTH: 7
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any amino acid

<400> SEQUENCE: 74

Xaa Ala Ser Asn Leu Glu Ser
 1               5

<210> SEQ ID NO 75
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any amino acid

<400> SEQUENCE: 75

Xaa Gln Ser Asn Glu Glu
 1               5

<210> SEQ ID NO 76
<211> LENGTH: 6
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid

<400> SEQUENCE: 76

Gln Gln Xaa Asn Glu Xaa
 1               5

<210> SEQ ID NO 77
```

```
<211> LENGTH: 17
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (16)..(16)
<223> OTHER INFORMATION: Xaa can be any amino acid

<400> SEQUENCE: 77

Trp Ile Asn Thr Xaa Ser Gly Val Pro Thr Tyr Ala Asp Asp Phe Xaa
1               5                   10                  15

Gly

<210> SEQ ID NO 78
<211> LENGTH: 10
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid or nothing
<220> FEATURE:
<221> NAME/KEY: misc_feature
<222> LOCATION: (9)..(9)
<223> OTHER INFORMATION: Xaa can be any amino acid or nothing

<400> SEQUENCE: 78

Xaa Xaa Tyr Tyr Gly Xaa Xaa Ala Xaa Tyr
1               5                   10

<210> SEQ ID NO 79
<211> LENGTH: 75
<212> TYPE: DNA
<213> ORGANISM: Mus musculus

<400> SEQUENCE: 79
gacaccaact tccccatctg catcttctgc tgtaaatgct gtaacaattc ccagtgtggt    60
atctgttgca aaaca                                                    75

<210> SEQ ID NO 80
<211> LENGTH: 25
<212> TYPE: PRT
<213> ORGANISM: Mus musculus

<400> SEQUENCE: 80

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 81
<211> LENGTH: 75
<212> TYPE: DNA
<213> ORGANISM: Rattus norvegicus

<400> SEQUENCE: 81
```

```
gacaccaact tccccatatg cctcttctgc tgtaaatgct gtaagaattc ctcctgtggt      60
ctctgttgca taaca                                                       75
```

<210> SEQ ID NO 82
<211> LENGTH: 25
<212> TYPE: PRT
<213> ORGANISM: Rattus norvegicus

<400> SEQUENCE: 82

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 83
<211> LENGTH: 78
<212> TYPE: DNA
<213> ORGANISM: Cercopithecus aethiops

<400> SEQUENCE: 83

```
gacacccact tccccatctg cattttctgc tgcggctgct gtcatcgatc aaagtgtggg      60
atgtgctgca ggacgtag                                                    78
```

<210> SEQ ID NO 84
<211> LENGTH: 25
<212> TYPE: PRT
<213> ORGANISM: Cercopithecus aethiops

<400> SEQUENCE: 84

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 85
<211> LENGTH: 75
<212> TYPE: DNA
<213> ORGANISM: Oryctolagus cuniculus

<400> SEQUENCE: 85

```
gacacccact tccccatctg catcttctgc tgcagctgct gtaggaattc aaaatgtggg      60
atctgctgca agacc                                                       75
```

<210> SEQ ID NO 86
<211> LENGTH: 25
<212> TYPE: PRT
<213> ORGANISM: Oryctolagus cuniculus

<400> SEQUENCE: 86

Asp Thr His Phe Pro Ile Cys Ile Phe Cys Cys Ser Cys Cys Arg Asn
1               5                   10                  15

Ser Lys Cys Gly Ile Cys Cys Lys Thr
            20                  25

<210> SEQ ID NO 87
<211> LENGTH: 75
<212> TYPE: DNA
<213> ORGANISM: Canis familiaris

<400> SEQUENCE: 87

```
gacacccact tccccatctg catattctgc tgtggctgct gtaaaacacc gaagtgtggg      60
```

```
ctctgctgca taaca                                                  75

<210> SEQ ID NO 88
<211> LENGTH: 25
<212> TYPE: PRT
<213> ORGANISM: Canis familiaris

<400> SEQUENCE: 88

Asp Thr His Phe Pro Ile Cys Ile Phe Cys Cys Gly Cys Cys Lys Thr
1               5                   10                  15

Pro Lys Cys Gly Leu Cys Cys Ile Thr
            20                  25

<210> SEQ ID NO 89
<211> LENGTH: 75
<212> TYPE: DNA
<213> ORGANISM: Canis familiaris

<400> SEQUENCE: 89
gacacccact tccccatctg catattctgc tgtggctgct gtaaaacacc gaagtgtggg  60
ttctgctgca ggacg                                                  75

<210> SEQ ID NO 90
<211> LENGTH: 25
<212> TYPE: PRT
<213> ORGANISM: Canis familiaris

<400> SEQUENCE: 90

Asp Thr His Phe Pro Ile Cys Ile Phe Cys Cys Gly Cys Cys Lys Thr
1               5                   10                  15

Pro Lys Cys Gly Phe Cys Cys Arg Thr
            20                  25

<210> SEQ ID NO 91
<211> LENGTH: 75
<212> TYPE: DNA
<213> ORGANISM: Canis familiaris

<400> SEQUENCE: 91
gacacccact tccccatctg catattctgc tgtggctgct gtaaaacacc gaagtgtggg  60
ttgtgctgca agacg                                                  75

<210> SEQ ID NO 92
<211> LENGTH: 25
<212> TYPE: PRT
<213> ORGANISM: Canis familiaris

<400> SEQUENCE: 92

Asp Thr His Phe Pro Ile Cys Ile Phe Cys Cys Gly Cys Cys Lys Thr
1               5                   10                  15

Pro Lys Cys Gly Leu Cys Cys Lys Thr
            20                  25

<210> SEQ ID NO 93
<211> LENGTH: 180
<212> TYPE: DNA
<213> ORGANISM: Homo sapiens

<400> SEQUENCE: 93
tctgttttcc cacaacagac gggacaactt gcagagctgc aacccagga cagagctgga   60 gccagggcca gctggatgcc catgttccag aggcgaagga ggcgagacac ccacttcccc  120
```

```
atctgcattt tctgctgcgg ctgctgtcat cgatcaaagt gtgggatgtg ctgcaagacg        180
```

<210> SEQ ID NO 94
<211> LENGTH: 60
<212> TYPE: PRT
<213> ORGANISM: Homo sapiens

<400> SEQUENCE: 94

Ser Val Phe Pro Gln Gln Thr Gly Gln Leu Ala Glu Leu Gln Pro Gln
1               5                   10                  15

Asp Arg Ala Gly Ala Arg Ala Ser Trp Met Pro Met Phe Gln Arg Arg
            20                  25                  30

Arg Arg Arg Asp Thr His Phe Pro Ile Cys Ile Phe Cys Cys Gly Cys
        35                  40                  45

Cys His Arg Ser Lys Cys Gly Met Cys Cys Lys Thr
    50                  55                  60

<210> SEQ ID NO 95
<211> LENGTH: 60
<212> TYPE: DNA
<213> ORGANISM: Homo sapiens

<400> SEQUENCE: 95

```
atctgcattt tctgctgcgg ctgctgtcat cgatcaaagt gtgggatgtg ctgcaagacg        60
```

<210> SEQ ID NO 96
<211> LENGTH: 20
<212> TYPE: PRT
<213> ORGANISM: Homo sapiens

<400> SEQUENCE: 96

Ile Cys Ile Phe Cys Cys Gly Cys Cys His Arg Ser Lys Cys Gly Met
1               5                   10                  15

Cys Cys Lys Thr
            20

<210> SEQ ID NO 97
<211> LENGTH: 66
<212> TYPE: DNA
<213> ORGANISM: Homo sapiens

<400> SEQUENCE: 97

```
ttccccatct gcatttctg ctgcggctgc tgtcatcgat caaagtgtgg gatgtgctgc        60
aagacg                                                                  66
```

<210> SEQ ID NO 98
<211> LENGTH: 22
<212> TYPE: PRT
<213> ORGANISM: Homo sapiens

<400> SEQUENCE: 98

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 99
<211> LENGTH: 1650
<212> TYPE: DNA
<213> ORGANISM: Mus musculus

<400> SEQUENCE: 99

```
agtccttaga ctgcacagca gaacagaagg catgatggca ctcagcactc ggacccaggc    60
tgcctgtctc ctgcttctcc tccttgccag cctgagcagc accacctatc tccatcaaca   120
ggtgagcacc ccaggcccat tgtggtggga gagccaggtc ccaggcaggc aggagctgct   180
caccactgag tagttagaat ggctcaggag tgatggcagc tgctgacaag gaagagggtg   240
gtccttagtg ggagctggga agctgcacag gtgtccttga atagctactc tgttgtccta   300
ctgtggaaaa tgaagcatgg tgggagccaa acaaaagtgt tccttggctg tcccaccccg   360
tcagggcatt cttaagcag cctttacatg agtattttat aaagaattac tgtggatagt   420
acaaaagaca atgggcagaa aaactctaat gaggaaggac cagaggtggg gctaagaggc   480
tgacagccag gcaaagtatt ctatgagaaa atgatacaga agtcgggcag tggtggcaca   540
tgcctttaat cccagcattt gggaggcaga ggcaggtgga tttctgagtt tgaatccagc   600
ctggtctaca aagtgagttt caagacagcc agggctacac agagaaatcc tgtctgaaaa   660
aaaaaaaaaa acaaaaaaag aaaaaaaaaa tgatacagaa gggtctggag agatggctta   720
gctgttagga acatttgatg cttgtgcata ggacctagag tcagttccca gcacccatgt   780
ggtggatcac aaccatcctg aactctactt ccagggtacc tgatgccttc tgccctagat   840
ggcagtcagc agtaagcatg catatgatac acataggcac tcaaggcaat cacaagaccc   900
ttggggactg tagggtctga taagtgaagc cagtgttggc aataaagggc tgtagaggtt   960
ctgctgtgcc gagctttgtg gacagctgtg cagatgatga tctgtcctgg aaagccacaa  1020
tccagatgaa tgtgctataa gcctttgtgc tatggggtga cctggttata agagataaga  1080
tgcagggaaa actgtccgga gtgtgcaaaa gcaagaaag tgggtgcttt taggagcatc   1140
caaggaatgg tgaggggaca cagggcagta ggagcccttc tagaaattct gtctaagcac  1200
agtccctaaa tctctgggga gaagctggca gagaaaagtc aggaagctat gccgggtact  1260
ccacaagatt caatacctct tctgctttca cagatgagac agactacaga gctgcagcct  1320
ttgcacgggg aagaaagcag ggcagacatt gcggtaagag catctgggac tccctccctg  1380
atccccagcc tctcccatgc ccaagctagg ctgcttacct ctctttcttt acacagatac  1440
caatgcagaa gagaaggaag agagacacca acttccccat ctgcatcttc tgctgtaaat  1500
gctgtaacaa ttcccagtgt ggtatctgtt gcaaaacata gcctagagcc acatcctgac  1560
ctctctacac ccctgcagcc cctcaacccc attatttatt cctgccctcc ccaccaatga  1620
ccttgaaata aagacgattt tattttcaaa                                   1650

<210> SEQ ID NO 100
<211> LENGTH: 2637
<212> TYPE: DNA
<213> ORGANISM: Homo sapiens

<400> SEQUENCE: 100
gactgtcact cggtcccaga caccagagca agctcaagac ccagcagtgg gacagccaga    60
cagacggcac gatggcactg agctcccaga tctgggccgc ttgcctcctg ctcctcctcc   120
tcctcgccag cctgaccagt ggctctgttt tcccacaaca ggtgagagcc cagtggcctg   180
ggtccttagc agggcagcag ggatgggaga gccaggcctc agcctagggc actggagaca   240
cccgagcact gagcagagct caggacgtct caggagtact ggcagctgaa caggaaccag   300
gacaggcacg gtggctcatg cctgtaatcc cagcactttg ggaggttgag gcaggcagcc   360
cacttgaggt cagtttgaga ccagcctggc caacatggta aaaccccgtc tctactaaaa   420
atacaaaagt tagccaggct tggtggcagg tgcctgtaat cccagctact cgggagactg   480
```

```
aggcaggaga attgcttgaa cccgcaaggt ggaggttgca cagtgagctg agattgcacc    540
actgcactcc agcctggcaa cagagcaaga ctccatctcc aaaaaagaac agaaatcaat    600
gaagcaccga gtgacaggga ctggaaggtc ctaattccat gggtatttac ggaaccccta    660
cgccgtgtgg agtcttattc tagacagtgg ggacgaggcc atgaacaagg tagatgagag    720
aggagatttc tccatcctgg tcagggaatt tgttaaagac tgatgaaaac atgaataaat    780
aattgtgtct agtacattct attcgtgaat ctcataacag acagtggtag agtgaccgtg    840
acccattcgc cacacagtag agtcactttt ttggtttgtt tttagagac agggtcttcc     900 tctgttgctg aggctggagt gcagtggtgc agtcatagtt cactgcagcc tcaacctcct    960
gtgctcaagc aatcctccca cctcagcgtc ccaagtagct gggacagcag gcacatgcca    1020 cggggttgggg gaccacaggc atggtcaagg ggctggcagt caagcaagtg tttcatgaga   1080
aagtgacagt tgaccttcgt cttggagggt gagagatgga ggcagcaaag acctaaggag   1140
aggacaagcc agcatagccc agggtcaggc tgaacaagag gagatggtgg gacttgggga   1200
taaggctgag gggtgggcag tccctaagtc ttgtgggcaa ccatgcagac actgattttt   1260
ccttggaata aagaggaagc ccccataagc tttttttttt ttttctgaga tagggtctcg   1320
ctctgtcgtt caggctggtg tgcagtggca tcatctgggc tcactgcaac ctccgcctcc   1380
cgggttcaag caattctcct gcctcagctt cccgagcagc tgggattaca gcggctgcc    1440 accacgcccg gctaattttt gtttttttag tagagacagg gtttcaccat gttggccaga   1500
ctggtcttga actcctgacc tcaggtgatt ctcccacctc ggcttcccaa agtgctggga   1560
ttacaggcgt gagccactgc gcccagcctc ctgtaggttt taaaatgga gaaaaccaca    1620 atctcactgg ccatgtttta aaaaacttaa tctgccagtc aggcaccatg gctcacacct   1680
gtaatcccag agttttggga ggccaaggta ggaagatcag ttgagcccag gagttcaaga   1740
ccagcttggg caacacaacc agaccccacc tctacaaaaa attaaaaaat tagccgggtg   1800
tggtggcgtg cacctgctgt cccagctact cgggaagctg aggcgggagc atcgcttgag   1860
cacaggaggt caaggctgca gggagctatg actgtgccac tgcactctgg cctgggcaac   1920
agaggaagac tctgtctaaa aaacaaacaa aaaagtgac tctgctgtgt ggcaaatgga    1980
ttgaggggca agaatgcagg gaggtgtgtt aggaggctgg cactggcatc caggcagggg   2040
aaggtgatat cccaaagaag agtagcagct gtggaaagag gaggaggcgg atctgggagg   2100
tttttttttt taggaaaagc cgcccatggg aaggtgagca gaagcaagaa agcaaggccc   2160
ctcctaagag tccatttgag ctctgggttt aaaccacttg gagaggagca ggttgccggg   2220
agccagtctc agaggtccac tgggccccct gccatcctct gcacccccct ctgctttcac   2280
agacgggaca acttgcagag ctgcaacccc aggacagagc tggagccagg gccagctgga   2340
tggtgagcgc aacagtgatg cctttcctag cccctgctc cctcccatg ctaaggccgg      2400 ttccctgctc acattccctt ccttcccaca gccatgttc cagaggcgaa ggaggcgaga    2460
cacccacttc cccatctgca ttttctgctg cggctgctgt catcgatcaa agtgtgggat   2520
gtgctgcaag acgtagaacc tacctgccct gcccccgtcc cctcccttcc ttatttattc   2580
ctgctgcccc agaacatagg tcttggaata aaatggctgg ttcttttgtt ttccaaa      2637
```

<210> SEQ ID NO 101
<211> LENGTH: 180
<212> TYPE: DNA
<213> ORGANISM: Homo sapiens

<400> SEQUENCE: 101

```
tctgttttcc cacaacagac gggacaactt gcagagctgc aaccccagga cagagctgga      60
gccagggcca gctggatgcc catgttccag aggcgaagga ggcgagacac ccacttcccc     120
atctgcattt tctgctgcgg ctgctgtcat cgatcaaagt gtgggatgtg ctgcaagacg     180
```

<210> SEQ ID NO 102
<211> LENGTH: 61
<212> TYPE: PRT
<213> ORGANISM: Homo sapiens

<400> SEQUENCE: 102

```
Gly Ser Val Phe Pro Gln Gln Thr Gly Gln Leu Ala Glu Leu Gln Pro
 1               5                  10                  15

Gln Asp Arg Ala Gly Ala Arg Ala Ser Trp Met Pro Met Phe Gln Arg
             20                  25                  30

Arg Arg Arg Arg Asp Thr His Phe Pro Ile Cys Ile Phe Cys Cys Gly
         35                  40                  45

Cys Cys His Arg Ser Lys Cys Gly Met Cys Cys Lys Thr
     50                  55                  60
```

<210> SEQ ID NO 103
<211> LENGTH: 301
<212> TYPE: DNA
<213> ORGANISM: Homo sapiens

<400> SEQUENCE: 103

```
tcggccccgc ctcctgccac cgcagattgg ccgctagccc tccccgagcg ccctgcctcc      60
gagggccggc gcaccataaa agaagccgcc ctagccacgt cccctcgcag ttcggcggtc     120
ccgcgggtct gtctcttgct tcaacagtgt ttggacggaa cagatccggg gactctcttc     180
cagcctccga ccgccctccg atttcctctc cgcttgcaac tccgggacc atcttctcgg      240 ccatctcctg cttctgggac ctgccagcac cgttttttgtg gttagctcct tcttgccaac    300
c                                                                     301
```

<210> SEQ ID NO 104
<211> LENGTH: 75
<212> TYPE: DNA
<213> ORGANISM: Homo sapiens

<400> SEQUENCE: 104

```
gacacccact tccccatctg cattttctgc tgcggctgct gtcatcgatc aaagtgtggg      60
atgtgctgca agacg                                                      75
```

<210> SEQ ID NO 105
<211> LENGTH: 66
<212> TYPE: DNA
<213> ORGANISM: Homo sapiens

<400> SEQUENCE: 105

```
ggggacaagt ttgtacaaaa aagcaggctt agatctgaat tcaatttacg cgtgggatcc      60
aaggtc                                                                66
```

<210> SEQ ID NO 106

<400> SEQUENCE: 106

000

<210> SEQ ID NO 107
<211> LENGTH: 336

```
<212> TYPE: DNA
<213> ORGANISM: Homo sapiens

<400> SEQUENCE: 107
gatattgtga tgacccagtc tccactctcc ctgcccgtca cccctggaga gccggcctcc      60
atctcctgca ggtctagtca gagcctcctg catagtgatg gatacaacta tttggattgg    120
tacctgcaga agtcagggca gtctccacag cgcctgatct atatgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccg    300
ctcactatcg gcggagggac caaggtggag atcaaa                              336

<210> SEQ ID NO 108
<211> LENGTH: 112
<212> TYPE: PRT
<213> ORGANISM: Homo sapiens

<400> SEQUENCE: 108

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Ser Gly Gln Ser
        35                  40                  45

Pro Gln Arg Leu Ile Tyr Met Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Ile Gly Gly Gly Thr Lys Val Glu Ile Lys
            100                 105                 110

<210> SEQ ID NO 109
<211> LENGTH: 366
<212> TYPE: DNA
<213> ORGANISM: Homo sapiens

<400> SEQUENCE: 109
caggtgcagc tggtggagtc tgggggaggc gtggtccagc ctgggaggtc cctgagactc      60
tcctgtgcag cctctggatt caccttcagt agttatggca tgcactgggt ccgtcaggct    120
ccaggcaagg ggctggagtg ggtggcagtt atttcatatg atggaagtaa tgaatactat    180
gcagactccg tgaagggccg attcaccatc tccagagaca attccaagaa cacgctgtat    240
ctgcaaatga acagcctgag agctgaggac acggctgtat attactgtgt gagagatgtg    300
tggttcgggg agtccctcca cggtttggac gtctggggcc aagggaccac ggtcaccgtc    360
tcctca                                                               366

<210> SEQ ID NO 110
<211> LENGTH: 122
<212> TYPE: PRT
<213> ORGANISM: Homo sapiens

<400> SEQUENCE: 110

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

-continued

```
                 20                  25                  30
Gly Met His Trp Val Arg Gln Ala Pro Gly Lys Gly Leu Glu Trp Val
            35                  40                  45

Ala Val Ile Ser Tyr Asp Gly Ser Asn Glu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Val Trp Phe Gly Glu Ser Leu His Gly Leu Asp Val Trp
            100                 105                 110

Gly Gln Gly Thr Thr Val Thr Val Ser Ser
        115                 120
```

<210> SEQ ID NO 111
<211> LENGTH: 16
<212> TYPE: PRT
<213> ORGANISM: Homo sapiens

<400> SEQUENCE: 111

```
Arg Ser Ser Gln Ser Leu Leu His Ser Asp Gly Tyr Asn Tyr Leu Asp
1               5                   10                  15
```

<210> SEQ ID NO 112
<211> LENGTH: 7
<212> TYPE: PRT
<213> ORGANISM: Homo sapiens

<400> SEQUENCE: 112

```
Met Gly Ser Asn Arg Ala Ser
1               5
```

<210> SEQ ID NO 113
<211> LENGTH: 9
<212> TYPE: PRT
<213> ORGANISM: Homo sapiens

<400> SEQUENCE: 113

```
Met Gln Ala Leu Gln Thr Pro Leu Thr
1               5
```

<210> SEQ ID NO 114
<211> LENGTH: 5
<212> TYPE: PRT
<213> ORGANISM: Homo sapiens

<400> SEQUENCE: 114

```
Ser Tyr Gly Met His
1               5
```

<210> SEQ ID NO 115
<211> LENGTH: 17
<212> TYPE: PRT
<213> ORGANISM: Homo sapiens

<400> SEQUENCE: 115

```
Val Ile Ser Tyr Asp Gly Ser Asn Glu Tyr Tyr Ala Asp Ser Val Lys
1               5                   10                  15

Gly
```

<210> SEQ ID NO 116
<211> LENGTH: 13

<212> TYPE: PRT
<213> ORGANISM: Homo sapiens

<400> SEQUENCE: 116

Asp Val Trp Phe Gly Glu Ser Leu His Gly Leu Asp Val
1               5                   10

<210> SEQ ID NO 117
<211> LENGTH: 333
<212> TYPE: DNA
<213> ORGANISM: Homo sapiens

<400> SEQUENCE: 117

```
cagtctgtgt tgacgcagcc gccctcactg tctggggccc cagggcagag ggtcaccatc    60
tcctgcactg ggggcagctc caacatcggg tcaggttttg ctatatactg gtaccagcag   120
cttccaggaa cagcccccaa actcctcatc tttggtgaca acattcggcc ctcaggggtc   180
cctgaccgat tctctggctc caagtctggc acctccgcct ccctggccat cactgggctc   240
caggctgagg atgaggctga ttattactgc cagtcctatg acagcagcct gagtggttcg   300
gttttcggcg gagggaccaa gctgaccgtc cta                                333
```

<210> SEQ ID NO 118
<211> LENGTH: 111
<212> TYPE: PRT
<213> ORGANISM: Homo sapiens

<400> SEQUENCE: 118

Gln Ser Val Leu Thr Gln Pro Pro Ser Leu Ser Gly Ala Pro Gly Gln
1               5                   10                  15

Arg Val Thr Ile Ser Cys Thr Gly Gly Ser Ser Asn Ile Gly Ser Gly
                20                  25                  30

Phe Ala Ile Tyr Trp Tyr Gln Gln Leu Pro Gly Thr Ala Pro Lys Leu
            35                  40                  45

Leu Ile Phe Gly Asp Asn Ile Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 119
<211> LENGTH: 351
<212> TYPE: DNA
<213> ORGANISM: Homo sapiens

<400> SEQUENCE: 119

```
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtga aaaaacact    180 gcacagaaac tccagggcag agtcaccatg accacagaca catccacgag cacagcctac   240
atggagctga ggagcctgag atctgacgac acggccgtgt attactgtgc gagagaggaa   300
ctaggggctt ttgatatctg gggccaaggg acaatggtca ccgtctcttc a            351
```

<210> SEQ ID NO 120
<211> LENGTH: 117

```
<212> TYPE: PRT
<213> ORGANISM: Homo sapiens

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Glu Lys Asn Thr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Leu Gly Ala Phe Asp Ile Trp Gly Gln Gly Thr Met
            100                 105                 110

Val Thr Val Ser Ser
        115

<210> SEQ ID NO 121
<211> LENGTH: 14
<212> TYPE: PRT
<213> ORGANISM: Homo sapiens

<400> SEQUENCE: 121

Thr Gly Gly Ser Ser Asn Ile Gly Ser Gly Phe Ala Ile Tyr
1               5                   10

<210> SEQ ID NO 122
<211> LENGTH: 7
<212> TYPE: PRT
<213> ORGANISM: Homo sapiens

<400> SEQUENCE: 122

Gly Asp Asn Ile Arg Pro Ser
1               5

<210> SEQ ID NO 123
<211> LENGTH: 11
<212> TYPE: PRT
<213> ORGANISM: Homo sapiens

<400> SEQUENCE: 123

Gln Ser Tyr Asp Ser Ser Leu Ser Gly Ser Val
1               5                   10

<210> SEQ ID NO 124
<211> LENGTH: 5
<212> TYPE: PRT
<213> ORGANISM: Homo sapiens

<400> SEQUENCE: 124

Ser Tyr Gly Ile Ser
1               5

<210> SEQ ID NO 125
<211> LENGTH: 17
<212> TYPE: PRT
<213> ORGANISM: Homo sapiens

<400> SEQUENCE: 125
```

Trp Ile Ser Ala Tyr Asn Gly Glu Lys Asn Thr Ala Gln Lys Leu Gln
1               5                   10                  15

Gly

<210> SEQ ID NO 126
<211> LENGTH: 8
<212> TYPE: PRT
<213> ORGANISM: Homo sapiens

<400> SEQUENCE: 126

Glu Glu Leu Gly Ala Phe Asp Ile
1               5

<210> SEQ ID NO 127
<211> LENGTH: 321
<212> TYPE: DNA
<213> ORGANISM: Homo sapiens

<400> SEQUENCE: 127
gaaattgtgt tgacgcagtc tccaggcacc ctgtctttgt ctccagggga aagagccacc      60
ctctcctgca gggccagtca gagtgttagc agcaactact tagcctggta ccagcagaaa     120
cctggccagg ctcccaggct cctcatctat ggtgcatcca gcagggccac tggcatccca     180
gacaggttca gtggcagtgg gtctgggaca gacttcactc tcatcatcag cagactggag     240
cctgaagatt ttgtagtgta ttactgtcag cagtatggta gctcactcac tttcggcgga     300
gggaccaagg tggagatcaa a                                               321

<210> SEQ ID NO 128
<211> LENGTH: 107
<212> TYPE: PRT
<213> ORGANISM: Homo sapiens

<400> SEQUENCE: 128

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ile Ile Ser Arg Leu Glu
65                  70                  75                  80

Pro Glu Asp Phe Val Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 129
<211> LENGTH: 366
<212> TYPE: DNA
<213> ORGANISM: Homo sapiens

<400> SEQUENCE: 129
caggttcagc tggtgcagtc tggagatgag gtgaagaagc ctggggcctc agtgaaggtc      60
tcctgcaagg cttctggtta cacctttatc aagtatggaa tcagttgggt gcgacaggcc     120
cctggacaag ggcttgagtg gatgggatgg atcggcgctt tcaatggtaa cacagactat    180

-continued

```
gcacggaacc tccaggccag agtcaccatg accacagaca catccacgag cacagcctac    240
atggagctga ggagcctgag atctgacgac acggccgtat attactgtgc gagagagggc    300
tggaacgacg actacttctg cggtttggac gtctggggcc aagggaccac ggtcaccgtc    360
tcctca                                                               366
```

```
<210> SEQ ID NO 130
<211> LENGTH: 122
<212> TYPE: PRT
<213> ORGANISM: Homo sapiens

<400> SEQUENCE: 130
```

Gln Val Gln Leu Val Gln Ser Gly Asp Glu Val Lys Lys Pro Gly Ala
1               5                   10                  15

Ser Val Lys Val Ser Cys Lys Ala Ser Gly Tyr Thr Phe Ile Lys Tyr
            20                  25                  30

Gly Ile Ser Trp Val Arg Gln Ala Pro Gly Gln Gly Leu Glu Trp Met
        35                  40                  45

Gly Trp Ile Gly Ala Phe Asn Gly Asn Thr Asp Tyr Ala Arg Asn Leu
    50                  55                  60

Gln Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Trp Asn Asp Asp Tyr Phe Cys Gly Leu Asp Val Trp
            100                 105                 110

Gly Gln Gly Thr Thr Val Thr Val Ser Ser
        115                 120

```
<210> SEQ ID NO 131
<211> LENGTH: 12
<212> TYPE: PRT
<213> ORGANISM: Homo sapiens

<400> SEQUENCE: 131
```

Arg Ala Ser Gln Ser Val Ser Ser Asn Tyr Leu Ala
1               5                   10

```
<210> SEQ ID NO 132
<211> LENGTH: 7
<212> TYPE: PRT
<213> ORGANISM: Homo sapiens

<400> SEQUENCE: 132
```

Gly Ala Ser Ser Arg Ala Thr
1               5

```
<210> SEQ ID NO 133
<211> LENGTH: 8
<212> TYPE: PRT
<213> ORGANISM: Homo sapiens

<400> SEQUENCE: 133
```

Gln Gln Tyr Gly Ser Ser Leu Thr
1               5

```
<210> SEQ ID NO 134
<211> LENGTH: 5
<212> TYPE: PRT
<213> ORGANISM: Homo sapiens

<400> SEQUENCE: 134
```

```
Lys Tyr Gly Ile Ser
1               5

<210> SEQ ID NO 135
<211> LENGTH: 17
<212> TYPE: PRT
<213> ORGANISM: Homo sapiens

<400> SEQUENCE: 135

Trp Ile Gly Ala Phe Asn Gly Asn Thr Asp Tyr Ala Arg Asn Leu Gln
1               5                   10                  15

Ala

<210> SEQ ID NO 136
<211> LENGTH: 13
<212> TYPE: PRT
<213> ORGANISM: Homo sapiens

<400> SEQUENCE: 136

Glu Gly Trp Asn Asp Asp Tyr Phe Cys Gly Leu Asp Val
1               5                   10

<210> SEQ ID NO 137
<211> LENGTH: 318
<212> TYPE: DNA
<213> ORGANISM: Homo sapiens

<400> SEQUENCE: 137
tatgagctga ctcagccacc ctcagtgtcc gtgtccccag gacagacagc cagcctcacc      60
tgctctggag ataaattggg ggatagatat gcttcctggt atcagcagaa gccaggccag     120 tccccttgtgc tggtcatcta tcaagatagc aagcggccct cagggatccc tgagcgattc    180
tctggctcca actctgggaa cacagccact ctgaccatca gcgggaccca ggctatggat     240
gaggctgact attactgtca ggcgtgggac agcagcactg catgtgtctt cggaactggg     300
accaaggtca ccgtccta                                                   318

<210> SEQ ID NO 138
<211> LENGTH: 106
<212> TYPE: PRT
<213> ORGANISM: Homo sapiens

<400> SEQUENCE: 138

Tyr Glu Leu Thr Gln Pro Pro Ser Val Ser Val Ser Pro Gly Gln Thr
1               5                   10                  15

Ala Ser Leu Thr Cys Ser Gly Asp Lys Leu Gly Asp Arg Tyr Ala Ser
                20                  25                  30

Trp Tyr Gln Gln Lys Pro Gly Gln Ser Pro Val Leu Val Ile Tyr Gln
            35                  40                  45

Asp Ser Lys Arg Pro Ser Gly Ile Pro Glu Arg Phe Ser Gly Ser Asn
        50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Asp Ser Ser Thr Ala Cys Val
                85                  90                  95

Phe Gly Thr Gly Thr Lys Val Thr Val Leu
            100                 105

<210> SEQ ID NO 139
<211> LENGTH: 363
```

```
<212> TYPE: DNA
<213> ORGANISM: Homo sapiens

<400> SEQUENCE: 139
caggtgcagc tggtggagtc tgggggaggc gtggtccagc ctgggaggtc cctgagactc      60
tcctgtgcag cgtctggatt caccctcagt agctatggca tgcactgggt ccgccaggct     120
ccaggcaagg gctggagtg gtggcagtt atatggtatg atgaaagtaa taaatactat       180
gcagactccg tgaagggccg attcaccatc tccagagaca attccaagaa cacgttgaat     240
ctgcaaatga acagcctgag agccgaggac acggctttgt attactgtgc gagagccggt     300
atagcagcag cccttgatgc ttttgatatc tggggccaag gacaatggt caccgtctct      360 tca                                                                   363

<210> SEQ ID NO 140
<211> LENGTH: 121
<212> TYPE: PRT
<213> ORGANISM: Homo sapiens

<400> SEQUENCE: 140

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Asn Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Leu Tyr Tyr Cys
                85                  90                  95

Ala Arg Ala Gly Ile Ala Ala Ala Leu Asp Ala Phe Asp Ile Trp Gly
            100                 105                 110

Gln Gly Thr Met Val Thr Val Ser Ser
        115                 120

<210> SEQ ID NO 141
<211> LENGTH: 11
<212> TYPE: PRT
<213> ORGANISM: Homo sapiens

<400> SEQUENCE: 141

Ser Gly Asp Lys Leu Gly Asp Arg Tyr Ala Ser
1               5                   10

<210> SEQ ID NO 142
<211> LENGTH: 7
<212> TYPE: PRT
<213> ORGANISM: Homo sapiens

<400> SEQUENCE: 142

Gln Asp Ser Lys Arg Pro Ser
1               5

<210> SEQ ID NO 143
<211> LENGTH: 10
<212> TYPE: PRT
<213> ORGANISM: Homo sapiens

<400> SEQUENCE: 143
```

Gln Ala Trp Asp Ser Ser Thr Ala Cys Val
1               5                   10

<210> SEQ ID NO 144
<211> LENGTH: 5
<212> TYPE: PRT
<213> ORGANISM: Homo sapiens

<400> SEQUENCE: 144

Ser Tyr Gly Met His
1               5

<210> SEQ ID NO 145
<211> LENGTH: 17
<212> TYPE: PRT
<213> ORGANISM: Homo sapiens

<400> SEQUENCE: 145

Val Ile Trp Tyr Asp Glu Ser Asn Lys Tyr Tyr Ala Asp Ser Val Lys
1               5                   10                  15

Gly

<210> SEQ ID NO 146
<211> LENGTH: 12
<212> TYPE: PRT
<213> ORGANISM: Homo sapiens

<400> SEQUENCE: 146

Ala Gly Ile Ala Ala Ala Leu Asp Ala Phe Asp Ile
1               5                   10

<210> SEQ ID NO 147
<211> LENGTH: 333
<212> TYPE: DNA
<213> ORGANISM: Homo sapiens

<400> SEQUENCE: 147
cagtctgtgt tgacgcagcc gccctcactg tctggggccc cagggcagag ggtcaccatc      60
tcctgcactg ggggcagctc caacatcggg tcaggttttg ctatatactg gtaccagcag     120
cttccaggaa cagcccccaa actcctcatc tatggtgaca acattcggcc ctcaggggtc     180
cctgaccgat tctctggctc caagtctggc acctccgcct ccctggccat cactgggctc     240
caggctgagg atgaggctga ttattactgc cagtcctatg acagcagcct gagtggttcg     300
gtattcggcg gagggaccaa gctgaccgtc cta                                  333

<210> SEQ ID NO 148
<211> LENGTH: 111
<212> TYPE: PRT
<213> ORGANISM: Homo sapiens

<400> SEQUENCE: 148

Gln Ser Val Leu Thr Gln Pro Pro Ser Leu Ser Gly Ala Pro Gly Gln
1               5                   10                  15

Arg Val Thr Ile Ser Cys Thr Gly Gly Ser Ser Asn Ile Gly Ser Gly
                20                  25                  30

Phe Ala Ile Tyr Trp Tyr Gln Gln Leu Pro Gly Thr Ala Pro Lys Leu
            35                  40                  45

Leu Ile Tyr Gly Asp Asn Ile Arg Pro Ser Gly Val Pro Asp Arg Phe
        50                  55                  60

Ser Gly Ser Lys Ser Gly Thr Ser Ala Ser Leu Ala Ile Thr Gly Leu

```
                65                  70                  75                  80
Gln Ala Glu Asp Glu Ala Asp Tyr Tyr Cys Gln Ser Tyr Asp Ser Ser
                    85                  90                  95

Leu Ser Gly Ser Val Phe Gly Gly Gly Thr Lys Leu Thr Val Leu
            100                 105                 110

<210> SEQ ID NO 149
<211> LENGTH: 351
<212> TYPE: DNA
<213> ORGANISM: Homo sapiens

<400> SEQUENCE: 149
caggttcagc tggtgcagtc tggagctgag gtgaagaagc ctggggcctc agtgaaggtc     60
tcctgcaagg cttctggtta cacctttacc agctatggta tcagctgggt gcgacaggcc    120
cctggacaag ggcttgagtg gatgggatgg atcagcgctt acaatggtga aacaaacact    180
gcacagaaac tccagggcag agtcaccatg accacagaca catccacgag cacagcctac    240
atggagctga ggagcctgag atctgacgac acggccgtgt attactgtgc gagagaggaa    300
ctaggggctt tgatatctg gggccaaggg acaatggtca ccgtctcttc a              351

<210> SEQ ID NO 150
<211> LENGTH: 117
<212> TYPE: PRT
<213> ORGANISM: Homo sapiens

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Glu Thr Asn Thr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Leu Gly Ala Phe Asp Ile Trp Gly Gln Gly Thr Met
            100                 105                 110

Val Thr Val Ser Ser
        115

<210> SEQ ID NO 151
<211> LENGTH: 14
<212> TYPE: PRT
<213> ORGANISM: Homo sapiens

<400> SEQUENCE: 151

Thr Gly Gly Ser Ser Asn Ile Gly Ser Gly Phe Ala Ile Tyr
1               5                   10

<210> SEQ ID NO 152
<211> LENGTH: 7
<212> TYPE: PRT
<213> ORGANISM: Homo sapiens

<400> SEQUENCE: 152

Gly Asp Asn Ile Arg Pro Ser
1               5
```

```
                                  -continued
1               5

<210> SEQ ID NO 153
<211> LENGTH: 11
<212> TYPE: PRT
<213> ORGANISM: Homo sapiens

<400> SEQUENCE: 153

Gln Ser Tyr Asp Ser Ser Leu Ser Gly Ser Val
1               5                   10

<210> SEQ ID NO 154
<211> LENGTH: 5
<212> TYPE: PRT
<213> ORGANISM: Homo sapiens

<400> SEQUENCE: 154

Ser Tyr Gly Ile Ser
1               5

<210> SEQ ID NO 155
<211> LENGTH: 17
<212> TYPE: PRT
<213> ORGANISM: Homo sapiens

<400> SEQUENCE: 155

Trp Ile Ser Ala Tyr Asn Gly Glu Thr Asn Thr Ala Gln Lys Leu Gln
1               5                   10                  15

Gly

<210> SEQ ID NO 156
<211> LENGTH: 8
<212> TYPE: PRT
<213> ORGANISM: Homo sapiens

<400> SEQUENCE: 156

Glu Glu Leu Gly Ala Phe Asp Ile
1               5

<210> SEQ ID NO 157
<211> LENGTH: 321
<212> TYPE: DNA
<213> ORGANISM: Homo sapiens

<400> SEQUENCE: 157
tcctatgagc tgactcagcc accctcagtg tccgtgtccc caggacagac agccaccatc      60
acctgctctg gagataaaatt gggggaaaga tatgcgtgtt ggtatcagca gaggccaggc    120
cagtcccctg tactggtcat ctatcaagat atcaagcggc cctcagggat ccctgagcga    180
ttctctggct ccaactctgg gaacacagcc actctgacca tcagcgggac ccaggctatg    240
gatgaggctg actatttctg tcaggcgtgg tacagcagca ccaatgtgct tttcggcgga    300
gggaccaagc tgaccgtcct a                                              321

<210> SEQ ID NO 158
<211> LENGTH: 107
<212> TYPE: PRT
<213> ORGANISM: Homo sapiens

<400> SEQUENCE: 158

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Glu Arg Tyr Ala
```

```
                    20                  25                  30
Cys Trp Tyr Gln Gln Arg Pro Gly Gln Ser Pro Val Leu Val Ile Tyr
            35                  40                  45
Gln Asp Ile Lys Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Met
 65                  70                  75                  80
Asp Glu Ala Asp Tyr Phe Cys Gln Ala Trp Tyr Ser Thr Asn Val
                    85                  90                  95
Leu Phe Gly Gly Gly Thr Lys Leu Thr Val Leu
            100                 105

<210> SEQ ID NO 159
<211> LENGTH: 363
<212> TYPE: DNA
<213> ORGANISM: Homo sapiens

<400> SEQUENCE: 159
caggtgcagc tggtggagtc tgggggaggc gtggtccagc ctggggaggtc cctgagactc      60
tcctgtgcag cgtctggatt caccttcagt agctatggca tgcactgggt ccgccaggct     120
ccaggcaagg ggctggagtg ggtggcagtt atatggtatg ctgaaagtaa taatactac     180
gcagactccg tgaagggccg attcaccatc tccagagaca attccaagaa cacgctgtat    240
ctgcaaatga acagcctgag agccgaggac acggctgtgt attactgtgc gagagcccag    300
gagggtatag cccctgacgc ttttgatatc tggggccaag gaacaatggt caccgtctct    360
tca                                                                   363

<210> SEQ ID NO 160
<211> LENGTH: 121
<212> TYPE: PRT
<213> ORGANISM: Homo sapiens

<400> SEQUENCE: 160

Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
            35                  40                  45
Ala Val Ile Trp Tyr Ala Glu Ser Asn Lys Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                    85                  90                  95
Ala Arg Ala Gln Glu Gly Ile Ala Pro Asp Ala Phe Asp Ile Trp Gly
            100                 105                 110
Gln Gly Thr Met Val Thr Val Ser Ser
        115                 120

<210> SEQ ID NO 161
<211> LENGTH: 11
<212> TYPE: PRT
<213> ORGANISM: Homo sapiens

<400> SEQUENCE: 161

Ser Gly Asp Lys Leu Gly Glu Arg Tyr Ala Cys
```

<210> SEQ ID NO 162
<211> LENGTH: 7
<212> TYPE: PRT
<213> ORGANISM: Homo sapiens

<400> SEQUENCE: 162

Gln Asp Ile Lys Arg Pro Ser
1               5

<210> SEQ ID NO 163
<211> LENGTH: 10
<212> TYPE: PRT
<213> ORGANISM: Homo sapiens

<400> SEQUENCE: 163

Gln Ala Trp Tyr Ser Ser Thr Asn Val Leu
1               5                   10

<210> SEQ ID NO 164
<211> LENGTH: 5
<212> TYPE: PRT
<213> ORGANISM: Homo sapiens

<400> SEQUENCE: 164

Ser Tyr Gly Met His
1               5

<210> SEQ ID NO 165
<211> LENGTH: 17
<212> TYPE: PRT
<213> ORGANISM: Homo sapiens

<400> SEQUENCE: 165

Val Ile Trp Tyr Ala Glu Ser Asn Lys Tyr Tyr Ala Asp Ser Val Lys
1               5                   10                  15

Gly

<210> SEQ ID NO 166
<211> LENGTH: 12
<212> TYPE: PRT
<213> ORGANISM: Homo sapiens

<400> SEQUENCE: 166

Ala Gln Glu Gly Ile Ala Pro Asp Ala Phe Asp Ile
1               5                   10

<210> SEQ ID NO 167
<211> LENGTH: 321
<212> TYPE: DNA
<213> ORGANISM: Homo sapiens

<400> SEQUENCE: 167

```
tcctatgagc tgactcagcc accctcagtg tccgtgtccc caggacagac agccaccatc    60
acctgctctg gagataaatt gggggaaaga tatgcgtgtt ggtatcagca gaggccaggc   120
cagtcccctg tactggtcat ctatcaagat agcaagcggc cctcagggat ccctgagcga   180
ttctctggct ccaactctgg gaacacagcc actctgacca tcagcgggac ccaggctatg   240
gatgaggctg actatttctg tcaggcgtgg tacagcagca ccaatgtgct tttcggcgga   300
gggaccaagc tgaccgtcct a                                             321
```

```
<210> SEQ ID NO 168
<211> LENGTH: 107
<212> TYPE: PRT
<213> ORGANISM: Homo sapiens

<400> SEQUENCE: 168

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Glu Arg Tyr Ala
            20                  25                  30

Cys Trp Tyr Gln Gln Arg Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Tyr Ser Ser Thr Asn Val
                85                  90                  95

Leu Phe Gly Gly Gly Thr Lys Leu Thr Val Leu
            100                 105

<210> SEQ ID NO 169
<211> LENGTH: 363
<212> TYPE: DNA
<213> ORGANISM: Homo sapiens

<400> SEQUENCE: 169
caggtgcagc tggtggagtc tgggggaggc gtggtccagc ctggggaggtc cctgagactc     60 tcctgtgcag cgtctggatt caccttcagt agctatggca tgcactgggt ccgccaggct    120
ccaggcaagg ggctggagtg ggtggcagtt atatggtatg ctgaaagtaa taaatactac    180
gcagactccg tgaagggccg attcaccatc tccagagaca attccaagaa cacgctgtat    240
ctgcaaatga acagcctgag agccgaggac acggctgtgt attactgtgc gagagcccag    300
gagggtatag cccctgacgc ttttgatatc tggggccaag gaacaatggt caccgtctct    360
tca                                                                  363

<210> SEQ ID NO 170
<211> LENGTH: 121
<212> TYPE: PRT
<213> ORGANISM: Homo sapiens

<400> SEQUENCE: 170

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Glu Gly Ile Ala Pro Asp Ala Phe Asp Ile Trp Gly
            100                 105                 110

Gln Gly Thr Met Val Thr Val Ser Ser
            115                 120
```

115             120

<210> SEQ ID NO 171
<211> LENGTH: 11
<212> TYPE: PRT
<213> ORGANISM: Homo sapiens

<400> SEQUENCE: 171

Ser Gly Asp Lys Leu Gly Glu Arg Tyr Ala Cys
1               5                   10

<210> SEQ ID NO 172
<211> LENGTH: 7
<212> TYPE: PRT
<213> ORGANISM: Homo sapiens

<400> SEQUENCE: 172

Gln Asp Ser Lys Arg Pro Ser
1               5

<210> SEQ ID NO 173
<211> LENGTH: 10
<212> TYPE: PRT
<213> ORGANISM: Homo sapiens

<400> SEQUENCE: 173

Gln Ala Trp Tyr Ser Ser Thr Asn Val Leu
1               5                   10

<210> SEQ ID NO 174
<211> LENGTH: 5
<212> TYPE: PRT
<213> ORGANISM: Homo sapiens

<400> SEQUENCE: 174

Ser Tyr Gly Met His
1               5

<210> SEQ ID NO 175
<211> LENGTH: 17
<212> TYPE: PRT
<213> ORGANISM: Homo sapiens

<400> SEQUENCE: 175

Val Ile Trp Tyr Ala Glu Ser Asn Lys Tyr Tyr Ala Asp Ser Val Lys
1               5                   10                  15

Gly

<210> SEQ ID NO 176
<211> LENGTH: 12
<212> TYPE: PRT
<213> ORGANISM: Homo sapiens

<400> SEQUENCE: 176

Ala Gln Glu Gly Ile Ala Pro Asp Ala Phe Asp Ile
1               5                   10

<210> SEQ ID NO 177
<211> LENGTH: 330
<212> TYPE: DNA
<213> ORGANISM: Homo sapiens

<400> SEQUENCE: 177
aattttatgc tgactcagcc ccactctgtg tcggagtctc cggggaagac ggtaaccatc      60

```
tcctgcaccc gcagcagtgg cagcattgcc agctactatg tgcagtggta ccagcagcgc    120
ccgggcagtt cccccaccac tgtgatctat gaggatagcc agagaccctc tggggtccct    180
gatcggttct ctggctccat cgacagctcc tccaactctg cctccctcac catctctgga    240
ctgaagactg aggacgaggc tgactattat tgtcagtctt atgatagcag caatgtggta    300
ttcggcggag ggaccaagct gaccgtccta                                     330
```

<210> SEQ ID NO 178
<211> LENGTH: 110
<212> TYPE: PRT
<213> ORGANISM: Homo sapiens

<400> SEQUENCE: 178

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Ser Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Leu Thr Val Leu
            100                 105                 110
```

<210> SEQ ID NO 179
<211> LENGTH: 366
<212> TYPE: DNA
<213> ORGANISM: Homo sapiens

<400> SEQUENCE: 179

```
caggtacagc tgcagcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacat actacaggtc caagtggttt    180
aatgattatg cagtatctgt gcaaagtcga ataaccatca cccagacac atccaagaac    240 cagttctccc tgcagctgaa ctctgtgact cccgaggaca cggctgtgta ttactgtgca    300
agagggattg tcttctccta cgctatggac gtctggggcc aagggaccac ggtcaccgtc    360
tcctca                                                              366
```

<210> SEQ ID NO 180
<211> LENGTH: 122
<212> TYPE: PRT
<213> ORGANISM: Homo sapiens

<400> SEQUENCE: 180

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Phe Asn Asp Tyr Ala
    50                  55                  60
```

```
Val Ser Val Gln Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Ile Val Phe Ser Tyr Ala Met Asp Val Trp
            100                 105                 110

Gly Gln Gly Thr Thr Val Thr Val Ser Ser
        115                 120
```

<210> SEQ ID NO 181  
<211> LENGTH: 13  
<212> TYPE: PRT  
<213> ORGANISM: Homo sapiens

<400> SEQUENCE: 181

```
Thr Arg Ser Ser Gly Ser Ile Ala Ser Tyr Tyr Val Gln
1               5                   10
```

<210> SEQ ID NO 182  
<211> LENGTH: 7  
<212> TYPE: PRT  
<213> ORGANISM: Homo sapiens

<400> SEQUENCE: 182

```
Glu Asp Ser Gln Arg Pro Ser
1               5
```

<210> SEQ ID NO 183  
<211> LENGTH: 9  
<212> TYPE: PRT  
<213> ORGANISM: Homo sapiens

<400> SEQUENCE: 183

```
Gln Ser Tyr Asp Ser Ser Asn Val Val
1               5
```

<210> SEQ ID NO 184  
<211> LENGTH: 7  
<212> TYPE: PRT  
<213> ORGANISM: Homo sapiens

<400> SEQUENCE: 184

```
Ser Asn Ser Ala Ala Trp Asn
1               5
```

<210> SEQ ID NO 185  
<211> LENGTH: 18  
<212> TYPE: PRT  
<213> ORGANISM: Homo sapiens

<400> SEQUENCE: 185

```
Arg Thr Tyr Tyr Arg Ser Lys Trp Phe Asn Asp Tyr Ala Val Ser Val
1               5                   10                  15

Gln Ser
```

<210> SEQ ID NO 186  
<211> LENGTH: 10  
<212> TYPE: PRT  
<213> ORGANISM: Homo sapiens

<400> SEQUENCE: 186

```
Gly Ile Val Phe Ser Tyr Ala Met Asp Val
1               5                   10
```

<210> SEQ ID NO 187
<211> LENGTH: 321
<212> TYPE: DNA
<213> ORGANISM: Homo sapiens

<400> SEQUENCE: 187

```
tcctatgagc tgactcagcc ccctcagtg tccgtgtccc caggacagac agccagcatc        60
acctgttctg gagataaaat gggggaaaga tatgcttgct ggtatcagca gaagccaggc       120
cagtccccta tactggtcat ctatcaagat accaagcggc cctcagggat ccctgagcga       180
ttctctggct ccaactctgg gaacacagcc actctgacca tcagcgggac ccaggctatg       240
gatgaggctg actattactg tcaggcgtgg tacagcagca ccaatgtggt attcggcgga       300
gggaccaagc tgaccgtcct a                                                 321
```

<210> SEQ ID NO 188
<211> LENGTH: 107
<212> TYPE: PRT
<213> ORGANISM: Homo sapiens

<400> SEQUENCE: 188

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Met Gly Glu Arg Tyr Ala
            20                  25                  30

Cys Trp Tyr Gln Gln Lys Pro Gly Gln Ser Pro Ile Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Tyr Ser Ser Thr Asn Val
                85                  90                  95

Val Phe Gly Gly Gly Thr Lys Leu Thr Val Leu
            100                 105

<210> SEQ ID NO 189
<211> LENGTH: 363
<212> TYPE: DNA
<213> ORGANISM: Homo sapiens

<400> SEQUENCE: 189

```
caggtgcagc tggtggagtc tgggggaggc gtggtccagc ctgggaggtc cctgagactc        60
tcctgtgcag cgtctggatt caccttcagt aactatggca tgcactgggt ccgccaggct       120
ccaggcaagg ggctggagtg ggtggcagtt atatggtatg ttggaagtaa taatactat        180
gcagactccg tgaagggccg attcaccatc tccagagaca attccaagaa cacgctgtat       240
ctgcaaatga acagcctgag agccgaggac acggctgtgt attactgtgc gagagcccag       300
gagggtatgg cccctgatgc ttttgatatc tggggccaag gacaatggtc accgtctct        360
tca                                                                     363
```

<210> SEQ ID NO 190
<211> LENGTH: 121
<212> TYPE: PRT
<213> ORGANISM: Homo sapiens

<400> SEQUENCE: 190

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Val Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Glu Gly Met Ala Pro Asp Ala Phe Asp Ile Trp Gly
            100                 105                 110

Gln Gly Thr Met Val Thr Val Ser Ser
        115                 120
```

<210> SEQ ID NO 191
<211> LENGTH: 11
<212> TYPE: PRT
<213> ORGANISM: Homo sapiens

<400> SEQUENCE: 191

```
Ser Gly Asp Lys Met Gly Glu Arg Tyr Ala Cys
1               5                   10
```

<210> SEQ ID NO 192
<211> LENGTH: 7
<212> TYPE: PRT
<213> ORGANISM: Homo sapiens

<400> SEQUENCE: 192

```
Gln Asp Thr Lys Arg Pro Ser
1               5
```

<210> SEQ ID NO 193
<211> LENGTH: 10
<212> TYPE: PRT
<213> ORGANISM: Homo sapiens

<400> SEQUENCE: 193

```
Gln Ala Trp Tyr Ser Ser Thr Asn Val Val
1               5                   10
```

<210> SEQ ID NO 194
<211> LENGTH: 5
<212> TYPE: PRT
<213> ORGANISM: Homo sapiens

<400> SEQUENCE: 194

```
Asn Tyr Gly Met His
1               5
```

<210> SEQ ID NO 195
<211> LENGTH: 17
<212> TYPE: PRT
<213> ORGANISM: Homo sapiens

<400> SEQUENCE: 195

```
Val Ile Trp Tyr Val Gly Ser Asn Lys Tyr Tyr Ala Asp Ser Val Lys
1               5                   10                  15

Gly
```

<210> SEQ ID NO 196
<211> LENGTH: 12
<212> TYPE: PRT
<213> ORGANISM: Homo sapiens

<400> SEQUENCE: 196

Ala Gln Glu Gly Met Ala Pro Asp Ala Phe Asp Ile
1               5                   10

<210> SEQ ID NO 197
<211> LENGTH: 717
<212> TYPE: DNA
<213> ORGANISM: Homo sapiens

<400> SEQUENCE: 197

```
atgaggctcc ctgctcagct cctggggctg ctaatgctct gggtctctgg atccagtggg      60
gatattgtga tgacccagtc tccactctcc ctgcccgtca cccctggaga gccggcctcc     120
atctcctgca ggtctagtca gagcctcctg catagtgatg gatacaacta tttggattgg     180
tacctgcaga agtcagggca gtctccacag cgcctgatct atatgggttc taatcgggcc     240
tccggggtcc ctgacaggtt cagtggcagt ggatcaggca cagattttac actgaaaatc     300
agcagagtgg aggctgagga tgttggggtt tattactgca tgcaagctct acaaactccg     360
ctcactatcg gcggagggac caaggtggag atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt       717
```

<210> SEQ ID NO 198
<211> LENGTH: 239
<212> TYPE: PRT
<213> ORGANISM: Homo sapiens

<400> SEQUENCE: 198

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu His Ser Asp Gly Tyr Asn Tyr Leu Asp Trp Tyr Leu Gln Lys
    50                  55                  60

Ser Gly Gln Ser Pro Gln Arg Leu Ile Tyr Met Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Leu Thr Ile Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu

```
                145                 150                 155                 160
Leu Asn Asn Phe Tyr Pro Arg Glu Ala Lys Val Gln Trp Lys Val Asp
                    165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
                210                 215                 220

Gly Leu Ser Ser Pro Val Thr Lys Ser Phe Asn Arg Gly Glu Cys
225                 230                 235

<210> SEQ ID NO 199
<211> LENGTH: 1401
<212> TYPE: DNA
<213> ORGANISM: Homo sapiens

<400> SEQUENCE: 199
atggagtttg ggctgagctg ggttttcctc gttgctcttt taagaggtgt ccagtgtcag     60
gtgcagctgg tggagtctgg gggaggcgtg gtccagcctg gaggtccct  gagactctcc   120 tgtgcagcct ctggattcac cttcagtagt tatggcatgc actgggtccg tcaggctcca   180 ggcaagggc  tggagtgggt ggcagttatt tcatatgatg aagtaatga  atactatgca   240 gactccgtga agggccgatt caccatctcc agagacaatt ccaagaacac gctgtatctg   300
caaatgaaca gcctgagagc tgaggacacg gctgtatatt actgtgtgag agatgtgtgg   360
ttcggggagt ccctccacgg tttggacgtc tggggccaag gaccacggt  caccgtctcc   420 tcagcctcca ccaagggccc atcggtcttc cccctggcgc cctgctccag gagcacctcc   480
gagagcacag cggccctggg ctgcctggtc aaggactact tccccgaacc ggtgacggtg   540
tcgtggaact caggcgctct gaccagcggc gtgcacacct tcccagctgt cctacagtcc   600
tcaggactct actccctcag cagcgtggtg accgtgccct ccagcaactt cggcacccag   660
acctacacct gcaacgtaga tcacaagccc agcaacacca aggtggacaa gacagttgag   720
cgcaaatgtt gtgtcgagtg cccaccgtgc ccagcaccac ctgtggcagg accgtcagtc   780
ttcctcttcc ccccaaaacc caaggacacc ctcatgatct cccggacccc tgaggtcacg   840
tgcgtggtgg tggacgtgag ccacgaagac cccgaggtcc agttcaactg gtacgtggac   900
ggcgtggagg tgcataatgc caagacaaag ccacgggagg agcagttcaa cagcacgttc   960
cgtgtggtca gcgtcctcac cgttgtgcac caggactggc tgaacggcaa ggagtacaag  1020
tgcaaggtct ccaacaaagg cctcccagcc cccatcgaga aaccatctc  caaaaccaaa  1080 gggcagcccc gagaaccaca ggtgtacacc ctgcccccat cccgggagga gatgaccaag  1140
aaccaggtca gcctgacctg cctggtcaaa ggcttctacc ccagcgacat cgccgtggag  1200
tgggagagca atgggcagcc ggagaacaac tacaagacca cacctcccat gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctccctgt ctccgggtaa a                                            1401

<210> SEQ ID NO 200
<211> LENGTH: 467
<212> TYPE: PRT
<213> ORGANISM: Homo sapiens

<400> SEQUENCE: 200
```

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Ser Tyr Asp Gly Ser Asn Glu Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Asp Val Trp Phe Gly Glu Ser Leu His Gly Leu
            115                 120                 125

Asp Val Trp Gly Gln Gly Thr Thr Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
        290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
```

```
                     420             425             430
Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
        450                 455                 460

Pro Gly Lys
465

<210> SEQ ID NO 201
<211> LENGTH: 366
<212> TYPE: DNA
<213> ORGANISM: Homo sapiens

<400> SEQUENCE: 201
caggttcagc tggtgcagtc tggagatgag gtgaagaagc ctggggcctc agtgaaggtc      60
tcctgcaagg cttctggtta cacctttatc aagtatggaa tcagtttggg tgcgacaggcc   120 cctggacaag gcttgagtg gatgggatgg atcggcgctt tcaatggtaa cacagactat     180
gcacggaacc tccaggccag agtcaccatg accacagaca catccacgag cacagcctac    240
atggagctga ggagcctgag atctgacgac acggccgtat attactgtgc gagagagggc    300
tggaacgacg actacttctc cggtttggac gtctggggcc aagggaccac ggtcaccgtc    360
tcctca                                                               366

<210> SEQ ID NO 202
<211> LENGTH: 122
<212> TYPE: PRT
<213> ORGANISM: Homo sapiens

<400> SEQUENCE: 202

Gln Val Gln Leu Val Gln Ser Gly Asp Glu Val Lys Lys Pro Gly Ala
1               5                   10                  15

Ser Val Lys Val Ser Cys Lys Ala Ser Gly Tyr Thr Phe Ile Lys Tyr
            20                  25                  30

Gly Ile Ser Trp Val Arg Gln Ala Pro Gly Gln Gly Leu Glu Trp Met
        35                  40                  45

Gly Trp Ile Gly Ala Phe Asn Gly Asn Thr Asp Tyr Ala Arg Asn Leu
    50                  55                  60

Gln Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Trp Asn Asp Asp Tyr Phe Ser Gly Leu Asp Val Trp
            100                 105                 110

Gly Gln Gly Thr Thr Val Thr Val Ser Ser
        115                 120

<210> SEQ ID NO 203
<211> LENGTH: 5
<212> TYPE: PRT
<213> ORGANISM: Homo sapiens

<400> SEQUENCE: 203

Lys Tyr Gly Ile Ser
1               5

<210> SEQ ID NO 204
<211> LENGTH: 17
<212> TYPE: PRT
```

<213> ORGANISM: Homo sapiens

<400> SEQUENCE: 204

Trp Ile Gly Ala Phe Asn Gly Asn Thr Asp Tyr Ala Arg Asn Leu Gln
1               5                   10                  15

Ala

<210> SEQ ID NO 205
<211> LENGTH: 13
<212> TYPE: PRT
<213> ORGANISM: Homo sapiens

<400> SEQUENCE: 205

Glu Gly Trp Asn Asp Asp Tyr Phe Ser Gly Leu Asp Val
1               5                   10

<210> SEQ ID NO 206
<211> LENGTH: 1401
<212> TYPE: DNA
<213> ORGANISM: Homo sapiens

<400> SEQUENCE: 206

```
atggactgga cctggagcat ccttttcttg gtggcagcag caacaggtgc ccactcccag      60
gttcagctgg tgcagtctgg agatgaggtg aagaagcctg gggcctcagt gaaggtctcc     120
tgcaaggctt ctggttacac ctttatcaag tatggaatca gttgggtgcg acaggcccct     180
ggacaagggc ttgagtggat gggatggatc ggcgctttca atggtaacac agactatgca     240
cggaacctcc aggccagagt caccatgacc acagacacat ccacgagcac agcctacatg     300
gagctgagga gcctgagatc tgacgacacg gccgtatatt actgtgcgag agagggctgg     360
aacgacgact acttctccgg tttggacgtc tggggccaag ggaccacggt caccgtctcc     420
tcagcctcca ccaagggccc atcggtcttc cccctggcgc cctgctccag gagcacctcc     480
gagagcacag cggccctggg ctgcctggtc aaggactact tccccgaacc ggtgacggtg     540
tcgtggaact caggcgctct gaccagcggc gtgcacacct tcccagctgt cctacagtcc     600
tcaggactct actccctcag cagcgtggtg accgtgccct ccagcaactt cggcacccag     660
acctacacct gcaacgtaga tcacaagccc agcaacacca aggtggacaa gacagttgag     720
cgcaaatgtt gtgtcgagtg cccaccgtgc ccagcaccac ctgtggcagg accgtcagtc     780
ttcctcttcc ccccaaaacc caaggacacc ctcatgatct cccggacccc tgaggtcacg     840
tgcgtggtgg tggacgtgag ccacgaagac cccgaggtcc agttcaactg gtacgtggac     900
ggcgtggagg tgcataatgc caagacaaag ccacgggagg agcagttcaa cagcacgttc     960
cgtgtggtca gcgtcctcac cgttgtgcac caggactggc tgaacggcaa ggagtacaag    1020
tgcaaggtct ccaacaaagg cctcccagcc cccatcgaga aaccatctc caaaaccaaa     1080
ggcagcccc gagaaccaca ggtgtacacc ctgcccccat cccggagga gatgaccaag     1140
aaccaggtca gcctgacctg cctggtcaaa ggcttctacc ccagcgacat cgccgtggag    1200
tgggagagca atgggcagcc ggagaacaac tacaagacca cacctcccat gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa a                                              1401
```

<210> SEQ ID NO 207
<211> LENGTH: 467
<212> TYPE: PRT

<213> ORGANISM: Homo sapiens

<400> SEQUENCE: 207

```
Met Asp Trp Thr Trp Ser Ile Leu Phe Leu Val Ala Ala Thr Gly
1               5                   10                  15

Ala His Ser Gln Val Gln Leu Val Gln Ser Gly Asp Glu Val Lys Lys
            20                  25                  30

Pro Gly Ala Ser Val Lys Val Ser Cys Lys Ala Ser Gly Tyr Thr Phe
        35                  40                  45

Ile Lys Tyr Gly Ile Ser Trp Val Arg Gln Ala Pro Gly Gln Gly Leu
    50                  55                  60

Glu Trp Met Gly Trp Ile Gly Ala Phe Asn Gly Asn Thr Asp Tyr Ala
65              70                  75                  80

Arg Asn Leu Gln Ala Arg Val Thr Met Thr Thr Asp Thr Ser Thr Ser
                85                  90                  95

Thr Ala Tyr Met Glu Leu Arg Ser Leu Arg Ser Asp Thr Ala Val
            100                 105                 110

Tyr Tyr Cys Ala Arg Glu Gly Trp Asn Asp Asp Tyr Phe Ser Gly Leu
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
```

```
                       405                 410                 415
Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460

Pro Gly Lys
465

<210> SEQ ID NO 208
<211> LENGTH: 708
<212> TYPE: DNA
<213> ORGANISM: Homo sapiens

<400> SEQUENCE: 208
atggcctggt ctcctctcct cctcactctc ctcgctcact gcacagggtc ctgggcccag     60
tctgtgttga cgcagccgcc ctcactgtct ggggccccag ggcagagggt caccatctcc    120
tgcactgggg gcagctccaa catcgggtca ggttttgcta tatactggta ccagcagctt    180
ccaggaacag ccccccaaact cctcatcttt ggtgacaaca ttcggccctc aggggtccct    240
gaccgattct ctggctccaa gtctggcacc tccgcctccc tggccatcac tgggctccag    300
gctgaggatg aggctgatta ttactgccag tcctatgaca gcagcctgag tggttcggtt    360
ttcggcggag ggaccaagct gaccgtccta agtcagccca aggctgcccc ctcggtcact    420
ctgttcccgc cctcctctga ggagcttcaa gccaacaagg ccacactggt gtgtctcata    480
agtgacttct acccgggagc cgtgacagtg gcctggaagg cagatagcag ccccgtcaag    540
gcgggagtgg agaccaccac accctccaaa caaagcaaca acaagtacgc ggccagcagc    600
tatctgagcc tgacgcctga gcagtggaag tcccacagaa gctacagctg ccaggtcacg    660
catgaaggga gcaccgtgga agaacagtg gcccctacag aatgttca                  708

<210> SEQ ID NO 209
<211> LENGTH: 236
<212> TYPE: PRT
<213> ORGANISM: Homo sapiens

<400> SEQUENCE: 209

Met Ala Trp Ser Pro Leu Leu Thr Leu Leu Ala His Cys Thr Gly
1               5                   10                  15

Ser Trp Ala Gln Ser Val Leu Thr Gln Pro Pro Ser Leu Ser Gly Ala
                20                  25                  30

Pro Gly Gln Arg Val Thr Ile Ser Cys Thr Gly Gly Ser Ser Asn Ile
            35                  40                  45

Gly Ser Gly Phe Ala Ile Tyr Trp Tyr Gln Gln Leu Pro Gly Thr Ala
        50                  55                  60

Pro Lys Leu Leu Ile Phe Gly Asp Asn Ile Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
            100                 105                 110

Asp Ser Ser Leu Ser Gly Ser Val Phe Gly Gly Gly Thr Lys Leu Thr
        115                 120                 125

Val Leu Ser Gln Pro Lys Ala Ala Pro Ser Val Thr Leu Phe Pro Pro
    130                 135                 140
```

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 210
<211> LENGTH: 1386
<212> TYPE: DNA
<213> ORGANISM: Homo sapiens

<400> SEQUENCE: 210
atggactgga cctggagcat ccttttcttg gtggcagcag caacaggtgc ccactcccag      60
gttcagctgg tgcagtctgg agctgaggtg aagaagcctg gggcctcagt gaaggtctcc     120
tgcaaggctt ctggttacac ctttaccagc tatggtatca gctgggtgcg acaggcccct     180
ggacaagggc ttgagtggat gggatggatc agcgcttaca atggtgaaaa aaacactgca     240
cagaaactcc agggcagagt caccatgacc acagacacat ccacgagcac agcctacatg     300
gagctgagga gcctgagatc tgacgacacg gccgtgtatt actgtgcgag agaggaacta     360
ggggcttttg atatctgggg ccaagggaca atggtcaccg tctcttcagc tccaccaag     420 ggcccatcgg tcttccccct ggcgccctgc tccaggagca cctccgagag cacagcggcc     480
ctgggctgcc tggtcaagga ctacttcccc gaaccggtga cggtgtcgtg gaactcaggc     540
gctctgacca gcggcgtgca caccttccca gctgtcctac agtcctcagg actctactcc     600
ctcagcagcg tggtgaccgt gccctccagc aacttcggca cccagaccta cacctgcaac     660
gtagatcaca agcccagcaa caccaaggtg gacaagacag ttgagcgcaa atgttgtgtc     720
gagtgcccac cgtgcccagc accacctgtg gcaggaccgt cagtcttcct cttcccccca     780
aaacccaagg acaccctcat gatctcccgg acccctgagg tcacgtgcgt ggtggtggac     840
gtgagccacg aagaccccga ggtccagttc aactggtacg tggacggcgt ggaggtgcat     900
aatgccaaga caaagccacg ggaggagcag ttcaacagca cgttccgtgt ggtcagcgtc     960
ctcaccgttg tgcaccagga ctggctgaac ggcaaggagt acaagtgcaa ggtctccaac    1020
aaaggcctcc cagcccccat cgagaaaacc atctccaaaa ccaaagggca gccccgagaa    1080
ccacaggtgt acaccctgcc cccatcccgg gaggagatga ccaagaacca ggtcagcctg    1140
acctgcctgg tcaaaggctt ctaccccagc gacatcgccg tggagtggga gagcaatggg    1200
cagccggaga caactacaa gaccacacct cccatgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaa                                                                1386

<210> SEQ ID NO 211
<211> LENGTH: 462
<212> TYPE: PRT
<213> ORGANISM: Homo sapiens

```
<400> SEQUENCE: 211

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Glu Lys Asn Thr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Glu Leu Gly Ala Phe Asp Ile Trp Gly Gln
        115                 120                 125

Gly Thr Met Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415
```

```
Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 212
<211> LENGTH: 318
<212> TYPE: DNA
<213> ORGANISM: Homo sapiens

<400> SEQUENCE: 212
tatgagctga ctcagccacc ctcagtgtcc gtgtccccag gacagacagc cagcctcacc      60
tgctctggag ataaattggg ggatagatat gcttcctggt atcagcagaa gccaggccag     120
tcccctgtgc tggtcatcta tcaagatagc aagcggccct cagggatccc tgagcgattc     180
tctggctcca actctgggaa cacagccact ctgaccatca gcgggaccca ggctatggat     240
gaggctgact attactgtca ggcgtgggac agcagcactg catctgtctt cggaactggg     300
accaaggtca ccgtccta                                                   318

<210> SEQ ID NO 213
<211> LENGTH: 106
<212> TYPE: PRT
<213> ORGANISM: Homo sapiens

<400> SEQUENCE: 213

Tyr Glu Leu Thr Gln Pro Pro Ser Val Ser Val Ser Pro Gly Gln Thr
1               5                   10                  15

Ala Ser Leu Thr Cys Ser Gly Asp Lys Leu Gly Asp Arg Tyr Ala Ser
            20                  25                  30

Trp Tyr Gln Gln Lys Pro Gly Gln Ser Pro Val Leu Val Ile Tyr Gln
        35                  40                  45

Asp Ser Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Asp Ser Ser Thr Ala Ser Val
                85                  90                  95

Phe Gly Thr Gly Thr Lys Val Thr Val Leu
            100                 105

<210> SEQ ID NO 214
<211> LENGTH: 11
<212> TYPE: PRT
<213> ORGANISM: Homo sapiens

<400> SEQUENCE: 214

Ser Gly Asp Lys Leu Gly Asp Arg Tyr Ala Ser
1               5                   10

<210> SEQ ID NO 215
<211> LENGTH: 7
<212> TYPE: PRT
<213> ORGANISM: Homo sapiens

<400> SEQUENCE: 215

Gln Asp Ser Lys Arg Pro Ser
1               5
```

<210> SEQ ID NO 216
<211> LENGTH: 10
<212> TYPE: PRT
<213> ORGANISM: Homo sapiens

<400> SEQUENCE: 216

Gln Ala Trp Asp Ser Ser Thr Ala Ser Val
1               5                   10

<210> SEQ ID NO 217
<211> LENGTH: 702
<212> TYPE: DNA
<213> ORGANISM: Homo sapiens

<400> SEQUENCE: 217

```
atggacatga gggtgcccgc tcagctcctg gggctcctgc tgctgtggct gagaggtgcc      60
agatgttatg agctgactca gccaccctca gtgtccgtgt ccccaggaca gacagccagc     120
ctcacctgct ctggagataa attgggggat agatatgctt cctggtatca gcagaagcca     180
ggccagtccc ctgtgctggt catctatcaa gatagcaagc ggccctcagg gatccctgag     240
cgattctctg gctccaactc tgggaacaca gccactctga ccatcagcgg gacccaggct     300
atggatgagg ctgactatta ctgtcaggcg tgggacagca gcactgcatc tgtcttcgga     360
actgggacca aggtcaccgt cctaggtcag cccaaggcca accccactgt cactctgttc     420
ccgccctcct ctgaggagct ccaagccaac aaggccacac tagtgtgtct gatcagtgac     480
ttctacccgg gagctgtgac agtggcctgg aaggcagatg gcagccccgt caaggcggga     540
gtggagacca ccaaaccctc aaacagagc aacaacaagt acgcggccag cagctacctg     600
agcctgacgc ccgagcagtg gaagtcccac agaagctaca gctgccaggt cacgcatgaa     660
gggagcaccg tggagaagac agtggcccct acagaatgtt ca                       702
```

<210> SEQ ID NO 218
<211> LENGTH: 234
<212> TYPE: PRT
<213> ORGANISM: Homo sapiens

<400> SEQUENCE: 218

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
                20                  25                  30

Val Ser Pro Gly Gln Thr Ala Ser Leu Thr Cys Ser Gly Asp Lys Leu
            35                  40                  45

Gly Asp Arg Tyr Ala Ser Trp Tyr Gln Gln Lys Pro Gly Gln Ser Pro
        50                  55                  60

Val Leu Val Ile Tyr Gln Asp Ser Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Tyr Cys Gln Ala Trp Asp
            100                 105                 110

Ser Ser Thr Ala Ser Val Phe Gly Thr Gly Thr Lys Val Thr Val Leu
        115                 120                 125

Gly Gln Pro Lys Ala Asn Pro Thr Val Thr Leu Phe Pro Pro Ser Ser
    130                 135                 140

Glu Glu Leu Gln Ala Asn Lys Ala Thr Leu Val Cys Leu Ile Ser Asp

```
               145                 150                 155                 160
Phe Tyr Pro Gly Ala Val Thr Val Ala Trp Lys Ala Asp Gly Ser Pro
                165                 170                 175

Val Lys Ala Gly Val Glu Thr Thr Lys Pro Ser Lys Gln Ser Asn Asn
                180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230

<210> SEQ ID NO 219
<211> LENGTH: 702
<212> TYPE: DNA
<213> ORGANISM: Homo sapiens

<400> SEQUENCE: 219
atggaaaccc cagcgcagct tctcttcctc ctgctactct ggctcccaga taccaccgga      60
gaaattgtgt tgacgcagtc tccaggcacc ctgtctttgt ctccagggga agagccacc     120
ctctcctgca gggccagtca gagtgttagc agcaactact tagcctggta ccagcagaaa    180
cctggccagg ctcccaggct cctcatctat ggtgcatcca gcagggccac tggcatccca    240
gacaggttca gtggcagtgg gtctgggaca gacttcactc tcatcatcag cagactggag    300
cctgaagatt ttgtagtgta ttactgtcag cagtatggta gctcactcac tttcggcgga    360
gggaccaagg tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag cacactgacg    600
ctgagcaaag cagactacga gaaacacaaa gtctacgcct gcgaagtcac ccatcagggc    660
ctgagctcgc ccgtcacaaa gagcttcaac aggggagagt gt                       702

<210> SEQ ID NO 220
<211> LENGTH: 234
<212> TYPE: PRT
<213> ORGANISM: Homo sapiens

<400> SEQUENCE: 220

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Asn Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Ile Ile
                85                  90                  95

Ser Arg Leu Glu Pro Glu Asp Phe Val Val Tyr Tyr Cys Gln Gln Tyr
            100                 105                 110

Gly Ser Ser Leu Thr Phe Gly Gly Gly Thr Lys Val Glu Ile Lys Arg
        115                 120                 125
```

```
Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 221
<211> LENGTH: 1401
<212> TYPE: DNA
<213> ORGANISM: Homo sapiens

<400> SEQUENCE: 221
atggactgga cctggagcat ccttttcttg gtggcagcag caacaggtgc ccactcccag    60
gttcagctgg tgcagtctgg agatgaggtg aagaagcctg gggcctcagt gaaggtctcc   120
tgcaaggctt ctggttacac ctttatcaag tatggaatca gttgggtgcg acaggcccct   180
ggacaagggc ttgagtggat gggatggatc ggcgctttca atggtaacac agactatgca   240
cggaacctcc aggccagagt caccatgacc acagacacat ccacgagcac agcctacatg   300
gagctgagga gcctgagatc tgacgacacg gccgtatatt actgtgcgag agagggctgg   360
aacgacgact acttctgcgg tttggacgtc tggggccaag gaccacggt caccgtctcc    420 tcagcctcca caagggccc atcggtcttc ccctggcgc cctgctccag gagcacctcc    480
gagagcacag cggccctggg ctgcctggtc aaggactact ccccgaacc ggtgacggtg    540 tcgtggaact caggcgctct gaccagcggc gtgcacacct tcccagctgt cctacagtcc   600
tcaggactct actccctcag cagcgtggtg accgtgccct ccagcaactt cggcacccag   660
acctacacct gcaacgtaga tcacaagccc agcaacacca aggtggacaa gacagttgag   720
cgcaaatgtt gtgtcgagtg cccaccgtgc ccagcaccac ctgtggcagg accgtcagtc   780
ttcctcttcc cccaaaaacc caaggacacc ctcatgatct cccggacccc tgaggtcacg   840
tgcgtggtgg tggacgtgag ccacgaagac cccgaggtcc agttcaactg gtacgtggac   900
ggcgtggagg tgcataatgc caagacaaag ccacgggagg agcagttcaa cagcacgttc   960
cgtgtggtca gcgtcctcac cgttgtgcac caggactggc tgaacggcaa ggagtacaag  1020
tgcaaggtct ccaacaaagg cctcccagcc ccatcgaga aaaccatctc caaaaccaaa   1080
gggcagcccc gagaaccaca ggtgtacacc ctgcccccat cccgggagga gatgaccaag  1140
aaccaggtca gcctgacctg cctggtcaaa ggcttctacc ccagcgacat cgccgtggag  1200
tgggagagca atgggcagcc ggagaacaac tacaagacca cacctcccat gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctccctgt ctccgggtaa a                                            1401

<210> SEQ ID NO 222
```

<211> LENGTH: 467
<212> TYPE: PRT
<213> ORGANISM: Homo sapiens

<400> SEQUENCE: 222

```
Met Asp Trp Thr Trp Ser Ile Leu Phe Leu Val Ala Ala Thr Gly
1               5                   10                  15

Ala His Ser Gln Val Gln Leu Val Gln Ser Gly Asp Glu Val Lys Lys
            20                  25                  30

Pro Gly Ala Ser Val Lys Val Ser Cys Lys Ala Ser Gly Tyr Thr Phe
        35                  40                  45

Ile Lys Tyr Gly Ile Ser Trp Val Arg Gln Ala Pro Gly Gln Gly Leu
    50                  55                  60

Glu Trp Met Gly Trp Ile Gly Ala Phe Asn Gly Asn Thr Asp Tyr Ala
65              70                  75                  80

Arg Asn Leu Gln Ala Arg Val Thr Met Thr Thr Asp Thr Ser Thr Ser
            85                  90                  95

Thr Ala Tyr Met Glu Leu Arg Ser Leu Arg Ser Asp Asp Thr Ala Val
        100                 105                 110

Tyr Tyr Cys Ala Arg Glu Gly Trp Asn Asp Asp Tyr Phe Cys Gly Leu
    115                 120                 125

Asp Val Trp Gly Gln Gly Thr Thr Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
            165                 170                 175

Pro Val Thr Val Ser Trp Asn Ser Gly Ala Leu Thr Ser Gly Val His
        180                 185                 190

Thr Phe Pro Ala Val Leu Gln Ser Ser Gly Leu Tyr Ser Leu Ser Ser
    195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
        340                 345                 350

Glu Lys Thr Ile Ser Lys Thr Lys Gly Gln Pro Arg Glu Pro Gln Val
    355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400
```

```
Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460

Pro Gly Lys
465

<210> SEQ ID NO 223
<211> LENGTH: 318
<212> TYPE: DNA
<213> ORGANISM: Homo sapiens

<400> SEQUENCE: 223
tatgagctga ctcagccacc ctcagtgtcc gtgtccccag gacagacagc caccatcacc      60
tgctctggag ataaattggg ggaaagatat gcgtcttggt atcagcagag gccaggccag     120
tcccctgtac tggtcatcta tcaagatatc aagcggccct cagggatccc tgagcgattc     180
tctggctcca actctgggaa cacagccact ctgaccatca gcgggaccca ggctatggat     240
gaggctgact atttctgtca ggcgtggtac agcagcacca atgtgctttt cggcggaggg     300
accaagctga ccgtccta                                                   318

<210> SEQ ID NO 224
<211> LENGTH: 106
<212> TYPE: PRT
<213> ORGANISM: Homo sapiens

<400> SEQUENCE: 224

Tyr Glu Leu Thr Gln Pro Pro Ser Val Ser Val Ser Pro Gly Gln Thr
1               5                   10                  15

Ala Thr Ile Thr Cys Ser Gly Asp Lys Leu Gly Glu Arg Tyr Ala Ser
            20                  25                  30

Trp Tyr Gln Gln Arg Pro Gly Gln Ser Pro Val Leu Val Ile Tyr Gln
        35                  40                  45

Asp Ile Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Phe Cys Gln Ala Trp Tyr Ser Ser Thr Asn Val Leu
                85                  90                  95

Phe Gly Gly Gly Thr Lys Leu Thr Val Leu
            100                 105

<210> SEQ ID NO 225
<211> LENGTH: 11
<212> TYPE: PRT
<213> ORGANISM: Homo sapiens

<400> SEQUENCE: 225

Ser Gly Asp Lys Leu Gly Glu Arg Tyr Ala Ser
1               5                   10

<210> SEQ ID NO 226
<211> LENGTH: 7
<212> TYPE: PRT
```

<213> ORGANISM: Homo sapiens

<400> SEQUENCE: 226

Gln Asp Ile Lys Arg Pro Ser
1               5

<210> SEQ ID NO 227
<211> LENGTH: 10
<212> TYPE: PRT
<213> ORGANISM: Homo sapiens

<400> SEQUENCE: 227

Gln Ala Trp Tyr Ser Ser Thr Asn Val Leu
1               5                   10

<210> SEQ ID NO 228
<211> LENGTH: 702
<212> TYPE: DNA
<213> ORGANISM: Homo sapiens

<400> SEQUENCE: 228

```
atggacatga gggtgcccgc tcagctcctg gggctcctgc tgctgtggct gagaggtgcc    60
agatgttatg agctgactca gccaccctca gtgtccgtgt ccccaggaca cagccacc    120
atcacctgct ctggagataa attgggggaa agatatgcgt cttggtatca gcagaggcca   180
ggccagtccc ctgtactggt catctatcaa gatatcaagc ggccctcagg gatccctgag   240
cgattctctg gctccaactc tgggaacaca gccactctga ccatcagcgg gacccaggct   300
atggatgagg ctgactattt ctgtcaggcg tggtacagca gcaccaatgt gcttttcggc   360
ggagggacca gctgaccgt cctaggtcag cccaaggctg cccctcggt cactctgttc   420
ccgcccctcct ctgaggagct tcaagccaac aaggccacac tggtgtgtct cataagtgac   480
ttctaccgg agccgtgac agtggcctgg aaggcagata gcagcccgt caaggcggga   540
gtggagacca ccacaccctc caaacaaagc aacaacaagt acgcggccag cagctatctg   600
agcctgacgc ctgagcagtg gaagtcccac agaagctaca gctgccaggt cacgcatgaa   660
gggagcaccg tggagaagac agtggcccct acagaatgtt ca                      702
```

<210> SEQ ID NO 229
<211> LENGTH: 234
<212> TYPE: PRT
<213> ORGANISM: Homo sapiens

<400> SEQUENCE: 229

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Thr Ile Thr Cys Ser Gly Asp Lys Leu
        35                  40                  45

Gly Glu Arg Tyr Ala Ser Trp Tyr Gln Gln Arg Pro Gly Gln Ser Pro
    50                  55                  60

Val Leu Val Ile Tyr Gln Asp Ile Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Phe Cys Gln Ala Trp Tyr
            100                 105                 110

Ser Ser Thr Asn Val Leu Phe Gly Gly Gly Thr Lys Leu Thr Val Leu

-continued

```
              115                 120                 125
Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 230
<211> LENGTH: 696
<212> TYPE: DNA
<213> ORGANISM: Homo sapiens

<400> SEQUENCE: 230
atggcatgga tccctctctt cctcggcgtc cttgcttact gcacaggatc cgtggcctcc      60
tatgagctga ctcagccacc ctcagtgtcc gtgtccccag acagacagc cagcctcacc      120 tgctctggag ataaaattgg ggatagatat gcttcctggt atcagcagaa gccaggccag     180
tcccctgtgc tggtcatcta tcaagatagc aagcggccct cagggatccc tgagcgattc     240
tctggctcca actctgggaa cacagccact ctgaccatca gcgggaccca ggctatggat     300
gaggctgact attactgtca ggcgtgggac agcagcactg catgtgtctt cggaactggg     360
accaaggtca ccgtcctagg tcagcccaag gccaacccca ctgtcactct gttcccgccc     420
tcctctgagg agctccaagc caacaaggcc acactagtgt gtctgatcag tgacttctac     480
ccgggagctg tgacagtggc ctggaaggca gatggcagcc ccgtcaaggc gggagtggag     540
accaccaaac cctccaaaca gagcaacaac aagtacgcgg ccagcagcta cctgagcctg     600
acgcccgagc agtggaagtc cacagaaagc tacagctgcc aggtcacgca tgaagggagc     660
accgtggaga agacagtggc ccctacagaa tgttca                                696

<210> SEQ ID NO 231
<211> LENGTH: 232
<212> TYPE: PRT
<213> ORGANISM: Homo sapiens

<400> SEQUENCE: 231

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Ser Leu Thr Cys Ser Gly Asp Lys Leu Gly Asp
        35                  40                  45

Arg Tyr Ala Ser Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95
```

Gln Ala Met Asp Glu Ala Asp Tyr Tyr Cys Gln Ala Trp Asp Ser Ser
            100                 105                 110

Thr Ala Cys Val Phe Gly Thr Gly Thr Lys Val Thr Val Leu Gly Gln
        115                 120                 125

Pro Lys Ala Asn Pro Thr Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Gly Ser Pro Val Lys
                165                 170                 175

Ala Gly Val Glu Thr Thr Lys Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 232
<211> LENGTH: 1398
<212> TYPE: DNA
<213> ORGANISM: Homo sapiens

<400> SEQUENCE: 232
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120 tgtgcagcgt ctggattcac cctcagtagc tatggcatgc actgggtccg ccaggctcca    180
ggcaaggggc tggagtgggt ggcagttata tggtatgatg aaagtaataa atactatgca    240
gactccgtga agggccgatt caccatctcc agagacaatt ccaagaacac gttgaatctg    300
caaatgaaca gcctgagagc cgaggacacg gctttgtatt actgtgcgag agccggtata    360
gcagcagccc ttgatgcttt tgatatctgg ggccaaggga caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tgcaggacc gtcagtcttc    780 ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320

```
gtcttctcat gctccgtgat gcatgaggct ctgcacaacc actacacgca gaagagcctc    1380
tccctgtctc cgggtaaa                                                   1398
```

<210> SEQ ID NO 233
<211> LENGTH: 466
<212> TYPE: PRT
<213> ORGANISM: Homo sapiens

<400> SEQUENCE: 233

| | | | | | | | | | | | | | | |
|---|---|---|---|---|---|---|---|---|---|---|---|---|---|---|
| Met | Glu | Phe | Gly | Leu | Ser | Trp | Val | Phe | Leu | Val | Ala | Leu | Leu | Arg | Gly |
| 1 | | | | 5 | | | | | 10 | | | | | 15 | |
| Val | Gln | Cys | Gln | Val | Gln | Leu | Val | Glu | Ser | Gly | Gly | Gly | Val | Val | Gln |
| | | | 20 | | | | | 25 | | | | | 30 | | |
| Pro | Gly | Arg | Ser | Leu | Arg | Leu | Ser | Cys | Ala | Ala | Ser | Gly | Phe | Thr | Leu |
| | | 35 | | | | | 40 | | | | | 45 | | | |
| Ser | Ser | Tyr | Gly | Met | His | Trp | Val | Arg | Gln | Ala | Pro | Gly | Lys | Gly | Leu |
| | 50 | | | | | 55 | | | | | 60 | | | | |
| Glu | Trp | Val | Ala | Val | Ile | Trp | Tyr | Asp | Glu | Ser | Asn | Lys | Tyr | Tyr | Ala |
| 65 | | | | | 70 | | | | | 75 | | | | | 80 |
| Asp | Ser | Val | Lys | Gly | Arg | Phe | Thr | Ile | Ser | Arg | Asp | Asn | Ser | Lys | Asn |
| | | | | 85 | | | | | 90 | | | | | 95 | |
| Thr | Leu | Asn | Leu | Gln | Met | Asn | Ser | Leu | Arg | Ala | Glu | Asp | Thr | Ala | Leu |
| | | | 100 | | | | | 105 | | | | | 110 | | |
| Tyr | Tyr | Cys | Ala | Arg | Ala | Gly | Ile | Ala | Ala | Leu | Asp | Ala | Phe | Asp |
| | | 115 | | | | | 120 | | | | | 125 | | |
| Ile | Trp | Gly | Gln | Gly | Thr | Met | Val | Thr | Val | Ser | Ala | Ser | Thr | Lys |
| | 130 | | | | | 135 | | | | | 140 | | | |
| Gly | Pro | Ser | Val | Phe | Pro | Leu | Ala | Pro | Cys | Ser | Arg | Ser | Thr | Ser | Glu |
| 145 | | | | | 150 | | | | | 155 | | | | | 160 |
| Ser | Thr | Ala | Ala | Leu | Gly | Cys | Leu | Val | Lys | Asp | Tyr | Phe | Pro | Glu | Pro |
| | | | | 165 | | | | | 170 | | | | | 175 | |
| Val | Thr | Val | Ser | Trp | Asn | Ser | Gly | Ala | Leu | Thr | Ser | Gly | Val | His | Thr |
| | | | 180 | | | | | 185 | | | | | 190 | | |
| Phe | Pro | Ala | Val | Leu | Gln | Ser | Ser | Gly | Leu | Tyr | Ser | Leu | Ser | Ser | Val |
| | | 195 | | | | | 200 | | | | | 205 | | | |
| Val | Thr | Val | Pro | Ser | Ser | Asn | Phe | Gly | Thr | Gln | Thr | Tyr | Thr | Cys | Asn |
| | 210 | | | | | 215 | | | | | 220 | | | | |
| Val | Asp | His | Lys | Pro | Ser | Asn | Thr | Lys | Val | Asp | Lys | Thr | Val | Glu | Arg |
| 225 | | | | | 230 | | | | | 235 | | | | | 240 |
| Lys | Cys | Cys | Val | Glu | Cys | Pro | Pro | Cys | Pro | Ala | Pro | Pro | Val | Ala | Gly |
| | | | | 245 | | | | | 250 | | | | | 255 | |
| Pro | Ser | Val | Phe | Leu | Phe | Pro | Pro | Lys | Pro | Lys | Asp | Thr | Leu | Met | Ile |
| | | | 260 | | | | | 265 | | | | | 270 | | |
| Ser | Arg | Thr | Pro | Glu | Val | Thr | Cys | Val | Val | Val | Asp | Val | Ser | His | Glu |
| | | 275 | | | | | 280 | | | | | 285 | | | |
| Asp | Pro | Glu | Val | Gln | Phe | Asn | Trp | Tyr | Val | Asp | Gly | Val | Glu | Val | His |
| | 290 | | | | | 295 | | | | | 300 | | | | |
| Asn | Ala | Lys | Thr | Lys | Pro | Arg | Glu | Glu | Gln | Phe | Asn | Ser | Thr | Phe | Arg |
| 305 | | | | | 310 | | | | | 315 | | | | | 320 |
| Val | Val | Ser | Val | Leu | Thr | Val | Val | His | Gln | Asp | Trp | Leu | Asn | Gly | Lys |
| | | | | 325 | | | | | 330 | | | | | 335 | |
| Glu | Tyr | Lys | Cys | Lys | Val | Ser | Asn | Lys | Gly | Leu | Pro | Ala | Pro | Ile | Glu |
| | | | 340 | | | | | 345 | | | | | 350 | | |
| Lys | Thr | Ile | Ser | Lys | Thr | Lys | Gly | Gln | Pro | Arg | Glu | Pro | Gln | Val | Tyr |
| | | 355 | | | | | 360 | | | | | 365 | | | |

```
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 234
<211> LENGTH: 318
<212> TYPE: DNA
<213> ORGANISM: Homo sapiens

<400> SEQUENCE: 234
tatgagctga ctcagccacc ctcagtgtcc gtgtccccag gacagacagc caccatcacc      60
tgctctggag ataaattggg ggaaagatat gcgtcttggt atcagcagag gccaggccag     120
tcccctgtac tggtcatcta tcaagatagc aagcggccct cagggatccc tgagcgattc     180
tctggctcca actctgggaa cacagccact ctgaccatca gcgggaccca ggctatggat     240
gaggctgact atttctgtca ggcgtggtac agcagcacca atgtgctttt cggcggaggg     300
accaagctga ccgtccta                                                   318

<210> SEQ ID NO 235
<211> LENGTH: 106
<212> TYPE: PRT
<213> ORGANISM: Homo sapiens

<400> SEQUENCE: 235

Tyr Glu Leu Thr Gln Pro Pro Ser Val Ser Val Ser Pro Gly Gln Thr
1               5                   10                  15
Ala Thr Ile Thr Cys Ser Gly Asp Lys Leu Gly Glu Arg Tyr Ala Ser
            20                  25                  30
Trp Tyr Gln Gln Arg Pro Gly Gln Ser Pro Val Leu Val Ile Tyr Gln
        35                  40                  45
Asp Ser Lys Arg Pro Ser Gly Ile Pro Glu Arg Phe Ser Gly Ser Asn
    50                  55                  60
Ser Gly Asn Thr Ala Thr Leu Thr Ile Ser Gly Thr Gln Ala Met Asp
65                  70                  75                  80
Glu Ala Asp Tyr Phe Cys Gln Ala Trp Tyr Ser Ser Thr Asn Val Leu
                85                  90                  95
Phe Gly Gly Gly Thr Lys Leu Thr Val Leu
            100                 105

<210> SEQ ID NO 236
<211> LENGTH: 11
<212> TYPE: PRT
<213> ORGANISM: Homo sapiens

<400> SEQUENCE: 236

Ser Gly Asp Lys Leu Gly Glu Arg Tyr Ala Ser
```

<210> SEQ ID NO 237
<211> LENGTH: 7
<212> TYPE: PRT
<213> ORGANISM: Homo sapiens

<400> SEQUENCE: 237

Gln Asp Ser Lys Arg Pro Ser
1               5

<210> SEQ ID NO 238
<211> LENGTH: 10
<212> TYPE: PRT
<213> ORGANISM: Homo sapiens

<400> SEQUENCE: 238

Gln Ala Trp Tyr Ser Ser Thr Asn Val Leu
1               5                   10

<210> SEQ ID NO 239
<211> LENGTH: 702
<212> TYPE: DNA
<213> ORGANISM: Homo sapiens

<400> SEQUENCE: 239

```
atggacatga gggtgcccgc tcagctcctg gggctcctgc tgctgtggct gagaggtgcc      60
agatgttatg agctgactca gccaccctca gtgtccgtgt ccccaggaca gacagccacc     120
atcacctgct ctggagataa attgggggaa agatatgcgt cttggtatca gcagaggcca     180
ggccagtccc ctgtactggt catctatcaa gatagcaagc ggccctcagg gatccctgag     240
cgattctctg gctccaactc tgggaacaca gccactctga ccatcagcgg gacccaggct     300
atggatgagg ctgactattt ctgtcaggcg tggtacagca gcaccaatgt gcttttcggc     360
ggagggacca agctgaccgt cctaggtcag cccaaggctg cccctcggt cactctgttc      420
ccgccctcct ctgaggagct tcaagccaac aaggccacac tggtgtgtct cataagtgac     480
ttctacccgg gagccgtgac agtggcctgg aaggcagata gcagccccgt caaggcggga     540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                        702
```

<210> SEQ ID NO 240
<211> LENGTH: 234
<212> TYPE: PRT
<213> ORGANISM: Homo sapiens

<400> SEQUENCE: 240

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Thr Ile Thr Cys Ser Gly Asp Lys Leu
        35                  40                  45

Gly Glu Arg Tyr Ala Ser Trp Tyr Gln Gln Arg Pro Gly Gln Ser Pro
    50                  55                  60

Val Leu Val Ile Tyr Gln Asp Ser Lys Arg Pro Ser Gly Ile Pro Glu
65                  70                  75                  80

Arg Phe Ser Gly Ser Asn Ser Gly Asn Thr Ala Thr Leu Thr Ile Ser

```
                         85                  90                  95
Gly Thr Gln Ala Met Asp Glu Ala Asp Tyr Phe Cys Gln Ala Trp Tyr
            100                 105                 110

Ser Ser Thr Asn Val Leu Phe Gly Gly Gly Thr Lys Leu Thr Val Leu
            115                 120                 125

Gly Gln Pro Lys Ala Ala Pro Ser Val Thr Leu Phe Pro Pro Ser Ser
            130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230

<210> SEQ ID NO 241
<211> LENGTH: 708
<212> TYPE: DNA
<213> ORGANISM: Homo sapiens

<400> SEQUENCE: 241
atggcctggt ctcctctcct cctcactctc ctcgctcact gcacagggtc ctgggcccag    60
tctgtgttga cgcagccgcc ctcactgtct ggggccccag ggcagagggt caccatctcc   120
tgcactgggg gcagctccaa catcgggtca ggttttgcta tatactggta ccagcagctt   180
ccaggaacag cccccaaact cctcatctat ggtgacaaca ttcggccctc aggggtccct   240
gaccgattct ctggctccaa gtctggcacc tcggcctccc tggccatcac tgggctccag   300
gctgaggatg aggctgatta ttactgccag tcctatgaca gcagcctgag tggttcggta   360
ttcggcggag ggaccaagct gaccgtccta agtcagccca aggctgcccc ctcggtcact   420
ctgttcccgc cctcctctga ggagcttcaa gccaacaagg ccacactggt gtgtctcata   480
agtgacttct acccgggagc cgtgacagtg gcctggaagg cagatagcag ccccgtcaag   540
gcgggagtgg agaccaccac accctccaaa caaagcaaca acaagtacgc ggccagcagc   600
tatctgagcc tgacgcctga gcagtggaag tcccacagaa gctacagctg ccaggtcacg   660
catgaaggga gcaccgtgga agacagtgcc cctacagaat gttca                   708

<210> SEQ ID NO 242
<211> LENGTH: 236
<212> TYPE: PRT
<213> ORGANISM: Homo sapiens

<400> SEQUENCE: 242

Met Ala Trp Ser Pro Leu Leu Leu Thr Leu Leu Ala His Cys Thr Gly
1               5                   10                  15

Ser Trp Ala Gln Ser Val Leu Thr Gln Pro Pro Ser Leu Ser Gly Ala
            20                  25                  30

Pro Gly Gln Arg Val Thr Ile Ser Cys Thr Gly Gly Ser Ser Asn Ile
        35                  40                  45

Gly Ser Gly Phe Ala Ile Tyr Trp Tyr Gln Gln Leu Pro Gly Thr Ala
    50                  55                  60
```

```
Pro Lys Leu Leu Ile Tyr Gly Asp Asn Ile Arg Pro Ser Gly Val Pro
 65                  70                  75                  80

Asp Arg Phe Ser Gly Ser Lys Ser Gly Thr Ser Ala Ser Leu Ala Ile
                 85                  90                  95

Thr Gly Leu Gln Ala Glu Asp Glu Ala Asp Tyr Tyr Cys Gln Ser Tyr
            100                 105                 110

Asp Ser Ser Leu Ser Gly Ser Val Phe Gly Gly Gly Thr Lys Leu Thr
        115                 120                 125

Val Leu Ser Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 243
<211> LENGTH: 1329
<212> TYPE: DNA
<213> ORGANISM: Homo sapiens

<400> SEQUENCE: 243
caggttcagc tggtgcagtc tggagctgag gtgaagaagc ctggggcctc agtgaaggtc     60
tcctgcaagg cttctggtta ccctttacc agctatggta tcagctgggt gcgacaggcc    120
cctggacaag gcttgagtg gatgggatgg atcagcgctt acaatggtga acaaacact    180 gcacagaaac tccagggcag agtcaccatg accacagaca catccacgag cacagcctac   240
atggagctga ggagcctgag atctgacgac acggccgtgt attactgtgc gagagaggaa   300
ctaggggctt tgatatctg gggccaaggg acaatggtca ccgtctcttc agcctccacc    360
aagggcccat cggtcttccc cctggcgccc tgctccagga gcacctccga gagcacagcg   420
gccctgggct gcctggtcaa ggactacttc cccgaaccgg tgacggtgtc gtggaactca   480
ggcgctctga ccagcggcgt gcacaccttc ccagctgtcc tacagtcctc aggactctac   540
tccctcagca gcgtggtgac cgtgccctcc agcaacttcg gcacccagac ctacacctgc   600
aacgtagatc acaagcccag caacaccaag gtggacaaga cagttgagcg caaatgttgt   660
gtcgagtgcc caccgtgccc agcaccacct gtggcaggac cgtcagtctt cctcttcccc   720
ccaaaaccca aggacaccct catgatctcc cggacccctg aggtcacgtg cgtggtggtg   780
gacgtgagcc acgaagaccc cgaggtccag ttcaactggt acgtggacgg cgtggaggtg   840
cataatgcca agacaaagcc acgggaggag cagttcaaca gcacgttccg tgtggtcagc   900
gtcctcaccg ttgtgcacca ggactggctg aacggcaagg agtacaagtg caaggtctcc   960
aacaaaggcc tcccagcccc catcgagaaa accatctcca aaaccaaagg cagccccga   1020 gaaccacagg tgtacaccct gcccccatcc cgggaggaga tgaccaagaa ccaggtcagc   1080
ctgacctgcc tggtcaaagg cttctacccc agcgacatcg ccgtggagtg ggagagcaat   1140
```

-continued

```
gggcagccgg agaacaacta caagaccaca cctcccatgc tggactccga cggctccttc    1200
ttcctctaca gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                              1329

<210> SEQ ID NO 244
<211> LENGTH: 443
<212> TYPE: PRT
<213> ORGANISM: Homo sapiens

<400> SEQUENCE: 244

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Glu Thr Asn Thr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Leu Gly Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
```

```
                340             345             350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
        370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440

<210> SEQ ID NO 245
<211> LENGTH: 318
<212> TYPE: DNA
<213> ORGANISM: Homo sapiens

<400> SEQUENCE: 245
tatgagctga ctcagccccc ctcagtgtcc gtgtccccag gacagacagc cagcatcacc      60
tgttctggag ataaaatggg ggaaagatat gcttcctggt atcagcagaa gccaggccag     120
tcccctatac tggtcatcta tcaagatacc aagcggccct cagggatccc tgagcgattc     180
tctggctcca actctgggaa cacagccact ctgaccatca gcgggaccca ggctatggat     240
gaggctgact attactgtca ggcgtggtac agcagcacca atgtggtatt cggcggaggg     300
accaagctga ccgtccta                                                   318

<210> SEQ ID NO 246
<211> LENGTH: 106
<212> TYPE: PRT
<213> ORGANISM: Homo sapiens

<400> SEQUENCE: 246

Tyr Glu Leu Thr Gln Pro Pro Ser Val Ser Val Ser Pro Gly Gln Thr
1               5                   10                  15
Ala Ser Ile Thr Cys Ser Gly Asp Lys Met Gly Glu Arg Tyr Ala Ser
            20                  25                  30
Trp Tyr Gln Gln Lys Pro Gly Gln Ser Pro Ile Leu Val Ile Tyr Gln
        35                  40                  45
Asp Thr Lys Arg Pro Ser Gly Ile Pro Glu Arg Phe Ser Gly Ser Asn
    50                  55                  60
Ser Gly Asn Thr Ala Thr Leu Thr Ile Ser Gly Thr Gln Ala Met Asp
65                  70                  75                  80
Glu Ala Asp Tyr Tyr Cys Gln Ala Trp Tyr Ser Ser Thr Asn Val Val
                85                  90                  95
Phe Gly Gly Gly Thr Lys Leu Thr Val Leu
            100                 105

<210> SEQ ID NO 247
<211> LENGTH: 11
<212> TYPE: PRT
<213> ORGANISM: Homo sapiens

<400> SEQUENCE: 247

Ser Gly Asp Lys Met Gly Glu Arg Tyr Ala Ser
1               5                   10
```

<210> SEQ ID NO 248
<211> LENGTH: 7
<212> TYPE: PRT
<213> ORGANISM: Homo sapiens

<400> SEQUENCE: 248

Gln Asp Thr Lys Arg Pro Ser
1               5

<210> SEQ ID NO 249
<211> LENGTH: 10
<212> TYPE: PRT
<213> ORGANISM: Homo sapiens

<400> SEQUENCE: 249

Gln Ala Trp Tyr Ser Ser Thr Asn Val Val
1               5                   10

<210> SEQ ID NO 250
<211> LENGTH: 702
<212> TYPE: DNA
<213> ORGANISM: Homo sapiens

<400> SEQUENCE: 250

```
atggacatga gggtgcccgc tcagctcctg gggctcctgc tgctgtggct gagaggtgcc      60
agatgttatg agctgactca gccccctca gtgtccgtgt ccccaggaca dacagccagc     120
atcacctgtt ctggagataa aatgggggaa agatatgctt cctggtatca gcagaagcca    180
ggccagtccc ctatactggt catctatcaa gataccaagc ggccctcagg gatccctgag    240
cgattctctg gctccaactc tgggaacaca gccactctga ccatcagcgg gacccaggct    300
atggatgagg ctgactatta ctgtcaggcg tggtacagca gcaccaatgt ggtattcggc    360
ggagggacca agctgaccgt cctaggtcag cccaaggctg ccccctcggt cactctgttc    420
ccgccctcct ctgaggagct tcaagccaac aaggccacac tggtgtgtct cataagtgac    480
ttctacccgg gagccgtgac agtggcctgg aaggcagata gcagccccgt caaggcggga    540
gtggagacca ccacaccctc caaacaaagc aacaacaagt acgcggccag cagctatctg    600
agcctgacgc ctgaacagtg gaagtcccac agaagctaca gctgccaggt cacgcatgaa    660
gggagcaccg tggagaagac agtggcccct acagaatgtt ca                       702
```

<210> SEQ ID NO 251
<211> LENGTH: 234
<212> TYPE: PRT
<213> ORGANISM: Homo sapiens

<400> SEQUENCE: 251

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Ser Ile Thr Cys Ser Gly Asp Lys Met
        35                  40                  45

Gly Glu Arg Tyr Ala Ser Trp Tyr Gln Gln Lys Pro Gly Gln Ser Pro
    50                  55                  60

Ile Leu Val Ile Tyr Gln Asp Thr Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

```
Gly Thr Gln Ala Met Asp Glu Ala Asp Tyr Tyr Cys Gln Ala Trp Tyr
            100                 105                 110

Ser Ser Thr Asn Val Val Phe Gly Gly Thr Lys Leu Thr Val Leu
    115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230
```

```
<210> SEQ ID NO 252
<211> LENGTH: 696
<212> TYPE: DNA
<213> ORGANISM: Homo sapiens

<400> SEQUENCE: 252
atggcatgga tccctctctt cctcggcgtc cttgcttact gcacaggatc cgtggcctcc      60
tatgagctga ctcagccacc ctcagtgtcc gtgtccccag acagacagc caccatcacc     120
tgctctggag ataaattggg ggaaagatat gcgtgttggt atcagcagag gccaggccag     180
tcccctgtac tggtcatcta tcaagatatc aagcggccct cagggatccc tgagcgattc     240
tctggctcca actctgggaa cacagccact ctgaccatca gcgggaccca ggctatggat     300
gaggctgact atttctgtca ggcgtggtac agcagcacca atgtgctttt cggcggaggg     360
accaagctga ccgtcctagg tcagcccaag gctgccccct cggtcactct gttcccgccc     420
tcctctgagg agcttcaagc caacaaggcc acactggtgt gtctcataag tgacttctac     480
ccgggagccg tgacagtggc ctggaaggca gatagcagcc ccgtcaaggc gggagtggag     540
accaccacac cctccaaaca aagcaacaac aagtacgcgg ccagcagcta tctgagcctg     600
acgcctgagc agtggaagtc ccacagaagc tacagctgcc aggtcacgca tgaagggagc     660
accgtggaga agacagtggc ccctacagaa tgttca                              696
```

```
<210> SEQ ID NO 253
<211> LENGTH: 232
<212> TYPE: PRT
<213> ORGANISM: Homo sapiens

<400> SEQUENCE: 253

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Thr Ile Thr Cys Ser Gly Asp Lys Leu Gly Glu
        35                  40                  45

Arg Tyr Ala Cys Trp Tyr Gln Gln Arg Pro Gly Gln Ser Pro Val Leu
    50                  55                  60

Val Ile Tyr Gln Asp Ile Lys Arg Pro Ser Gly Ile Pro Glu Arg Phe
```

```
              65                  70                  75                  80
Ser Gly Ser Asn Ser Gly Asn Thr Ala Thr Leu Thr Ile Ser Gly Thr
                         85                  90                  95

Gln Ala Met Asp Glu Ala Asp Tyr Phe Cys Gln Ala Trp Tyr Ser Ser
                100                 105                 110

Thr Asn Val Leu Phe Gly Gly Gly Thr Lys Leu Thr Val Leu Gly Gln
            115                 120                 125

Pro Lys Ala Ala Pro Ser Val Thr Leu Phe Pro Pro Ser Ser Glu Glu
        130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
210                 215                 220

Thr Val Ala Pro Thr Glu Cys Ser
225                 230

<210> SEQ ID NO 254
<211> LENGTH: 1398
<212> TYPE: DNA
<213> ORGANISM: Homo sapiens

<400> SEQUENCE: 254
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120 tgtgcagcgt ctggattcac cttcagtagc tatggcatgc actgggtccg ccaggctcca    180
ggcaaggggc tggagtgggt ggcagttata tggtatgctg aaagtaataa atactacgca    240
gactccgtga agggccgatt caccatctcc agagacaatt ccaagaacac gctgtatctg    300
caaatgaaca gcctgagagc cgaggacacg gctgtgtatt actgtgcgag agcccaggag    360
ggtatagccc ctgacgcttt tgatatctgg ggccaaggaa caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tgcaggacc gtcagtcttc    780 ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
```

-continued

```
gagagcaatg ggcagccgga gaacaactac aagaccacac ctcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                   1398

<210> SEQ ID NO 255
<211> LENGTH: 466
<212> TYPE: PRT
<213> ORGANISM: Homo sapiens

<400> SEQUENCE: 255

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Ile Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
```

-continued

```
                340                 345                 350
Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 256
<211> LENGTH: 696
<212> TYPE: DNA
<213> ORGANISM: Homo sapiens

<400> SEQUENCE: 256
atggcatgga tccctctctt cctcggcgtc cttgcttact gcacaggatc cgtggcctcc      60
tatgagctga ctcagccacc ctcagtgtcc gtgtccccag acagacagc caccatcacc      120 tgctctggag ataaattggg ggaaagatat gcgtgttggt atcagcagag gccaggccag      180
tcccctgtac tggtcatcta tcaagatagc aagcggccct cagggatccc tgagcgattc      240
tctggctcca actctgggaa cacagccact ctgaccatca gcgggaccca ggctatggat      300
gaggctgact atttctgtca ggcgtggtac agcagcacca atgtgctttt cggcggaggg      360
accaagctga ccgtcctagg tcagcccaag gctgcccct cggtcactct gttcccgccc      420
tcctctgagg agcttcaagc caacaaggcc acactggtgt gtctcataag tgacttctac      480
ccgggagccg tgacagtggc ctggaaggca gatagcagcc cgtcaaggc gggagtggag      540 accaccacac cctccaaaca aagcaacaac aagtacgcgg ccagcagcta tctgagcctg      600
acgcctgagc agtggaagtc cacagaagc tacagctgcc aggtcacgca tgaagggagc      660
accgtggaga agacagtggc ccctacagaa tgttca                                696

<210> SEQ ID NO 257
<211> LENGTH: 232
<212> TYPE: PRT
<213> ORGANISM: Homo sapiens

<400> SEQUENCE: 257

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Thr Ile Thr Cys Ser Gly Asp Lys Leu Gly Glu
        35                  40                  45

Arg Tyr Ala Cys Trp Tyr Gln Gln Arg Pro Gly Gln Ser Pro Val Leu
    50                  55                  60

Val Ile Tyr Gln Asp Ser Lys Arg Pro Ser Gly Ile Pro Glu Arg Phe
65                  70                  75                  80
```

```
Ser Gly Ser Asn Ser Gly Asn Thr Ala Thr Leu Thr Ile Ser Gly Thr
                85                  90                  95
Gln Ala Met Asp Glu Ala Asp Tyr Phe Cys Gln Ala Trp Tyr Ser Ser
            100                 105                 110
Thr Asn Val Leu Phe Gly Gly Gly Thr Lys Leu Thr Val Leu Gly Gln
        115                 120                 125
Pro Lys Ala Ala Pro Ser Val Thr Leu Phe Pro Pro Ser Ser Glu Glu
    130                 135                 140
Leu Gln Ala Asn Lys Ala Thr Leu Val Cys Leu Ile Ser Asp Phe Tyr
145                 150                 155                 160
Pro Gly Ala Val Thr Val Ala Trp Lys Ala Asp Ser Ser Pro Val Lys
                165                 170                 175
Ala Gly Val Glu Thr Thr Thr Pro Ser Lys Gln Ser Asn Asn Lys Tyr
            180                 185                 190
Ala Ala Ser Ser Tyr Leu Ser Leu Thr Pro Glu Gln Trp Lys Ser His
        195                 200                 205
Arg Ser Tyr Ser Cys Gln Val Thr His Glu Gly Ser Thr Val Glu Lys
    210                 215                 220
Thr Val Ala Pro Thr Glu Cys Ser
225                 230

<210> SEQ ID NO 258
<211> LENGTH: 1398
<212> TYPE: DNA
<213> ORGANISM: Homo sapiens

<400> SEQUENCE: 258
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120
tgtgcagcgt ctggattcac cttcagtagc tatggcatgc actgggtccg ccaggctcca     180
ggcaaggggc tggagtgggt ggcagttata tggtatgctg aaagtaataa atactacgca     240
gactccgtga agggccgatt caccatctcc agagacaatt ccaagaacac gctgtatctg     300
caaatgaaca gcctgagagc cgaggacacg gctgtgtatt actgtgcgag agcccaggag     360
ggtatagccc ctgacgcttt tgatatctgg ggccaaggaa caatggtcac cgtctcttca     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggacccctga ggtcacgtgc     840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagccccc atcgagaaaa ccatctccaa accaaagggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
```

```
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                  1398
```

<210> SEQ ID NO 259
<211> LENGTH: 466
<212> TYPE: PRT
<213> ORGANISM: Homo sapiens

<400> SEQUENCE: 259

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Gly Ile Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350
```

```
Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 260
<211> LENGTH: 705
<212> TYPE: DNA
<213> ORGANISM: Homo sapiens

<400> SEQUENCE: 260
atggcctggg ctccactact tctcaccctc ctcgctcact gcacaggttc ttgggccaat    60
tttatgctga ctcagcccca ctctgtgtcg gagtctccgg ggaagacggt aaccatctcc   120
tgcacccgca gcagtggcag cattgccagc tactatgtgc agtggtacca gcagcgcccg   180
ggcagttccc ccaccactgt gatctatgag gatagccaga gaccctctgg ggtccctgat   240
cggttctctg gctccatcga cagctcctcc aactctgcct ccctcaccat ctctggactg   300
aagactgagg acgaggctga ctattattgt cagtcttatg atagcagcaa tgtggtattc   360
ggcggaggga ccaagctgac cgtcctaggt cagcccaagg ctgccccctc ggtcactctg   420
ttcccgccct cctctgagga gcttcaagcc aacaaggcca cactggtgtg tctcataagt   480
gacttctacc cgggagccgt gacagtggcc tggaaggcag atagcagccc cgtcaaggcg   540
ggagtggaga ccaccacacc tccaaacaa agcaacaaca gtacgcggc cagcagctat   600 ctgagcctga cgcctgagca gtggaagtcc cacagaagct acagctgcca ggtcacgcat   660
gaagggagca ccgtggagaa gacagtggcc cctacagaat gttca                  705

<210> SEQ ID NO 261
<211> LENGTH: 235
<212> TYPE: PRT
<213> ORGANISM: Homo sapiens

<400> SEQUENCE: 261

Met Ala Trp Ala Pro Leu Leu Leu Thr Leu Leu Ala His Cys Thr Gly
1               5                   10                  15

Ser Trp Ala Asn Phe Met Leu Thr Gln Pro His Ser Val Ser Glu Ser
            20                  25                  30

Pro Gly Lys Thr Val Thr Ile Ser Cys Thr Arg Ser Ser Gly Ser Ile
        35                  40                  45

Ala Ser Tyr Tyr Val Gln Trp Tyr Gln Gln Arg Pro Gly Ser Ser Pro
    50                  55                  60

Thr Thr Val Ile Tyr Glu Asp Ser Gln Arg Pro Ser Gly Val Pro Asp
65                  70                  75                  80
```

```
Arg Phe Ser Gly Ser Ile Asp Ser Ser Asn Ser Ala Ser Leu Thr
                 85                  90                  95
Ile Ser Gly Leu Lys Thr Glu Asp Glu Ala Asp Tyr Tyr Cys Gln Ser
            100                 105                 110
Tyr Asp Ser Ser Asn Val Val Phe Gly Gly Gly Thr Lys Leu Thr Val
        115                 120                 125
Leu Gly Gln Pro Lys Ala Ala Pro Ser Val Thr Leu Phe Pro Pro Ser
130                 135                 140
Ser Glu Glu Leu Gln Ala Asn Lys Ala Thr Leu Val Cys Leu Ile Ser
145                 150                 155                 160
Asp Phe Tyr Pro Gly Ala Val Thr Val Ala Trp Lys Ala Asp Ser Ser
                165                 170                 175
Pro Val Lys Ala Gly Val Glu Thr Thr Thr Pro Ser Lys Gln Ser Asn
            180                 185                 190
Asn Lys Tyr Ala Ala Ser Ser Tyr Leu Ser Leu Thr Pro Glu Gln Trp
        195                 200                 205
Lys Ser His Arg Ser Tyr Ser Cys Gln Val Thr His Glu Gly Ser Thr
    210                 215                 220
Val Glu Lys Thr Val Ala Pro Thr Glu Cys Ser
225                 230                 235

<210> SEQ ID NO 262
<211> LENGTH: 1404
<212> TYPE: DNA
<213> ORGANISM: Homo sapiens

<400> SEQUENCE: 262
atgtctgtct ccttcctcat cttcctgccc gtgctgggcc tcccatgggg tgtcctgtca    60
caggtacagc tgcagcagtc aggtccagga ctggtgaagc cctcgcagac cctctcactc   120
acctgtgcca tctccgggga cagtgtctct agcaacagtg ctgcttggaa ctggatcagg   180
cagtccccat cgagaggcct tgagtggctg gaaggacact actacaggtc caagtggttt   240
aatgattatg cagtatctgt gcaaagtcga ataaccatca cccagacac atccaagaac   300 cagttctccc tgcagctgaa ctctgtgact cccgaggaca cggctgtgta ttactgtgca   360
agagggattg tcttctccta cgctatggac gtctggggcc aagggaccac ggtcaccgtc   420
tcctcagcct ccaccaaggg cccatcggtc ttccccctgg cgccctgctc caggagcacc   480
tccgagagca cagcggccct gggctgcctg gtcaaggact acttccccga accggtgacg   540
gtgtcgtgga actcaggcgc tctgaccagc ggcgtgcaca ccttcccagc tgtcctacag   600
tcctcaggac tctactccct cagcagcgtg gtgaccgtgc cctccagcaa cttcggcacc   660
cagacctaca cctgcaacgt agatcacaag cccagcaaca ccaaggtgga caagacagtt   720
gagcgcaaat gttgtgtcga gtgcccaccg tgcccagcac cacctgtggc aggaccgtca   780
gtcttcctct tccccccaaa acccaaggac accctcatga tctcccggac ccctgaggtc   840
acgtgcgtgg tggtggacgt gagccacgaa gaccccgagg tccagttcaa ctggtacgtg   900
gacggcgtgg aggtgcataa tgccaagaca aagccacggg aggagcagtt caacagcacg   960
ttccgtgtgg tcagcgtcct caccgttgtg caccaggact ggctgaacgg caaggagtac  1020
aagtgcaagg tctccaacaa aggcctccca gcccccatcg agaaaaccat ctccaaaacc  1080
aaagggcagc cccgagaacc acaggtgtac accctgcccc catcccggga ggagatgacc  1140
aagaaccagg tcagcctgac ctgcctggtc aaaggcttct accccagcga catcgccgtg  1200
gagtgggaga gcaatgggca gccggagaac aactacaaga ccacacctcc catgctggac  1260
```

```
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                          1404
```

<210> SEQ ID NO 263
<211> LENGTH: 468
<212> TYPE: PRT
<213> ORGANISM: Homo sapiens

<400> SEQUENCE: 263

```
Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Phe
65                  70                  75                  80

Asn Asp Tyr Ala Val Ser Val Gln Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Gly Ile Val Phe Ser Tyr Ala
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350
```

```
Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 264
<211> LENGTH: 696
<212> TYPE: DNA
<213> ORGANISM: Homo sapiens

<400> SEQUENCE: 264
atggcatgga tccctctctt cctcggcgtc cttgcttact gcacaggatc cgtggcctcc      60
tatgagctga ctcagccccc ctcagtgtcc gtgtccccag acagacagc cagcatcacc      120 tgttctggag ataaaatggg ggaaagatat gcttgctggt atcagcagaa gccaggccag      180
tcccctatac tggtcatcta tcaagatacc aagcggccct cagggatccc tgagcgattc      240
tctggctcca actctgggaa cacagccact ctgaccatca gcgggaccca ggctatggat      300
gaggctgact attactgtca ggcgtggtac agcagcacca atgtggtatt cggcggaggg      360
accaagctga ccgtcctagg tcagcccaag gctgcccct cggtcactct gttcccgccc      420
tcctctgagg agcttcaagc caacaaggcc acactggtgt gtctcataag tgacttctac      480
ccgggagccg tgacagtggc ctggaaggca gatagcagcc cgtcaaggc gggagtggag      540 accaccacac cctccaaaca aagcaacaac aagtacgcgg ccagcagcta tctgagcctg      600
acgcctgaac agtggaagtc cacagaaagc tacagctgcc aggtcacgca tgaagggagc      660
accgtggaga agacagtggc ccctacagaa tgttca                               696

<210> SEQ ID NO 265
<211> LENGTH: 232
<212> TYPE: PRT
<213> ORGANISM: Homo sapiens

<400> SEQUENCE: 265

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
                20                  25                  30

Pro Gly Gln Thr Ala Ser Ile Thr Cys Ser Gly Asp Lys Met Gly Glu
            35                  40                  45

Arg Tyr Ala Cys Trp Tyr Gln Gln Lys Pro Gly Gln Ser Pro Ile Leu
        50                  55                  60

Val Ile Tyr Gln Asp Thr Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
```

```
                        85                  90                  95
Gln Ala Met Asp Glu Ala Asp Tyr Tyr Cys Gln Ala Trp Tyr Ser Ser
                100                 105                 110

Thr Asn Val Val Phe Gly Gly Gly Thr Lys Leu Thr Val Leu Gly Gln
            115                 120                 125

Pro Lys Ala Ala Pro Ser Val Thr Leu Phe Pro Pro Ser Ser Glu Glu
        130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 266
<211> LENGTH: 1398
<212> TYPE: DNA
<213> ORGANISM: Homo sapiens

<400> SEQUENCE: 266
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120 tgtgcagcgt ctggattcac cttcagtaac tatggcatgc actgggtccg ccaggctcca    180
ggcaaggggc tggagtgggt ggcagttata tggtatgttg aagtaataa atactatgca     240 gactccgtga agggccgatt caccatctcc agagacaatt ccaagaacac gctgtatctg    300
caaatgaaca gcctgagagc cgaggacacg gctgtgtatt actgtgcgag agcccaggag    360
ggtatggccc tgatgctttt tgatatctgg ggccaaggga caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggaccctga ggtcacgtgc     840 gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac tcccatgct ggactccgac    1260 ggctccttct cctctacag caagctcacc gtggacaaga gcaggtggca gcaggggaac   1320
```

```
gtcttctcat gctccgtgat gcatgaggct ctgcacaacc actacacgca gaagagcctc    1380
tccctgtctc cgggtaaa                                                  1398
```

<210> SEQ ID NO 267
<211> LENGTH: 466
<212> TYPE: PRT
<213> ORGANISM: Homo sapiens

<400> SEQUENCE: 267

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Gly Met His Trp Val Arg Gln Ala Pro Gly Lys Gly Leu
    50                  55                  60

Glu Trp Val Ala Val Ile Trp Tyr Val Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Met Ala Pro Asp Ala Phe Asp
        115                 120                 125

Ile Trp Gly Gln Gly Thr Met Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
```

```
              355                 360                 365
Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
    450                 455                 460

Gly Lys
465

<210> SEQ ID NO 268
<211> LENGTH: 711
<212> TYPE: DNA
<213> ORGANISM: Mus musculus

<400> SEQUENCE: 268
atggagacag acacactcct gctatgggtg ctgctgctct gggttccagg ttccacaggt        60
aacatcgtgc tgacccaatc tccagcttct ttggctgtgt ctctagggca gagggccacc       120
atatcctgca gagccagtga aagtgttgat agttatggca atagttttat gcactggtac       180
cagcagaaac aggacagcc acccaaactc ctcatctatc ttgcatccaa cctagaatct        240
ggggtccctg ccaggttcag tggcagtggg tctaggacag acttcaccct caccattgat       300
cctgtggagg ctgatgatgc tgcaacctat tactgtcagc aaaataatga ggatcggacg       360
ttcggtggag gcaccaagct ggaaatcaaa cgggctgatg ctgcaccaac tgtatccatc       420
ttcccaccat ccagtgagca gttaacatct ggaggtgcct cagtcgtgtg cttcttgaac       480
aacttctacc ccaaagacat caatgtcaag tggaagattg atggcagtga acgacaaaat       540
ggcgtcctga cagttggac tgatcaggac agcaaagaca gcacctacag catgagcagc       600
accctcacgt tgaccaagga cgagtatgaa cgacataaca gctatacctg tgaggccact       660
cacaagacat caacttcacc cattgtcaag agcttcaaca ggaatgagtg t                711

<210> SEQ ID NO 269
<211> LENGTH: 237
<212> TYPE: PRT
<213> ORGANISM: Mus musculus

<400> SEQUENCE: 269

Met Glu Thr Asp Thr Leu Leu Leu Trp Val Leu Leu Leu Trp Val Pro
1               5                   10                  15

Gly Ser Thr Gly Asn Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Arg Thr Asp Phe Thr
                85                  90                  95
```

Leu Thr Ile Asp Pro Val Glu Ala Asp Ala Ala Thr Tyr Tyr Cys
            100                 105                 110

Gln Gln Asn Asn Glu Asp Arg Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 270
<211> LENGTH: 1419
<212> TYPE: DNA
<213> ORGANISM: Mus musculus

<400> SEQUENCE: 270
atgggttggc tgtggaactt gctattcctg atggcagctg cccaaagtgc ccaagcacag    60
atccagttgg tacagtctgg acctgagctg aagaagcctg agagacagt caagatctcc    120 tgcaaggctt ctgggtatac cttcacaacc tatggaatga gctgggtgaa acaggctcca    180
ggaaagggtt taaagtggat gggctggata aacaccctact ctggagtgcc aacatatgct    240
gatgacttca agggacggtt tgccttctct ttggaaacct ctgccagcac tgcctatttg    300
cagatcaaca acctcaaaaa tgaggacacg gctacatatt tctgtgcaag cttatggtac    360
tacggtaggg cctttgacta ctggggccaa ggcaccactc tcacagtctc ctcagccaaa    420
acaacagccc catcggtcta tccactggcc ctgtgtgtg aggtacaac tggctcctcg    480 gtgactctag gatgcctggt caagggttat ttccctgagc cagtgacctt gacctggaac    540
tctggatccc tgtccagtgg tgtgcacacc ttcccagctc tcctgcagtc tggcctctac    600
accctcagca gctcagtgac tgtaacctcg aacacctggc ccagccagac catcacctgc    660
aatgtggccc acccggcaag cagcaccaaa gtggacaaga aaattgagcc cagagtgccc    720
ataacacaga ccccctgtcc tccactcaaa gagtgtcccc catgcgcagc tccagacctc    780
ttgggtggac catccgtctt catcttccct ccaaagatca aggatgtact catgatctcc    840
ctgagcccca tggtcacatg tgtggtggtg gatgtgagcg aggatgaccc agacgtccag    900
atcagctggt ttgtgaacaa cgtggaagta cacacagctc agacacaaac ccatagagag    960
gattacaaca gtactctccg ggtggtcagt gccctcccca tccagcacca ggactggatg    1020
agtggcaagg agttcaaatg caaggtcaac aacagagccc tcccatcccc catcgagaaa    1080
accatctcaa aacccagagg gccagtaaga gctccacagg tatatgtctt gcctccacca    1140
gcagaagaga tgactaagaa agagttcagt ctgacctgca tgatcacagg cttcttacct    1200
gccgaaattg ctgtggactg gaccagcaat gggcgtacag agcaaaacta caagaacacc    1260
gcaacagtcc tggactctga tggttcttac ttcatgtaca gcaagctcag agtacaaaag    1320

```
agcacttggg aaagaggaag tctttccgcc tgctcagtgg tccacgaggg tctgcacaat    1380
caccttacga ctaagaccat ctcccggtct ctgggtaaa                           1419
```

<210> SEQ ID NO 271
<211> LENGTH: 473
<212> TYPE: PRT
<213> ORGANISM: Mus musculus

<400> SEQUENCE: 271

```
Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Ser Leu Trp Tyr Tyr Gly Arg Ala Phe Asp Tyr Trp
        115                 120                 125

Gly Gln Gly Thr Thr Leu Thr Val Ser Ser Ala Lys Thr Thr Ala Pro
    130                 135                 140

Ser Val Tyr Pro Leu Ala Pro Val Cys Gly Gly Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Leu Leu Gln Ser Gly Leu Tyr Thr Leu Ser Ser Ser Val Thr Val
        195                 200                 205

Thr Ser Asn Thr Trp Pro Ser Gln Thr Ile Thr Cys Asn Val Ala His
    210                 215                 220

Pro Ala Ser Ser Thr Lys Val Asp Lys Lys Ile Glu Pro Arg Val Pro
225                 230                 235                 240

Ile Thr Gln Asn Pro Cys Pro Pro Leu Lys Glu Cys Pro Pro Cys Ala
                245                 250                 255

Ala Pro Asp Leu Leu Gly Gly Pro Ser Val Phe Ile Phe Pro Pro Lys
            260                 265                 270

Ile Lys Asp Val Leu Met Ile Ser Leu Ser Pro Met Val Thr Cys Val
        275                 280                 285

Val Val Asp Val Ser Glu Asp Asp Pro Asp Val Gln Ile Ser Trp Phe
    290                 295                 300

Val Asn Asn Val Glu Val His Thr Ala Gln Thr Gln Thr His Arg Glu
305                 310                 315                 320

Asp Tyr Asn Ser Thr Leu Arg Val Val Ser Ala Leu Pro Ile Gln His
                325                 330                 335

Gln Asp Trp Met Ser Gly Lys Glu Phe Lys Cys Lys Val Asn Asn Arg
            340                 345                 350

Ala Leu Pro Ser Pro Ile Glu Lys Thr Ile Ser Lys Pro Arg Gly Pro
        355                 360                 365
```

Val Arg Ala Pro Gln Val Tyr Val Leu Pro Pro Ala Glu Glu Met
    370                 375                 380

Thr Lys Lys Glu Phe Ser Leu Thr Cys Met Ile Thr Gly Phe Leu Pro
385                 390                 395                 400

Ala Glu Ile Ala Val Asp Trp Thr Ser Asn Gly Arg Thr Glu Gln Asn
            405                 410                 415

Tyr Lys Asn Thr Ala Thr Val Leu Asp Ser Asp Gly Ser Tyr Phe Met
            420                 425                 430

Tyr Ser Lys Leu Arg Val Gln Lys Ser Thr Trp Glu Arg Gly Ser Leu
        435                 440                 445

Phe Ala Cys Ser Val Val His Glu Gly Leu His Asn His Leu Thr Thr
    450                 455                 460

Lys Thr Ile Ser Arg Ser Leu Gly Lys
465                 470

<210> SEQ ID NO 272
<211> LENGTH: 711
<212> TYPE: DNA
<213> ORGANISM: Mus musculus

<400> SEQUENCE: 272
atggagacag acacactcct gctatgggtg ctgctgctct gggttccagg ttccacaggt      60
gacattgtgc tgacccaatc tccagcttct ttggctgtgt ctctagggca gagggccacc     120
atatcctgca gagccagtga aagtgttgat agttatggca atagttttat gcactggtac     180
cagcagaaac aggacagcc acccaaactc ctcatctatc gtgcatccaa cctagaatct     240
gggatccctg ccaggttcag tggcagtggg tctaggacag acttcaccct caccattaat     300
cctgtggagg ctgatgatgt tgcaacctat tactgtcacc aaagtaatga ggagtacacg     360
ttcggagggg ggaccaagct ggaaataaaa cgggctgatg ctgccaccaa ctgtatccatc     420
ttcccaccat ccagtgagca gttaacatct ggaggtgcct cagtcgtgtg cttcttgaac     480
aacttctacc ccaaagacat caatgtcaag tggaagattg atggcagtga acgacaaaat     540
ggcgtcctga acagttggac tgatcaggac agcaaagaca gcacctacag catgagcagc     600
accctcacgt tgaccaagga cgagtatgaa cgacataaca gctatacctg tgaggccact     660
cacaagacat caacttccacc cattgtcaag agcttcaaca ggaatgagtg t             711

<210> SEQ ID NO 273
<211> LENGTH: 237
<212> TYPE: PRT
<213> ORGANISM: Mus musculus

<400> SEQUENCE: 273

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

His Gln Ser Asn Glu Glu Tyr Thr Phe Gly Gly Gly Thr Lys Leu Glu
            115                 120                 125

Ile Lys Arg Ala Asp Ala Ala Pro Thr Val Ser Ile Phe Pro Pro Ser
        130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 274
<211> LENGTH: 1383
<212> TYPE: DNA
<213> ORGANISM: Mus musculus

<400> SEQUENCE: 274
atgggttggc tgtggaactt gctattcctg atggcagctg cccaaagtgc ccaagcacag      60
atccagttgg tacagtctgg acctgagctg aagaagcctg agagacagtc aagatctcc     120
tgcaaggctt ctgggtatac cttcacaacc tatggaatga gctgggtgaa acaggctcca    180
ggaaagggtt taaagtggat gggctggata aatacctact ctggagtgcc aacatatgct    240
gatgacttca aggacggttt gccttctct ttggaaacct ctgccagcac tgcctatttg      300
cagatcaaca acctcaaaaa tgaggacacg gctacatatt tctgtggaag agaccactac    360
tacggggagt tgcttactg gggccaaggg actctggtca ctgtctctgc agccaaaacg      420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gccagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacga aaccccggga ggagcagatc aacagcactt tccgttcagt cagtgaactt    960
cccatcatgc accaggactg gctcaatggc aaggagttca atgcagggt caacagtgca   1020
gctttccctg cccccatcga gaaaaccatc tccaaaacca aggcagacc gaaggctcca   1080
caggtgtaca ccattccacc tcccaaggag cagatggcca aggataaagt cagtctgacc   1140
tgcatgataa caaacttctt ccctgaagac attactgtgg agtggcagtg gaatgggcag   1200
ccagcggaga actacaagaa cactcagccc atcatggaca cagatggctc ttacttcgtc   1260
tacagcaagc tcaatgtgca gaagagcaac tgggaggcag gaaatacttt cacctgctct   1320
gtgttacatg agggcctgca caaccaccat actgagaaga gcctctccca ctctcctggt   1380

```
aaa                                                      1383

<210> SEQ ID NO 275
<211> LENGTH: 461
<212> TYPE: PRT
<213> ORGANISM: Mus musculus

<400> SEQUENCE: 275

Met Gly Trp Leu Trp Asn Leu Leu Phe Leu Met Ala Ala Ala Gln Ser
 1               5                  10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Gly Arg Asp His Tyr Tyr Gly Glu Val Ala Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Gln Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Lys
    290                 295                 300

Pro Arg Glu Glu Gln Ile Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365
```

Lys Glu Gln Met Ala Lys Asp Lys Val Ser Leu Thr Cys Met Ile Thr
            370                 375                 380

Asn Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
            435                 440                 445

His His Thr Glu Lys Ser Leu Ser His Ser Pro Gly Lys
            450                 455                 460

<210> SEQ ID NO 276
<211> LENGTH: 711
<212> TYPE: DNA
<213> ORGANISM: Mus musculus

<400> SEQUENCE: 276
atggagacag acacactcct gctatgggtg ctgctgctct ggttccagg ttccacaggt      60
gacattgtgc tgacccaatc tccagcttct ttggctgtgt ctctagggca gagggccacc     120
atatcctgca gagccagtga aagtgttgat agttttggca atagttttat gcactggtac     180
cagctgaaaac aggacagcc acccaaactc ctcatctatc gtgcatccaa cctagaatct    240
gggatccctg ccaggttcag tggcagtggg tctaggacag acttcaccct caccattaat     300
cctgtggagg ctgatgatgt tgcaattat tactgtcagc aaagtaatga ggagtacacg      360
ttcggagggg ggaccaagct ggaaataaaa cgggctgatg ctgcaccaac tgtatccatc    420
ttcccaccat ccagtgagca gttaacatct ggaggtgcct cagtcgtgtg cttcttgaac    480
aacttctacc ccaaagacat caatgtcaag tggaagattg atggcagtga acgacaaaat    540
ggcgtcctga caggttggac tgatcaggac agcaaagaca gcacctacag catgagcagc    600
accctcacgt tgaccaagga cgagtatgaa cgacataaca gctatacctg tgaggccact    660
cacaagacat caacttcacc cattgtcaag agcttcaaca ggaatgagtg t              711

<210> SEQ ID NO 277
<211> LENGTH: 237
<212> TYPE: PRT
<213> ORGANISM: Mus musculus

<400> SEQUENCE: 277

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Phe Gly Asn Ser Phe Met His Trp Tyr Gln Leu Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Ile Tyr Tyr Cys
            100                 105                 110

Gln Gln Ser Asn Glu Glu Tyr Thr Phe Gly Gly Gly Thr Lys Leu Glu

```
                115                 120                 125
Ile Lys Arg Ala Asp Ala Ala Pro Thr Val Ser Ile Phe Pro Pro Ser
            130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
                195                 200                 205

Tyr Glu Arg His Asn Ser Tyr Thr Cys Glu Ala Thr His Lys Thr Ser
            210                 215                 220

Thr Ser Pro Ile Val Lys Ser Phe Asn Arg Asn Glu Cys
225                 230                 235
```

<210> SEQ ID NO 278
<211> LENGTH: 1383
<212> TYPE: DNA
<213> ORGANISM: Mus musculus

<400> SEQUENCE: 278

```
atgggttggc tgtggaactt gctattcctg atggcagctg cccaaagtgc ccaagcacag      60
atccagttgg tacagtctgg acctgagctg aagaagcctg agagacagtc aagatctcc     120
tgcaaggctt ctgggtatac cttcacaacc tatggaatga ctgggtgaa acaggctcca     180
ggaaagggtt taaagtggat gggctggata acacctcct ctggagtgcc aacatatgct     240
gatgacttca tgggacggtt tgccttctct ttggaaacct ctgccagcac tgcctatttg     300
cagatcaaca acctcaaaaa tgaggacacg gctacgtatt tctgtgcaag agaccgctac     360
tacggggagt tgcttactg gggccaaggg actctggtca ccgtctctgc agccaaaacg     420
acaccccat ctgtctatcc actggcccct ggatctgctg cccaaactaa ctccatggtg     480
accctgggat gcctggtcaa gggctatttc cctgagccag tgacagtgac ctggaactct     540
ggatccctgt ccagcggtgt gcacaccttc ccagctgtcc tgcagtctga cctctacact     600
ctgagcagct cagtgactgt cccctccagc acctggccca gcgagaccgt cacctgcaac     660
gttgcccacc cggccagcag caccaaggtg gacaagaaaa ttgtgcccag ggattgtggt     720
tgtaagcctt gcatatgtac agtcccagaa gtatcatctg tcttcatctt ccccccaaag     780
cccaaggatg tgctcaccat tactctgact cctaaggtca cgtgtgttgt ggtagacatc     840
agcaaggatg atcccgaggt ccagttcagc tggtttgtag atgatgtgga ggtgcacaca     900
gctcagacgc aaccccggga ggagcagttc aacagcactt tccgctcagt cagtgaactt     960
cccatcatgc atcaggactg gctcaatggc aaggagttca atgcagggt caacagtgca    1020
gctttccctg cccccatcga gaaaaccatc tccaaaacca aggcagacc gaaggctcca    1080
caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggaca cagatggctc ttacttcgtc    1260
tacagcaagc tcaatgtgca gaagagcaac tgggaggcag gaaatacttt cacctgctct    1320
gtgttacatg agggcctgca caaccaccat actgagaaga gcctctccca ctctcctggt    1380
aaa                                                                    1383
```

```
<210> SEQ ID NO 279
<211> LENGTH: 461
<212> TYPE: PRT
<213> ORGANISM: Mus musculus

<400> SEQUENCE: 279

Met Gly Trp Leu Trp Asn Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
            35                  40                  45

Thr Thr Tyr Gly Met Ser Trp Val Lys Gln Ala Pro Gly Lys Gly Leu
    50                  55                  60

Lys Trp Met Gly Trp Ile Asn Thr Ser Ser Gly Val Pro Thr Tyr Ala
65                  70                  75                  80

Asp Asp Phe Met Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Arg Tyr Gly Glu Val Ala Tyr Trp Gly
        115                 120                 125

Gln Gly Thr Leu Val Thr Val Ser Ala Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
```

```
385                 390                 395                 400
Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
    450                 455                 460

<210> SEQ ID NO 280
<211> LENGTH: 696
<212> TYPE: DNA
<213> ORGANISM: Rattus norvegicus

<400> SEQUENCE: 280
atggctccag tccaacttct agggcttttg ctgctctgcc tccgagccat gagatgtgac      60
atccagatga cccagtctcc ttcactcctg tcagcatctg tgggagacag agtcactctc     120
agctgcaaag caagtcagaa tatttacaag tacttaaact ggtatcagca aaagcttgga     180
gaagctccca aactcctgat atattataca aacagtttgc aaacgggcat cccatcaagg     240
ttcagtggca gtggatctgg tacagatttc acacttacca tcagcagcct gcagcctgaa     300
gatgttgcca catattactg ctatcagtat aacagtgggc cacgtttgga gctgggacc      360 aagctggaac tgaaacgggc tgatgctgca ccaactgtat ctatcttccc accatccacg     420
gaacagttag caactggagg tgcctcagtc gtgtgcctca tgaacaactt ctatcccaga     480
gacatcagtg tcaagtggaa gattgatggc actgaacgac agatggtgt cctggacagt     540 gttactgatc aggacagcaa agacagcacg tacagcatga gcagcaccct ctcgttgacc     600
aaggctgact atgaaagtca taacctctat acctgtgagg ttgttcataa gacatcatcc     660
tcacccgtcg tcaagagctt caacaggaat gagtgt                               696

<210> SEQ ID NO 281
<211> LENGTH: 232
<212> TYPE: PRT
<213> ORGANISM: Rattus norvegicus

<400> SEQUENCE: 281

Met Ala Pro Val Gln Leu Leu Gly Leu Leu Leu Leu Cys Leu Arg Ala
1               5                   10                  15

Met Arg Cys Asp Ile Gln Met Thr Gln Ser Pro Ser Leu Leu Ser Ala
            20                  25                  30

Ser Val Gly Asp Arg Val Thr Leu Ser Cys Lys Ala Ser Gln Asn Ile
        35                  40                  45

Tyr Lys Tyr Leu Asn Trp Tyr Gln Gln Lys Leu Gly Glu Ala Pro Lys
    50                  55                  60

Leu Leu Ile Tyr Tyr Thr Asn Ser Leu Gln Thr Gly Ile Pro Ser Arg
65              70                  75                  80

Phe Ser Gly Ser Gly Ser Gly Thr Asp Phe Thr Leu Thr Ile Ser Ser
                85                  90                  95

Leu Gln Pro Glu Asp Val Ala Thr Tyr Tyr Cys Tyr Gln Tyr Asn Ser
            100                 105                 110

Gly Pro Thr Phe Gly Ala Gly Thr Lys Leu Glu Leu Lys Arg Ala Asp
        115                 120                 125

Ala Ala Pro Thr Val Ser Ile Phe Pro Pro Ser Thr Glu Gln Leu Ala
    130                 135                 140
```

Thr Gly Gly Ala Ser Val Val Cys Leu Met Asn Asn Phe Tyr Pro Arg
145                 150                 155                 160

Asp Ile Ser Val Lys Trp Lys Ile Asp Gly Thr Glu Arg Arg Asp Gly
            165                 170                 175

Val Leu Asp Ser Val Thr Asp Gln Asp Ser Lys Asp Ser Thr Tyr Ser
        180                 185                 190

Met Ser Ser Thr Leu Ser Leu Thr Lys Ala Asp Tyr Glu Ser His Asn
        195                 200                 205

Leu Tyr Thr Cys Glu Val Val His Lys Thr Ser Ser Pro Val Val
        210                 215                 220

Lys Ser Phe Asn Arg Asn Glu Cys
225                 230

```
<210> SEQ ID NO 282
<211> LENGTH: 1395
<212> TYPE: DNA
<213> ORGANISM: Rattus norvegicus

<400> SEQUENCE: 282
atgggcaggc ttacttcctc attcctgctg ctgattatcc ctgcatatgt cttgtctcag      60
gttactctga aagagtctgg ccctgggata ttgcagcctt cccagaccct cagtctgact     120
tgctctttct ctgggttttc actgagcact tctggtatat gtgtgagctg gattcgtcag     180
ccttcaggga agggtctgga gtggctggca actatttgtt gggaggatag taagggctac     240
aaccccttctc tgaagaaccg gctcacaatc tccaaggaca cctccaacaa ccaagcattc     300
ctcaagatca ccagtgtgga cactgcagat accgccatat actactgtgc tcggccccctt    360
aactacggag ggtatagtga gctagaattg gattactggg gccaaggagt catggtcaca     420
gtctcctcag ctgaaacaac agccccatct gtctatccac tggctcctgg aactgctctc     480
aaaagtaact ccatggtgac cctgggatgc ctggtcaagg gctatttccc tgagccagtc     540
accgtgacct ggaactctgg agccctgtcc agcggtgtgc acaccttccc agctgtcctg     600
cagtctggac tctacactct caccagctca gtgactgtac cctccagcac ctggtccagc     660
caggccgtca cctgcaacgt agcccacccg gccagcagca ccaaggtgga caagaaaatt     720
gtgccaaggg aatgcaatcc ttgtggatgt acaggctcag aagtatcatc tgtcttcatc     780
ttcccccccaa agaccaaaga tgtgctcacc atcactctga ctcctaaggt cacgtgtgtt     840
gtggtagaca ttagccagaa tgatcccgag gtccggttca gctggtttat agatgacgtg     900
gaagtccaca cagctcagac tcatgccccg gagaagcagt ccaacagcac tttacgctca     960
gtcagtgaac tccccatcgt gcaccgggac tggctcaatg gcaagacgtt caaatgcaaa    1020
gtcaacagtg agcattccc tgcccccatc gagaaaagca tctccaaacc cgaaggcaca     1080
ccacgaggtc cacaggtata caccatggcg cctcccaagg aagagatgac ccagagtcaa    1140
gtcagtatca cctgcatggt aaaaggcttc tatccccag acatttatac ggagtggaag    1200
atgaacgggc agccacagga aaactacaag aacactccac ctacgatgga cacagatggg    1260
agttacttcc tctacagcaa gctcaatgta aagaaagaaa catggcagca gggaaacact    1320
ttcacgtgtt ctgtgctgca tgagggcctg cacaaccacc atactgagaa gagtctctcc    1380
cactctccgg gtaaa                                                      1395

<210> SEQ ID NO 283
<211> LENGTH: 465
<212> TYPE: PRT
<213> ORGANISM: Rattus norvegicus
```

<400> SEQUENCE: 283

Met Gly Arg Leu Thr Ser Ser Phe Leu Leu Ile Ile Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Ile Cys Val Ser Trp Ile Arg Gln Pro Ser Gly Lys
50                  55                  60

Gly Leu Glu Trp Leu Ala Thr Ile Cys Trp Asp Ser Lys Gly Tyr
65                  70                  75                  80

Asn Pro Ser Leu Lys Asn Arg Leu Thr Ile Ser Lys Asp Thr Ser Asn
            85                  90                  95

Asn Gln Ala Phe Leu Lys Ile Thr Ser Val Asp Thr Ala Asp Thr Ala
            100                 105                 110

Ile Tyr Tyr Cys Ala Arg Pro Leu Asn Tyr Gly Gly Tyr Ser Glu Leu
            115                 120                 125

Glu Leu Asp Tyr Trp Gly Gln Gly Val Met Val Thr Val Ser Ser Ala
130                 135                 140

Glu Thr Thr Ala Pro Ser Val Tyr Pro Leu Ala Pro Gly Thr Ala Leu
145                 150                 155                 160

Lys Ser Asn Ser Met Val Thr Leu Gly Cys Leu Val Lys Gly Tyr Phe
            165                 170                 175

Pro Glu Pro Val Thr Val Thr Trp Asn Ser Gly Ala Leu Ser Ser Gly
            180                 185                 190

Val His Thr Phe Pro Ala Val Leu Gln Ser Gly Leu Tyr Thr Leu Thr
            195                 200                 205

Ser Ser Val Thr Val Pro Ser Ser Thr Trp Ser Ser Gln Ala Val Thr
210                 215                 220

Cys Asn Val Ala His Pro Ala Ser Ser Thr Lys Val Asp Lys Lys Ile
225                 230                 235                 240

Val Pro Arg Glu Cys Asn Pro Cys Gly Cys Thr Gly Ser Glu Val Ser
            245                 250                 255

Ser Val Phe Ile Phe Pro Pro Lys Thr Lys Asp Val Leu Thr Ile Thr
            260                 265                 270

Leu Thr Pro Lys Val Thr Cys Val Val Val Asp Ile Ser Gln Asn Asp
            275                 280                 285

Pro Glu Val Arg Phe Ser Trp Phe Ile Asp Asp Val Glu Val His Thr
            290                 295                 300

Ala Gln Thr His Ala Pro Glu Lys Gln Ser Asn Ser Thr Leu Arg Ser
305                 310                 315                 320

Val Ser Glu Leu Pro Ile Val His Arg Asp Trp Leu Asn Gly Lys Thr
            325                 330                 335

Phe Lys Cys Lys Val Asn Ser Gly Ala Phe Pro Ala Pro Ile Glu Lys
            340                 345                 350

Ser Ile Ser Lys Pro Glu Gly Thr Pro Arg Gly Pro Gln Val Tyr Thr
            355                 360                 365

Met Ala Pro Pro Lys Glu Glu Met Thr Gln Ser Gln Val Ser Ile Thr
            370                 375                 380

Cys Met Val Lys Gly Phe Tyr Pro Pro Asp Ile Tyr Thr Glu Trp Lys
385                 390                 395                 400

Met Asn Gly Gln Pro Gln Glu Asn Tyr Lys Asn Thr Pro Pro Thr Met
            405                 410                 415

```
Asp Thr Asp Gly Ser Tyr Phe Leu Tyr Ser Lys Leu Asn Val Lys Lys
            420                 425                 430

Glu Thr Trp Gln Gln Gly Asn Thr Phe Thr Cys Ser Val Leu His Glu
        435                 440                 445

Gly Leu His Asn His His Thr Glu Lys Ser Leu Ser His Ser Pro Gly
        450                 455                 460

Lys
465

<210> SEQ ID NO 284
<211> LENGTH: 17
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid

<400> SEQUENCE: 284

Val Ile Xaa Tyr Xaa Xaa Ser Asn Lys Tyr Tyr Ala Asp Ser Val Lys
1               5                   10                  15

Gly

<210> SEQ ID NO 285
<211> LENGTH: 17
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (8)..(11)
<223> OTHER INFORMATION: Xaa can be any amino acid
<220> FEATURE:
<221> NAME/KEY: misc_feature
<222> LOCATION: (13)..(15)
<223> OTHER INFORMATION: Xaa can be any amino acid
<220> FEATURE:
<221> NAME/KEY: misc_feature
<222> LOCATION: (17)..(17)
<223> OTHER INFORMATION: Xaa can be any amino acid

<400> SEQUENCE: 285

Trp Ile Xaa Ala Xaa Asn Gly Xaa Xaa Xaa Xaa Ala Xaa Xaa Xaa Gln
1               5                   10                  15

Xaa

<210> SEQ ID NO 286
<211> LENGTH: 12
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any amino acid

<400> SEQUENCE: 286

Ala Gln Glu Gly Xaa Ala Pro Asp Ala Phe Asp Ile
```

```
1               5                   10
```

<210> SEQ ID NO 287
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any amino acid

<400> SEQUENCE: 287

```
Gln Ala Trp Tyr Ser Ser Thr Asn Val Xaa
1               5                   10
```

<210> SEQ ID NO 288
<211> LENGTH: 10
<212> TYPE: PRT
<213> ORGANISM: Homo sapiens
<220> FEATURE:
<221> NAME/KEY: misc_feature
<222> LOCATION: (9)..(10)
<223> OTHER INFORMATION: Xaa can be any amino acid

<400> SEQUENCE: 288

```
Gln Ala Trp Asp Ser Ser Thr Ala Xaa Xaa
1               5                   10
```

<210> SEQ ID NO 289
<211> LENGTH: 11
<212> TYPE: PRT
<213> ORGANISM: Homo sapiens
<220> FEATURE:
<221> NAME/KEY: misc_feature
<222> LOCATION: (7)..(9)
<223> OTHER INFORMATION: Xaa can be any amino acid
<220> FEATURE:
<221> NAME/KEY: misc_feature
<222> LOCATION: (10)..(11)
<223> OTHER INFORMATION: Xaa can be any amino acid or nothing

<400> SEQUENCE: 289

```
Gln Ser Asp Tyr Ser Ser Xaa Xaa Xaa Xaa Xaa
1               5                   10
```

<210> SEQ ID NO 290
<211> LENGTH: 330
<212> TYPE: DNA
<213> ORGANISM: Homo sapiens

<400> SEQUENCE: 290

```
cagtctgtgc tgactcagcc accctcaacg tctgggaccc ccgggcagag ggtcaccatc      60
tcttgttctg gaagcaactc caacatcgga agtcaaactg ttaactggta ccagcaactc     120
ccaggaacgg cccccaaact cctcatcttt agtcatcatc accggccctc agggggtccct   180
gaccgattct ctggctccaa gtctggcacc tcagcctccc tggccatcag tgggctccag     240
tctgaggatg aggctgatta ttactgtgca gcatgggatg acagcctgaa tggtgtggta     300
ttcggcggag ggaccaaact gaccgtccta                                      330
```

<210> SEQ ID NO 291
<211> LENGTH: 110
<212> TYPE: PRT
<213> ORGANISM: Homo sapiens

<400> SEQUENCE: 291

```
Gln Ser Val Leu Thr Gln Pro Pro Ser Thr Ser Gly Thr Pro Gly Gln
```

```
                1               5                   10                  15
Arg Val Thr Ile Ser Cys Ser Gly Ser Asn Ser Asn Ile Gly Ser Gln
                    20                  25                  30

Thr Val Asn Trp Tyr Gln Gln Leu Pro Gly Thr Ala Pro Lys Leu Leu
                    35                  40                  45

Ile Phe Ser His His His Arg Pro Ser Gly Val Pro Asp Arg Phe Ser
            50                  55                  60

Gly Ser Lys Ser Gly Thr Ser Ala Ser Leu Ala Ile Ser Gly Leu Gln
65                      70                  75                  80

Ser Glu Asp Glu Ala Asp Tyr Tyr Cys Ala Ala Trp Asp Asp Ser Leu
                        85                  90                  95

Asn Gly Val Val Phe Gly Gly Gly Thr Lys Leu Thr Val Leu
                        100                 105                 110

<210> SEQ ID NO 292
<211> LENGTH: 375
<212> TYPE: DNA
<213> ORGANISM: Homo sapiens

<400> SEQUENCE: 292
gaggtgcagc tggtggagtc tgggggaggc ttggtaaagc ctggggggtc ccttagactc      60
tcctgtgcag cctctggatt cactttcagt gacgcctgga tgagctgggt ccgccaggct    120
ccagggaagg ggctggagtg ggttggccgt attaaaagca aaactgatgg tgggacaaca    180
gacttcgctg cacccgtgaa aggcagattc accatctcaa gagatgattc aaaaacacg     240 ctgtatctgc aaatgaacag cctgaacacc gaggacacag cagtgtatta ctgtacctca    300
tctcatagca gcgcctggta cggctacttc ggtatggacg tctggggcca agggaccacg    360
gtcaccgtct cctca                                                    375

<210> SEQ ID NO 293
<211> LENGTH: 125
<212> TYPE: PRT
<213> ORGANISM: Homo sapiens

<400> SEQUENCE: 293

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                    20                  25                  30

Trp Met Ser Trp Val Arg Gln Ala Pro Gly Lys Gly Leu Glu Trp Val
                35                  40                  45

Gly Arg Ile Lys Ser Lys Thr Asp Gly Gly Thr Thr Asp Phe Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Asn Thr Glu Asp Thr Ala Val Tyr
                        85                  90                  95

Tyr Cys Thr Ser Ser His Ser Ser Ala Trp Tyr Gly Tyr Phe Gly Met
                    100                 105                 110

Asp Val Trp Gly Gln Gly Thr Thr Val Thr Val Ser Ser
            115                 120                 125

<210> SEQ ID NO 294
<211> LENGTH: 13
<212> TYPE: PRT
<213> ORGANISM: Homo sapiens
```

```
<400> SEQUENCE: 294

Ser Gly Ser Asn Ser Asn Ile Gly Ser Gln Thr Val Asn
1               5                   10

<210> SEQ ID NO 295
<211> LENGTH: 7
<212> TYPE: PRT
<213> ORGANISM: Homo sapiens

<400> SEQUENCE: 295

Ser His His His Arg Pro Ser
1               5

<210> SEQ ID NO 296
<211> LENGTH: 11
<212> TYPE: PRT
<213> ORGANISM: Homo sapiens

<400> SEQUENCE: 296

Ala Ala Trp Asp Asp Ser Leu Asn Gly Val Val
1               5                   10

<210> SEQ ID NO 297
<211> LENGTH: 10
<212> TYPE: PRT
<213> ORGANISM: Homo sapiens

<400> SEQUENCE: 297

Gly Phe Thr Phe Ser Asp Ala Trp Met Ser
1               5                   10

<210> SEQ ID NO 298
<211> LENGTH: 19
<212> TYPE: PRT
<213> ORGANISM: Homo sapiens

<400> SEQUENCE: 298

Arg Ile Lys Ser Lys Thr Asp Gly Gly Thr Thr Asp Phe Ala Ala Pro
1               5                   10                  15

Val Lys Gly

<210> SEQ ID NO 299
<211> LENGTH: 14
<212> TYPE: PRT
<213> ORGANISM: Homo sapiens

<400> SEQUENCE: 299

Ser His Ser Ser Ala Trp Tyr Gly Tyr Phe Gly Met Asp Val
1               5                   10

<210> SEQ ID NO 300
<211> LENGTH: 330
<212> TYPE: DNA
<213> ORGANISM: Homo sapiens

<400> SEQUENCE: 300
cagtctgtgc tgactctgtc accctcagcg tctgggaccc ccgggcagag ggtcaccatc      60
tcttgttctg gaagcacctc caacatcgga agtaatactg taaattggtt ccagcagctc     120
ccaggaacgg ccccccaaact cctcatcttt agtaataatc agcggccctc aggggtccct    180
gaccgatttt ctgcctccaa gtctggcacc tcagcctccc tggccatcag tgggctccag    240
tctgaggatg aggctgatta ttactgtgca gcgtgggatg acagcctgaa tggtgtggta    300
```
ttcggcggag ggaccaagct gaccgtccta 330

<210> SEQ ID NO 301
<211> LENGTH: 110
<212> TYPE: PRT
<213> ORGANISM: Homo sapiens

<400> SEQUENCE: 301

Gln Ser Val Leu Thr Leu Ser Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Thr Val Asn Trp Phe Gln Gln Leu Pro Gly Thr Ala Pro Lys Leu Leu
        35                  40                  45

Ile Phe Ser Asn Asn Gln Arg Pro Ser Gly Val Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 302
<211> LENGTH: 375
<212> TYPE: DNA
<213> ORGANISM: Homo sapiens

<400> SEQUENCE: 302
gaggtgcagc tggtggagtc tgggggaggc ttggtaaagc ctggggggtc ccttagactc    60
tcctgtgcag cctctggaat cactttcagt aacgcctgga tgagctgggt ccgccaggct   120
ccagggaagg ggctggagtg ggttggccgt atcaaaagca agactgatga tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
tctgatagca gcggctggta cggctactac ggtatggacg tctggggcca agggaccacg   360
gtcaccgtct cctca                                                    375

<210> SEQ ID NO 303
<211> LENGTH: 125
<212> TYPE: PRT
<213> ORGANISM: Homo sapiens

<400> SEQUENCE: 303

Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Asp Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ser Asp Ser Ser Gly Trp Tyr Gly Tyr Tyr Gly Met

```
              100                 105                 110
Asp Val Trp Gly Gln Gly Thr Thr Val Thr Val Ser Ser
        115                 120                 125
```

<210> SEQ ID NO 304
<211> LENGTH: 13
<212> TYPE: PRT
<213> ORGANISM: Homo sapiens

<400> SEQUENCE: 304

```
Ser Gly Ser Thr Ser Asn Ile Gly Ser Asn Thr Val Asn
1               5                   10
```

<210> SEQ ID NO 305
<211> LENGTH: 7
<212> TYPE: PRT
<213> ORGANISM: Homo sapiens

<400> SEQUENCE: 305

```
Ser Asn Asn Gln Arg Pro Ser
1               5
```

<210> SEQ ID NO 306
<211> LENGTH: 11
<212> TYPE: PRT
<213> ORGANISM: Homo sapiens

<400> SEQUENCE: 306

```
Ala Ala Trp Asp Asp Ser Leu Asn Gly Val Val
1               5                   10
```

<210> SEQ ID NO 307
<211> LENGTH: 10
<212> TYPE: PRT
<213> ORGANISM: Homo sapiens

<400> SEQUENCE: 307

```
Gly Ile Thr Phe Ser Asn Ala Trp Met Ser
1               5                   10
```

<210> SEQ ID NO 308
<211> LENGTH: 19
<212> TYPE: PRT
<213> ORGANISM: Homo sapiens

<400> SEQUENCE: 308

```
Arg Ile Lys Ser Lys Thr Asp Gly Thr Thr Asp Tyr Ala Ala Pro
1               5                   10                  15

Val Lys Gly
```

<210> SEQ ID NO 309
<211> LENGTH: 14
<212> TYPE: PRT
<213> ORGANISM: Homo sapiens

<400> SEQUENCE: 309

```
Ser Asp Ser Ser Gly Trp Tyr Gly Tyr Tyr Gly Met Asp Val
1               5                   10
```

<210> SEQ ID NO 310
<211> LENGTH: 330
<212> TYPE: DNA
<213> ORGANISM: Homo sapiens

<400> SEQUENCE: 310

```
cagtctgtgc tgactcagcc accctcagcg tctgggaccc ccgggcagag ggtcaccatc    60
tcttgttttg gaagcagctc caacatcgga agtaattctg taaactggta ccagcagctc   120
ccaggaacgg cccccaaact cctcatcttt agtaatgatc agcggccctc aggggtccct   180
gaccgattct ctgggtccaa gtctggcacc tcagattccc tggccatcag tgggctccag   240
tctgaggatg aagctgatta ttactgtgca gcatgggatg acagcctgaa tggtgtggta   300
ttcggcggag ggaccaagct gaccgtccta                                    330
```

<210> SEQ ID NO 311
<211> LENGTH: 110
<212> TYPE: PRT
<213> ORGANISM: Homo sapiens

<400> SEQUENCE: 311

```
Gln Ser Val Leu Thr Gln Pro Pro Ser Ala Ser Gly Thr Pro Gly Gln
1               5                   10                  15

Arg Val Thr Ile Ser Cys Phe Gly Ser Ser Asn Ile Gly Ser Asn
            20                  25                  30

Ser Val Asn Trp Tyr Gln Gln Leu Pro Gly Thr Ala Pro Lys Leu Leu
            35                  40                  45

Ile Phe Ser Asn Asp Gln Arg Pro Ser Gly Val Pro Asp Arg Phe Ser
    50                  55                  60

Gly Ser Lys Ser Gly Thr Ser Asp Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Asn Gly Val Val Phe Gly Gly Gly Thr Lys Leu Thr Val Leu
                100                 105                 110
```

<210> SEQ ID NO 312
<211> LENGTH: 375
<212> TYPE: DNA
<213> ORGANISM: Homo sapiens

<400> SEQUENCE: 312

```
gaggtgcagc tggtggagtc tgggggaggc ttggtaaagc ctggggggtc ccttagactc    60
tcctgtgcag cctctggatt cactttcagt aatgcctgga tgagctgggt ccgccaggct   120
ccagggaagg ggctggagtg ggttggccgt attaaaagca aaactgatgg tgggacaaca   180
gactacgctg ctcccgtgaa aggcagattc accatctcaa gagatgattc aaaagacacg   240
ctgtatctgc aaatgaacag cctgaaaacc gaggacacag ccgtgtatta ctgtaccaca   300
tctgatagca gcggctggtt cgggtactac ggaatggacg tctggggcca agggaccacg   360
gtcaccgtct cctca                                                    375
```

<210> SEQ ID NO 313
<211> LENGTH: 125
<212> TYPE: PRT
<213> ORGANISM: Homo sapiens

<400> SEQUENCE: 313

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45
```

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asp Thr
 65                  70                  75                  80

Leu Tyr Leu Gln Met Asn Ser Leu Lys Thr Glu Asp Thr Ala Val Tyr
                 85                  90                  95

Tyr Cys Thr Thr Ser Asp Ser Ser Gly Trp Phe Gly Tyr Tyr Gly Met
            100                 105                 110

Asp Val Trp Gly Gln Gly Thr Thr Val Thr Val Ser Ser
            115                 120                 125

<210> SEQ ID NO 314
<211> LENGTH: 13
<212> TYPE: PRT
<213> ORGANISM: Homo sapiens

<400> SEQUENCE: 314

Phe Gly Ser Ser Ser Asn Ile Gly Ser Asn Ser Val Asn
 1               5                   10

<210> SEQ ID NO 315
<211> LENGTH: 7
<212> TYPE: PRT
<213> ORGANISM: Homo sapiens

<400> SEQUENCE: 315

Ser Asn Asp Gln Arg Pro Ser
 1               5

<210> SEQ ID NO 316
<211> LENGTH: 11
<212> TYPE: PRT
<213> ORGANISM: Homo sapiens

<400> SEQUENCE: 316

Ala Ala Trp Asp Asp Ser Leu Asn Gly Val Val
 1               5                   10

<210> SEQ ID NO 317
<211> LENGTH: 10
<212> TYPE: PRT
<213> ORGANISM: Homo sapiens

<400> SEQUENCE: 317

Gly Phe Thr Phe Ser Asn Ala Trp Met Ser
 1               5                   10

<210> SEQ ID NO 318
<211> LENGTH: 19
<212> TYPE: PRT
<213> ORGANISM: Homo sapiens

<400> SEQUENCE: 318

Arg Ile Lys Ser Lys Thr Asp Gly Gly Thr Thr Asp Tyr Ala Ala Pro
 1               5                   10                  15

Val Lys Gly

<210> SEQ ID NO 319
<211> LENGTH: 14
<212> TYPE: PRT
<213> ORGANISM: Homo sapiens

<400> SEQUENCE: 319

Ser Asp Ser Ser Gly Trp Phe Gly Tyr Tyr Gly Met Asp Val
1               5                   10

<210> SEQ ID NO 320
<211> LENGTH: 330
<212> TYPE: DNA
<213> ORGANISM: Homo sapiens

<400> SEQUENCE: 320
cagtctgtgc tgactcagcc accctcaacg tctgggaccc ccgggcagag ggtcaccatc    60
tcttgttttg gaagcaactc caacatcgga agtcaaactg ttaactggta ccagcaactc   120
ccaggaacgg cccccaaact cctcatcttt agtcatcatc accggccctc aggggtccct   180
gaccgattct ctggctccaa gtctggcacc tcagcctccc tggccatcag tgggctccag   240
tctgaggatg aggctgatta ttactgtgca acatgggatg acagcctgaa tggtgtggta   300
ttcggcggag ggaccaaact gaccgtccta                                    330

<210> SEQ ID NO 321
<211> LENGTH: 110
<212> TYPE: PRT
<213> ORGANISM: Homo sapiens

<400> SEQUENCE: 321

Gln Ser Val Leu Thr Gln Pro Pro Ser Thr Ser Gly Thr Pro Gly Gln
1               5                   10                  15

Arg Val Thr Ile Ser Cys Phe Gly Ser Asn Ser Asn Ile Gly Ser Gln
            20                  25                  30

Thr Val Asn Trp Tyr Gln Gln Leu Pro Gly Thr Ala Pro Lys Leu Leu
        35                  40                  45

Ile Phe Ser His His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Val Val Phe Gly Gly Gly Thr Lys Leu Thr Val Leu
            100                 105                 110

<210> SEQ ID NO 322
<211> LENGTH: 375
<212> TYPE: DNA
<213> ORGANISM: Homo sapiens

<400> SEQUENCE: 322
gaggtgcagc tggtggagtc tgggggaggc ttggtaaagc ctggggggtc ccttagactc    60
tcctgtgcag cctctggatt cactttcagt gacgcctgga tgagctgggt ccgccaggct   120
ccagggaagg gactggggtg ggttggccgt attaaaagca aaactgatgg tgggacaaca   180
gacttcgctg cacccgtgaa aggcagattc accatctcaa gagatgattc aaaaaacacg   240
ctgtatctgc aaatgaacag cctgaaaacc gaggacacag ccgtgtatta ctgtacctca   300
tctcatagca gcgcctggta cggctacttc ggtatggacg tctggggcca agggaccacg   360
gtcaccgtct cctca                                                   375

<210> SEQ ID NO 323
<211> LENGTH: 125
<212> TYPE: PRT
<213> ORGANISM: Homo sapiens

<400> SEQUENCE: 323

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Ala
            20                  25                  30
Trp Met Ser Trp Val Arg Gln Ala Pro Gly Lys Gly Leu Gly Trp Val
        35                  40                  45
Gly Arg Ile Lys Ser Lys Thr Asp Gly Gly Thr Thr Asp Phe Ala Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Ser Ser His Ser Ser Ala Trp Tyr Gly Tyr Phe Gly Met
            100                 105                 110
Asp Val Trp Gly Gln Gly Thr Thr Val Thr Val Ser Ser
            115                 120                 125

<210> SEQ ID NO 324
<211> LENGTH: 13
<212> TYPE: PRT
<213> ORGANISM: Homo sapiens

<400> SEQUENCE: 324

Phe Gly Ser Asn Ser Asn Ile Gly Ser Gln Thr Val Asn
1               5                   10

<210> SEQ ID NO 325
<211> LENGTH: 7
<212> TYPE: PRT
<213> ORGANISM: Homo sapiens

<400> SEQUENCE: 325

Ser His His His Arg Pro Ser
1               5

<210> SEQ ID NO 326
<211> LENGTH: 11
<212> TYPE: PRT
<213> ORGANISM: Homo sapiens

<400> SEQUENCE: 326

Ala Thr Trp Asp Asp Ser Leu Asn Gly Val Val
1               5                   10

<210> SEQ ID NO 327
<211> LENGTH: 10
<212> TYPE: PRT
<213> ORGANISM: Homo sapiens

<400> SEQUENCE: 327

Gly Phe Thr Phe Ser Asp Ala Trp Met Ser
1               5                   10

<210> SEQ ID NO 328
<211> LENGTH: 19
<212> TYPE: PRT
<213> ORGANISM: Homo sapiens

<400> SEQUENCE: 328

Arg Ile Lys Ser Lys Thr Asp Gly Gly Thr Thr Asp Phe Ala Ala Pro

```
                   1               5              10              15
Val Lys Gly

<210> SEQ ID NO 329
<211> LENGTH: 14
<212> TYPE: PRT
<213> ORGANISM: Homo sapiens

<400> SEQUENCE: 329

Ser His Ser Ser Ala Trp Tyr Gly Tyr Phe Gly Met Asp Val
1               5                   10
```

HEPCIDIN, HEPCIDIN ANTAGONISTS AND METHODS OF USE

CROSS-REFERENCE TO RELATED APPLICATIONS

The present application claims the benefit of priority of U.S. Provisional Application No. 60/888,059, filed Feb. 2, 2007, and U.S. Provisional Application No. 61/015,138, filed Dec. 19, 2007. Each of the priority applications are incorporated herein by reference in their entireties.

FIELD OF THE INVENTION

The invention relates to hepcidin, hepcidin antagonists (including antibodies that bind hepcidin) and their ability to modulate hepcidin activity.

BACKGROUND

Iron is an essential trace element required for growth and development of all living organisms. Iron content in mammals is regulated by controlling iron absorption, iron recycling, and release of iron from the cells in which it is stored. Iron is absorbed predominantly in the duodenum and upper jejunum by enterocytes. A feedback mechanism exists that enhances iron absorption in individuals who are iron deficient, and that reduces iron absorption in individuals with iron overload (Andrews *Ann. Rev. Genomics Hum. Genet.* 1:75 (2000); Philpott, *Hepatology* 35:993(2002); Beutler et al., *Drug-Metab. Dispos.* 29:495(2001)). Iron is recycled from degraded red cells by reticuloendothelial macrophages in bone marrow, hepatic Kupffer cells and spleen. Iron release is controlled by ferroportin, a major iron export protein located on the cell surface of enterocytes, macrophages and hepatocytes, the main cells capable of releasing iron into plasma. Hepcidin binds to ferroportin and decreases its functional activity by causing it to be internalized from the cell surface and degraded. (Nemeth et al., *Science,* 306:2090-3, 2004; De domenico et al., Mol. Biol. Cell., 8:2569-2578, 2007).

Hepcidin is the key signal regulating iron homeostasis (Philpott, *Hepatology* 35:993 (2002); Nicolas et al., *Proc. Natl. Acad. Sci. USA* 99:4396 (2002)). High levels of human hepcidin result in reduced iron levels, and vice versa. Mutations in the hepcidin gene which result in lack of hepcidin activity are associated with juvenile hemochromatosis, a severe iron overload disease (Roetto et al., Nat. Genet., 33:21-22, 2003). Studies in mice have demonstrated a role of hepcidin in control of normal iron homeostasis (Nicolas et al., Nat. Genet., 34:97-101, 2003; Nicolas et al., Proc. Natl. Acad. Sci. USA, 99:4596-4601, 2002; Nicolas et al., Proc. Natl. Acad. Sci. USA, 98:8780-8785, 2001.).

In addition, data is accumulating implicating hepcidin in iron sequestration during inflammation (See, e.g., Weinstein et al., Blood, 100:3776-36781, 2002; Kemna et al., Blood, 106:1864-1866, 2005; Nicolas et al., J. Clin. Invest., 110:1037-1044, 2002; Nemeth et al., J. Clin. Invest., 113:1271-1276, 2004; Nemeth et al., Blood, 101:2461-2463, 2003 and Rivera et al., Blood, 105:1797-1802, 2005). Hepcidin gene expression has been observed to be robustly upregulated after inflammatory stimuli, such as infections, which induce the acute phase response of the innate immune systems of vertebrates. In mice, hepcidin gene expression was shown to be upregulated by lipopolysaccharide (LPS), turpentine, Freund's complete adjuvant, and adenoviral infections. Hepcidin expression is induced by the inflammatory cytokine interleukin-6 (IL-6). A strong correlation between hepcidin expression and anemia of inflammation was also found in patients with chronic inflammatory diseases, including bacterial, fungal, and viral infections.

Human hepcidin, a 25 amino acid peptide with anti-microbial and iron-regulating activity, was discovered independently by two groups investigating novel anti-microbial peptides. (Krause et al., *FEBS Lett.* 480:147 (2000); Park et al., *J. Biol. Chem.* 276:7806 (2001)). It has also been referred to as LEAP-1 (liver-expressed antimicrobial peptide). A hepcidin cDNA encoding an 83 amino acid pre-propeptide in mice and an 84 amino acid pre-propeptide in rat and human were subsequently identified in a search for liver specific genes that were regulated by iron (Pigeon et al., *J. Biol. Chem.* 276:7811 (2001)). The 24 residue N-terminal signal peptide is first cleaved to produce pro-hepcidin, which is then further processed to produce mature hepcidin, found in both blood and urine. In human urine, the predominant form contains 25 amino acids, although shorter 22 and 20 amino acid peptides are also present.

The mature peptide is notable for containing eight cysteine residues linked as four disulfide bridges. The structure of hepcidin was studied by Hunter et al., *J. Biol. Chem.,* 277:37597-37603 (2002), by NMR using chemically synthesized hepcidin with an identical HPLC retention time to that of native hepcidin purified from urine. Hunter et al. reported their determination that hepcidin folded into a hairpin loop structure containing a vicinal disulfide bond (C1-C8, C2-C7, C3-C6, C4-C5). More recently, determination of the structure of bass hepcidin was also reported, using the structural information of Hunter et al. and inferential NMR data to deduce an identical disulfide connectivity assignment (Lauth et al., *J. Biol. Chem.,* 280:9272-9282 (2005). However, as discovered and disclosed herein by the present inventors, the structure of hepcidin was determined to have a disulfide bond connectivity that is different from that taught by the prior art.

U.S. Patent Publication Nos. 2003/0187228, 2004/0096987, 2004/0096990, 2005/0148025, 2006/0019339, 2005/0037971 and 2007/0224186; U.S. Pat. Nos. 7,232,892 and 7,294,690 and International Publication No. WO 02/98444 discuss hepcidin antibodies but fail to disclose or suggest the structural conformation of hepcidin disclosed herein.

Thus, the specification illustrates the determination of the structure of hepcidin, as well as the central role of hepcidin and its key functions in iron regulation and in the innate immune response to infection. Furthermore, the application provides, inter alia, bioactive hepcidin, monoclonal antibodies to the bioactive hepcidin, methods to produce the same, methods to determine bioactive hepcidin, and methods to modulate hepcidin activity or its expression, and methods for treating disorder of iron homeostasis as well as hepcidin antagonists and hepcidin agonists.

SUMMARY OF THE INVENTION

Various embodiments of the invention generally relate to purified, correctly folded human hepcidin, monoclonal antibodies thereto, hepcidin variants that retain one or more of the disulfide bonds of properly folded human hepcidin, methods for producing such materials, and methods for using such materials to detect hepcidin or to modulate hepcidin activity.

This application is believed to be the first report of bioactive human hepcidin disulfide connectivity in which disulfide bonds are formed between C1-C8, C2-C4, C3-C6 and C5-C7, and which predicts a compact and tightly folded molecule. In some embodiments, the invention provides for large scale production of hepcidin, expressed recombinantly or generated synthetically, which possesses identical disulfide connectivity and equivalent biological activity to native material. Such recombinant or synthetic material is useful for treatment of subjects in need of additional hepcidin, as well as for preparation of known hepcidin standards in detection methods and kits. The production of large batches of correctly-folded human hepcidin also permits the generation and testing of monoclonal antibodies that bind to hepcidin, especially monoclonal antibodies of high affinity and/or specificity. Such monoclonal antibodies are useful, for example, in hepcidin detection methods and in diagnostic and therapeutic methods.

In one aspect, the hepcidin activity antagonist is a monoclonal antibody that binds to mature, correctly-folded, bioactive human hepcidin (SEQ ID NO: 9), with the desired affinity. Also provided is a monoclonal antibody that binds hepcidin (SEQ ID NO: 9) and inhibits the iron-regulating activity of hepcidin. In one embodiment, the monoclonal antibody decreases intracellular iron concentration and/or increases circulating iron concentration at an $EC_{50}$ of about $10^{-8}$ M or less. In other embodiments, the monoclonal antibody exhibits the property in mammals of increasing red blood cell count (number) or hemoglobin or hematocrit levels, and/or normalizing reticulocyte count, reticulocyte mean cell volume and/or reticulocyte hemoglobin content.

In various embodiments, the monoclonal antibody binds to a conformational epitope of hepcidin, the conformational epitope comprising: any one of amino acids 1 through 5 (e.g., amino acid 1, 2, 3, 4 or 5) of SEQ ID NO: 9, and/or any one of amino acids 10 through 13 (e.g., amino acid 10, 11, 12 or 13) of SEQ ID NO: 9, and/or any one of amino acids 14 through 22 (e.g., amino acid 14, 15, 16, 17, 18, 19, 20, 21 or 22) of SEQ ID NO: 9. In a related aspect, the monoclonal antibody binds to a conformational loop comprising the Cys at position 10 and the Cys at position 13 of SEQ ID NO: 9 and/or a conformational loop comprising the Cys at position 14 and the Cys at position 22 of SEQ ID NO: 9.

In various embodiments monoclonal antibodies can include any of antibodies Ab43, 2.7, 2.41, R9, 1C9, 1S1, 1S2, 1S3, 1S4, 1S5, 3B3; 4E1, 7A3, 9D12, 12B9, 15E1, 18D8, 19C1, 19D12, 19H6, 23F11, and 26F11, or antibodies that retain any one, two, three, four, five, or six of CDRH1, CDRH2, CDRH3, CDRL1, CDRL2 or CDRL3 of such antibodies, optionally including one or two mutations in such CDR(s), or antibodies that retain a light or heavy chain variable region of any of such antibodies, or antibodies that bind to the same epitope on human hepcidin as antibodies Ab43, 2.7, 2.41, R9, 1C9, 1S1, 1S2, 1S3, 1S4, 1S5, 3B3; 4E1, 7A3, 9D12, 12B9, 15E1, 18D8, 19C1, 19D12, 19H6, 23F11, and 26F11, or that compete with such antibodies for binding to human hepcidin by at least 75%. Such competitive binding may be assessed by competitive ELISA or by the methods described for evaluating epitope specificity in Example 17 or by other methods described herein or known in the art.

Various embodiments also provide nucleic acids encoding any of the monoclonal antibodies described herein, vectors comprising such nucleic acid sequences, and host cells comprising such nucleic acids or vectors. In a related aspect, methods for recombinant production of such monoclonal antibodies are provided which include culturing the aforementioned host cell such that the nucleic acid is expressed to produce the antibody, and optionally recovering the antibody from the host cell or culture medium. In a related embodiment, an isolated antibody or agent produced by the aforementioned method is provided.

In another aspect, a method is provided of detecting human hepcidin in a sample, comprising contacting a sample from a human with any of the aforementioned antibodies under conditions that allow binding of the antibody to human hepcidin, and detecting the bound antibody. In one embodiment, a first antibody to hepcidin is immobilized on a solid support, as a capture reagent, and a second antibody to hepcidin is used as a detection reagent. In a related aspect, the amount of hepcidin in the sample is quantitated by measuring the amount of the bound antibody. The detection methods can be used in a variety of diagnostic, prognostic and monitoring methods, including methods of diagnosing a hepcidin-related disorder, methods of differentiating an inflammatory disease from a non-inflammatory disease and methods of monitoring therapy with a hepcidin antagonist. In such methods, a level of hepcidin above a certain threshold is correlated with the presence of hepcidin-related disorder, such as hepcidin-related anemia, while a level below said threshold indicates that the patient is unlikely to have hepcidin-related disorder. Similarly, a level of hepcidin above a certain threshold is correlated with the presence of an inflammatory disease, while a level below said threshold indicates that the patient is unlikely to have an inflammatory disease. In some embodiments, such methods will diagnose patients having iron deficiency anemia, anemia of inflammation or mixed anemia. For monitoring of therapy aimed at suppressing hepcidin levels, a level of hepcidin below a certain threshold indicates that the dose of hepcidin antagonist is therapeutically effective, and a level above said threshold indicates that the dose of hepcidin antagonist is not therapeutically effective.

In another aspect, pharmaceutical compositions are provided comprising a therapeutically effective amount of any of the antibodies described herein and a pharmaceutically acceptable carrier, diluent or excipient. Also provided is the use of such antibodies in preparation of a medicament for treatment of a human with an elevated level of hepcidin, a hepcidin-related disorder, a disorder of iron homeostasis or an anemia. It is understood that co-administration methods involving administration of antibodies with a second therapeutic agent, as described herein, encompass not only the use of the antibody in preparation of a medicament for co-administration with the second therapeutic agent, but also the use of the second therapeutic agent in preparation of a medicament for co-administration with the antibody.

Various embodiments further provide methods of using such antibodies, for example, to treat a mammal with an elevated level of hepcidin, or a hepcidin-related disorder, or a disorder of iron homeostasis, or a mammal with anemia, by administering a therapeutically effective amount of such antibody. In exemplary embodiments, the mammal is a human suffering from a condition selected from the group consisting of African iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pyelori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

In yet another aspect, methods are provided for treating a mammal with anemia by administration of (a) a hepcidin activity antagonist or a hepcidin expression inhibitor and (b) an erythropoiesis stimulator, in therapeutically effective amounts. Exemplary hepcidin activity antagonists include antibodies that bind human hepcidin. Exemplary hepcidin expression inhibitors include polynucleotides or oligonucleotides that bind a human hepcidin nucleic acid. Exemplary erythropoiesis stimulators include erythropoietin, erythropoietin agonist variants, and peptides or antibodies that bind and activate erythropoietin receptor. Erythropoiesis stimulators include, but are not limited to, epoetin alfa, epoetin beta, epoetin delta, epoetin omega, epoetin iota, epoetin zeta, and analogs thereof, mimetic peptides, mimetic antibodies and HIF inhibitors (see U.S. Patent Publication No. 2005/0020487, the disclosure of which is incorporated by reference in its entirety). In particular, erythropoietin includes, but is not limited to, erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,955,422 and 5,856,298; and WO 91/05867; WO 95/05465; WO 00/24893 and WO 01/81405. In certain exemplary embodiments, the erythropoiesis stimulator is selected from the group consisting of human erythropoietin (SEQ ID NO: 72) and darbepoetin alfa (SEQ ID NO: 73). Exemplary forms of anemia that may be treated according to such methods include anemia of inflammation, anemia of cancer, chemotherapy induced anemia, iron deficiency anemia, a disorder of iron homeostasis, ferroportin disease, or anemia resulting from kidney disease. Also provided are methods of treating a mammal with anemia that is hypo-responsive, or even resistant, to therapy with an erythropoiesis stimulator, comprising administering a therapeutically effective amount of a hepcidin activity antagonist, or alternatively a therapeutically effective amount of a hepcidin expression inhibitor.

In another related aspect, kits for treating a disorder associated with elevated hepcidin levels, or a hepcidin-related disorder, or a disorder of iron homeostasis, or a mammal with anemia, are also provided. In one exemplary embodiment, the kit includes (a) a hepcidin activity antagonist or a hepcidin expression inhibitor, and (b) an erythropoiesis stimulator, and optionally, iron. In another exemplary embodiment, the kit includes a hepcidin activity antagonist, or a hepcidin expression inhibitor, and a label attached to or packaged with the container, the label describing use of the hepcidin activity antagonist, or the hepcidin expression inhibitor, with an erythropoiesis stimulator. In yet another exemplary embodiment, the kit includes an erythropoiesis stimulator and a label attached to or packaged with the container, the label describing use of the erythropoiesis stimulator with a hepcidin activity antagonist, or a hepcidin expression inhibitor. Also provided is the use of a hepcidin activity antagonist or a hepcidin expression inhibitor in preparation of a medicament for administration with an erythropoiesis stimulator, as well as use of an erythropoiesis stimulator in preparation of a medicament for administration with a hepcidin activity antagonist or a hepcidin expression inhibitor. In any of these kits or uses, the hepcidin activity antagonist (or hepcidin expression inhibitor) and the erythropoiesis stimulator can be in separate vials or can be combined together in a single pharmaceutical composition. In yet another embodiment, the hepcidin activity antagonist (or hepcidin expression inhibitor) or the erythropoiesis stimulator, or both, can be combined with iron in a single pharmaceutical composition or can be in separate vials.

In a different aspect, a composition of purified, bioactive, correctly-folded, non-urinary human hepcidin is provided comprising SEQ ID NO: 96 wherein at least 80%, 85%, 90%, 95%, 98% or 99% of the human hepcidin in the composition has a C2-C4 disulfide bond, a C5-C7 disulfide bond, a C1-C8 disulfide bond, and a C3-C6 disulfide bond. In some embodiments, the human hepcidin has been chemically synthesized or produced in bacteria or other non-mammalian cells. The amount of a properly folded protein in a solution can be quantitated by methods known in the art (including heteronuclear single quantum correlation (HSQC), Morita et al., Protein Science, 12(6), 1216-1221 (2003)). In a related embodiment, methods of using such purified human hepcidin compositions are provided, for example, to generate or screen for monoclonal antibodies, to identify a hepcidin binding partner, or to test a composition comprising an antibody or specific binding agent for ability to bind human hepcidin. Generation of antibodies involves, e.g., contacting an immunoglobulin producing cell with the purified human hepcidin composition and isolating an immunoglobulin produced by said cell. Screening for antibodies or specific binding agents generally involve, for example, contacting a candidate hepcidin binding partner with the purified human hepcidin composition and detecting a complex formed between the candidate hepcidin binding partner and human hepcidin in the composition. In another related embodiment, the method further comprises administering the candidate hepcidin binding partner to a mammal. Testing an antibody or specific binding agent for ability to bind human hepcidin involves, e.g., contacting it with the purified human hepcidin composition or fragment thereof retaining proper folding, and detecting a complex formed between the human hepcidin and the antibody or specific binding agent.

In a related aspect, a method of refolding a human hepcidin polypeptide is provided comprising SEQ ID NO: 96 to a correctly-folded, bioactive form comprising (a) exposing a human hepcidin polypeptide to a chaotropic agent under conditions that promote denaturing, and (b) exposing the product of (a) to an oxidizing agent under conditions that promote renaturing into a properly folded and bioactive form, and (c) recovering a solution comprising the bioactive human hepcidin polypeptide, wherein at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% or more of the human hepcidin polypeptide has a C2-C4 disulfide-bond and a C5-C7 disulfide-bond. The amount of a properly folded protein in a solution can be quantitated by methods known in the art (including heteronuclear single quantum correlation (HSQC), Morita et al., Protein Science, 12(6), 1216-1221 (2003). In one embodiment, the correctly-folded bioactive hepcidin has an $EC_{50}$ of <100 nM in a cell-based assay. In another embodiment, the correctly-folded bioactive hepcidin has an $EC_{50}$ of <30 nM in a cell-based assay. In a related embodiment, (b) further comprises contacting the human hepcidin polypeptide with an oxidizing agent other than air. In another embodiment, the oxidizing takes place at a pH of greater than 8 and in a solution containing less than 0.1% acetic acid.

In a different aspect, a variant of human hepcidin is provided that retains the same or similar disulfide connectivity, and/or the same or similar predicted three-dimensional structure. In exemplary embodiments, the variant retains all eight cysteine residues and further retains the C2-C4 disulfide bond and/or the C5-C7 disulfide bond. Such variants may exhibit agonist or antagonist activity, i.e. retain or inhibit hepcidin biological activity (anti-microbial or iron-regulating activity). In exemplary embodiments, a hepcidin analog peptide is provided that comprises an amino acid sequence at least 70%, at least 75%, at least 80%, at least 85%, at least 90%, at least 95%, at least 96%, at least 97%, at least 98%, or at least 99% identical over its length to SEQ ID NO: 96. Hepcidin variants may exhibit one or more of the following: retains ferroportin-binding activity (i.e., activates ferroportin or inhibits ferroportin iron transport), promotes or inhibits iron-regulating activity of mature human hepcidin (SEQ ID NO: 9) and/or decreases or increases circulating iron levels in vivo.

In another aspect, an antibody that detects purified mature human hepcidin of SEQ ID NO: 9 as a principal band having an approximate molecular weight of less than 6 kd (e.g., 3 kd±2) as determined by a sodium dodecyl sulfate polyacrylamide gel electrophoresis (SDS-PAGE) under reducing conditions is provided.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention can include, as an additional aspect, all embodiments of the invention narrower in scope in any way than the variations defined by specific paragraphs herein. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It should also be understood that when describing a range of values, the characteristic being described could be an individual value found within the range. For example, "a pH from about pH 4 to about pH 6," could be, but is not limited to, pH 4, 4.2, 4.6, 5.1 5.5 etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH. In some embodiments, when the term "about" is used, it means the recited number plus or minus 5%, 10%, 15% or more of that recited number. The actual variation intended is determinable from the context. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 3A shows HPLC analysis of partially reduced and alkylated hepcidin at pH2.

FIG. 3B shows HPLC analysis of partially reduced and alkylated hepcidin at pH3.

FIG. 16 shows that neutralization of hepcidin by anti-hepcidin antibody treatment restores responsiveness to erythropoietin in human hepcidin knock-in mice with anemia of inflammation.

FIGS. 24A-B show that hepcidin levels are related to inflammatory status as assessed by C-reactive protein (A), and prohepcidin levels are not (B).

FIGS. 26A-B demonstrate that hepcidin levels correlate with diagnosis of inflammatory anemia (A), and prohepcidin levels do not (B).

FIG. 33 comparison of hepcidin levels detected in random human donors measured using the sandwich ELISA, competitive ELISA and mass spectrometric techniques.

DETAILED DESCRIPTION OF THE INVENTION

Figure 1:
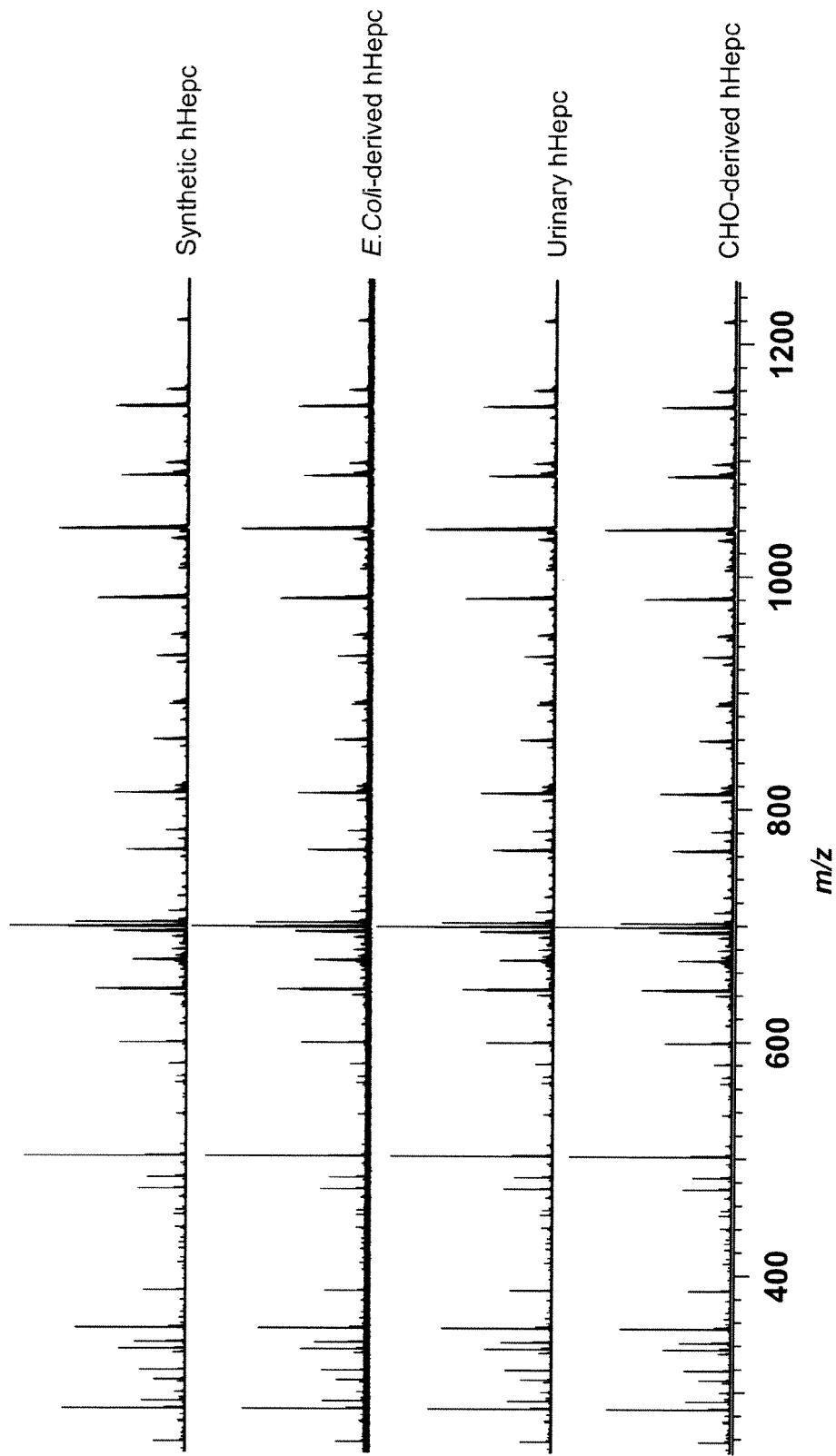
FIG. 1 shows an IRMPD FTMS spectra of all four preparations of human hepcidin demonstrating equivalence of all three synthetic and recombinant preparations to urinary hepcidin.

The human hepcidin gene encodes an 84 residue pre-propeptide (SEQ ID NO: 8). The corresponding cDNA and genomic sequences are set forth in SEQ ID NOs: 7 and 100, respectively. The 24-residue N-terminal signal peptide (residues 1-24 of SEQ ID NO: 8) is first cleaved to produce pro-hepcidin, which is then further processed by cleavage of the prodomain (residues 25-59 of SEQ ID NO: 8) to produce the 25-residue mature hepcidin (residues 60-84 of SEQ ID NO: 8, set forth in SEQ ID NO: 9). In addition to the primary 25 amino acid form, further N-terminally truncated forms that are 20 or 22 amino acids in length can be identified in urine (20 amino acids, SEQ ID NO: 96; and 22 amino acids, SEQ ID NO: 98). Mature human hepcidin contains eight cysteine residues, which are referred to herein sequentially as C1 through C8 (numbered from the N-terminus to the C-terminus).

The novel disulfide connectivity reported herein and the corresponding modeled three-dimensional structure of hepcidin also permits the production of hepcidin variants that retain the same or similar disulfide connectivity and that are useful as modulators of hepcidin biological activity. For example, molecules that bind to and activate hepcidin receptor, molecules that bind to and cause internalization of ferroportin, or molecules that act as competitive inhibitors relative to hepcidin can be designed and produced.

I. Purified, Correctly-Folded Human Hepcidin Compositions

Hepcidin polypeptides may need to be "refolded" and oxidized into a proper tertiary structure and generating disulfide linkages in order to be biologically active. Refolding can be accomplished using the procedures described herein and others well known in the art. Such methods include, for example, exposing the solubilized polypeptide agent to a pH usually above 7 in the presence of a chaotropic agent. A chaotropic agent is a compound, including, without limitation, guanidine hydrochloride (guanidinium hydrochloride, GdnHCl), guanidine sulfate, urea, sodium thiocyanate, sarcosyl, sodium dodecyl sulfate, sodium octyl sulfate and/or other compounds which disrupt the noncovalent intermolecular bonding within the protein, permitting the polypeptide chain to assume a substantially random conformation.

In most cases, the refolding/oxidation solution will also contain a reducing agent plus its oxidized form in a specific ratio to generate a particular redox potential which allows for disulfide shuffling to occur for the formation of cysteine bridges. A reducing agent is capable of transferring electrons and, in so doing, "reducing" bonds between various atoms. In the context of various embodiments of the invention, a reducing agent will disrupt intra- and intermolecular interactions, in particular, those involving disulfide bridges. Exemplary reducing agents, according to the various embodiments of the invention include diothiothreitol, glutathione, dithioerythritol, or β-mercaptoethanol. Some commonly used redox couples include cysteine/cystamine, glutathione/dithio-bisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

Once refolded, the disulfide connectivity of a hepcidin polypeptide can be assessed by a variety of techniques known in the art. In one aspect, the technique is NEM partial reductive alkylation; in another it is Fourier transform mass spectrometry (FT-MS). NEM partial reductive alkylation and FT-MS are discussed in more detail in Examples 1 and 4.

FT-MS (Fourier transform mass spectrometry) can be used to assess disulfide connectivity. As known in the art, FT-MS is based on the principle of a charged particle orbiting in a strong, stable magnetic field. By detecting the current generated by the orbiting ions, a Fourier transform may be used to determine the m/z of the ions. Advantageously, this procedure allows for very high mass resolution and the ability to perform convenient tandem mass spectroscopy experiments. Together, this allows for the unequivocal assignment of the proteolytic fragments under analysis. (See, e.g., Marshall et al., Mass Spectrometry Reviews, 17:1-35, 1998; Lewis et al., Proc Natl Acad Sci USA., 95:8596-601, 1998; Li et al., Anal Chem, 66:2077-83, 1994) FT-MS is discussed in more detail in Examples 1 and 4.

The amount of a properly folded protein in a solution can be quantitated by methods known in the art (including heteronuclear single quantum correlation (HSQC), Morita et al., Protein Science, 12(6), 1216-1221 (2003)). A misfolded protein such as hepcidin will have unique cross-peaks in an HSQC spectrum. By integrating these peaks, in principle, the percentage of misfolding is quantitated.

II. Hepcidin Antagonists

Various embodiments of the invention provide for the production and the use of two different categories of hepcidin antagonists: (a) hepcidin activity antagonists or (b) hepcidin expression inhibitors.

As used herein, "hepcidin activity antagonist" means a substance that inhibits human hepcidin's iron-regulating activity but that does not inhibit expression of the hepcidin gene or hepcidin mRNA.

As used herein, "hepcidin expression inhibitor" means a substance that inhibits expression of hepcidin gene or hepcidin mRNA.

Hepcidin activity antagonists and hepcidin expression inhibitors are mutually exclusive categories, although both fall under a general category of "hepcidin antagonist."

In one aspect, the hepcidin activity antagonist can be a substance that inhibits the function of hepcidin, for example, by inhibiting binding between hepcidin and ferroportin, by inhibiting hepcidin-controlled cellular iron retention, or by facilitating ferroportin dependent iron transport. Hepcidin activity antagonists in this category include antibodies or peptide-based specific binding agents that bind hepcidin and inhibit its activity, including any of the antibodies described herein; hepcidin variants and derivatives thereof that bind to ferroportin but do not activate ferroportin iron transport; and small organic chemical compounds, optionally of less than about 1000 Daltons in molecular weight that bind hepcidin and inhibits its activity.

Hepcidin expression inhibitors include polynucleotides or oligonucleotides that bind to hepcidin DNA or mRNA and inhibit hepcidin expression, including antisense oligonucleotides, inhibitory RNA, DNA enzyme, ribozyme, an aptamer or pharmaceutically acceptable salts thereof that inhibit the expression of hepcidin.

A. Anti-Hepcidin Antibodies and Specific Binding Agents

Various embodiments of the invention provide antibodies, including monoclonal antibodies, that bind human hepcidin, methods of producing such antibodies, methods of using such antibodies for detecting hepcidin, pharmaceutical formulations including such antibodies, methods of preparing the pharmaceutical formulations, and methods of treating patients with the pharmaceutical formulations, including combination therapy with erythropoiesis stimulators as described below. Nucleic acids encoding such antibodies, vectors and recombinant host cells comprising such nucleic acids, and methods of producing such antibodies are also provided.

The term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)$_2$, Fv, single chain antibodies, diabodies), and recombinant peptides comprising the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

In some embodiments, the antibodies exhibit desirable characteristics such as binding affinity as measured by $K_D$ (equilibrium dissociation constant) for hepcidin in the range of $1 \times 10^{-6}$ M or less, or ranging down to $10^{-16}$ M or lower, (e.g., about $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ M or less). The equilibrium dissociation constant can be determined in solution equilibrium assay using BIAcore and/or KinExA, such as described in. Examples 13 and 14.

In other embodiments, the antibodies exhibit specificity for hepcidin. As used herein, an antibody is "specific for" human hepcidin when it has a significantly higher binding affinity for, and consequently is capable of distinguishing, human hepcidin compared to other unrelated proteins in different families. In some embodiments, such antibodies may also cross-react with hepcidin of other species, such as murine, rat, or primate hepcidin; while in other embodiments, the antibodies bind only to human or primate hepcidin and not significantly to rodent hepcidin. In exemplary embodiments, antibodies bind to human and cynomologous monkey hepcidin but not significantly to rodent hepcidin. In some embodiments, antibodies specific for hepcidin cross-react with other proteins in the same family, while in other embodiments, the antibodies distinguish hepcidin from other related family members, including defensins or mouse hepc2.

In yet other embodiments, the monoclonal antibodies inhibit (or neutralize) hepcidin iron-regulating activity, in vitro and preferably also in vivo. Such hepcidin-neutralizing antibodies are therapeutically useful for hepcidin-related disorders or disorders of iron homeostasis. Hepcidin neutralizing activity can be measured through a number of markers, for example, ferritin/iron levels, red blood cell count, red blood cell characteristics (hemoglobin content and/or cell volume), early red blood cell characteristics (reticulocyte numbers, hemoglobin content or cell volume) (Clinical Hematology, third edition, Lippincott, Williams and Wilkins; editor Mary L. Turgeon, 1999) ferroportin internalization, or iron transport. In an exemplary embodiment, the monoclonal antibody decreases intracellular iron concentration at an $EC_{50}$ of about $10^{-8}$ M or less and/or increases circulating iron concentration.

In some embodiments, a monoclonal antibody as described herein antagonizes the effect of human hepcidin or inhibits hepcidin iron-regulating activity. In some embodiments, a monoclonal antibody as described herein exerts an effect at an $EC_{50}$ of about $1 \times 10^{-8}$ M or less, or about $1 \times 10^{-7}$ M or less. For example, an antibody may decrease the intracellular iron level in a cell at an $EC_{50}$ of about $1 \times 10^{-8}$ M or less, or may reduce ferritin expression at an $EC_{50}$ of about $1 \times 10^{-8}$ M or less, as determined by a ferritin assay. In other embodiments, a monoclonal antibody as described herein may reduce free serum hepcidin levels by at least about 20%, by at least about 30%, by at least about 40%, by at least about 50%, by at least about 60%, by at least about 70%, by at least about 80%, or by at least about 90%. In other embodiments, a monoclonal antibody as described herein may increase red blood cell count (number), red blood cell mean cell volume or red blood cell hemoglobin content, increase hemoglobin, increase hematocrit, increase Tsat, increase circulating (or serum) iron levels, and/or increase or normalize reticulocyte count, reticulocyte mean cell volume, reticulocyte hemoglobin content or reticulocyte numbers.

In specific exemplary embodiments, the invention contemplates:

1) a monoclonal antibody that retains any one, two, three, four, five, or six of CDRH1, CDRH2, CDRH3, CDRL1, CDRL2 or CDRL3 of any of antibody Ab43, 2.7, 2.41, R9, 1C9; 1S1, 1S2, 1S3, 1S4, 1S5, 3B3; 4E1, 7A3, 9D12, 12B9, 15E1, 18D8, 19C1, 19D12, 19H6, 23F11, and 26F11, optionally including one or two mutations in such CDR(s), 2) a monoclonal antibody that retains all of CDRH1, CDRH2, CDRH3, or the heavy chain variable region of any of antibody Ab43, 2.7, 2.41, R9, 1C9; 1S1, 1S2, 1S3, 1S4, 1S5, 3B3; 4E1, 7A3, 9D12, 12B9, 15E1, 18D8, 19C1, 19D12, 19H6, 23F11, and 26F11, optionally including one or two mutations in such CDR(s), 3) a monoclonal antibody that retains all of CDRL1, CDRL2, CDRL3, or the light chain variable region of any of antibody Ab43, 2.7, 2.41, R9, 1C9; 1S1, 1S2, 1S3, 1S4, 1S5, 3B3; 4E1, 7A3, 9D12, 12B9, 15E1, 18D8, 19C1, 19D12, 19H6, 23F11, and 26F11, optionally including one or two mutations in such CDR(s), 4) a monoclonal antibody that binds to the same epitope of mature human hepcidin as antibody Ab43, 2.7, 2.41, R9, 1C9; 1S1, 1S2, 1S3, 1S4, 1S5, 3B3; 4E1, 7A3, 9D12, 12B9, 15E1, 18D8, 19C1, 19D12, 19H6, 23F11, and 26F11, e.g. as determined through X-ray crystallography, or a conformational epitope comprising an amino acid within amino acids 1-5 of SEQ ID NO: 9 and/or an amino acid within a loop formed by amino acids 10-13 of SEQ ID NO: 9 and/or an amino acid within a loop formed by amino acids 14-22 of SEQ ID NO: 9; and 5) a monoclonal antibody that competes with antibody Ab43, 2.7, 2.41, R9, 1C9; 1S1, 1S2, 1S3, 1S4, 1S5, 3B3; 4E1, 7A3, 9D12, 12B9, 15E1, 18D8, 19C1, 19D12, 19H6, 23F11, and 26F11 for binding to mature human hepcidin by more than about 75%, more than about 80%, or more than about 81%, 82%, 83%, 84%, 85%, 86%, 87%, 88%, 89%, 90%, 91%, 92%, 93%, 94% or 95%.

In one embodiment, the antibody comprises at least one, two, three, four, five or all of the amino acid sequences selected from the group consisting of SEQ ID NOs: 16-21. In another embodiment, the antibody comprises at least one, two, three, four, five or all of the amino acid sequences selected from the group consisting of SEQ ID NOs: 28-33 (2.7 CDRs). In another embodiment, the antibody comprises at least one, two, three, four, five or all of the amino acid sequences selected from the group consisting of SEQ ID NOs: 40-45 (2.41 CDRs). In yet another embodiment, the antibody comprises at least one, two, three, four, five or all of the amino acid sequences selected from the group consisting of SEQ ID NOs: 52-57 (R9 CDRs). In another embodiment, the antibody comprises at least one, two, three, four, five or all of the amino acid sequences selected from the group consisting of SEQ ID NOs: 111-116 (1C9 CDRs). In another embodiment, the antibody comprises at least one, two, three, four, five or all of the amino acid sequences selected from the group consisting of SEQ ID NOs: 121-126 (3B3 CDRs). In yet another embodiment, the antibody comprises at least one, two, three, four, five or all of the amino acid sequences selected from the group consisting of SEQ ID NOs: 131-136 (4E1 CDRs). In another embodiment, the antibody comprises at least one, two, three, four, five or all of the amino acid sequences selected from the group consisting of SEQ ID NOs: 141-146 (7A3 CDRs). In another embodiment, the antibody comprises at least one, two, three, four, five or all of the amino acid sequences selected from the group consisting of SEQ ID NOs: 151-156 (9D12 CDRs). In another embodiment, the antibody comprises at least one, two, three, four, five or all of the amino acid sequences selected from the group consisting of SEQ ID NOs: 161-166 (12B9 CDRs). In yet another embodiment, the antibody comprises at least one, two, three, four, five or all of the amino acid sequences selected from the group consisting of SEQ ID NOs: 171-176 (15E1 CDRs). In another embodiment, the antibody comprises at least one, two, three, four, five or all of the amino acid sequences selected from the group consisting of SEQ ID NOs: 314-319 (18D8 CDRs). In another embodiment, the antibody comprises at least one, two, three, four, five or all of the amino acid sequences selected from the group consisting of SEQ ID NOs: 324-329 (19C1 CDRs). In yet another embodiment, the antibody comprises at least one, two, three, four, five or all of the amino acid sequences selected from the group consisting of SEQ ID NOs: 294-299 (19D12 CDRs). In another embodiment, the antibody comprises at least one, two, three, four, five or all of the amino acid sequences selected from the group consisting of SEQ ID NOs: 304-309 (19H6 CDRs). In yet another embodiment, the antibody comprises at least one, two, three, four, five or all of the amino acid sequences selected from the group consisting of SEQ ID NOs: 181-186 (23F11 CDRs). In another embodiment, the antibody comprises at least one, two, three, four, five or all of the amino acid sequences selected from the group consisting of SEQ ID NOs: 191-196 (26F11 CDRs). In another embodiment, the antibody comprises at least one, two, three, four, five or all of the amino acid sequences selected from the group consisting of SEQ ID NOs: 203-205 and 131-133 (1S1 CDRs). In another embodiment, the antibody comprises at least one, two, three, four, five or all of the amino acid sequences selected from the group consisting of SEQ ID NOs: 214-216 and 144-146 (1S2 CDRs). In yet another embodiment, the antibody comprises at least one, two, three, four, five or all of the amino acid sequences selected from the group consisting of SEQ ID NOs: 225-227 and 164-166 (1S3 CDRs). In another embodiment, the antibody comprises at least one, two, three, four, five or all of the amino acid sequences selected from the group consisting of SEQ ID NOs: 236-238 and 174-176 (1S4 CDRs). In another embodiment, the antibody comprises at least one, two, three, four, five or all of the amino acid sequences selected from the group consisting of SEQ ID NOs: 247-249 and 184-186 (1S5 CDRs).

In some embodiments, the antibody comprises all three light chain CDRs, all three heavy chain CDRs, or all six CDRs. In some exemplary embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous.

Consensus CDRs may also be used. In an exemplary embodiment, the antibody comprises one or more of the amino acid sequences set forth in SEQ ID NO: 74 (XASNLES), SEQ ID NO: 75 (XQSNEE) and SEQ ID NO: 76

(QQXNEX), SEQ ID NO: 28 (RASESVDSYGNSFMH), SEQ ID NO: 77 (WINTXSGVPTYADDFXG), SEQ ID NO: 78 (XXYYGX*A*Y), SEQ ID NO: 19 (TYGMS), SEQ ID NO: 284 (VIXYXXSNKYYADSVKG), SEQ ID NO: 285 (WIXAXNGXXXXAXXXQX), SEQ ID NO: 286 (AQEGXAPDAFDI), SEQ ID NO: 287 (QAWYSSTNVX), SEQ ID NO: 288 (QAWDSSTAXX), SEQ ID NO: 289 (QS-DYSSXXX**), wherein X is any amino acid and * can be absent or any amino acid.

In yet another exemplary embodiment, the antibody comprises the light and/or heavy chain variable region of an antibody, e.g., SEQ ID NO: 15 (Ab43 heavy chain variable region), and/or SEQ ID NO: 13 (Ab43 light chain variable region); SEQ ID NO: 27 (2.7 heavy chain variable region), and/or SEQ ID NO: 25 (2.7 light chain variable region); SEQ ID NO: 39 (2.41 heavy chain variable region), and/or SEQ ID NO: 37 (2.41 light chain variable region); or SEQ ID NO: 51 (R9 heavy chain variable region), and/or SEQ ID NO: 49 (R9 light chain variable region), SEQ ID NO: 110 (1C9 heavy chain variable region) and/or SEQ ID NO: 108 (1C9 light chain variable region); or SEQ ID NO: 120 (3B3 heavy chain variable region) and/or SEQ ID NO: 118 (3B3 light chain variable region); SEQ ID NO: 130 (4E1 heavy chain variable region) and/or SEQ ID NO: 128 (4E1 light chain variable region); or SEQ ID NO: 140 (7A3 heavy chain variable region) and/or SEQ ID NO:138 (7A3 light chain variable region); or SEQ ID NO: 150 (9D12 heavy chain variable region) and/or SEQ ID NO: 148 (9D12 light chain variable region); SEQ ID NO: 160 (12B9 heavy chain variable region), and/or SEQ ID NO: 158 (12B9 light chain variable region); SEQ ID NO: 170 (15E1 heavy chain variable region) and/or SEQ ID NO: 168 (15E1 light chain variable region); SEQ ID NO: 313 (18D8 heavy chain variable region) and/or SEQ ID NO: 311 (18D8 light chain variable region); SEQ ID NO: 323 (19C1 heavy chain variable region) and/or SEQ ID NO: 321 (19C1 light chain variable region); SEQ ID NO: 293 (19D12 heavy chain variable region) and/or SEQ ID NO: 291 (19D12 light chain variable region); SEQ ID NO: 303 (19H6 heavy chain variable region) and/or SEQ ID NO: 301 (19H6 light chain variable region); SEQ ID NO: 180 (23F11 heavy chain variable region) and/or SEQ ID NO: 178 (23F11 light chain variable region); SEQ ID NO: 190 (26F11 heavy chain variable region) and/or SEQ ID NO: 188 (26F11 light chain variable region); or SEQ ID NO: 202 (1S1 heavy chain variable region) and/or SEQ ID NO: 128 (1S1 light chain variable region); SEQ ID NO: 213 (1S2 light chain variable region) and/or SEQ ID NO: 140 (1S2 heavy chain variable region); SEQ ID NO: 224 (1S3 light chain variable region) and/or SEQ ID NO: 160 (1S3 heavy chain variable region); SEQ ID NO: 235 (1S4 light chain variable region) and/or SEQ ID NO: 170 (1S4 heavy chain variable region; or SEQ ID NO: 246 (1S5 light chain variable region) and/or SEQ ID NO: 190 (1S5 heavy chain variable region.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to an amino acid sequence selected from the group consisting of SEQ ID NOs: 15 (Ab43 heavy chain variable region), 27 (2.7 heavy chain variable region), 39 (2.41 heavy chain variable region), 51 (R9 heavy chain variable region), 110 (1C9 heavy chain variable region), 120 (3B3 heavy chain variable region), 130 (4E1 heavy chain variable region), 140 (7A3 heavy chain variable region), 150 (9D12 heavy chain variable region), 160 (12B9 heavy chain variable region), 170 (15E1 heavy chain variable region), 313 (18D8 heavy chain variable region), 323 (19C1 heavy chain variable region), 293 (19D12 heavy chain variable region), 303 (19H6 heavy chain variable region), 180 (23F11 heavy chain variable region), 190 (26F11 heavy chain variable region), 202 (1S1 heavy chain variable region), 13 (Ab43 light chain variable region), 25 (2.7 light chain variable region), 37 (2.41 light chain variable region), 49 (R9 light chain variable region), 108 (1C9 light chain variable region), 118 (3B3 light chain variable region), 128 (4E1 light chain variable region), 138 (7A3 light chain variable region), 148 (9D12 light chain variable region), 158 (12B9 light chain variable region), 168 (15E1 light chain variable region), 311 (18D8 light chain variable region), 321 (19C1 light chain variable region), 291 (19D12 light chain variable region), 301 (19H6 light chain variable region), 178 (23F11 light chain variable region), 188 (26F11 light chain variable region), 213 (1S2 light chain variable region), 224 (1S3 light chain variable region), 235 (1S4 light chain variable region), and 246 (1S5 light chain variable region) the polypeptide further comprising at least one or more of the amino acid sequences set forth in SEQ ID NOs: 16-21 (Ab43 CDRs), 28-33 (2.7 CDRs), 40-45 (2.41 CDRs), 52-57 (R9 CDRs), 111-116 (1C9 CDRs), 121-126 (3B3 CDRs), 131-136 (4E1 CDRs), 141-146 (7A3 CDRs), 151-156 (9D12 CDRs), 161-166 (12B9 CDRs), 171-176 (15E1 CDRs), 314-319 (18D8 CDRs), 324-329 (19C1 CDRs), 294-299 (19D12 CDRs), 304-309 (19H6 CDRs), 181-186 (23F11 CDRs), 191-196 (26F11 CDRs), 203-205 and 131-133 (1S1 heavy chain CDRs), 214-216 and 144-146 (1S2 light chain CDRs), 225-227 and 164-166 (1S3 light chain CDRs), 236-238 and 174-176 (1S4 light chain CDRs) and 247-249 and 184-186 (1S5 light chain CDRs). In any of the foregoing embodiments, the polypeptide includes a sequence comprising one or two modifications to any of the amino acid sequences set forth in SEQ ID NOs: 16-21 (Ab43 CDRs), 28-33 (2.7 CDRs), 40-45 (2.41 CDRs), 52-57 (R9 CDRs), 111-116 (1C9 CDRs), 121-126 (3B3 CDRs), 131-136 (4E1 CDRs), 141-146 (7A3 CDRs), 151-156 (9D12 CDRs), 161-166 (12B9 CDRs), 171-176 (15E1 CDRs), 314-319 (18D8 CDRs), 324-329 (19C1 CDRs), 294-299 (19D12 CDRs), 304-309 (19H6 CDRs), 181-186 (23F11 CDRs), 191-196 (26F11 CDRs), 203-205 and 131-133 (1S1 heavy chain CDRs), 214-216 and 144-146 (1S2 light chain CDRs), 225-227 and 164-166 (1S3 light chain CDRs), 236-238 and 174-176 (1S4 light chain CDRs) and 247-249 and 184-186 (1S5 light chain CDRs).

The cDNA and amino acid sequences for the full length light and heavy chains of each of antibodies 1C9, 3B3, 4E1, 7A3, 9D12, 12B9, 15E1, 23F11 and 26F11 are also provided. The cDNA sequences encoding the full length light chain of antibodies 1C9, 3B3, 4E1, 7A3, 9D12, 12B9, 15E1, 23F11, 26F11, 1S2, 1S3, 1S4 and 1S5, including the constant region, are set forth in SEQ ID NOs: 197, 208, 219, 230, 241, 252, 256, 260, 264, 217, 228, 239 and 250, respectively. The amino acid sequences of the full length light chain of antibodies 1C9, 3B3, 4E1, 7A3, 9D12, 12B9, 15E1, 23F11, 26F11, 1S2, 1S3, 1S4 and 1S5, including the constant region, are set forth in SEQ ID NOs: 198 (of which residues 1-20 correspond to the signal peptide and the remainder is the mature polypeptide), 209 (of which residues 1-19 correspond to the signal peptide and the remainder is the mature polypeptide), 220 (of which residues 1-20 correspond to the signal peptide and the remainder is the mature polypeptide), 231 (of which residues 1-20 correspond to the signal peptide and the remainder is the mature polypeptide), 242 (of which residues 1-19 correspond to the signal peptide and the remainder is the mature polypeptide), 253 (of which residues 1-20 correspond to the signal peptide and the remainder is the mature polypeptide), 257 (of which residues 1-20 correspond to the signal peptide and the remainder is the mature polypeptide), 261 (of which residues 1-19 correspond to the signal peptide and the remainder is the mature polypeptide), 265 (of which residues 1-19 correspond to the signal peptide and the remainder is the mature polypeptide), 218 (of which residues 1-22 correspond to the signal peptide and the remainder is the mature polypeptide), 229 (of which residues 1-22 correspond to the signal peptide and the remainder is the mature polypeptide), 240 (of which residues 1-22 correspond to the signal peptide and the remainder is the mature polypeptide) and 251 (of which residues 1-22 correspond to the signal peptide and the remainder is the mature polypeptide), respectively.

The cDNA sequences encoding the full length heavy chain of antibodies 1C9, 3B3, 4E1, 7A3, 9D12, 12B9, 15E1, 23F11, 26F11 and 1S1, including the constant region, are set forth in SEQ ID NOs: 199, 210, 221, 232, 243, 254, 258, 262, 266 and 206, respectively. The amino acid sequences of the full length heavy chain of antibodies 1C9, 3B3, 4E1, 7A3, 9D12, 12B9, 15E1, 23F11, 26F11 and 1S1, including the constant region, are set forth in SEQ ID NOs: 200 (of which residues 1-19 correspond to the signal peptide and the remainder is the mature polypeptide), 211 (of which residues 1-19 correspond to the signal peptide and the remainder is the mature polypeptide), 222 (of which residues 1-19 correspond to the signal peptide and the remainder is the mature polypeptide), 233 (of which residues 1-19 correspond to the signal peptide and the remainder is the mature polypeptide), 244 (no signal peptide), 255 (of which residues 1-19 correspond to the signal peptide and the remainder is the mature polypeptide), 259 (of which residues 1-19 correspond to the signal peptide and the remainder is the mature polypeptide), 263 (of which residues 1-20 correspond to the signal peptide and the remainder is the mature polypeptide), 267 (of which residues 1-19 correspond to the signal peptide and the remainder is the mature polypeptide) and 207 (of which residues 1-19 correspond to the signal peptide and the remainder is the mature polypeptide), respectively.

In some embodiments of the invention, antibodies comprise amino acids 20-467 of SEQ ID NO: 207 (1S1 heavy chain) and amino acids 21-234 of SEQ ID NO: 220 (1S1 light chain); or amino acids 20-466 of SEQ ID NO: 233 (1S2 heavy chain) and amino acids 23-234 of SEQ ID NO: 218 (1S2 light chain); or amino acids 20-466 of SEQ ID NO: 255 (1S3 heavy chain) and amino acids 23-234 of SEQ ID NO: 229 (1S3 light chain); or amino acids 20-466 of SEQ ID NO: 259 (1S4 heavy chain) and wherein amino acids 23-234 of SEQ ID NO: 240 (1S4 light chain); or amino acids 20-466 of SEQ ID NO: 267 (1S5 heavy chain) and amino acids 23-234 of SEQ ID NO: 251 (1S5 light chain).

The term "monoclonal antibody" as used herein refers to an antibody, as that term is defined herein, obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab', F'(ab)$_2$, Fv, single chain antibodies, diabodies), maxibodies, nanobodies, and recombinant peptides comprising the foregoing as long as they exhibit the desired biological activity, or variants or derivatives thereof. Humanizing or modifying antibody sequence to be more human-like is described in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference in its entirety. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. patent application publication nos. 20030194404, 20030031667 or 20020199213; each incorporated herein by reference in its entirety.

An "isolated" antibody refers to an antibody, as that term is defined herein, that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

Allotypes are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

For a detailed description of the structure and generation of antibodies, see Roth, D. B., and Craig, N. L., *Cell,* 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md. (1991)). Even a single CDR may recognize and bind antigen, although with a lower affinity than the entire antigen binding site containing all of the CDRs.

An alternative definition of residues from a hypervariable "loop" is described by Chothia et al., *J. Mol. Biol.* 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact immunoglobulin, preferably an antigen binding or variable region of the intact antibody, and include multi specific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a VH domain) (Ward et al., Nature 341:544-546, 1989), complementarity determining region (CDR) fragments, single-chain antibodies (scFv, containing VH and VL domains on a single polypeptide chain) (Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain) (EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. April 2004;17(4):315-23), linear antibodies (tandem Fd segments (VH-CH1-VH-CH1) (Zapata et al., Protein Eng., 8(10):1057-1062 (1995)); chelating recombinant antibodies (crAb, which can bind to two adjacent epitopes on the sane antigen) (Neri et al., J Mol Biol. 246: 367-73, 1995), bibodies (bispecific Fab-scFv) or tribodies (trispecific Fab-(scFv)(2)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO03/041600, U.S. Patent publication 20030133939 and US Patent Publication 20030118592), an antigen-binding-domain immunoglobulin fusion protein, a camelized antibody (in which VH recombines with a constant region that contains hinge, CH1, CH2 and CH3 domains) (Desmyter et al., J. Biol. Chem. 276:26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "variant" when used in connection with antibodies refers to a polypeptide sequence of an antibody that contains at least one amino acid substitution, deletion, or insertion in the variable region or the portion equivalent to the variable region, provided that the variant retains the desired binding affinity or biological activity. In addition, the antibodies as described herein may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9):

6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "modification" when used in connection with antibodies or polypeptides described herein, includes but is not limited to, one or more amino acid change (including substitutions, insertions or deletions); chemical modifications that do not interfere with hepcidin-binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) of the invention will retain the binding properties of unmodified molecules of the invention.

The term "derivative" when used in connection with antibodies or polypeptides of the invention refers to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives of the invention will retain the binding properties of underivatized molecules of the invention.

Methods for making bispecific or other multispecific antibodies are known in the art and include chemical cross-linking, use of leucine zippers [Kostelny et al., J. Immunol. 148:1547-1553, 1992]; diabody technology [Hollinger et al., Proc. Natl. Acad. Sci. USA 90:6444-48, 1993]; scFv dimers [Gruber et al., J. Immunol. 152: 5368, 1994], linear antibodies [Zapata et al., Protein Eng. 8:1057-62, 1995]; and chelating recombinant antibodies [Neri et al., J Mol Biol. 246:367-73, 1995].

Thus, a variety of compositions comprising one, two, and/or three CDRs of a heavy chain variable region or a light chain variable region of an antibody may be generated by techniques known in the art.

Recombinant Production of Antibodies

Isolated nucleic acids encoding monoclonal antibodies described herein are also provided, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

Relevant amino acid sequence from an immunoglobulin of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies).

Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

Once isolated, the DNA may be operably linked to expression control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells (i.e., a multicellular organism). Prokaryotic host cells include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis, Pseudomonas, and Streptomyces. Eukaryotic microbes such as filamentous fungi or yeast are suitable cloning or expression hosts for recombinant polypeptides or antibodies. Saccharomyces cerevisiae, or common baker's yeast, is the most commonly used among lower eukaryotic host microorganisms. However, a number of other genera, species, and strains are commonly available and useful herein, such as Pichia, e.g. P. pastoris, Schizosaccharomyces pombe; Kluyveromyces, Yarrowia; Candida; Trichoderma reesia; Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger.

Host cells for the expression of glycosylated polypeptide or antibody can be derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection of such cells are publicly available, e.g., the L-1 variant of Autographa califomica NPV and the Bm-5 strain of Bombyx mori NPV.

Vertebrate host cells are also suitable hosts, and recombinant production of polypeptide or antibody from such cells has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells or FS4 cells; or mammalian myeloma cells.

Host cells are transformed or transfected with the above-described nucleic acids or vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antibodies.

The host cells used to produce an antibody described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody can be purified using, for example, hydroxylapatite chromatography, cation or anion exchange chromatography, or preferably affinity chromatography, using the antigen of interest or protein A or protein G as an affinity ligand. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Chimeric and Humanized Antibodies

Because chimeric or humanized antibodies are less immunogenic in humans than the parental rodent monoclonal antibodies, they can be used for the treatment of humans with far less risk of anaphylaxis. Thus, these antibodies are contemplated in therapeutic applications that involve in vivo administration to a human.

For example, a murine antibody on repeated in vivo administration in man either alone or as a conjugate will bring about an immune response in the recipient, sometimes called a HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like.

The phrase "chimeric antibody," as used herein, refers to an antibody containing sequence derived from two different antibodies which typically originate from different species. Most typically, chimeric antibodies comprise variable Ig domains of a rodent monoclonal antibody fused to human constant Ig domains. Such antibodies can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). Although some chimeric monoclonal antibodies have proved less immunogenic in humans, the rodent variable Ig domains can still lead to a significant human anti-rodent response.

The phrase "humanized antibody" refers to an antibody derived from a non-human antibody, typically a rodent monoclonal antibody. Alternatively, a humanized antibody may be derived from a chimeric antibody.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239: 1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference in its entirety.

CDR grafting involves introducing one or more of the six CDRs from the mouse heavy and light chain variable Ig domains into the appropriate framework regions of a human variable Ig domain. This technique (Riechmann, L., et al., Nature 332, 323 (1988)), utilizes the conserved framework regions (FR1-FR4) as a scaffold to support the CDR loops which are the primary contacts with antigen. A significant disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089).

A number of humanizations of mouse monoclonal antibodies by rational design have been reported (See, for example, 20020091240 published Jul. 11, 2002, WO 92/11018 and U.S. Pat. Nos. 5,693,762, 5,766,866).

Human Engineered™ Antibodies

The phrase "Human Engineered™ antibody" refers to an antibody derived from a non-human antibody, typically a rodent monoclonal antibody or possibly a chimeric antibody. Human Engineering™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody can be Human Engineered™ by substituting human amino acids at positions determined to be unlikely to adversely effect either antigen binding or protein folding, but likely to reduce immunogenicity in a human environment. Although any human variable region can be used, including an individual VH or VL sequence or a human consensus VH or VL sequence or an individual or consensus human germline sequence, generally a human sequence with highest identity or homology to the rodent sequence is used to minimize the number of substitutions. The amino acid residues at any number of the low risk positions, or at all of the low risk positions, can be changed. For example, at each low risk position where the aligned murine and human amino acid residues differ, an amino acid modification is introduced that replaces the rodent residue with the human residue. In addition, the amino acid residues at any number or all of the moderate risk positions can be changed. In exemplary embodiments, all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions of any class or subclass may be used in combination with the Human Engineered™ antibody variable regions.

Antibodies From Transgenic Animals Engineered to Contain Human Immunoglobulin Loci Antibodies to hepcidin can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369, 5,545,807; and U.S Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. Nos. 6,054,287; 5,877,293.

Watkins, "Screening of Phage-Expressed Antibody Libraries by Capture Lift," Methods in Molecular Biology, Antibody Phage Display: Methods and Protocols 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

Antibody Fragments

As noted above, antibody fragments comprise a portion of an intact full length antibody, preferably an antigen binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., *Science* 242:423-426, 1988, and Huston et al., *Proc. Natl. Acad. Sci. USA* 85:5879-5883, 1988). An Fd fragment consists of the $V_H$ and $C_H1$ domains.

Additional antibody fragments include a domain antibody (dAb) fragment (Ward et al., *Nature* 341:544-546, 1989) which consists of a $V_H$ domain.

"Linear antibodies" comprise a pair of tandem Fd segments ($V_H$-$C_H1$-$V_H$-$C_H1$) which form a pair of antigen binding regions. Linear antibodies can be bispecific or monospecific (Zapata et al. Protein Eng. 8:1057-62 (1995)).

A "minibody" consisting of scFv fused to CH3 via a peptide linker (hingeless) or via an IgG hinge has been described in Olafsen, et al., Protein Eng Des Sel. 2004 April; 17 (4): 315-23.

The term "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001).

Functional heavy-chain antibodies devoid of light chains are naturally occurring in certain species of animals, such as nurse sharks, wobbegong sharks and *Camelidae*, such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain. Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Camelized $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Methods for generating antibodies having camelized heavy chains are described in, for example, in U.S. Patent Publication Nos. 20050136049 and 20050037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001).

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody contruct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Additionally, the anti-hepcidin antibodies disclosed herein can also be constructed to fold into multivalent forms, which may improve binding affinity, specificity and/or increased half-life in blood. Multivalent forms of anti-hepcidin antibodies can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., Hum Antibodies Hybridomas 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments have also been described in the literature. For example, bispecific or trispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific or multispecific antibody fragments directly from recombinant cell culture have also been described. For example, bispecific antibodies have been produced using leucine zippers, e.g. GCN4. (See generally Kostelny et al., J. Immunol. 148(5): 1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

Diabodies, described above, are one example of a bispecific antibody. See, for example, Hollinger et al., Proc. Natl. Acad. Sci. USA, 90:6444-6448 (1993). Bivalent diabodies can be stabilized by disulfide linkage.

Stable monospecific or bispecific Fv tetramers can also be generated by noncovalent association in (scFv$_2$)$_2$ configuration or as bis-tetrabodies. Alternatively, two different scFvs can be joined in tandem to form a bis-scFv.

Another strategy for making bispecific antibody fragments by the use of single-chain Fv (sFv) dimers has also been reported. See Gruber et al., J. Immunol. 152: 5368 (1994). One approach has been to link two scFv antibodies with linkers or disulfide bonds (Mallender and Voss, J. Biol. Chem. 269:199-2061994, WO 94/13806, and U.S. Pat. No. 5,989, 830, the disclosures of which are incorporated herein by reference in their entireties).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol.* 246:367-73, 1995).

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

In yet another method, dimers, trimers, and tetramers are produced after a free cysteine is introduced in the parental protein. A peptide-based cross linker with variable numbers (two to four) of maleimide groups was used to cross link the protein of interest to the free cysteines (Cochran et al., Immunity 12(3): 241-50 (2000), the disclosure of which is incorporated herein in its entirety).

Antibody Screening Methods

Methods of identifying antibodies which bind hepcidin, which cross-block exemplary antibodies herein, and/or which inhibit hepcidin activity are also provided. Such methods may utilize the composition of highly purified, bioactive, correctly-folded, non-urinary human hepcidin (either chemically synthesized or produced in bacteria or non-mammalian cells) provided herein.

Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies which bind to the desired epitope on the target antigen, a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995).

In one variation of an in vitro binding assay, a method is provided comprising (a) contacting an immobilized hepcidin with a candidate antibody and (b) detecting binding of the candidate antibody to the hepcidin. In an alternative embodiment, the candidate antibody is immobilized and binding of hepcidin is detected. Immobilization is accomplished using any of the methods well known in the art, including covalent bonding to a support, a bead, or a chromatographic resin, as well as non-covalent, high affinity interaction such as antibody binding, or use of streptavidinibiotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Antibodies that inhibit or neutralize human hepcidin activity may be identified by contacting hepcidin with an antibody, comparing hepcidin activity in the presence and absence of the test antibody, and determining whether the presence of the antibody decreases activity of the hepcidin. The biological activity of a particular antibody, or combination of antibodies, may be evaluated in vivo using a suitable animal model, including any of those described herein.

In exemplary embodiments, the invention includes high throughput screening (HTS) assays to identify antibodies that interact with or inhibit biological activity (i.e., inhibit phosphorylation, dimerization, ligand induced-receptor activation, or intracellular signaling, etc.) of target antigen. HTS assays permit screening of large numbers of compounds in an efficient manner. Cell-based HTS systems are contemplated to investigate the interaction between target antigen and its binding partners. HTS assays are designed to identify "hits" or "lead compounds" having the desired property, from which modifications can be designed to improve the desired property.

In another embodiment of the invention, high throughput screening for antibody fragments or CDRs with 1, 2, 3 or more modifications to amino acids within the CDRs having suitable binding affinity to a target antigen polypeptide is employed.

Specific Binding Agents

Other hepcidin-specific binding agents can be prepared, for example, based on CDRs from an antibody or by screening libraries of diverse peptides or organic chemical compounds for peptides or compounds that exhibit the desired binding properties for human hepcidin. Hepcidin specific binding agent include peptides containing amino acid sequences that are at least 80%, 81%, 82%, 83%, 84%, 85%, 86%, 87%, 88%, 89%, 90%, 91%, 92%, 93%, 94%, 95%, 96%, 97%, 98%, 99% or more identical to one or more CDRs of murine antibody Ab43 (SEQ ID NOs: 16-21); murine antibody 2.7 (SEQ ID NOs: 28-33); murine antibody 2.41 (SEQ ID NOs: 40-45), rat antibody R9 (SEQ ID NOs: 52-57) or human antibody 1C9 (SEQ ID NOs: 111-116), human antibody 3B3 (SEQ ID NOs: 121-126), human antibody 4E1 (SEQ ID NOs: 131-136), human antibody 7A3 (SEQ ID NOs: 141-46), human antibody 9D12 (SEQ ID NOs: 151-156), human antibody 12B9 (SEQ ID NOs: 161-166), human antibody 15E1 (SEQ ID NOs: 171-176), human antibody 18D8 (SEQ ID NOs: 314-319), human antibody 19C1 (SEQ ID NOs: 324-329), human antibody 19D12 (SEQ ID NOs: 294-299), human antibody 19H6 (SEQ ID NOs: 304-309), human antibody 23F11 (SEQ ID NOs: 181-186), human antibody 26F11 (SEQ ID NOs: 191-196), or human antibody 1S1 (SEQ ID NOs: 203-205 and 131-133) or human antibody 1S2 (SEQ ID NOs: 214-216 and 144-146) or human antibody 1S3 (SEQ ID NOs: 225-227 and 164-166) or human antibody 1S4 (SEQ ID NOs: 236-238 and 174-176) or human antibody 1S5 (SEQ ID NO: 247-249 and 184-186).

Hepcidin-specific binding agents also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example, the carboxyl terminus may be capped with an amino group, cysteines may be cappe, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct. 26: 401-24 (1997). Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

The development of hepcidin peptibodies is also contemplated. The interaction of a protein ligand with its receptor often takes place at a relatively large interface. However, as demonstrated for human growth hormone and its receptor, only a few key residues at the interface contribute to most of the binding energy. Clackson et al., Science 267: 383-6 (1995). The bulk of the protein ligand merely displays the binding epitopes in the right topology or serves functions unrelated to binding. Thus, molecules of only "peptide" length (generally 2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display technology has emerged as a powerful method in identifying such peptide agonists and antagonists. See, for example, Scott et al. Science 249: 386 (1990); Devlin et al., Science 249: 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). In peptide phage display libraries, random peptide sequences can be displayed by fusion with coat proteins of filamentous phage. The displayed peptides can be affinity-eluted against an antibody-immobilized extracellular domain of a receptor, if desired. The retained phage may be enriched by successive rounds of affinity purification and repropagation. The best binding peptides may be sequenced to identify key residues within one or more structurally related families of peptides. See, e.g., Cwirla et al., Science 276: 1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, Ann. Rev. Biophys. Biomol. Struct. 26: 401-24 (1997).

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al., Nature Biotech 15: 1266-70 (1997). These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA. See, for example, Roberts and Szostak, Proc Natl Acad Sci USA, 94: 12297-303 (1997). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, Curr. Opin. Biotechnol., 3: 355-62 (1992).

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. See, e.g., Cortese et al., Curr. Opin. Biotech. 7: 616-21 (1996). Peptide libraries are now being used most often in immunological studies, such as epitope mapping. See Kreeger, The Scientist 10(13):19-20 (1996).

Sources for compounds that may be screened for ability to bind to or modulate (i.e., increase or decrease) the activity of the hepcidin polypeptides described herein include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see *Science* 282:63-68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). For reviews and examples of peptidomimetic libraries, see Al-Obeidi et al., Mol. Biotechnol, 9(3):205-23 (1998); Hruby et al., Curr Opin Chem Biol, 1(1):114-19 (1997); Dorner et al., Bioorg Med Chem, 4(5):709-15 (1996) (alkylated dipeptides).

Hepcidin-specific binding agents may also include scaffolding proteins, as described by Hays et al. Trends In Biotechnology, 23(10):514-522 (2005), herein incorporated by reference in its entirety, and Avimer protein technology, as described in US Publication Nos. 2006-0286603 and 2006-0223114, both herein incorporated by reference in their entireties.

Screening Methods for Antibodies or Specific Binding Agents

Methods of identifying antibodies or specific binding agents which bind hepcidin and/or which cross-block exemplary antibodies described herein, and/or which inhibit hepcidin activity are also provided. Such methods may utilize the composition of highly purified, bioactive, correctly-folded, non-urinary human hepcidin (either chemically synthesized or produced in bacteria or non-mammalian cells) provided herein.

Antibodies or specific binding agents may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies or specific binding agents which bind to the desired epitope on the target antigen, a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995).

In one variation of an in vitro binding assay, the invention provides a method comprising (a) contacting an immobilized hepcidin with a candidate antibody or specific binding agent and (b) detecting binding of the candidate antibody or specific binding agent to the hepcidin. In an alternative embodiment, the candidate antibody or specific binding agent is immobilized and binding of hepcidin is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

In some embodiments, antibodies or specific binding agents that inhibit or neutralize human hepcidin activity may be identified by contacting hepcidin with the antibody (or specific binding agent), comparing hepcidin activity in the presence and absence of the test antibody (or specific binding agent), and determining whether the presence of the antibody (or specific binding agent) decreases activity of the hepcidin. The biological activity of a particular antibody, or specific binding agent, or combination of antibodies or specific binding agents, may be evaluated in vivo using a suitable animal model, including any of those described herein.

In some embodiments, the invention also contemplates high throughput screening (HTS) assays to identify antibodies that interact with or inhibit biological activity (i.e., inhibit phosphorylation, dimerization, ligand induced-receptor activation, or intracellular signaling, etc.) of target antigen. HTS assays permit screening of large numbers of compounds in an efficient manner. Cell-based HTS systems are contemplated to investigate the interaction between target antigen and its binding partners. HTS assays are designed to identify "hits" or "lead compounds" having the desired property, from which modifications can be designed to improve the desired property.

In another embodiment, high throughput screening for antibody fragments or CDRs with 1, 2, 3 or more modifications to amino acids within the CDRs having suitable binding affinity to a target antigen polypeptide is employed.

B. Inhibitory Oligonucleotides

Hepcidin expression inhibitors that may be used according to the methods described herein include inhibitor oligonucleotides or polynucleotides, including pharmaceutically acceptable salts thereof, e.g. sodium salts. Nonlimiting examples include: antisense oligonucleotides [Eckstein, *Antisense Nucleic Acid Drug Dev.,* 10: 117-121 (2000); Crooke, *Methods Enzymol.,* 313: 3-45 (2000); Guvakova et al., *J. Biol. Chem.,* 270: 2620-2627 (1995); Manoharan, *Biochim. Biophys. Acta,* 1489: 117-130 (1999); Baker et al., *J. Biol. Chem.,* 272: 11994-12000 (1997); Kurreck, *Eur. J. Biochem.,* 270:1628-1644 (2003); Sierakowska et al., *Proc. Natl. Acad. Sci. USA,* 93: 12840-12844 (1996); Marwick, *J. Am. Med. Assoc.* 280: 871 (1998); Tomita and Morishita, *Curr. Pharm. Des.,* 10: 797-803 (2004); Gleave and Monia, *Nat. Rev. Cancer,* 5: 468-479 (2005) and Patil, *AAPS J.* 7: E61-E77 (2005), triplex oligonucleotides [Francois et al., *Nucleic Acids Res.,* 16: 11431-11440 (1988) and Moser and Dervan, *Science,* 238: 645-650 (1987)], ribozymes/deoxyribozymes (DNAzymes) [Kruger et al., *Tetrahymena. Cell,* 31: 147-157 (1982); Uhlenbeck, *Nature,* 328: 596-600 (1987); Sigurdsson and Eckstein, *Trends Biotechnol.,* 13 286-289 (1995); Kumar et al., *Gene Ther.,* 12: 1486-1493 (2005); Breaker and Joyce, *Chem. Biol.,* 1: 223-229 (1994); Khachigian, *Curr. Pharm. Biotechnol.,* 5: 337-339 (2004); Khachigian, *Biochem. Pharmacol.,* 68: 1023-1025 (2004) and Trulzsch and Wood, *J. Neurochem.,* 88: 257-265 (2004)], small-interfering RNAs/ RNAi [Fire et al., *Nature,* 391: 806-811 (1998); Montgomery et al., *Proc. Natl. Acad. Sci. U.S.A.,* 95: 15502-15507 (1998); Cullen, *Nat. Immunol.,* 3: 597-599 (2002); Hannon, *Nature,* 418: 244-251 (2002); Bernstein et al., *Nature,* 409: 363-366 (2001); Nykanen et al., *Cell,* 107: 309-321 (2001); Gilmore et al., *J. Drug Target.,* 12: 315-340 (2004); Reynolds et al., *Nat. Biotechnol.,* 22: 326-330 (2004); Soutschek et al., *Nature,* 432173-178 (2004); Ralph et al., *Nat. Med.,* 11: 429-433 (2005); Xia et al., *Nat. Med.,* 10816-820 (2004) and Miller et al., *Nucleic Acids Res.,* 32: 661-668 (2004)], aptamers [Ellington and Szostak, *Nature,* 346: 818-822 (1990); Doudna et al., *Proc. Natl. Acad. Sci. U.S.A.,* 92: 2355-2359 (1995); Tuerk and Gold, *Science,* 249: 505-510 (1990); White et al., *Mol. Ther.,* 4: 567-573 (2001); Rusconi et al., *Nature,* 419: 90-94 (2002); Nimjee et al., *Mol. Ther.,* 14: 408-415 (2006); Gragoudas et al., *N. Engl. J. Med.,* 351: 3805-2816 (2004); Vinores, *Curr. Opin. Mol. Ther.,* 5673-679 (2003) and Kourlas and Schiller et al., *Clin. Ther.,* 28 36-44 (2006)] or decoy oligonucleotides [Morishita et al., *Proc. Natl. Acad. Sci. U.S.A.,* 92: 5855-5859 (1995); Alexander et al., *J. Am. Med. Assoc.,* 294: 2446-2454 (2005); Mann and Dzau, *J. Clin. Invest.,* 106: 1071-1075 (2000) and Nimjee et al., *Annu. Rev. Med.,* 56: 555-583 (2005). The foregoing documents are hereby incorporated by reference in their entirety herein, with particular emphasis on those sections of the documents relating to methods of designing, making and using inhibitory oligonucleotides. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.).

Inhibitory oligonucleotides may be complementary to the coding portion of a target gene, 3' or 5' untranslated regions, or intronic sequences in a gene, or alternatively coding or intron sequences in the target mRNA. Intron sequences are generally less conserved and thus may provide greater specificity. In one embodiment, the inhibitory oligonucleotide inhibits expression of a gene product of one species but not its homologue in another species; in other embodiments, the inhibitory oligonucleotide inhibits expression of a gene in two species, e.g. human and primate, or human and murine.

In certain embodiments, the inhibitory oligonucleotide is capable of hybridizing to at least 8, 9, 10, 11, or 12 consecutive bases of the hepcidin gene or mRNA (SEQ ID NO: 99 (mouse) or SEQ ID NO: 100 (human) or the reverse strand thereof) under moderate or high stringency conditions. In some cases, depending on the length of the complementary region, one, two or more mismatches may be tolerated without affecting inhibitory function. In certain embodiments, the inhibitory oligonucleotide is an antisense oligonucleotide, an inhibitory RNA (including siRNA or RNAi, or shRNA), a DNA enzyme, a ribozyme (optionally a hammerhead ribozyme), an aptamer, or pharmaceutically acceptable salts thereof. In one embodiment, the oligonucleotide is complementary to at least 10 bases of SEQ ID NO: 104. In one embodiment, the oligonucleotide targets the nucleotides located in the vicinity of the 3' untranslated region of the hepcidin mRNA.

Selection of mRNA Site to Target with Inhibitory Oligonucleotide

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference in its entirety.

Most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al., 1989, Proc. Natl. Acad. Sci. USA 86:7706; and Turner et al., 1988, Annu. Rev. Biophys. Biophys. Chem. 17:167). The rules are useful in identification of RNA structural elements and, in particular, for identifying single stranded RNA regions which may represent segments of the mRNA to target for siRNA, ribozyme or antisense technologies.

Antisense Oligonucleotides

The constitutive expression of antisense oligonucleotides in cells has been shown to inhibit gene expression, possibly via the blockage of translation or prevention of splicing. Suitable inhibitory oligonucleotides may be single stranded and contain a segment, e.g. at least 12, 15 or 18 bases in length, that is sufficiently complementary to, and specific for, an mRNA or DNA molecule such that it hybridizes to the mRNA or DNA molecule and inhibits transcription, splicing or translation. Generally complementarity over a length of less than 30 bases is more than sufficient.

Factors that govern a target site for the inhibitory oligonucleotide sequence include the length of the oligonucleotide, binding affinity, and accessibility of the target sequence. Sequences may be screened in vitro for potency of their inhibitory activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

Phosphorothioate antisense oligonucleotides may be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides which are stable, have a high resistance to nucleases, possess suitable pharmacokinetics to allow them to traffic to target tissue site at non-toxic doses, and have the ability to cross through plasma membranes are contemplated for use as a therapeutic.

Short Interfering RNA

Short interfering (si) RNA technology (also known as RNAi) generally involves degradation of an mRNA of a particular sequence induced by double-stranded RNA (dsRNA) that is homologous to that sequence, thereby "interfering" with expression of the corresponding gene. Any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Exemplary siRNAs have sense and antisense strands of about 21 nucleotides that form approximately 19 nucleotide of doublestranded RNA with overhangs of two nucleotides at each 3' end. Indeed the use of relatively short homologous dsRNAs may have certain advantages.

Mammalian cells have at least two pathways that are affected by double-stranded RNA (dsRNA). In the sequence-specific siRNA pathway, the initiating dsRNA is first broken into short interfering RNAs, as described above. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are contemplated to effect gene repression by RNAi (see Hunter et al., 1975, J. Biol. Chem. 250:409-17; Manche et al., 1992, Mol. Cell. Biol. 12:5239-48; Minks et al., 1979, J. Biol. Chem. 254:10180-3; and Elbashir et al., 2001, Nature 411: 494-8).

siRNA has proven to be an effective means of decreasing gene expression in a variety of cell types. siRNA typically decreases expression of a gene to lower levels than that achieved using antisense techniques, and frequently eliminates expression entirely (see Bass, 2001, Nature 411:428-9). In mammalian cells, siRNAs are effective at concentrations that are several orders of magnitude below the concentrations typically used in antisense experiments (Elbashir et al., 2001, Nature 411:494-8).

The double stranded oligonucleotides used to effect RNAi are preferably less than 30 base pairs in length, for example, about 25, 24, 23, 22, 21, 20, 19, 18 or 17 base pairs or less in length, and contain a segment sufficiently complementary to the target mRNA to allow hybridization to the target mRNA. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., 2001, Nature 411:494-8). Exemplary dsRNAs may be synthesized chemically or produced in vitro or in vivo using appropriate expression vectors (see e.g. Elbashir et al., 2001, Genes Dev. 15:188-200). Longer RNAs may be transcribed from promoters, such as T7 RNA polymerase promoters, known in the art.

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan.

Further compositions, methods and applications of siRNA technology are provided in U.S. Pat. Nos. 6,278,039, 5,723, 750 and 5,244,805, which are incorporated herein by reference in its entirety.

Short Hairpin RNA

Compared to siRNA, shRNA offers advantages in silencing longevity and delivery options. See, e.g., Hannon et al., Nature, 431:371-378, 2004, for review. Vectors that produce shRNAs, which are processed intracellularly into short duplex RNAs having siRNA-like properties have been reported (Brummelkamp et al., Science 296, 550-553, 2000; Paddison et al., Genes Dev. 16, 948-958 (2002). Such vectors provide a renewable source of a gene-silencing reagent that can mediate persistent gene silencing after stable integration of the vector into the host-cell genome. Furthermore, the core silencing 'hairpin' cassette can be readily inserted into retroviral, lentiviral or adenoviral vectors, facilitating delivery of shRNAs into a broad range of cell types (Brummelkamp et al., Cancer Cell 2:243-247, 2002; Dirac, et al., J. Biol. Chem. 278:11731-11734, 2003; Michiels et al., Nat. Biotechnol. 20:1154-1157, 2002; Stegmeie et al., Proc. Natl. Acad. Sci. USA 102:13212-13217, 2005; Khvorova et al., Cell, 115: 209-216 (2003) in any of the innumerable ways that have been devised for delivery of DNA constructs that allow ectopic mRNA expression.

A hairpin can be organized in either a left-handed hairpin (i.e., 5'-antisense-loop-sense-3') or a right-handed hairpin (i.e., 5'-sense-loop-antisense-3'). The siRNA may also contain overhangs at either the 5' or 3' end of either the sense strand or the antisense strand, depending upon the organization of the hairpin. Preferably, if there are any overhangs, they are on the 3' end of the hairpin and comprise between 1 to 6 bases. The overhangs can be unmodified, or can contain one or more specificity or stabilizing modifications, such as a halogen or O-alkyl modification of the 2' position, or internucleotide modifications such as phosphorothioate, phosphorodithioate, or methylphosphonate modifications. The overhangs can be ribonucleic acid, deoxyribonucleic acid, or a combination of ribonucleic acid and deoxyribonucleic acid.

Additionally, a hairpin can further comprise a phosphate group on the 5'-most nucleotide. The phosphorylation of the 5'-most nucleotide refers to the presence of one or more phosphate groups attached to the 5' carbon of the sugar moiety of the 5'-terminal nucleotide. Preferably, there is only one phosphate group on the 5' end of the region that will form the antisense strand following Dicer processing. In one exemplary embodiment, a right-handed hairpin can include a 5' end (i.e., the free 5' end of the sense region) that does not have a 5' phosphate group, or can have the 5' carbon of the free 5'-most nucleotide of the sense region being modified in such a way that prevents phosphorylation. This can be achieved by a variety of methods including, but not limited to, addition of a phosphorylation blocking group (e.g., a 5'-O-alkyl group), or elimination of the 5'-OH functional group (e.g., the 5'-most nucleotide is a 5'-deoxy nucleotide). In cases where the hairpin is a left-handed hairpin, preferably the 5' carbon position of the 5'-most nucleotide is phosphorylated.

Hairpins that have stem lengths longer than 26 base pairs can be processed by Dicer such that some portions are not part of the resulting siRNA that facilitates mRNA degradation. Accordingly the first region, which may comprise sense nucleotides, and the second region, which may comprise antisense nucleotides, may also contain a stretch of nucleotides that are complementary (or at least substantially complementary to each other), but are or are not the same as or complementary to the target mRNA. While the stem of the shRNA can be composed of complementary or partially complementary antisense and sense strands exclusive of overhangs, the shRNA can also include the following: (1) the portion of the molecule that is distal to the eventual Dicer cut site contains a region that is substantially complementary/ homologous to the target mRNA; and (2) the region of the stem that is proximal to the Dicer cut site (i.e., the region adjacent to the loop) is unrelated or only partially related (e.g., complementary/homologous) to the target mRNA. The nucleotide content of this second region can be chosen based on a number of parameters including but not limited to thermodynamic traits or profiles.

Modified shRNAs can retain the modifications in the post-Dicer processed duplex. In exemplary embodiments, in cases in which the hairpin is a right handed hairpin (e.g., 5'-S-loop-AS-3') containing 2-6 nucleotide overhangs on the 3' end of the molecule, 2'-O-methyl modifications can be added to nucleotides at position 2, positions 1 and 2, or positions 1, 2, and 3 at the 5' end of the hairpin. Also, Dicer processing of hairpins with this configuration can retain the 5' end of the sense strand intact, thus preserving the pattern of chemical modification in the post-Dicer processed duplex. Presence of a 3' overhang in this configuration can be particularly advantageous since blunt ended molecules containing the prescribed modification pattern can be further processed by Dicer in such a way that the nucleotides carrying the 2' modifications are removed. In cases where the 3' overhang is present/retained, the resulting duplex carrying the sense-modified nucleotides can have highly favorable traits with respect to silencing specificity and functionality. Examples of exemplary modification patterns are described in detail in U.S. patent application publication number 2005/0223427, International Publication Nos. WO 2004/090105 and WO/2005/078094 the disclosures of each of which are incorporated by reference herein in their entirety.

shRNA may comprise sequences that were selected at random, or according to any rational design selection procedure. For example, the rational design algorithms are described in International Publication No. WO 2004/045543 A2, U.S. Patent Application Publication No. 2005/0255487, the disclosures of which are incorporated herein by reference in their entireties. Additionally, it may be desirable to select sequences in whole or in part based on average internal stability profiles ("AISPs") or regional internal stability profiles ("RISPs") that may facilitate access or processing by cellular machinery.

Ribozymes

Ribozymes are enzymatic RNA molecules capable of catalyzing specific cleavage of mRNA, thus preventing translation. (For a review, see Rossi, 1994, Current Biology 4:469-471). The mechanism of ribozyme action involves sequence specific hybridization of the ribozyme molecule to complementary target RNA, followed by an endonucleolytic cleavage event. The ribozyme molecules preferably include (1) one or more sequences complementary to a target mRNA, and (2) the well known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site-specific recognition sequences can be used to destroy target mRNAs, hammerhead ribozymes may alternatively be used. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach, 1988, Nature 334:585-591; and PCT Application. No. WO89/05852, the contents of which are incorporated herein by reference in its entirety.

Gene targeting ribozymes may contain a hybridizing region complementary to two regions of a target mRNA, each of which is at least 5, 6, 7, 8, 9, 10, 11, 12, 13, 14, 15, 16, 17, 18, 19 or 20 contiguous nucleotides (but which need not both be the same length).

Hammerhead ribozyme sequences can be embedded in a stable RNA such as a transfer RNA (tRNA) to increase cleavage efficiency in vivo (Perriman et al., 1995, Proc. Natl. Acad. Sci. USA, 92:6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase III-mediated expression of tRNA fusion ribozymes are well known in the art (see Kawasaki et al., 1998, Nature 393:284-9; Kuwabara et al., 1998, Nature Biotechnol. 16:961-5; and Kuwabara et al., 1998, Mol. Cell 2:617-27; Koseki et al., 1999, J. Virol 73:1868-77; Kuwabara et al., 1999, Proc. Natl. Acad. Sci. USA, 96:1886-91; Tanabe et al., 2000, Nature 406:473-4). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the target mRNA would allow the selective targeting of one or the other target genes.

The ribozymes of the present invention also include RNA endoribonucleases ("Cech-type ribozymes") such as the one which occurs naturally in Tetrahymena thermophila (known as the IVS, or L-19 IVS RNA) and which has been extensively described in Zaug, et al., 1984, Science, 224:574-578; Zaug, et al., 1986, Science 231:470-475; Zaug, et al., 1986, Nature 324:429-433; published International patent application No. WO88/04300; and Been, et al., 1986, Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should can be chemically synthesized or produced through an expression vector. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. Portions of the same sequence may then be incorporated into a ribozyme.

Triple Helix Formation

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C., 1991, Anticancer Drug Des., 6:569-84; Helene, C., et al., 1992, Ann. N.Y. Acad. Sci., 660:27-36; and Maher, L. J., 1992, Bioassays 14:807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the target sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

DNA Enzymes

Alternatively, DNA enzymes may be used to inhibit expression of target gene. DNA enzymes incorporate some of the mechanistic features of both antisense and ribozyme technologies. DNA enzymes are designed so that they recognize a particular target nucleic acid sequence, much like an antisense oligonucleotide. They are, however, also catalytic and specifically cleave the target nucleic acid.

There are currently two basic types of DNA enzymes, both of which were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Preferably, the unique or substantially unique sequence is a G/C rich of approximately 18 to 22 nucleotides. High G/C content helps insure a stronger interaction between the DNA enzyme and the target sequence. The specific antisense recognition sequence that will target the enzyme to the message may be divided between the two arms of the DNA enzyme.

Methods of making and administering DNA enzymes can be found, for example, in U.S. Pat. No. 6,110,462. Additionally, one of skill in the art will recognize that, like antisense oligonucleotide, DNA enzymes can be optionally modified to improve stability and improve resistance to degradation.

Delivery of Inhibitory Oligonucleotides

Inhibitory oligonucleotides can be administered directly or delivered to cells by transformation or transfection via a vector, including viral vectors or plasmids, into which has been placed DNA encoding the inhibitory oligonucleotide with the appropriate regulatory sequences, including a promoter, to result in expression of the inhibitory oligonucleotide in the desired cell. Known methods include standard transient transfection, stable transfection and delivery using viruses ranging from retroviruses to adenoviruses. Delivery of nucleic acid inhibitors by replicating or replication-deficient vectors is contemplated. Expression can also be driven by either constitutive or inducible promoter systems (Paddison et al., Methods Mol. Biol. 265:85-100, 2004). In other embodiments, expression may be under the control of tissue or development-specific promoters.

For example, vectors may be introduced by transfection using carrier compositions such as Lipofectamine 2000 (Life Technologies) or Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141: 863-74).

The delivery route will be the one that provides the best inhibitory effect as measured according to the criteria described above. Delivery mediated by cationic liposomes, delivery by retroviral vectors and direct delivery are efficient.

Other known delivery methods are described below in the section entitled "Gene Therapy."

The effectiveness of the inhibitory oligonucleotide may be assessed by any of a number of assays, including reverse transcriptase polymerase chain reaction or Northern blot analysis to determine the level of existing human hepcidin mRNA, or Western blot analysis using antibodies which recognize the human hepcidin protein, after sufficient time for turnover of the endogenous pool after new protein synthesis is repressed. While the "normal" range of hepcidin levels is less than about 25 ng/mL, a measurement below about 10 ng/mL may indicate suppression of hepcidin. In another embodiment, the "normal" range of hepcidin levels is less than about 10 ng/ml (as assessed by mass-spectometry), and a measurement below about 2.5 ng/ml (as assessed by mass-spectometrt) may indicate suppression of hepcidin.

C. Hepcidin Polypeptide Variants with Antagonist Activity

With respect to human hepcidin polypeptide, antagonist variants are contemplated that include one or more substitutions, insertions or deletions relative to the native mature human hepcidin sequence, but which retain all eight cysteines and which inhibit hepcidin biological activity (e.g. anti-microbial and/or iron-regulating activity). Variants may maintain the C2-C4 and/or C5-C7 disulfide bond and optionally the C1-C8 and C3-C6 disulfide bonds as well. Also contemplated are hepcidin variants that retain ferroportin binding activity but which do not cause internalization or degradation of ferroportin, as well as hepcidin variants that retain hepcidin receptor binding activity but which do not activate the ferroportin receptor.

Antagonist variants are readily prepared as described in section IV (Production of Polypeptide Variants), and can be screened for ability to inhibit hepcidin iron-regulating activity in any of the in vitro or in vivo assays described herein.

III. Hepcidin Polypeptide Variants with Agonist Activity

Agonist variants of human hepcidin polypeptide are also contemplated that include one or more substitutions, insertions or deletions relative to the native mature human hepcidin sequence, but which retain all eight cysteines and which retain hepcidin biological activity (e.g. anti-microbial and/or iron-regulating activity). Variants may maintain the C2-C4 and/or C5-C7 disulfide bond and optionally the C1-C8 and C3-C6 disulfide bonds as well. Also contemplated are hepcidin variants that retain ferroportin binding activity and/or retain hepcidin receptor binding activity.

Agonist variants are readily prepared as described in section IV (Production of Polypeptide Variants), and can be screened for retention of hepcidin iron-regulating activity in any of the in vitro or in vivo assays described herein.

IV. Production of Polypeptide Variants and Derivatives

The hepcidin polypeptides of the invention (including hepcidin variants) or anti-hepcidin antibodies of the invention can readily be modified by techniques well-known to one of ordinary skill in the art. Potential mutations include insertion, deletion or substitution of one or more residues. Insertions or deletions are preferably in the range of about 1 to 5 amino acids, more preferably 1 to 3, and most preferably 1 or 2 amino acids.

Deletion variants are polypeptides wherein at least one amino acid residue of any amino acid sequence is removed. Deletions can be effected at one or both termini of the protein, or with removal of one or more residues within (i.e., internal to) the polypeptide. Methods for preparation of deletion variants are routine in the art. See, e.g., Sambrook et al. (1989) Molecular Cloning: A Laboratory Guide, Vols 1-3, Cold Spring Harbor Press, the disclosure of which is incorporated herein by reference in its entirety.

Amino acid sequence insertions include amino- and/or carboxyl-terminal fusions ranging in length from one residue to polypeptides containing hundreds or more residues, as well as internal sequence insertions of one or more amino acids. As with any of the different variant types described herein, insertional variants can be designed such that the resulting polypeptide retains the same biological properties or exhibits a new physical, chemical and/or biological property not associated with the parental polypeptide from which it was derived. Methods for preparation of insertion variants are also routine and well known in the art (Sambrook et al., supra).

Fusion proteins comprising a polypeptide of the invention (including a hepcidin variant) or antibody of the invention, and a heterologous polypeptide, are a specific type of insertion variant contemplated by the invention. Nonlimiting examples of heterologous polypeptides which can be fused to polypeptides of interest include proteins with long circulating half-life, such as, but not limited to, immunoglobulin constant regions (e.g., Fc region); marker sequences that permit identification of the polypeptide of interest; sequences that facilitate purification of the polypeptide of interest; and sequences that promote formation of multimeric proteins.

Methods of making antibody fusion proteins are well known in the art. See, e.g., U.S. Pat. No. 6,306,393, the disclosure of which is incorporated herein by reference in its entirety. In certain embodiments of the invention, fusion proteins are produced which may include a flexible linker, which connects the chimeric scFv antibody to the heterologous protein moiety. Appropriate linker sequences are those that do not affect the ability of the resulting fusion protein to be recognized and bind the epitope specifically bound by the V domain of the protein (see, e.g., WO 98/25965, the disclosure of which is incorporated herein by reference in its entirety).

Substitution variants are those in which at least one residue in the polypeptide amino acid sequence is removed and a different residue is inserted in its place. Modifications in the biological properties of the polypeptide or antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. In certain embodiments of the invention, substitution variants are designed, i.e., one or more specific (as opposed to random) amino acid residues are substituted with a specific amino acid residue. Typical changes of these types include conservative substitutions and/or substitution of one residue for another based on similar properties of the native and substituting residues.

Conservative substitutions are shown in Table 1. The most conservative substitution is found under the heading of "preferred substitutions." If such substitutions result in no change in biological activity, then more substantial changes may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |

TABLE 1-continued

| Original | Exemplary | Preferred Residue Substitutions |
|---|---|---|
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Amino acid residues which share common side-chain properties are often grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Antibody Variants

In certain instances, antibody variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which antibody amino acid residues are important for epitope recognition and binding, alanine scanning mutagenesis can be performed to produce substitution variants. See, for example, Cunningham et al., Science, 244:1081-1085 (1989), the disclosure of which is incorporated herein by reference in its entirety. In this method, individual amino acid residues are replaced one-at-a-time with an alanine residue and the resulting anti-hepcidin antibody is screened for its ability to bind its specific epitope relative to the unmodified antibody. Modified antibodies with reduced binding capacity are sequenced to determine which residue was changed, indicating its significance in binding or biological properties.

Substitution variants of antibodies can be prepared by affinity maturation wherein random amino acid changes are introduced into the parent antibody sequence. See, for example, Ouwehand et al., Vox Sang 74 (Suppl 2):223-232, 1998; Rader et al., Proc. Natl. Acad. Sci. USA 95:8910-8915, 1998; Dall'Acqua et al., Curr. Opin. Struct. Biol. 8:443-450, 1998, the disclosures of which are incorporated herein by reference in their entireties. Affinity maturation involves preparing and screening the anti-hepcidin antibodies, or variants thereof and selecting from the resulting variants those that have modified biological properties, such as increased binding affinity relative to the parent anti-hepcidin antibody. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of M13 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68, 1996), and saturation mutagenesis (Nishimiya et al., *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA.* 102:8466-71, 2005). Nonstochastic techniques often use alanine-scanning or site-directed mutagenesis to generate limited collections of specific muteins. Some methods are described in further detail below.

Affinity maturation via panning methods—Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA.* 97:2029-34, 2000).

Look-through mutagenesis—Look-through mutagenesis (LTM) (Rajpal et al., *Proc Natl Acad Sci USA.* 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-prone PCR—Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol Biol. 226:889-96, 1992). After the mutation cycles, clones with improved affinity for the antigen are selected using routine methods in the art.

Techniques utilizing gene shuffling and directed evolution may also be used to prepare and screen anti-hepcidin antibodies, or variants thereof, for desired activity. For example, Jermutus et al., Proc Natl Acad Sci USA., 98(1):75-80 (2001) showed that tailored in vitro selection strategies based on ribosome display were combined with in vitro diversification by DNA shuffling to evolve either the off-rate or thermodynamic stability of scFvs; Fermer et al., Tumour Biol. January-April 2004;25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

Antibody with Modified Carbohydrate

Antibody variants can also be produced that have a modified glycosylation pattern relative to the parent antibody, for example, adding or deleting one or more of the carbohydrate moieties bound to the specific binding agent or antibody, and/or adding or deleting one or more glycosylation sites in the specific binding agent or antibody.

Glycosylation of polypeptides, including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent or antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent or antibody by inserting or substituting one or more serine or threonine residues to the sequence of the original specific binding agent or antibody.

Altered Effector Function

Cysteine residue(s) may be removed or introduced in the Fc region of an antibody or Fc-containing polypeptide, thereby eliminating or increasing interchain disulfide bond formation in this region. A homodimeric specific binding agent or antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric specific binding agents or antibodies may also be prepared using heterobifunctional cross-linkers as described in Wolff et al., Cancer Research 53: 2560-2565 (1993). Alternatively, a specific binding agent or antibody can be engineered which has dual Fc regions and may thereby have enhanced complement lysis and ADCC capabilities. See Stevenson et al., *Anti-CancerDrug Design* 3: 219-230 (1989).

It has been shown that sequences within the CDR can cause an antibody to bind to MHC Class II and trigger an unwanted helper T-cell response. A conservative substitution can allow the specific binding agent or antibody to retain binding activity yet reduce its ability to trigger an unwanted T-cell response. It is also contemplated that one or more of the N-terminal 20 amino acids of the heavy or light chain are removed.

In some embodiments, the invention also contemplates production of antibody molecules with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. Sep. 5, 2004;87(5):614-22). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol Immunol. December 1989; 26(12):1113-23). Some host cell strains, e.g. Lec13 or rat hybridoma YB2/0 cell line naturally produce antibodies with lower fucosylation levels. Shields et al., J Biol Chem. Jul. 26, 2002;277(30):26733-40; Shinkawa et al., J Biol Chem. Jan. 31, 2003;278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. February 1999;17(2):176-80. It has been predicted that the absence of only one of the two fucose residues may be sufficient to increase ADCC activity. (Ferrara et al., J Biol Chem. Dec. 5, 2005).

Other Covalent Modifications

Covalent modifications of a polypeptide, or antibody are also included within the scope of this invention. They may be made by chemical synthesis or by enzymatic or chemical cleavage of the polypeptide or antibody, if applicable. Other types of covalent modifications can be introduced by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the polypeptide or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the polypeptide or antibody may be accomplished chemically or enzymatically. Chemical deglycosylation requires exposure of the specific binding agent or antibody to the compound trifluoromethanesulfonic acid, or an equivalent compound. This treatment results in the cleavage of most or all sugars except the linking sugar (N-acetylglucosamine or N-acetylgalactosamine), while leaving the specific binding agent or antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on a specific binding agent or antibody can be achieved by the use of a variety of endo- and exo-glycosidases as described by Thotakura et al. Meth. Enzymol. 138: 350 (1987).

Another type of covalent modification of the hepcidin activity antagonists of the invention (including anti-hepcidin antibody or hepcidin variant) comprises linking the polypeptide, specific binding agent or antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

V. Gene Therapy

Delivery of a hepcidin agonist or antagonist to appropriate cells can be effected via gene therapy ex vivo, in situ, or in vivo by use of any suitable approach known in the art. For example, for in vivo therapy, a nucleic acid encoding the desired hepcidin activity antagonist or hepcidin expression inhibitor, either alone or in conjunction with a vector, liposome, or precipitate may be injected directly into the subject, and in some embodiments, may be injected at the site where the expression of the hepcidin activity antagonist or hepcidin expression inhibitor is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl)trimethylammonium bromide, commercialized as Lipofectin by GIBCO-BRL))(Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES)(J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC) (Leventis et al. (1990) Biochim. Inter. 22, 235-241); 3beta[N-(N', N'-dimethylaminoethane)-carbamoyl]cholesterol (DC-Chol), dioleoylphosphatidyl ethanolamine (DOPE)/3beta[N-(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cre-soxy]ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997;235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP, linear dextran nonasaccharide, glycerol, cholesteryl groups tethered at the 3'-terminal internucleoside link of an oligonucleotide (Letsinger, R. L. 1989 Proc Natl Acad Sci USA 86: (17): 6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

VI. Diagnostic Methods for Hepcidin-Related Disorders and Monitoring of Therapy with Hepcidin Antagonists Also provided are methods for diagnosing hepcidin-related disorders, such as hepcidin-related anemia, or other diseases of hepcidin excess or hepcidin deficiency, and for monitoring the effectiveness of therapy for such a disease, including therapy with hepcidin activity antagonists or hepcidin expression inhibitors. To determine the presence or absence of hepcidin-related anemia, a biological sample from a patient is contacted with one or more of the anti-hepcidin antibodies disclosed herein under conditions and for a time sufficient to allow immunocomplexes to form. Immunocomplexes formed between an anti-hepcidin antibody and hepcidin in the biological sample are then detected. The amount of hepcidin in the sample is quantitated by measuring the amount of the immunocomplex formed between the antibody and hepcidin. Within certain methods, a biological sample is isolated from a patient and is incubated with one or more of the anti-hepcidin antibodies disclosed herein, and the level of the antibody-hepcidin complex above a certain threshold is correlated with the presence of hepcidin-related anemia, and a level below said threshold indicates that the patient is unlikely to have hepcidin-related anemia. For example, a level within the normal range indicates the patient is unlikely to have hepcidin-related anemia. Normal range of serum hepcidin is generally less than 10 ng/ml when determined by certain assays, i.e., mass spectrometry techniques described in co-owned U.S. patent application Ser. No. 11/880,313 and International Patent Application No. PCT/US2007/016477, the disclosures of which are incorporated herein by reference in their entirety, but will vary depending on the assay and depending on the subset of population tested.

Also provided are methods for differentiating an inflammatory disease from a non-inflammatory disease. To determine the presence or absence of an inflammatory disease, a biological sample from a patient is contacted with one or more of the anti-hepcidin antibodies disclosed herein under conditions and for a time sufficient to allow immunocomplexes to form. Various immunoassays known in the art can be used, including but are not limited to: competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. Antibodies: A Laboratory Manual (1988) by Harlow & Lane or more recent editions; Immunoassays: A Practical Approach, Oxford University Press, Gosling, J. P. (ed.) (2001) or more recent editions; and/or Current Protocols in Molecular Biology (Ausubel et al.), which is regularly updated. Examples of such assays usually involve the antibody attached to a surface or matrix, patient serum added and time allowed for a complex to form; suitable washing procedures to remove unbound complex, followed by either the addition of a second antibody to allow detection of the complex (a sandwich ELISA) or a detectable version of hepcidin to detect free hepcidin binding sites on the antibody surface (a competition ELISA). The level of hepcidin, as detected by the foregoing methods, above a certain threshold is correlated with the presence of an inflammatory disease, and a level below said threshold indicates that the patient is unlikely to have an inflammatory disease. A patient is unlikely to have an inflammatory disease when the hepcidin level is within the normal range. A patient is likely to have an inflammatory disease when the hepcidin level exceeds the normal range, for example 20 ng/ml, in particular, when the level is between 20 and 1000 ng/ml. Exemplary hepcidin-related inflammatory diseases include anemia of cancer, anemia of chronic disease, anemia of inflammation, chemotherapy-induced anemia, chronic kidney disease (stage I, II, III, IV or V), end stage renal disease, chronic renal failure congestive heart failure, cancer, rheumatoid arthritis, systemic lupus erythematosus, Crohn's disease, *H. pyelori* infection or other bacterial infections, hepatitis C, HIV, and other viral illnesses, arteriosclerosis, atherosclerosis, cirrhosis of the liver, pancreatitis, sepsis, vasculitis, iron-deficiency, hypochromic microcytic anemia and conditions with hepcidin excess.

Within other methods, a biological sample obtained from a patient is tested for the level of hepcidin. The biological sample is incubated with one or more of the anti-hepcidin antibodies disclosed herein under conditions and for a time sufficient to allow immunocomplexes to form. Immunocomplexes formed between the hepcidin and antibodies in the biological sample that specifically bind to the hepcidin are then detected. A biological sample for use within such methods may be any sample obtained from a patient that is expected to contain hepcidin. Suitable biological samples include blood, sera, plasma, urine and bone marrow. Suitable antibodies include antibodies from human cells, rodent, rabbit, goat, camel, or any other species.

The biological sample is incubated with antibodies in a reaction mixture under conditions and for a time sufficient to permit immunocomplexes to form between hepcidin and antibodies that are immunospecific for hepcidin. For example, a biological sample and one or more anti-hepcidin antibodies may be incubated at 4° C. for 24-48 hours.

Following the incubation, the reaction mixture is tested for the presence of immuno-complexes. Detection of immuno-complexes formed between an anti-hepcidin antibody and hepcidin present in the biological sample may be accomplished by a variety of known techniques, such as radioimmunoassays (RIA) and enzyme linked immunosorbent assays (ELISA). Suitable assays are well known in the art and are amply described in the scientific and patent literature (Harlow and Lane, 1988). Assays that may be used include, but are not limited to, the double monoclonal antibody sandwich immunoassay technique (U.S. Pat. No. 4,376,110); monoclonal-polyclonal antibody sandwich assays (Wide et al., 1970); the "western blot" method (U.S. Pat. No. 4,452,901); immunoprecipitation of labeled ligand (Brown et al., 1980); enzyme-linked immunosorbent assays (Raines and Ross, 1982); immunocytochemical techniques, including the use of fluorochromes (Brooks et al., 1980); and neutralization of activity (Bowen-Pope et al., 1984). Other immunoassays include, but are not limited to, those described in U.S. Pat. Nos. 3,817,827; 3,850,752; 3,901,654; 3,935,074; 3,984,533; 3,996,345; 4,034,074; and 4,098,876.

For detection purposes, an anti-hepcidin antibody may either be labeled or unlabeled. Unlabeled antibodies may be used in agglutination assays or in combination with labeled detection reagents that bind to the immunocomplexes (e.g., anti-immunoglobulin, protein G, Protein A or a lectin and secondary antibodies, or antigen-binding fragments thereof, capable of binding to the antibodies that specifically bind to the hepcidin). If the anti-hepcidin antibody is labeled, the reporter group may be any suitable reporter group known in the art, including radioisotopes, fluorescent groups (e.g. fluorescein or rhodamine), luminescent groups, enzymes, biotin and dye particles. Labels that are themselves directly detectable include fluorescent or luminescent dyes, metals or metal chelates, electrochemical labels, radionuclides (e.g., 32P, 14C, 125I, 3H, or 131I), magnetic labels or beads (e.g., DYNABEADS), paramagnetic labels, or colorimetric labels (e.g., colloidal gold, colored glass or plastic beads). Such detectable labels may be directly conjugated to the anti-hepcidin antibody or detection reagent or may be associated with a bead or particle that is attached to the anti-hepcidin antibody or detection reagent. Labels that are detectable through binding of a labeled specific binding partner include biotin, digoxigenin, maltose, oligohistidine, 2,4-dinitrobenzene, phenylarsenate, ssDNA, or dsDNA). Indirect labels that can be indirectly detected by their production of a detectable reaction product include various enzymes well known in the art, such as alkaline phosphatase, horseradish peroxidase, β-galactosidase, xanthine oxidase, glucose oxidase or other saccharide oxidases, or luciferases, which cleave appropriate substrate to form a colored or fluorescent reaction product.

Within certain assays, an unlabeled anti-hepcidin antibody is immobilized on a solid support, for use as a "capture agent" (or reagent) that captures the hepcidin within a biological sample. The solid support may be any material known to those of ordinary skill in the art to which the antibody may be attached. For example, the solid support may be a test well in a microtiter plate or a nitrocellulose or other suitable membrane. Alternatively, the support may be a tube, bead, particle or disc, such as glass, fiberglass, latex or a plastic material such as polyethylene, polypropylene, polystyrene or polyvinylchloride or a porous matrix. Other materials include agarose, dextran, polyacrylamide, nylon, Sephadex, cellulose or polysaccharides. The support may also be a magnetic particle or a fiber optic sensor, such as those disclosed, for example, in U.S. Pat. No. 5,359,681. The immobilized anti-hepcidin antibody may be a polyclonal antibody, or one or more monoclonal antibodies such as those described herein, or a combination of polyclonal and one or more monoclonal antibodies. The antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is contemplated. In such cases, adsorption may be achieved by contacting the anti-hepcidin antibody, in a suitable buffer, with the solid support for a suitable amount of time. The contact time varies with temperature, but is typically between about 1 hour and about 1 day. In general, contacting a well of a plastic microtiter plate (including polystyrene or polyvinylchloride) with an amount of peptide ranging from about 10 ng to about 10 µg, and preferably about 100 ng to about 1 µg, is sufficient to immobilize an adequate amount of peptide.

Following immobilization, the remaining protein binding sites on the support are typically blocked. Any suitable blocking agent known to those of ordinary skill in the art, including bovine serum albumin, Tween™ 20™ (Sigma Chemical Co., St. Louis, Mo.), heat-inactivated normal goat serum (NGS), or BLOTTO (buffered solution of nonfat dry milk which also contains a preservative, salts, and an antifoaming agent) can be used. The support is then incubated with a biological sample suspected of containing hepcidin. The sample can be applied neat, or, more often, it can be diluted, usually in a buffered solution which contains a small amount (0.1%-5.0% by weight) of protein, such as BSA, NGS, or BLOTTO. In general, an appropriate contact time (i.e., incubation time) is a period of time that is sufficient to detect the presence of antibody or an antigen binding fragment that is immunospecific for the hepcidin within a sample containing hepcidin. Preferably, the contact time is sufficient to achieve a level of binding that is at least about 95% of that achieved at equilibrium between bound and unbound antibody or antibody fragment. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween™ 20. A detection reagent that binds to the hepcidin in the immunocomplexes (formed by binding of the capture agent and the hepcidin from the sample) may then be added. Such detection reagent may be a polyclonal antibody, or one or more monoclonal antibodies such as those described herein, or a combination of polyclonal and one or more monoclonal antibodies such as those described herein or a Fab fraction of any antibody. The detection reagent may be directly labeled, i.e., comprises at least a first detectable label or "reporter" molecule. Alternatively, the detection reagent may be an unlabeled anti-hepcidin antibody. This unlabeled anti-hepcidin (primary) antibody is then detected by the binding of a labeled secondary antibody or reagent to the primary antibody. For example, if the primary antibody is a murine immunoglobulin, the secondary antibody may be a labeled anti-murine immunoglobulin antibody. Similarly, if the primary antibody is a rabbit immunoglobulin, the secondary antibody may be a labeled anti-rabbit immunoglobulin antibody.

The detection reagent is incubated with the immunocomplex for an amount of time sufficient to detect the bound antibody or antigen binding fragment thereof. An appropriate amount of time may generally be determined by assaying the level of binding that occurs over a period of time. Unbound label or detection reagent is then removed and bound label or detection reagent is detected using a suitable assay or analytical instrument. The method employed for detecting the reporter group depends upon the nature of the reporter group. For radioactive labels, scintillation counting or autoradiographic methods are generally appropriate. Spectroscopic methods may be used to detect dyes, luminescent or chemiluminescent moieties and various chromogens, fluorescent labels and such like. Biotin may be detected using avidin, coupled to a different reporter group (commonly a radioactive or fluorescent group or an enzyme). Enzyme reporter groups (including horseradish peroxidase, β-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from an individual with a normal level of hepcidin) indicates the presence of a disorder associated with expression of hepcidin.

In alternative embodiments, the sample and detection reagent may be contacted simultaneously with the capture agent, rather than sequentially added. In yet another alternative, the sample and detection reagent may be pre-incubated together, then added to the capture agent. Other variations are readily apparent to one of ordinary skill in the art.

In another embodiment, the amount of hepcidin present in a sample is determined by a competitive binding assay. Competitive binding assays rely on the ability of a labeled standard (e.g., a hepcidin polypeptide, or an immunologically reactive portion thereof) to compete with the test sample analyte (a hepcidin polypeptide) for binding with a limited amount of an anti-hepcidin antibody. Following separation of free and bound hepcidin, the hepcidin is quantitated by relating ratio of bound/unbound hepcidin to known standards. The amount of a hepcidin polypeptide in the test sample is inversely proportional to the amount of standard that becomes bound to the antibodies. To facilitate determining the amount of standard that becomes bound, the antibodies typically are immobilized on a solid support so that the standard and analyte that are bound to the antibodies may conveniently be separated from the standard and analyte which remain unbound. Thus, in such embodiments, the invention contemplates contacting a biological sample with labeled mature hepcidin (or a labeled fragment thereof that retains the antigenicity of hepcidin) and an antibody that binds to mature hepcidin, and detecting the amount of antibody-labeled hepcidin complex formed.

Preparation of conjugates to solid supports or detectable labels often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, whereas pyridyl disulfides react with sulfhydryls to produce mixed disulfides. The pyridyl disulfide product is cleavable. Imidoesters are also very useful for protein-protein cross-links.

Heterobifunctional cross-linkers possess two or more different reactive groups that allow for sequential conjugations with specific groups of proteins, minimizing undesirable polymerization or self-conjugation. Heterobifunctional reagents are also used when modification of amines is problematic. Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups. A variety of heterobifunctional cross-linkers, each combining different attributes for successful conjugation, are commercially available. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

As shown herein in Examples 27-28, it is the level of mature hepcidin (amino acids 60-84 of SEQ ID NO: 8) rather than the level of prohepcidin (amino acids 25-84 of SEQ ID NO: 8) which is diagnostic for certain disease states such as anemia of inflammation and anemia of cancer. Thus, in one preferred embodiment, antibody(ies) that bind to mature, properly folded, hepcidin (SEQ ID NO: 9) are used as both capture agent and detection reagent. Antibodies that bind to the naturally occurring N-terminally truncated versions (e.g. lacking up to two or up to five of the N-terminal amino acids of mature hepcidin) may also be used. Various combinations of capture agent and detection reagent are contemplated. For example, the capture agent may be a monoclonal antibody that binds to a first epitope of mature hepcidin and the detection reagent may be a different monoclonal antibody that binds to a second epitope of mature hepcidin. Preferably antibodies specific for different epitopes of hepcidin are used, in order to minimize competition or interference between the capture agent and detection reagent. Alternatively, the capture agent may be a polyclonal antibody that binds to mature hepcidin and the detection reagent may be a monoclonal antibody. As yet another alternative, the capture agent may be a monoclonal antibody that binds to mature hepcidin and the detection reagent may be a polyclonal antibody. In any of the preceding embodiments, either the capture agent or the detection reagent may be a combination of a polyclonal and a monoclonal antibody.

In some embodiments, a mature-hepcidin-specific monoclonal antibody is used as either the capture agent or detection reagent or both. A mature-hepcidin-specific antibody does not bind prohepcidin at all, or binds to prohepcidin with such low affinity that the antibody can differentiate mature hepcidin from prohepcidin. For example, such a monoclonal antibody may bind to the N-terminus of mature hepcidin, or it may bind an epitope of mature hepcidin that is not detectable in prohepcidin (e.g. due to masking by the prodomain).

In embodiments utilizing a monoclonal antibody that binds to an epitope present in both mature hepcidin and prohepcidin, an optional further refinement is contemplated. The amount of mature hepcidin alone is determined by subtracting the amount of prohepcidin present in the sample from the amount of total hepcidin (prohepcidin plus mature hepcidin) present in the same sample. The amount of prohepcidin can be determined by using prohepcidin-specific polyclonal and/or monoclonal antibodies in techniques like those described above. A prohepcidin-specific antibody does not bind mature hepcidin at all, or binds to mature hepcidin with such low affinity that the antibody can differentiate prohepcidin from mature hepcidin. For example, such antibodies may bind to a linear or conformational epitope present uniquely in the prodomain of hepcidin (amino acids 25-59 of SEQ ID NO: 8). In such embodiments, the amount of total hepcidin and prohepcidin may be determined sequentially or simultaneously. Because prohepcidin is rapidly degraded in serum to hepcidin, in some embodiments furin inhibitors are added to the biological sample in order to prevent or reduce degradation of prohepcidin.

In some embodiments utilizing a monoclonal antibody that binds to the 25-amino acid mature hepcidin, the monoclonal antibody does not bind the degradation products (i.e., hepcidin-22 and hepcidin-20).

In one embodiment of a simultaneous assay for detecting total hepcidin and prohepcidin, the capture agent is an antibody that binds to an epitope present in both mature hepcidin and prohepcidin, and two detection reagents are applied simultaneously. The first detection reagent is a labeled antibody that binds to an epitope present in both mature hepcidin and prohepcidin and the second detection reagent is a differently labeled prohepcidin-specific antibody. For example, the first detection reagent is labeled with a fluorescent dye detectable at a first wavelength while the second detection reagent is labeled with a fluorescent dye detectable at a second wavelength. Thus, in such an example, the capture agent will bind total hepcidin (mature hepcidin plus prohepcidin) in the sample, the first detection reagent will detect the amount of total hepcidin, and the second detection reagent will detect the amount of prohepcidin. Subtracting the amount of prohepcidin from amount of the total hepcidin will yield the amount of mature hepcidin. In other alternative embodiments, two different capture agents may be used: a first capture agent that binds to an epitope present in both mature hepcidin and prohepcidin, and a second capture agent that is a prohepcidin-specific antibody, optionally with a detection reagent that binds an epitope present in both mature hepcidin and prohepcidin.

Other embodiments for carrying out simultaneous assays are well known in the art, including the multiplex system described, e.g., in Khan et al., Clin. Vaccine Immunol., 13(1) 45-52 (January 2006) involving differentially coded sets of fluorescent microbeads. Other embodiments for performing multiple simultaneous assays on a single surface include surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and capillary devices (see, e.g., U.S. Pat. No. 6,019,944). In these embodiments, each discrete surface location has a different antibody that immobilizes a different analyte for detection at each location. Surfaces can alternatively have one or more discrete particles (e.g., microparticles or nanoparticles) immobilized at discrete locations of a surface, of which each set of particles contains a different capture agent for a different analyte.

Complementary antibody pairs (antibodies that bind to different epitopes on hepcidin such that the pairs are suitable for use in sandwich assays) were difficult to identify. Use of complementary pairs that minimize competition or interference can increase sensitivity of the assay by 20-fold to 50-fold. In some embodiments, the immunoassays of the invention are capable of measuring hepcidin levels ranging from 0.01 ng/mL to 10 μg/mL.

Antibody pairs suitable for use in sandwich immunoassays include the following:

(1) when one antibody of the pair is an antibody binds to the ame epitope as antibody is 1S1, or competes with antibody 1S1 for binding to mature human hepcidin of SEQ ID NO: 9 by at least about 75%, 80%, 85%, 90% or more, a suitable second antibody may be:
- (a) an antibody that binds to the same epitope as antibody is 23F11, or competes wth antibody 23F11 for binding to mature human hepcidin of SEQ ID NO: 9 by at least about 75%, 80%, 85%, 90% or more; or
- (b) an antibody that binds to the same epitope as antibody is 15E1, or competes wth antibody 15E1 for binding to mature human hepcidin of SEQ ID NO: 9 by at least about 75%, 80%, 85%, 90% or more; or
- (c) an antibody that binds to the same epitope as antibody is 12B9, or competes wth antibody 12B9 for binding to mature human hepcidin of SEQ ID NO: 9 by at least about 75%, 80%, 85%, 90% or more;

(2) when one antibody of the pair is an antibody that binds to the same epitope as antibody 12B9 or competes with antibody 12B9 for binding to mature human hepcidin of SEQ ID NO: 9 by at least about 75%, 80%, 85%, 90% or more, a suitable second antibody may be:
- (a) an antibody that binds to the same epitope as antibody 18D8, or competes wth antibody 18D8 for binding to mature human hepcidin of SEQ ID NO: 9 by at least about 75%, 80%, 85%, 90% or more, or
- (b) an antibody that binds to the same epitope as antibody 19C1, or competes wth antibody 19C1 for binding to mature human hepcidin of SEQ ID NO: 9 by at least about 75%, 80%, 85%, 90% or more, or
- (c) an antibody that binds to the same epitope as antibody 19D12, or competes with antibody 19D12 for binding to mature human hepcidin of SEQ ID NO: 9 by at least about 75%, 80%, 85%, 90% or more, or
- (d) an antibody that binds to the same epitope as antibody 19H6, or competes with antibody 19H6 for binding to mature human hepcidin of SEQ ID NO: 9 by at least about 75%, 80%, 85%, 90% or more; or
- (e) an antibody that binds to the same epitope as antibody 1S1 or competes wth antibody 1S1 for binding to mature human hepcidin of SEQ ID NO: 9 by at least about 75%, 80%, 85%, 90% or more; or (3) when one antibody o the pair is an antibody that binds to the same epitope as antibody 23F11, or competes with antibody 23F11 for binding to mature human hepcidin of SEQ ID NO: 9 by at least about 75%, 80%, 85%, 90% or more, a suitable second antibody may be:
- (a) an antibody that binds to the same epitope as antibody 18D8, or competes wth antibody 18D8 for binding to mature human hepcidin of SEQ ID NO: 9 by at least about 75%, 80%, 85%, 90% or more, or
- (b) an antibody that binds to the same epitope as antibody 19C1, or competes wth antibody 19C1 for binding to mature human hepcidin of SEQ ID NO: 9 by at least about 75%, 80%, 85%, 90% or more, or
- (c) an antibody that binds to the same epitope as antibody 19D12, or competes with antibody 19D12 for binding to mature human hepcidin of SEQ ID NO: 9 by at least about 75%, 80%, 85%, 90% or more, or
- (d) an antibody that binds to the same epitope as antibody 19H6, or competes with antibody 19H6 for binding to mature human hepcidin of SEQ ID NO: 9 by at least about 75%, 80%, 85%, 90% or more; or
- (e) an antibody that binds to the same epitope as antibody 1S1 or competes wth antibody 4E1 for binding to mature human hepcidin of SEQ ID NO: 9 by at least about 75%, 80%, 85%, 90% or more; or
- (f) an antibody that binds to the same epitope as antibody 3B3 or competes wth antibody 3B3 for binding to mature human hepcidin of SEQ ID NO: 9 by at least about 75%, 80%, 85%, 90% or more;

(4) when one antibody of the pair is an antibody binds to the same epitope as antibody 15E1, or competes with antibody 15E1 for binding to mature human hepcidin of SEQ ID NO: 9 by at least about 75%, 80%, 85%, 90% or more, a suitable second antibody may be:
- (a) an antibody that binds to the same epitope as antibody 1S1, or competes wth antibody 1S1 for binding to mature human hepcidin of SEQ ID NO: 9 by at least about 75%, 80%, 85%, 90% or more.

In some embodiments, methods for monitoring the effectiveness of therapy with a hepcidin antagonist include monitoring changes in the level of hepcidin in a sample, or in an animal such as a human patient. Methods in which hepcidin levels are monitored may comprise (a) incubating a first biological sample, obtained from a patient prior to a therapy with one or more of the anti-hepcidin antibodies disclosed herein, wherein the incubation is performed under conditions and for a time sufficient to allow immunocomplexes to form; (b) detecting immunocomplexes formed between the hepcidin in the biological sample and antibodies or antigen binding fragments that specifically bind hepcidin; and optionally (c) repeating steps (a) and (b) using a second biological sample taken from the patient at later time, such as for example, following therapy with one or more of the anti-hepcidin antibodies disclosed herein; and (d) comparing the number of immunocomplexes detected in the first and second biological samples.

Other monitoring methods include measuring (a) the blood (e.g., serum or plasma) circulating level of complexes between hepcidin and the therapeutic agent, and optionally (b) the amount of free hepcidin present in circulation. For example, complexes between hepcidin and therapeutic antibody can be detected using an anti-human Fc antibody that binds to the therapeutic antibody part of the complex and an Fab fragment of a "pairing" anti-hepcidin antibody that binds to the hepcidin part of the complex. Alternatively, an anti-idiotypic antibody can be used in place of the anti-human Fc antibody. As another alternative, an anti-hepcidin antibody containing a non-human Fc (e.g. a human Fc is replaced with murine Fc) can be used in place of the Fab fragment.

As another example, free hepcidin can be detected after removing hepcidin-therapeutic antibody complexes from the biological sample, using either an anti-human Fc antibody or an anti-idiotypic antibody that has been immobilized on a solid support. The amount of free hepcidin which remains unbound to the solid support is then measured. This level of free hepcidin may reflect the effectiveness of the therapeutic antibody in removing available circulating hepcidin.

A biological sample for use within such methods may be any sample obtained from a patient that would be expected to contain hepcidin. Exemplary biological samples include blood, plasma, sera, urine and bone marrow. A first biological sample may be obtained prior to initiation of therapy or part way through a therapy regime. The second biological sample should be obtained in a similar manner, but at a time following additional therapy. The second biological sample may be obtained at the completion of, or part way through, therapy, provided that at least a portion of therapy takes place between the isolation of the first and second biological samples.

Incubation and detection procedures for both samples may generally be performed as described above. A decrease in the number of immunocomplexes in the second sample relative to the first sample indicates a decrease in hepcidin levels and reflects successful therapy. Free serum hepcidin may also be analyzed in a similar manner, and a decrease in free serum hepcidin indicates successful therapy.

Hepcidin-related disorders, inflammatory diseases, and diseases or disorders of iron homeostasis for which the diagnostic or monitoring methods may be useful include but are not limited to african iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pyelori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hepcidin deficiency, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

Methods of setting an appropriate threshold for diagnosis of the disease states described herein and prognostic monitoring as described herein are well known in the art. By way of example, levels of hepcidin in a fluid sample from a sufficient representative number of normal subjects (e.g. healthy population without the condition to be detected) are analyzed relative to the hepcidin level from a sufficient representative number of diseased subjects (e.g. population confirmed to have the disease or condition) using the same protocols. A threshold cutoff can be determined that differentiates most of the normal population from most of the diseased population. Alternatively, useful end point values for negative, uncertain and positive results can be determined from the data. For example, a normal range (indicative of a negative result) can be determined, which includes hepcidin of most of the normal population but which exclude almost all of the diseased population. Correspondingly, a range indicative of a positive result can be determined, which includes hepcidin of most of the diseased population but which exclude almost all of the normal population. Similarly, a threshold differentiating hepcidin levels in a population suffering from anemia of inflammation from hepcidin levels in a population suffering from iron deficiency anemia can be determined. Useful endpoint values may indicate that the patient is suffering from anemia of inflammation, iron deficiency anemia or mixed anemia. Appropriate endpoint values for the threshold may be determined to optimize the desired specificity or sensitivity, and may also take account of overall medical and epidemiological factors. Factors to be considered include the clinical objective of the laboratory test and whether it is necessary to have a high positive predictive value, or a high negative predictive value, as well as prevalence of the disease in the test population.

VII. Therapeutic Uses for Hepcidin Activity Antagonists

Also provided is the use of hepcidin activity antagonists, including monoclonal antibodies described herein that bind human hepcidin, to treat subjects in need thereof. In exemplary embodiments, the subject may be at risk of or suffering from an elevated level of hepcidin, a hepcidin-related disorder, a disorder of iron homeostasis, or anemia.

As used herein, "treatment" or "treat" refers to both prophylactic treatment of a subject at risk of, or having a predisposition toward, a disease or disorder, and to therapeutic treatment of a subject suffering from a disease or disorder.

Administration of a therapeutic agent in a prophylactic method can occur prior to the manifestation of symptoms of an undesired disease or disorder, such that the disease or disorder is prevented or, alternatively, delayed in its progression. Thus, when used in conjunction with prophylactic methods, the term "therapeutically effective" means that, after treatment, a fewer number of subjects (on average) develop the undesired disease or disorder or progress in severity of symptoms.

When used in conjunction with therapeutic methods involving administration of a therapeutic agent after the subject manifests symptoms of a disease or disorder, the term "therapeutically effective" means that, after treatment, one or more signs or symptoms of the disease or disorder is ameliorated or eliminated.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, a "hepcidin-related disorder" refers to a condition caused by or associated with an abnormal level of hepcidin (e.g., hepcidin excess or hepcidin deficiency relative to the degree of anemia or iron stored) which disrupts iron homeostasis. A disruption in iron homeostasis can in turn result in secondary diseases such as anemia. Acute or chronic inflammatory conditions can result in upregulation of hepcidin expression, which can result in decreased circulating iron levels, which can cause anemia or worsen existing anemia. Exemplary hepcidin-related inflammatory diseases include anemia of cancer, anemia of chronic disease, anemia of inflammation, chemotherapy-induced anemia, chronic kidney disease (stage I, II, III, IV or V), end stage renal disease, chronic renal failure congestive heart failure, cancer, rheumatoid arthritis, systemic lupus erythematosus, Crohn's disease, *H. pyelori* infection or other bacterial infections, hepatitis C, HIV, and other viral illnesses, arteriosclerosis, atherosclerosis, cirrhosis of the liver, pancreatitis, sepsis, vasculitis, iron-deficiency, hypochromic microcytic anemia and conditions with hepcidin excess.

As used herein, the phrase "disease (or disorder) of iron homeostasis" refers to a condition in which a subject's iron levels require modulation. It includes hepcidin-related disorders; conditions not associated with elevated levels of hepcidin that nevertheless would benefit from inhibition of hepcidin activity, such as a disruption in iron homeostasis not caused by hepcidin; diseases where aberrant iron absorption, recycling, metabolism or excretion causes a disruption in normal iron blood levels or tissue distribution; diseases where iron dysregulation is a consequence of another disease or condition, such as inflammation, cancer or chemotherapy; diseases or disorders resulting from abnormal iron blood levels or tissue distribution; and diseases or disorders that can be treated by modulating iron levels or distribution. Nonlimiting examples of such diseases or disorders of iron homeostasis, hepcidin-related disorders and inflammatory conditions which can result in hepcidin excess include african iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pyelori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease Non-inflammatory conditions which are implicated in a disruption of iron regulation include, but are not limited to, vitamin B6 deficiency, vitamin B12 deficiency, folate deficiency, pellagra, funicular myelosis, pseudoencephalitis, Parkinson's disease (Fasano et al., *J. Neurochem.* 96:909 (2006) and Kaur et al., *Ageing Res. Rev.*, 3:327 (2004)), Alzheimer's disease, coronary heart disease, osteopenia and osteoporosis (Guggenbuhl et al., *Osteoporos. Int.* 16:1809 (2005)), hemoglobinopathies and other disorders of red cell metabolism (Papanikolaou et al., *Blood* 105:4103 (2005)), and peripheral occlusive arterial disease.

Various other iron indices and their normal ranges of concentrations are listed in Table 2.

TABLE 2

| Iron Index | Normal Level (Range) |
|---|---|
| Serum iron | 50-170 µg/dL |
| Hemoglobin | 11.5-18 g/dL |
| Hematocrit | 37-54% |
| Red blood cell count (RBC) | $4.6$-$6.2 \times 10^{12}$ cells/L (men) |
|  | $4.25$-$5.4 \times 10^{12}$ cells/L (women) |
| Mean Corpuscular Hemoglobin (MCH) | 27-32 pg |
| Mean Corpuscular Hemoglobin Concentration (MCHC) | 32-36% |
| Mean Corpuscular Volume (MCV) | 80-96 fL |
| Red Cell Distribution Width (RDW) | 11.5-14.5% (electrical impedence method) or 10.2-11.8% (laser light method) |
| Reticulocyte count | $18$-$158 \times 10^9$ cells/L (0.8-2.5% in men; 0.8-4% in women) |
| Total Iron Binding Capacity (TIBC) | 250-450 µg/dL |
| Transferrin Iron Saturation Percentage (Tsat) | 15-50% |
| Ferritin | 12-120 µg/L |
| Folate | 3-16 ng/mL (serum) and 130-628 ng/mL (red blood cell) |
| Vitamin B12 | 200-900 pg/ml |

A patient's iron index level outside of the normal ranges listed in Table 2 indicates that the patient may benefit from treatment with a hepcidin activity antagonist. Since hepcidin plays a key role in iron homeostasis, hepcidin levels and activity will correlate to a disruption of iron homeostasis and/or iron indices. Elevated hepcidin levels correlate with serum iron levels below the normal ranges indicated in Table 2, low hemoglobin, and hematocrit, reduced or normal Tsat and high or normal ferritin values, and elevated inflammatory status as measured by C-reactive protein (CRP) elevation or other markers of inflammation.

As used herein, the phrase "therapeutically effective amount" of a hepcidin activity antagonist refers to an amount that results in the desired therapeutic effect (i.e. that provides "therapeutic efficacy"). Exemplary therapeutic effects include increased circulating iron levels or increased iron availability, increased red blood cell count, increased red blood cell mean cell volume, increased red blood cell hemoglobin content, increased hemoglobin (e.g., increased by ≥0.5 g/dL), increased hematocrit, increased Tsat, increased reticulocyte count, increased or normalized reticulocyte mean cell volume, increased reticulocyte hemoglobin content, or reduced free hepcidin levels in serum or plasma, or normalization of any of the parameters described above. Returning such a parameter to its normal range is not required for therapeutic efficacy; for example, a measurable change (increase or reduction) in the direction of normal can be considered to be a desired therapeutic effect by a clinician. When applied to an individual active ingredient, administered alone, the term refers to that ingredient alone. When applied to a combination, the term refers to combined amounts of the active ingredients that result in the therapeutic effect, whether administered in combination, serially or simultaneously. For example, in aspects where the hepcidin activity antagonist (or hepcidin expression inhibitor) is administered in conjunction with an enrythropoiesis stimulator, a therapeutically effective amount is meant to refer to the combined amount that increases or normalizes any of the parameters stated above.

In order to facilitate the diagnosis of patients, decision trees, such as that of FIG. 9B, can be used to interpret the level of the hepcidin, and which is used to assist the user or interpreter in determining a course of treatment and the significance of the concentration reading. Hepcidin values are predicted to be elevated in patients with inflammation iron overload and ferroportin disease and suppressed in patients with hemochromatosis, hemoglobinopathies, and other red cell disorders. The decision tree of FIG. 9B shows how measurement of hepcidin levels simplifies diagnosis and/or assessment of a patient suspected of having iron metabolism disorders. FIG. 9A shows the decision tree assessment without a measurement of hepcidin levels.

The compositions for and methods of treatment described herein may utilize one or more hepcidin activity antagonists (or hepcidin expression inhibitors) used singularly or in combination with other therapeutic agents to achieve the desired effects.

Combination Therapy

It may be further advantageous to mix two or more antibodies together (which bind to the same or different target antigens) or to co-administer an antibody of the invention with a second therapeutic agent to provide still improved efficacy. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In exemplary embodiments, the methods of the invention include the administration of single antibodies, as well as combinations, or "cocktails", of different antibodies. Such antibody cocktails may have certain advantages inasmuch as they contain antibodies which exploit different effector mechanisms. Such antibodies in combination may exhibit synergistic therapeutic effects.

Combination therapy using a hepcidin activity antagonist (or hepcidin expression inhibitor) and an erythropoiesis stimulator is specifically contemplated. In various embodiments, hepcidin activity antagonists (or hepcidin expression inhibitors) and erythropoiesis stimulators can be used to improve treatment of a patient with anemia. In particular, patients who are hypo-responsive to, including unresponsive to, erythropoiesis stimulator therapy, such as erythropoietin or analogs thereof (Epoetin alfa, Epoetin beta, darbepoetin alfa), among others, will benefit from co-treatment with a hepcidin activity antagonist or hepcidin expression inhibitor. In one embodiment, combination therapy includes treatment with at least one antibody that binds to human hepcidin and at least one erythropoiesis stimulator.

Combination therapy using a hepcidin activity antagonist (or hepcidin expression inhibitor) and an iron chelator to redistribute iron stores in the body is also contemplated. An iron chelator is an agent capable of binding iron and removing it from a tissue or from circulation. Examples include deferoxamine (Desferal®) and deferasirox (Exjade®), and deferiprone (1,2-dimethyl-3-hydroxypyridin-4-one). In some embodiments, hepcidin activity antagonists (or hepcidin expression inhibitors) and erythropoiesis stimulators can be used to improve treatment of a patient an iron loading disorder secondary to transfusion-dependent iron overload, or have an iron maldistribution disorder such as Friedreich's ataxia.

As used herein, "erythropoiesis stimulator" means a chemical compound that directly or indirectly causes activation of the erythropoietin receptor, for example, by binding to and causing dimerization of the receptor or by stimulating endogenous erythropoietin expression. Erythropoiesis stimulators include erythropoietin and variants, analogs, or derivatives thereof that bind to and activate erythropoietin receptor; antibodies that bind to erythropoietin receptor and activate the receptor; or peptides that bind to and activate erythropoietin receptor; or small organic chemical compounds, optionally less than about 1000 Daltons in molecular weight, that bind to and activate erythropoietin receptor. Erythropoiesis stimulators include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), mimetic antibodies and HIF inhibitors (see U.S. Patent Publication No. 2005/0020487, the disclosure of which is incorporated by reference in its entirety). Exemplary erythropoiesis stimulators include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; US 2006/0111279.

Erythropoietin includes, but is not limited to, a polypeptide comprising the amino acid sequence as set forth in SEQ ID NO: 72. Amino acids 1 through 165 of SEQ ID NO: 72 constitute the mature protein of any molecules designated as an epoetin, e.g., epoetin alfa, epoetin beta, epoetin delta, epoetin omega, epoetin iota, epoetin gamma, epoetin zeta, and the like. Additionally, an epoetin also includes any of the aforementioned epoetin which are chemically modified, e.g., with one or more water-soluble polymers such as, e.g., polyethylene glycol (including PEG-EPO-beta). Also contemplated are analogs of erythropoietin, with 65%, 70%, 75%, 80%, 85%, 90%, 91%, 92%, 93%, 94%, 95%, 96%, 97%, 98%, or 99% identity to SEQ. ID NO: 72 still retaining erythropoietic activity.

Exemplary sequences, manufacture, purification and use of recombinant human erythropoietin are described in a number of patent publications, including but not limited to Lin U.S. Pat. No. 4,703,008 and Lai et al. U.S. Pat. No. 4,667,016, each of which is incorporated herein by reference in its entirety. Darbepoetin is a hyperglycosylated erythropoietin analog having five changes in the amino acid sequence of rHuEPO which provide for two additional carbohydrate chains. More specifically, darbepoetin alfa contains two additional N-linked carbohydrate chains at amino acid residues 30 and 88 of SEQ ID NO: 72. Exemplary sequences, manufacture, purification and use of darbepoetin and other erythropoietin analogs are described in a number of patent publications, including Strickland et al., 91/05867, Elliott et al., WO 95/05465, Egrie et al., WO 00/24893, and Egrie et al. WO 01/81405, each of which is incorporated herein by reference in its entirety. Derivatives of naturally occurring or analog polypeptides include those which have been chemically modified, for example, to attach water soluble polymers (e.g., pegylated), radionuclides, or other diagnostic or targeting or therapeutic moieties.

The term "erythropoietic activity" means activity to stimulate erythropoiesis as demonstrated in an in vivo assay, for example, the exhypoxic polycythemic mouse assay. See, e.g., Cotes and Bangham, *Nature* 191:1065 (1961).

Administration and Preparation of Pharmaceutical Formulations

In some embodiments, the hepcidin activity antagonists or antibodies used in the practice of a method of the invention may be formulated into pharmaceutical compositions comprising a carrier suitable for the desired delivery method. Suitable carriers include any material which, when combined with a hepcidin activity antagonist or antibody, retains the high-affinity binding of hepcidin and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antibody concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antibody, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated antibody and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the hepcidin activity antagonist or antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5-5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. In some embodiments, the compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In some embodiments, the formulations of the invention may be designed to be short-acting, fast-releasing, long-acting, or sustained-releasing as described herein. Thus, the pharmaceutical formulations may also be formulated for controlled release or for slow release.

Therapeutically effective amounts of a composition will vary and depend on the severity of the disease and the weight and general state of the subject being treated, but generally range from about 1.0 µg/kg to about 100 mg/kg body weight, or about 10 µg/kg to about 30 mg/kg, or about 0.1 mg/kg to about 10 mg/kg or about 1 mg/kg to about 10 mg/kg per application. Administration can be daily, on alternating days, weekly, twice a month, monthly or more or less frequently, as necessary depending on the response to the disorder or condition and the subject's tolerance of the therapy. Maintenance dosages over a longer period of time, such as 4, 5, 6, 7, 8, 10 or 12 weeks or longer may be needed until a desired suppression of disorder symptoms occurs, and dosages may be adjusted as necessary. The progress of this therapy is easily monitored by conventional techniques and assays.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The hepcidin activity antagonist or antibody is administered by any suitable means, either systemically or locally, including via parenteral, subcutaneous, intraperitoneal, intrapulmonary, and intranasal, and, if desired for local treatment, intralesional administration. Parenteral routes include intravenous, intraarterial, intraperitoneal, epidural, intrathecal administration. In addition, the specific binding agent or antibody is suitably administered by pulse infusion, particularly with declining doses of the specific binding agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. In some embodiments, the specific binding agent or antibody of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

VIII. Diagnostic and Therapeutic Kits

As a matter of convenience, an antibody disclosed herein can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic reagents and kits comprising one or more such reagents for use in a variety of diagnostic assays, including for example, immunoassays such as ELISA (sandwich-type or competitive format). In some embodiments, such kits may include at least a first peptide (optionally a properly folded mature hepcidin standard as described herein), or a first antibody or antigen binding fragment of the invention, a functional fragment thereof, or a cocktail thereof, and means for signal generation. The kit's components may be pre-attached to a solid support, or may be applied to the surface of a solid support when the kit is used. In some embodiment, the signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. Preferably, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising a hepcidin activity antagonist (or hepcidin expression inhibitor) and an erythropoiesis stimulator packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating a disorder associated with elevated hepcidin levels and comprises a hepcidin activity antagonist (or hepcidin expression inhibitor) and an erythropoiesis stimulator. The kit may optionally further include iron for oral or parenteral, e.g. intravenous, administration. In another aspect, the kit comprises a hepcidin activity antagonist (or hepcidin expression inhibitor) and a label attached to or packaged with the container describing use of the hepcidin activity antagonist (or hepcidin expression inhibitor) with an erythropoiesis stimulator. In yet another aspect, the kit comprises an erythropoiesis stimulator and a label attached to or packaged with the container describing use of the erythropoiesis stimulator with a hepcidin activity antagonist (or hepcidin expression inhibitor). In certain embodiments, a hepcidin activity antagonist (or hepcidin expression inhibitor) and an erythropoiesis stimulator, and optionally the iron, are in separate vials or are combined together in the same pharmaceutical composition. In yet another aspect, a hepcidin activity antagonist (or hepcidin expression inhibitor) is combined with iron in a single pharmaceutical composition. In yet another embodiment, the erythropoiesis stimulator is combined with iron in a single pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and diagnostic kits disclosed herein may also be prepared that comprise at least one of the antibody, peptide, antigen binding fragment, or polynucleotide disclosed herein and instructions for using the composition as a diagnostic reagent or therapeutic agent. Containers for use in such kits may typically comprise at least one vial, test tube, flask, bottle, syringe or other suitable container, into which one or more of the diagnostic and/or therapeutic composition(s) may be placed, and preferably suitably aliquoted. Where a second therapeutic agent is also provided, the kit may also contain a second distinct container into which this second diagnostic and/or therapeutic composition may be placed. Alternatively, a plurality of compounds may be prepared in a single pharmaceutical composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the diagnostic or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In related embodiments, also provided is a processor, a computer readable memory, and a routine stored on the computer readable memory and adapted to be executed on the processor to perform any of the methods described herein, and/or to generate as output the detected level of hepcidin and a threshold or range of threshold levels considered "normal", such that levels outside the "normal" range correlate with one or more of the conditions as described herein. In some embodiments, the invention further provides computer readable media containing programs or routines to perform similar functions. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

Non-Therapeutic Uses for Hepcidin Activity Antagonists

The antibodies disclosed herein may be used as affinity purification agents for target antigen or in diagnostic assays for target antigen, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the site can be localized using immunoscintiography.

The antibodies disclosed herein may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label cell samples using methods known in the art.

EXAMPLES

Example 1

Purification of Hepcidin from Urine

Purification: Human hepcidin was isolated from urine of sepsis patients (S. aureus and S. peumoniae infected, obtained commercially and purified using methods that are described by Park et al., Journal Biol. Chem., 276:7806-7810, 2001). Briefly, approximately 2 L of frozen urine were thawed and filtered through 0.45 and 0.22 µ filters and loaded onto a 10 mL bed volume CM macroprep (BioRad) column and equilibrated with PBS at a flow rate of 80 mL per hour. The column was washed with PBS until the OD280 of the eluent was less than 0.1. Hepcidin was eluted with 5% acetic acid in water. Because the eluent contained several other peptides, the material was further purified by RP-HPLC (C18) using a gradient of acetonitrile containing 0.1% TFA versus 0.1% aqueous TFA. HPLC fractions containing hepcidin were analyzed by mass spectrometry.

Peptide Quantification: CLND analyses were performed on an Agilent 1100 high-performance liquid chromatography (HPLC) system with a model 7000 CLND nitrogen-specific detector from Antek Instruments (Houston, Tex., USA)16. Chromatographic separations were achieved on an Agilent C3 reversed phase column (5 µm, 0.2 cm×5 cm) using linear gradients of buffer B versus A (A=0.04% aqueous TFA; B=MeOH containing 0.04% TFA), 0-80% B over 14 min at a flow rate of 0.5 mL/min. CLND conditions were 1050° C. pyrolysis temperature, PMT voltage 700 V, range 25 X, and detector output of 1 V; UV absorbance detection at 214 nm. A CLND response calibration curve was prepared with caffeine standards (99%, Sigma-Aldrich) dissolved in DMSO (Standards: 8, 80, 160, 320, 640, 1280, 1920 and 4480 nanograms (ng) equivalent of nitrogen). Hepcidin samples were dissolved in known volume of (50% MeOH/H2O) and the concentration determined by mathematical correlation of the CLND response with the hepcidin injection volume and nitrogen-count. This method was used for quantification of all subsequent hepcidin preparation methods.

Example 2

CHO-Derived Recombinant Human Hepcidin (rhHepc) Expression and Purification

Human hepcidin was stably expressed by transfection of AM-1/cyclin D Chinese hamster ovary (AM-1/D CHO) cells (see U.S. Pat. No. 6,210,924, incorporated herein by reference in its entirety) with DNA comprising SEQ ID NO: 101, which encodes human prohepcidin (SEQ ID NO: 102). Transfection was performed using Lipofectamine™ 2000 (LF2000) Reagent (Invitrogen Corporation, Carlsbad, Calif.) according to the manufacturer's suggestions. Briefly, 4×106 AM-1/D CHO cells were plated 24 hours prior to transfection in 100-mm diameter plastic BD-Falcon™ Petri dishes (BD Biosciences, Bedford, Mass.,) in 10 mL of Dulbecco's Modified Eagles Medium (D-MEM, Invitrogen) supplemented with 5% fetal bovine serum, 1× penicillin-streptomycin, and glutamine (Invitrogen), non-essential amino acids (Invitrogen), sodium pyruvate, and sodium hypoxanthine/thymidine (HT) supplement (Invitrogen). Approximately 30 µg of human prohepcidin plasmid DNA was linearized using the restriction enzyme Pvu I (New England Biolabs, Inc., Ipswich, Mass.) and diluted in 2 mL of OptiMEM (Invitrogen). The diluted DNAs were mixed with 75 µL of LF2000 diluted in 2 mL of OptiMEM, and the mixture was incubated for 20 minutes at room temperature. The DNA-LF2000 mixture was added to the cells and incubated overnight for transfection. The following day, fresh growth medium was added and cells were cultured for 48 hours at 37° C. with 5% CO2, and then plated in HT selection medium at 1:20 and 1:50 dilutions.

Approximately 2 weeks after transfection, surviving cells were single cell cloned into a 96 well plate by limiting dilution. Expression of hepcidin by the clones was determined using an anti-prohepcidin polyclonal antibody. Based on Western analysis we expanded clone 118-34 for large scale production. Approximately 2-3×10⁷ cells were used to seed one Corning® CellBIND® 850 cm2 polystyrene roller bottle (Corning Incorporated, Corning, N.Y.), and cells were subsequently expanded 1:10. Each roller bottle was inoculated with 250 mL of high-glucose DMEM, 10% dialyzed fetal bovine serum (FBS), 1× glutamine, 1× non-essential amino acids, and 1× sodium pyruvate (all from Invitrogen). Ten percent $CO_2$/balance air was bubbled into the medium for 2-3 seconds before each roller bottle was capped. Roller bottles were incubated at 37° C. on roller racks spinning at 0.75 revolutions per minute (rpm). When the cells were approximately 85-90% confluent (after approximately 5-6 days in culture), the growth medium was discarded, and the cells were washed with 100 mL phosphate-buffered saline (PBS) and 200 mL production medium, consisting of 50% D-MEM/ 50% Ham's F12, 1× glutamine, 1× non-essential amino acids, 1× sodium pyruvate (all from Invitrogen), and 1.5% dimethyl sulfoxide (Sigma-Aldrich, St. Louis, Mo.). The conditioned medium containing human hepcidin was harvested every 7 days and then filtered through a 0.45/0.1 μm cellulose acetate filter (Corning Incorporated) onto a 10 ml bed volume CM macroprep (BioRad) column and equilibrated with PBS at a flow rate of 80 ml per hour. The column was washed with PBS until the $OD_{280}$ of elute was less than 0.1. Hepcidin was eluted with 5% acetic acid in water. CM fractions were assayed by analytical RP-HPLC (C4 column). rhHepc 25, rhHepc 24, rhHepc 22, rhHepc 21, rhHepc 27 and rhHepc 24 with one internal clip were detected. The CM pool was loaded onto a semi-prep C4 Vydac column (10×250 mm). The fractions were collected and assayed by analytical RP-HPLC/MS. rhHepc 25 fractions were pooled according to proper mass and retention time.

Example 3

E. coli Derived Recombinant Human Hepcidin Expression and Refolding

DNA comprising SEQ ID NO: 101, which encodes human prohepcidin (SEQ ID NO: 102) was expressed in E. coli. After culturing, cells were harvested by centrifugation, lysed by microfluidizer, and washed. Inclusion bodies from the E. coli paste were solubilized with a weight to volume ratio of 1:10 in 6M guanidine hydrochloride, 50 mM Tris-HCl, 6 mM DTT, pH 8.5 for 1 hour at room temperature. The mixture was then diluted 1:25 into 2M urea, 50 mM Tris-HCl, 160 mM arginine, 3 mM cysteine, pH 8.5 at 4° C., stirring for 3-4 days. This solution was clarified by 0.45 μM filtration and brought to 5 mM citrate before lowering the pH to 3.0 using concentrated HCl. A ten-fold concentration was performed with a 3 MWCO membrane and buffer exchanged with 2M urea, 5 mM citric acid, pH 3.0. The mixture was again clarified by centrifugation and adjusted to pH 4.5 with NaOH before S-HP column loading. The column was run in 20 mM sodium acetate, 250 mM NaCl, 2M urea, pH 4.5. A gradient up to 750 mM NaCl was run whilst assaying the fractions by RP-MS and pooled according to expected mass and retention time. The pro-region of the protein was enzymatically cleaved by incubation with Kex protease, achieved by addition of 3 mU protease per mg prohepcidin. The mixture was incubated for 1.5 hrs at room temperature in a buffer comprising 30 mM TRIS pH 7.0 and 5 mM $CaCl_2$. The pool was again purified using reverse-phase HPLC.

Example 4

Chemical Synthesis of Hepcidin, Purification and Characterization

The human hepcidin peptide sequence, hydrogen-DTHF-PICIFCCGCCHRSKCGMCCKT-free acid, SEQ ID NO: 9, was chemically synthesized using an ABI433 synthesizer (Applied Biosystems, Foster City, Calif.) employing a $N^\alpha$-Fmoc/side-chain ᵗBu orthogonal protection strategy with 1.0 M N,N'-dicyclohexylcarbodiimide (DCC)/1-hydroxybenzotriazole hydrate (HOBT) (1:1) coupling chemistry in N-methyl-pyrrolidone (NMP) and 20% (v/v) piperidine/NMP deprotection chemistry (E. Atherton and R. C. Sheppard, *Solid Phase Peptide Synthesis: A Practical Approach*, IRL Press, Oxford, 1989). Single amino acid coupling cycles at 1 mmol scale were used for the synthesis, and consisted of 58 minute coupling times and 3+15 minute Fmoc-deprotection times. Fmoc-Thr(ᵗBu)-Wang resin (0.12 mmol equiv scale, Novabiochem) was used for the synthesis. The following side-chain protection strategy was used with $N^\alpha$-Fmoc-protected amino acids (Novabiochem): Asp(ᵗBu), Asn(Trt), Gln (Trt), Thr(ᵗBu), His(Trt), Cys(Trt), Arg(Pbf), Ser(ᵗBu) and Lys(Boc). Following on-resin chain-assembly and removal of the N-terminal Fmoc group, the side-chain protected and resin-bound human hepcidin peptide derivative was washed with dichloromethane (DCM) and dried. Side-chain deprotection and cleavage from the solid-support was achieved by treatment with a freshly prepared mixture of trifluoroacetic acid (TFA)/$H_2O$/triisopropylsilane (TIS)/3,6-dioxa-1,8-octane-dithiol (DODT) (92.5:2.5:2.5:2.5 v/v) in a total volume of 20 mL with slow stirring typically for 2 to 3 h. The solution was filtered to remove the polymeric solid-support and then evaporated. The residue was treated with ice-cold diethyl ether (50 mL) and the precipitated peptide collected by centrifugation (10 min at 2,000 rpm), the ether solution was then decanted, and the peptide was dried in vacuo.

The dried peptide was reconstituted in neat TFA (2 mL) with stirring and sonication, and then diluted dropwise with stirring into a fresh buffered solution (100 mL) prepared by the 1:1 combination of 6M guanidine pH 4.5 and 6M guanidine/0.5M Tris/20 mM EDTA pH 8.5. Tris(2-carboxyethyl) phosphine hydrochloride (TCEP, 1 mmol) was added to the solution and stirred for 2 h. The reduced human hepcidin containing solution was then loaded onto a Phenomenex Jupiter 10 μm 300 Å $C_{18}$ 250×21.2 mm column for preparative purification. Chromatographic separations were achieved using linear gradients of acetonitrile containing 0.1% TFA versus 0.1% aqueous TFA. The elution gradient method was 10-25% B in 15 min followed by 25-40% B in 30 min at a flow rate 20 mL/min. Fractions containing the expected molecular mass of reduced human hepcidin and <30% of any other mass detectable impurity were identified by LC/MS analysis using a Waters Acquity UPLC-LCT Premier system (Z-spray ionization coupled time-of-flight (TOF) mass spectrometer; column: Agilent Eclipse XDB-$C_{18}$ 2.1×50 mm, 1.8 μm) and pooled. Retention time $(R_t)$=5.27 min; $C_{113}H_{178}N_{34}O_{31}S_9$, calculated molecular weight=2795.09 Da (monoisotopic); experimental observed molecular weight 2795.70 Da. The pooled fractions were then diluted to 1 L with water and acetonitrile to give an approximate final acetonitrile composition of 25% (v/v). Disulfide bond formation was carried out for 16-24 hours in the presence of a glutathione/glutathione disulfide (GSH/GSSG) redox system (300 mg GSSG and 152 mg GSH) at pH 8.0~8.3 (solution adjusted with 28-30%

NH$_4$OH, Baker) with 50-60 RPM stirring. The progress of disulfide bond formation was monitored by analytical LC/MS.

After 16-24 hours folding, the human hepcidin containing solution was then adjusted to pH 2 with neat TFA and the acetonitrile solvent component was evaporated. The crude folding solution containing human hepcidin was then loaded onto a Phenomenex Jupiter 10 μm, 300 Å, C$_{18}$, 250×21.2 mm column for preparative purification. The elution linear gradient method was 10-25% buffer B in 15 min followed by 25-35% buffer B in 40 min at a flow rate 20 mL/min. Fractions were analyzed by LC/MS on a Waters Acquity UPLC-LCT Premier system, and fractions containing >95% human hepcidin were pooled and lyophilized. Fractions containing material of a molecular weight corresponding to folded human hepcidin but with poor LC purity (50-95%) were pooled, lyophilized, re-suspended in TFA-free 30% acetonitrile/water (to a concentration of approximately 0.1 mg peptide/mL), adjusted to pH 7.5-8.0 with saturated ammonium carbonate, and left for 24 hours. Semi-preparative scale purification of this second human hepcidin pool was performed using a Phenomenex Jupiter 10 μm, 300 Å, C$_{18}$, 250×10 mm column at 5 mL/min, and fractions containing >95% human hepcidin were pooled and lyophilized. The total yield of human hepcidin was 35 mg. Retention time (R$_t$)=5.05 min; C$_{113}$H$_{170}$N$_{34}$O$_{31}$S$_9$, calculated molecular weight=2787.03 Da (monoisotopic); experimental observed molecular weight 2787.70 Da. The disulfide connectivity of chemically synthesized human hepcidin was determined by reductive alkylation-peptide mapping methodologies as well as by Fourier-transform ion cyclotron resonance mass spectrometry analysis.

Example 5

Analysis and Comparison of Synthetic, Recombinant and Urinary Hepcidins

To demonstrate the equivalence of natural, recombinant and synthetic material, human hepcidin purified from urine as set forth in Example 1 was compared against CHO-derived recombinantly-generated material (Example 2), E. coli derived recombinantly-generated material (Example 3) and chemically-synthesized material (Example 4). IRMPD fragmentation spectra were compared (FIG. 1). Although direct sequence assignment is not possible for all of the observed fragments, the MS/MS fingerprints of all samples were identical. The samples were also dissociated by collisionally-activated dissociation (CAD), as well as ECD and the spectra were consistent for all preparations. Even small changes in the structure of biomolecular ions can profoundly alter their tandem mass spectra. Therefore, the equivalence of all four hepcidin preparations by these distinct dissociation techniques indicates that the disulfide connectivity is identical for all four forms of hepcidin analyzed.

Figure 2:
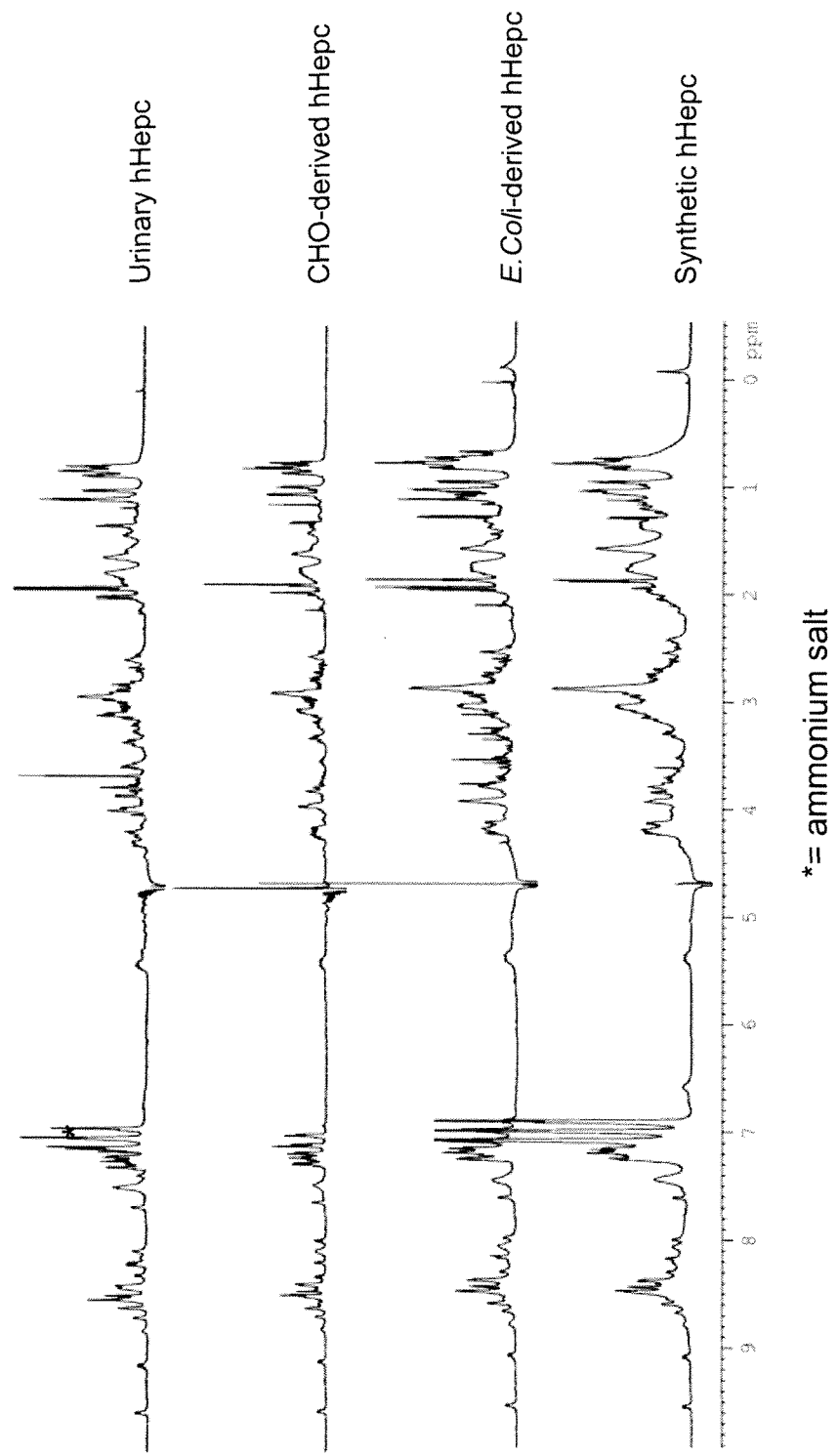
FIG. 2 shows 1D $^1$H NMR spectra of the four preparations of human hepcidin demonstrating equivalence of all three synthetic and recombinant preparations to urinary hepcidin.

The one-dimensional $^1$H NMR spectra of all four hepcidin preparations were also compared in FIG. 2 and supported that all preparations are equivalent. Methods used are stated in Example 2. Small differences in the ID spectrum of uhHepc are due to the slight pH and salt mismatch between the samples; this has the most pronounced effect on the histidine ring proton resonances and on the resonances from two flanking threonine residues which are in close proximity to the carboxyl groups, and are involved in different conformational forms. Some samples show small peaks from a minor form which has the proline residue in a cis conformation. The CHO-derived rhHepc contains small amounts (<5%) of the 24-residue peptide where the N-terminal aspartic acid has been enzymatically cleaved during the purification process.

The structural identity of synthetic, recombinantly expressed and natural hepcidin allows the production of large batches of correctly-folded manufactured material for antibody generation and testing.

Example 6

In Vitro Hepcidin Activity Ferritin Assay

Human hepcidin purified or produced according to Examples 1, 2, 3 and 4 was assayed for iron-regulating bioactivity in an in vitro cellular assay. Ferroportin expressed inducibly in 293 cells stimulates iron export and lowers intracellular iron and hence ferritin levels (Nemeth et al., Science, 306:2090-2093, 2004). The action of ferroportin can be reduced in a dose-dependent manner by hepcidin treatment. This action has been shown to be due to hepcidin-induced internalization and degradation of ferroportin and hence a reduction in iron export.

293 cells expressing a tetracycline-inducible ferroportin gene were plated at 50,000 cells per well (70-80% density) in a 96 well BioCoat poly-D Lysine-coated plate in DMEM supplemented with 5% fetal bovine serum and a penicillin/streptomycin/glutamine supplement (Gibco BRL). After an overnight incubation at 37° C. with 5% CO2, the medium was replaced with assay medium (as above, but supplemented with 2.5 μg/ml doxycycline for hepcidin induction, 2.5 μg/ml iron citrate for iron supplemented wells and 1 μg/ml hepcidin for hepcidin treatment wells). The plate was further incubated for 17-20 hours as above before washing the wells in cold PBS and lysing in 120 μl of 1% Triton lysis buffer on ice for 15 minutes. 100 μl of lysates were used for ferritin analysis (Olympus AU400 clinical chemistry analyzer) and 10 μl for BCA protein assay (Pierce). Ferritin results were normalized for protein content.

Treating the cells with either urinary, recombinant or synthetic hepcidin produced an increase in iron retention, indicating that all three preparations were biologically active. Since all three preparations exhibited the same disulfide connectivity and biological activity, they can be regarded as equivalent, allowing the use of synthetic and recombinant preparations for antibody production and testing.

Example 7

Disulfide Mapping of Urinary Hepcidin by Partial Reductive Alkylation

The disulfide connectivity of endogenous human hepcidin peptide purified from urine was investigated with two different techniques, NEM partial reductive-alkylation and fourier-transform mass spectroscopy (FT-MS).

Briefly, human hepcidin was purified from urine of sepsis patients as described below. Partial reduction with 3 mM TCEP allowed the step-wise reduction of disulfides in hepcidin over time. Disulfides which have been chemically reduced by TCEP treatment are susceptible to alkylation by NEM, and the NEM-alkylated cysteines can be identified by sequence analysis of the peptide. This technique demonstrated that the disulfide connectivity of hepcidin is different from that inferred by Hunter et al., supra. The directly determined hepcidin disulfide connectivity, C1-C8, C2-C4, C3-C6 and C5-C7, gives a compact and tightly folded molecule.

Method: Purified hepcidin (20-30 μg) was dissolved in 0.1M citrate buffer (100 ul), pH3.0, or 0.1% TFA (100 ul)(pH 2.0) and treated with 3 μl of 0.1M tris-(2-carboxyethyl)phosphine hydrochloride (TCEP). The final concentration of TCEP was 3 mM. Reduction was allowed to proceed for 8 min at 37° C. The partially reduced hepcidin was immediately treated with 20 μl of 0.5M NEM, followed by the addition of 30 μl of 1M Tris buffer (pH 7.0) and 100 μl 8M guanidinium hydrochloride. The pH of the solution was maintained below 6 to prevent disulfide rearrangement. The NEM-alkylation was performed at room temperature for 20 min. The reactant was directly subjected to reversed phase HPLC using a Vydac C18 column (2.1×150 mm) to purify the alkylated peptides. The NEM-modified peptides were eluted with a linear gradient from 25% B to 50% B over 30 min, using 0.1% TFA for solvent A and 90% acetonitrile-0.1% TFA for solvent B at a flow rate of 0.25 ml per min. NEM-derivatives were collected, dried and analyzed by MALDI mass spectrometry after dissolving in 15 μl of 0.2% TFA-50% acetonitrile. One aliquot of the sample was loaded on to a stainless steel plate or gold plate and co-crystallized with matrix α-cyano-4 hydroxycinnamic acid (4-HCCA). MALDI mass spectra were acquired on a Voyager DE-STR time-of-flight mass spectrometer (Perkin-ElmerBiosystems Inc.) equipped with a 337-nm nitrogen laser. The measurements were made in linear mode with the accelerating voltage set typically to 25000V with the grid voltage at 95%, guide wire at 0.05%, and extraction delay time at 150 ns. Time-of-flight to mass conversion was achieved by external calibration using a standard of an oxidized insulin B chain (MH+=3496.96).

From various NEM derivatives, the 2-NEM-Cys containing derivative was selected to determine the preferentially reduced cysteines and the sequence analysis was performed on the further reduced sample as follows: the 2-NEM-derivative was dissolved in 20 μl of 0.05% TEA and reduced with 0.5 μl of 2-mercaptoethanol at 45° C. for 20 min. The sample was directly subjected to peptide sequencing. An NEM-labeled cysteine appeared as double peaks between PTH-Pro and PTH-Met due to the isomeric forms. Both peaks were integrated for quantification of the NEM-Cys. The fractions containing 4 to 6 NEM-derivatives of hepcidin were combined, and proteolytically digested. The dried sample was again reconstituted in 0.1M Tris buffer, pH 6.6, and was digested with thermolysin (1 μg). The digestion was allowed to proceed overnight at 37° C. The sample was subjected to reversed phase HPLC using a Vydac C18 column (2.1×150 mm). Peptides were purified with a linear gradient from 2% B to 35% B for 30 min, and were finally washed with 60% B. The thermolytic peptides were dried and reconstituted in 0.2% TFA-50% acetonitrile (15 μl). One aliquot (1 μl) of the sample was loaded onto the plate and dried. Above matrix 4-HCCA was added and crystallized for MALDI mass spectrometry. The remaining samples were sequenced to determine the sites of the NEM-labeling.

Tandem Mass Spectrometry (FTMS method): All FTMS (Fourier-transformed mass spectrometry) data were acquired on a modified Bruker Q-FTMS operating at 7 Tesla. The instrument has been equipped with a cathode electron filament placed in the fringing field of the magnetic field, ~0.3 m from the back trapping plate of the ion cell. The instrument was externally calibrated with a PEG300/600 solution using the standard Francel equation. The calculated mass error for each calibrant ion was less than 1.0 ppm from the measured value. Individual ions were isolated using the front end quadrupole; ions were trapped in the FTMS cell employing gas-assisted dynamic trapping with Argon as the collision gas.

For IRMPD (Infrared Multi-Photon dissociation) experiments a Synrad CO2 laser was turned on for 200 ms at a laser power of 15% -40%. Ions were detected with direct mode detection at an acquisition bandwidth of 900 kHz and 512 K data points were collected. The time domain signal was zero-filled once and apodized using a sine window prior to performing a magnitude mode Fourier Transform.

For ECD (Electron Capture Dissociation) tandem MS experiments the electron filament was heated with 1.8 A (8.5 V). A+0.5 V bias was applied to the filament relative the voltage on the trapping plates. For MS3 experiments, after IRMPD the daughter ion of interest was isolated with a CHEF chirp pulse, with a notch at the RF amplitude corresponding to the cyclotron frequency of the ion of interest. The isolated daughter ion was further fragmented by "low energy" ECD; Argon gas was pulsed into the ion cell at the start of electron irradiation.

Results: Hepcidin was partially reduced with TCEP at pH 2, resulting in the primary reduction (cleavage) of only one disulfide bond and forming two closely-eluting peaks, both corresponding in molecular weight to a 2NEM alkylated product (designated 2a and 2b, FIG. 3A). In order to determine the NEM labeling sites in peaks 2a and 2b, purified peptides were sequenced by Edman degradation. Detection of PTH-NEM-cysteine at position C5 demonstrated that this residue was reduced and alkylated. Alkylation of C7 was also seen, but C8 also appeared to be alkylated. Sequence carry-over, a well-known phenomenon often conferring a false positive signal to the residue after a labeled residue (particularly in a longer sequenced product), was a significant obstacle in this analysis presumably due to the high cysteine and proline content of hepcidin (Grant et al., Meth. Emzymol., 289:395-419, 1997; Hunkapiller et al., Methods in protien sequence analysis. Clifton, N.J.: Humana Press; 1982). To verify the second NEM-labeling site, the sequenced sample was treated with cyanogen bromide (CNBr) on glass fiber filter and sequenced again. The results showed that C7 (and not C8) was significantly alkylated by NEM. Thus, it was concluded that C5 and C7 were the major alkylated species and hence a C5-C7 bond had existed prior to reduction. C4 was completely unlabeled in peak 2a, indicating that there was no C4-C5 linkage present in the major species of endogenous human hepcidin.

A similar analysis was conducted on peak 2b. C2 was clearly identified as the first NEM alkylated site with both C4 and C5 having a significant amount of alkylated product detected. The presence of alkylation in the C5 position was judged to be caused by the carry-over phenomenon described above. The possibility of C2-C5 linkage was eliminated by previous data showing that no C2-C5 or C4-C5 linkage is seen. These results are consistent with the fact that if a disulfide linkage between the adjacent cysteines C4 and C5 is present in an endogenous hepcidin preparation, it would have to be present at a concentration too low to be detected. This data indicated that C2 and C4 were the major NEM-alkylated forms thereby indicating a C2-C4 disulfide connectivity.

In order to reduce more disulfide bonds, the sample was further treated with 3 mM TCEP at pH 3. The MALDI mass spectral analysis indicated that the major peaks in the chromatogram correspond to 4-, 6-, and 8-NEM alkylated products respectively (FIG. 3B). The partially reduced and alkylated 4- and 6-NEM products still contained intact disulfide bonds whereas the 8-NEM product was a fully alkylated form and hence not useful for analysis. In order to determine the remaining disulfides, these 4-and 6-NEM derivatives were combined and further digested with thermolysin at pH 6.6 (maintained below pH7 to prevent disulfide rearrangement and thus allowing isolation of fragments still containing disulfide bonds, or peptides joined together by a disulfide bond). Partially-alkylated peptide fragments were identified by Edman sequencing. Cysteine pairs identified in the isolated peptide fragments which were not NEM labeled still involved in disulfide bond formation after alkylation. Peptide Th-1 showed two sequences corresponding to IC (residues 6-7 of SEQ ID NO: 9) and GMCCKT (residues 20-25 of SEQ ID NO: 9). Residue 22 (C7) was shown to be NEM-labeled and hence was not involved in the disulfide bridge connecting both peptides. Residues 7 and 23 (C1 and C8) were both unlabelled, indicating that the linkage between the two peptides was C1-C8. Peptide Th-2 showed a single sequence (IFCCGCCHRSKC; residues 8-19 of SEQ ID NO: 9), in which residues 10, 13, and 14 (C2, C4 and C5) were modified with NEM and hence not connected by a disulfide. Residues 11 and 19 (C3 and C6) were detected as unmodified cysteine. Because a monomeric peptide was isolated, the possibility of an inter-peptide disulfide linkage was eliminated and the presence of a C3-C6 disulfide bond was indicated. MALDI analysis of these peptides supported these assignments.

FTMS analysis of partial reductive alkylation peptide products also confirmed the disulfide connectivity and is not susceptible to the carryover phenomenon seen by Ednam degradation.

Figure 6:
FIG. 6 is a schematic of human hepcidin polypeptide indicating the various disulfide bonds determined by two partial alkylative reduction techniques and confirmed by NMR.

FIG. 6 shows a composite disulfide connectivity assignment generated from all NEM partial alkylation analyses, demonstrating that in human urinary hepcidin, the native disulfide connectivity is C1-C8, C2-C4, C3-C6 and C5-C7.

FTMS was also employed to assess disulfide connectivity. The resulting spectrum was complex, and direct sequence assignment was difficult since a standard b/y ion series was not directly observed. This was presumably due to the four intact disulfide bonds in the peptide. Several assignments can be postulated based on exact mass measurements. For example, a doubly charged ion is observed at m/z 698.7794, corresponding to a neutral mass of 1395.5443 Da. This exact mass suggests that this fragment contains two internal fragments of the peptide (DTHFPIC, residues 1-7 of SEQ ID NO: 9 and MCCKT, residues 21-25 of SEQ ID NO: 9) joined by a single disulfide bond. The theoretical monoisotopic mass of this fragment is 1395.5444 (0.1 ppm mass agreement). No other fragment ion can be postulated (without internal rearrangements) that agree with this mass to better than 10 ppm. The formation of internal fragment ions are not typically observed with low energy fragmentation methods such as IRMPD. Observation of these internal fragments is presumably facilitated by the cyclic structure induced by the four disulfide bonds in the intact molecule which appears to cause a novel fragmentation process. These internal fragments were not observed in IRMPD spectra of the fully disulfide reduced material.

A subsequent low energy ECD MS3 experiment exhibited a doubly charged daughter ion of m/z 698.7794. The primary fragments observed in this MS3 spectrum were two singly charged ions of m/z 831.3585 and 550.212, corresponding to the two internal fragments DTHFPIC, residues 1-7 of SEQ ID NO: 9, and MCCKT, residues 21-25 of SEQ ID NO: 9, respectively. Lower intensity ions corresponding to loss of an SH group were also observed. These assignments imply that these two peptide regions are connected by a disulfide bond in the intact structure; indicating C1 is connected to either C7 or C8.

Similar MS3 experiments were performed on most of the abundant multiply charged ions in the IRMPD spectra. From exact mass measurements the MS3 fragments were assigned as the internal peptides CHRSK (residues 14-18 of SEQ ID NO: 9) and MCC (residues 21-23 of SEQ ID NO: 9) implying that these peptides are connected by a disulfide in the intact molecule as shown in FIG. 6

Figure 7:
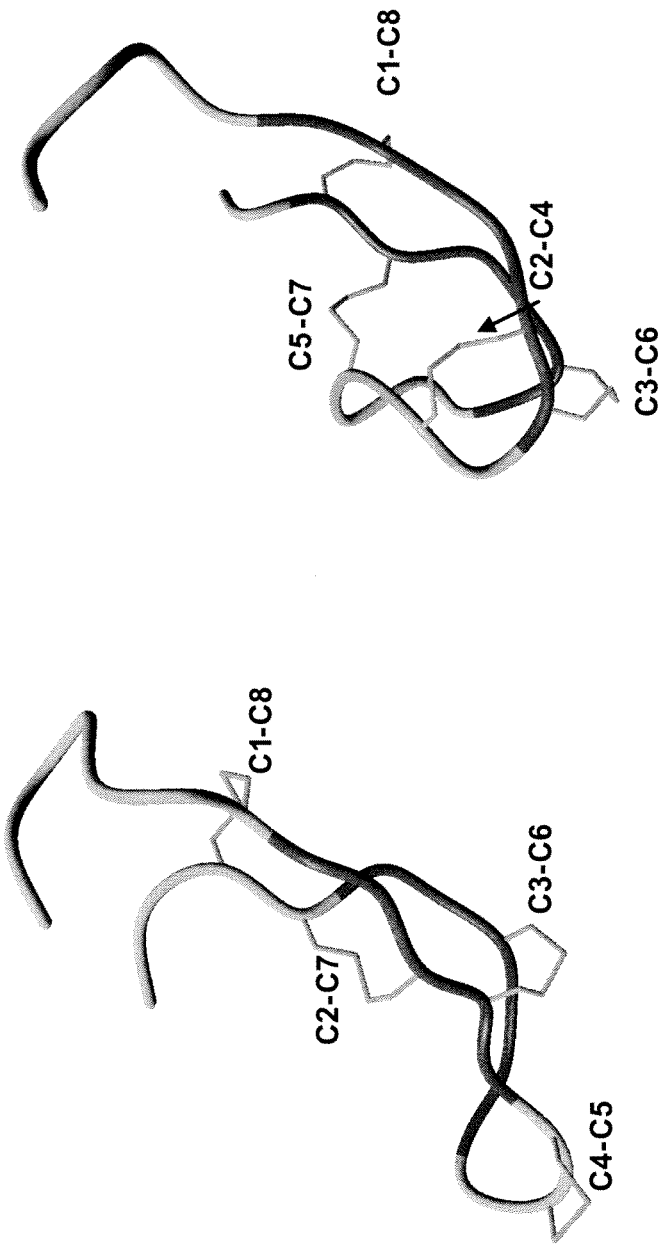
FIG. 7 shows the average backbone structures of human hepcidin obtained by Hunter et al. (J. Biol. Chem., 277: 37597-603, 2002) (left) and as determined in Example 8 (right).

A proposed model of the three-dimensional structure of human hepcidin with the disulfide connectivity is depicted in FIG. 7 (right).

Example 8

NMR Disulfide Bond and Structural Analysis of Human Hepcidin

The structure of human hepcidin was also determined by NMR spectroscopy. [These data, in which NOEs (Nuclear Overhauser Enhancement) are directly observed between the protons of all cysteine residues which form disulfide bonds, reveal the disulfide connectivities as follows: C7-C23 (C1-C8), C11-C19 (C3-C6), C10-C13 (C2-C4) and C14-C22 (C5-C7) in agreement with the partial alkylative reduction results quoted previously. These experimental observations allowed the determination of a three-dimensional structure of hepcidin that differs significantly from the previously published structure (Hunter et al. 2002). Results were generated from the CHO-derived recombinant human hepcidin as it demonstrated the best stability profile over time under the concentration and temperature conditions used in these experiments, important for high quality solution NMR studies. The stability-indicating parameters were the percentage of material aggregation and the degree of mono-dispersity of the molecules in solution as measured by NMR 1H linewidth shown in FIG. 2.

NMR Sample and Experiments: The NMR samples were prepared by adding 5% of $D_2O$ into the aqueous solution of uhHepc obtained from the last purification step. For NMR structural studies, 1 mM solutions of CHO-derived rhHepcidin in 90% $H_2O$/10% $D_2O$ and 99.999% $D_2O$ (Sigma-Aldrich) were prepared. The nonadjusted pH was close to 3. All experiments were conducted at 325K on a Bruker DRX-600 instrument equipped with TXI cryoprobe. Spectral assignments and a majority of the NOE constraints were obtained by standard 2D NMR methods (see Wuthrich, John Wiley & Sons, 1986). The $^{13}C$ chemical shifts of the alpha and beta carbons were obtained from the 2D $^{13}C$ HSQC spectrum. These spectral assignments were further confirmed and stereospecific assignments obtained by analysis of the 2D 2H-$^{13}C$ HMBC experiment (see Hansen, Biochemistry, 30:10457-66, 1991). The inter-cysteine NOEs were obtained either from 2D NOESY or hybrid TOCSY-NOESY experiments (Kessler et al., Angew. Chem. Int. Edn Engl., 27:564, 1988). The $^3J_{H}N_{H}\alpha$ (three-bond J couplings) were obtained from the 2D TOCSY experiment recorded with high digital resolution (0.5 Hz). Stereospecific proton assignments for all residues but C22 were obtained based on the vicinal H$\alpha$-H$\beta$ and C-H$\beta$ and two-bond C$\alpha$-H$\beta$ coupling patterns. C22 exhibited H$\beta$ protons with degenerate chemical shifts which precluded stereospecific assignment of this residue. The H-D exchange was tracked by recording 1D proton spectra after reconstitution of CHO-derived rhHepc from $H_2O$ into $D_2O$ solutions. Water suppression was achieved by use of the excitation sculpting pulse sequence. All NMR spectra were referenced externally to DSS (2,2-Dimethyl-2-silapentane-5-sulfonate sodium salt) at 0.0 ppm.

Figure 4:
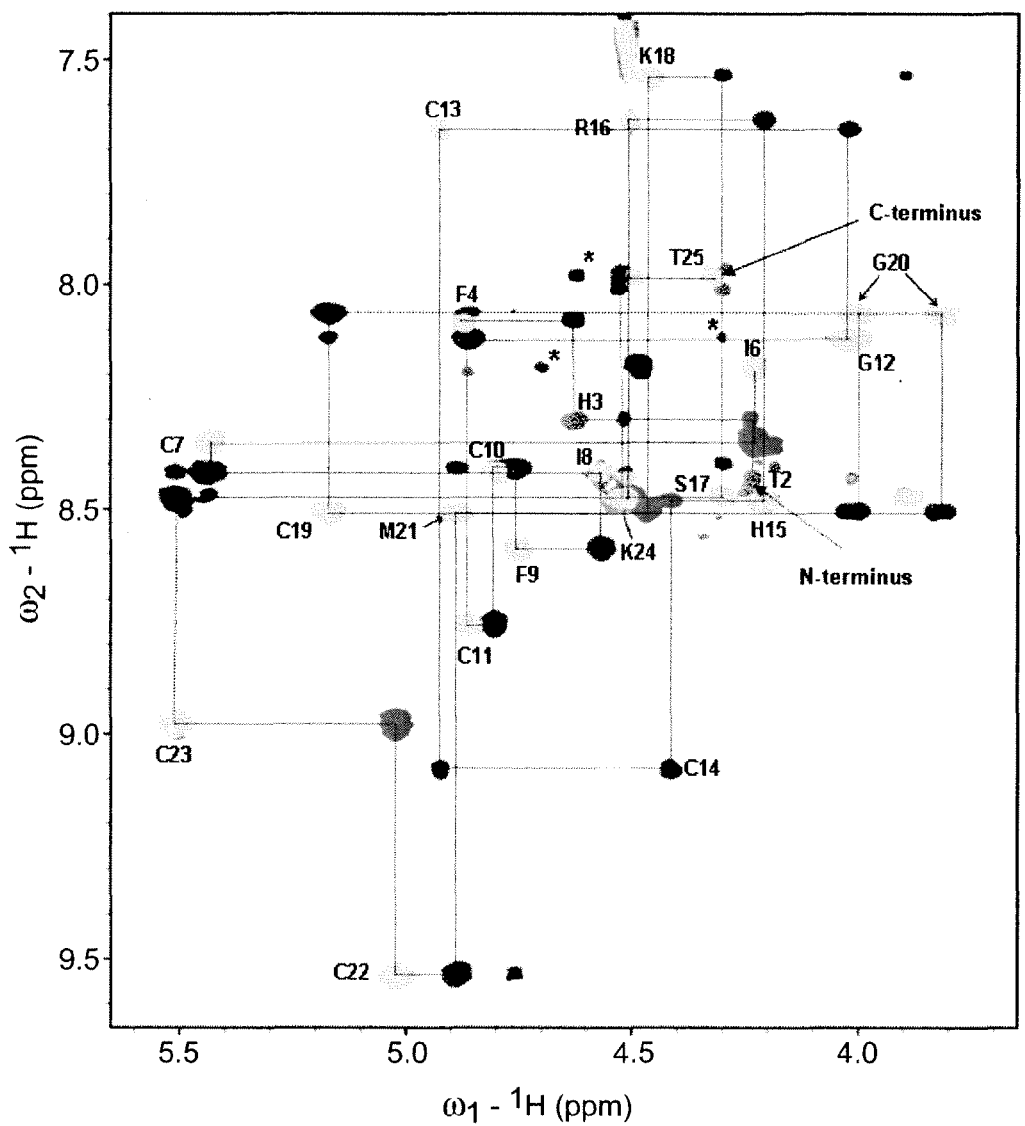
FIG. 4 shows a two-dimensional NOESY(dark)-TOCSY (light) overlay of backbone fingerprint region of recombinant human hepcidin showing backbone resonance assignments.

Disulfide Bond Connectivities: The proton spectrum of the CHO-derived rhHepc was fully assigned by the combination of homonuclear 2D TOCSY and 2D NOESY experiment; sequential connectivity assignment shown in FIG. 4. The resonances belonging to C13 and C14 (FIG. 2) are broadened by chemical exchange and only readily observable at elevated temperatures and low pH values.

The NOESY spectra were processed using NMRPipe and analyzed using the Sparky software package. The two-dimensional data were zero-filled once in each dimension and Fourier-transformed with a shifted sine-bell squared apodization function. Distance restraints were calibrated based on the NOESY peak volumes and by using the "isolated spin-pair approximation". The tumbling time was estimated from the cross-relaxation rates between methylene protons to be ~1.5 ns at 293 K and ~65 ns at 325 K which agrees with the Stoke's law, $$\left( \frac{\eta_{325} \times 293}{\eta_{293} \times 325} \approx 2.4 \right).$$

These correlation times correspond to the tumbling of a single molecule in aqueous solution and justify the two-spin approximation.

Figure 5:
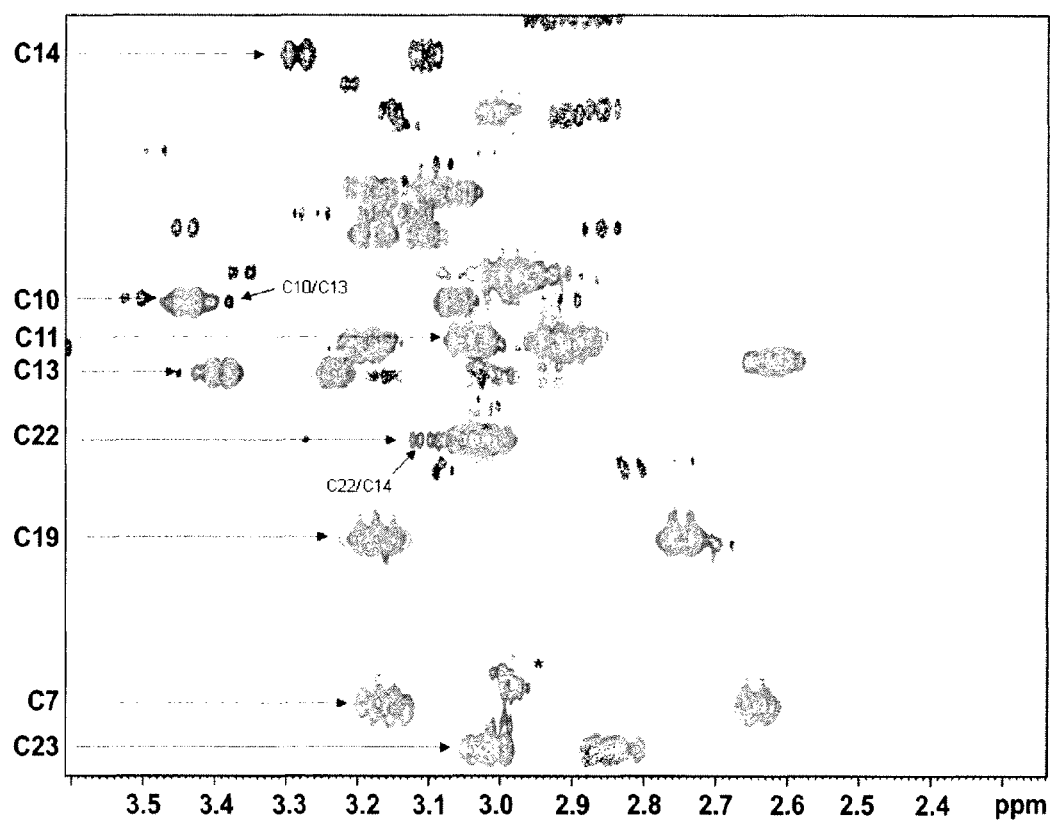
FIG. 5 shows an overlay of the $\omega_1$-decoupled 2D TOCSY and $\omega_1$-decoupled 2D TOCSY-NOESY experiments, as discussed in Example 8. The resonance positions of Hα protons are marked with the broken arrows. The asterisk denotes a folding artifact.

The disulfide bond connectivities for the C7-C23 (C1-C8) and C11-C19 (C3-C6) disulfides appear as very strong (2.1 Å) NOE interactions between the corresponding Hα protons. Since the beta proton resonances in peptides are highly congested it is often difficult to observe direct NOE connectivities between these protons. However, in the TOCSY-NOESY relay experiment, the Hβ-Hβ NOE peaks appear away from the diagonal and can be unambiguously assigned. The C10 (Hβ)-C13(Hβ) (C2-C4) and C14(Hβ)-C22(Hβ) (C5-C7) NOE interactions observed in this experiment are shown in FIG. 5. The relatively strong (~2.7 Å) C10(Hβ)-C13(Hβ) (C2-C4) NOE cross peak is also observed in 2D NOESY spectra recorded at pH~7 and 321K, where the Hβ resonances are well separated (~60 Hz). The C14(Hβ)-C22(Hβ) (C5-C7) relay NOE peak has a small contribution from the weak direct C14(Hα)-C22(Hβ) (C5-C7) interaction which appears at short mixing times in the 2D NOESY spectra. To remove this contribution, the 2D TOCSY-NOESY experiment was acquired using presaturation of Hα resonances during the 500 ms NOESY mixing time. This experiment showed almost the same C14(Hβ)-C22(Hβ) (C5-C7) cross-peak intensity confirming that it originates predominantly from the interaction between the Hβ protons (<3 Å). No additional NOE connectivities were observed between different cysteine residue pairs. In summary, these results support the disulfide connectivity disclosed in FIG. 6 and contradict the previously reported disulfide connectivity (Hunter et al. 2002).

Solution NMR Structure of Hepcidin: The 3-dimensional structure calculations were based on inter-proton NOE restraints, three bond J-coupling constants ($^3J_{H^N H^\alpha}$) for the φ angle and loose angular restraints for ψ angles obtained from the Cα and Cβ chemical shift values using the TALOS software package. Structures were calculated by CYANA 2.1 (See Guntert, Meth. Mol. Biol. 278:353-78, 2004) from extended geometry and were allowed to converge based on 20,000 steps of torsion angle dynamics-based-simulated annealing. In the last stage of calculations, after achieving convergence, hydrogen bond restraints were incorporated based on amides determined to be in slow exchange (obtained from $^2$H exchange experiments). At this point, disulfide bond constraints were then added according to the proposed connectivity pattern. The average structure of hepcidin, calculated from 20 lowest-energy structures, is compared in FIG. 7 with the average structure obtained from previously published ensemble of structures (Hunter et al., 2002, supra). Both studies show similar β-sheet elements and exhibit a β-hairpin loop. The most significant difference between both structures is the curl of this loop, which, in our structure, is most likely determined by the C2-C4 and C5-C7 disulfide bonds. This significant difference in the structure from that reported would represent a drastically different epitope to antibodies binding to the molecule.

Example 9

Synthesis and Activity of Hepcidin Variants

A number of hepcidin variants were chemically synthesized according to the general procedure described in Example 4. A variant of hepcidin lacking the five amino acids at the N-terminus, designated "hepcidin 20" or "hepc20," was synthesized. A linear hepcidin variant in which all eight cysteine residues were replaced with 2-aminobutyric acid, thus completely abolishing the ability to form disulfide bonds, was also synthesized. A C1-C8, C3-C6 hepcidin variant, in which cysteines 2, 4, 5 and 7 were substituted with 2-aminobutyric acid to allow formation of only two disulfide bonds (C1-C8 and C3-C6), was also synthesized.

Agreeing with published results (Nemeth et al., Blood, 107:328-333, 2006), the N-terminally truncated variant hepc20 had severely diminished biological activity. The linear hepcidin variant in which all eight cysteine residues were replaced was also inactive. Similar results were produced using hepcidin containing its native cysteine residues, when the molecule was in a fully-reduced state (i.e., no disulfide connectivity). This reduced material was not stable, however, and regained biological activity over time.

Example 10

Preparation of Murine Anti-Human Hepcidin Monoclonal Antibodies Against KLH-Conjugated Material Human hepcidin-specific monoclonal antibodies (mAbs) 2.7 and 2.41 were generated in mice as follows. Recombinantly expressed and refolded human hepcidin was conjugated to the carrier protein KLH using standard EDC chemistry before administering to animals. Briefly, a 4-fold molar excess of EDC (Pierce) was added directly to a MES buffered solution containing equal amounts of human Hepcidin and KLH. The reaction was allowed to proceed for 2 hrs at RT. The human hepcidin-KLH conjugate was then emulsified in a 1:1 ratio of Complete Freund's Adjuvant (Pierce) or RIBI (Sigma) and PBS (Gibco). BDF1 mice and C57BL/6 were immunized subcutaneously at the nape of the neck and hind leg with 50 ug of the hepcidin-KLH/adjuvant emulsification. 14 days later a second immunization of 25 ug human hepcidin-KLH in RIBI adjuvant was delivered subcutaneously as well as intraperitoneally. 10 days following this immunization, bleeds were taken to assess anti-human hepcidin serum levels.

Approximately 2 weeks following the titer bleeds, 1 C57Bl/6 mouse was boosted intraperitoneally with 75 ug of human hepcidin suspended in PBS. 5 days following this boost, the spleen was removed aseptically and processed for fusion. Briefly, the spleen was disrupted into a single cell suspension and the RBC were lysed. SP2/0.AG14 myeloma cells were mixed with the splenocytes in a 1:2.5 ratio of SP2/0 to splenocytes. This cell suspension was then fused using Electrofusion techniques. The resulting hybridomas were plated into 96 well plates using a rich growth media and maintained by 2 complete media exchanges. 3 days after the second media change, the hybridomas were screened for anti-human Hepcidin specific IgG via ELISA. Briefly, 100 ng/well of Neutravidin (Pierce) was coated on a standard ELISA plate. These plates were washed and then blocked with a 1% BSA, 1% gt serum 0.5% Tween 20 solution in PBS. 1 ng/well of biotinylated-human hepcidin was then added to the plates and incubated for 1 hour. After washing, 50 ul of the relevant hybridoma supernatants were transferred from the culture plates onto the screening plates and these were again incubated for 1 hour. After washing, a polyclonal goat anti-mu IgG Fc specific HRP labeled Ab was used to detect the murine IgG-human Hepcidin complexes. After appropriate washes, TMB (Pierce) was used to visualize the complexes. Positive clones identified by this method were then transferred to a 48 well plate for expansion.

Example 11

Preparation of Murine Anti-Human Hepcidin Monoclonal Antibody, Ab43, by Viral Immunization Human hepcidin-specific monoclonal antibody Ab43 was generated in mice by the following viral immunization method. ViraPower Adenoviral Expression System (Cat. #K4930-00, Invitrogen, Carlsbad, Calif.) was used to generate adenovirus expressing human hepcidin. Recombinant adenovirus carrying human hepcidin cDNA (rAd-hHepc) was constructed as follows: Briefly, pENTR-hHepc was constructed by inserting the human hepcidin gene into pENTR1A (Invitrogen). The resulting human hepcidin gene is flanked by attP DNA fragments allowing recombination with attB DNA fragments in pAd/CMV/V5-DEST. PAd/CMV-hHepc was constructed by recombination reaction between pENTR-hHepc and pAd/CMV/V5-DEST using LR clonase. To generate rAd-hHepc, pAd/CMV-hHepc was linearized by Pac I and transfected into 293T cells using Lipofectamine 2000. Transfected 293T cells were cultured until approximately 80% cytopathic effect (CPE) was observed. Transfected cells show enlarged and rounded morphology, lysed cells and visible plaques. RAd-hHepc containing cells were harvested and used for the amplification of rAd-hHepc. RAd-hHepC was purified by CsC1 gradient method and titered using Adeno-X rapid titer kit (BD Biosciences, Palo Alto, Calif.).

C57Bl/6 mice were immunized into quadriceps of both hind legs with 50 µl of $1.25 \times 10^9$ infectious units (i.f.u) of rAd-hHepc. Spleen was removed aseptically and processed for fusion at 10 days after rAd-hHepc immunization.

Example 12

Generation of Rat Anti-Human Hepcidin Monoclonal Antibody R9

Human hepcidin-specific monoclonal antibodies (mAbs) were generated in rats using the RIMMS method with modifications. Briefly, two 8-10 week old female Lewis rats (Charles River Laboratory) each received five rounds of immunizations with human hepcidin-KLH conjugated protein over the course of 11 days. Before each immunization, rats were anesthetized with a gas mixture of oxygen and isoflurane. For the first immunization on day 0, 10 ug antigen emulsified in Freund's complete adjuvant (DIFCO) in a volume of 600 ul, 300 ul of such antigen mix was administered subcutaneously to six sites proximal to draining lymph nodes, at 50 ul/site, along the back of the rats, with two at the nape of the neck and two bilaterally to the groin and calf. Another 300 ul of antigen mix was administered to six juxtaposed sites along the abdomen, with two bilaterally to the axilla, thigh, and calf. Boost immunizations were given on day 3, day 6, day 8, and day 11 in a similar fashion except RIBI (Corixa CORP, cat#R700) adjuvant was used throughout.

One day after the final immunization, rats were euthanized by asphyxiation with carbon dioxide. Bilateral popliteal, superficial inguinal, axillary, and branchial lymph nodes were isolated aseptically and washed twice with 2× Penicillin-Streptomycin-Glutamine (Gibco) BD medium. Lymphocytes were released from the lymph nodes and single-cell suspension was washed again in BD medium before fused with mouse myeloma cells, Sp2/0-Ag14 (ATCC, CRL-1581), at a ratio of 2.5:1 by electrofusion. Briefly, cells were washed and resuspended in 2 ml of Cytofusion Medium C (Cytopulse Sciences) at $1 \times 10^7$ cells/ml and transferred to a fusion chamber. Electrofusion was carried out by applying 3 pulses at 1500V for 30 µs, followed by a pulse of 60V for 3 sec using ECM 2001 with Enhancer 400 (BTX Inc. San Diego). Cells were allowed to recover at RT for 30 min before resuspended gently and seeded in 96-well plates at $3 \times 10^4$ cells/well in 100 ul of BD media supplemented with 10% FBS, 5% Origen Cloning Factor (BioVeris™), 1× Penicillin-Streptomycin-Glutamine (Gibco), and 1×OPI (oxaloacetate, pyruvate, and insulin) (Sigma). After 24 hrs in culture, 100 ul of 2×HAT (0.1 mM hypoxanthine, 0.16 mM thymidine, 4 mM aminopterin) (Sigma) was added to each well. Medium was changed 5 days later and the conditioned media collected after one week of incubation for primary screening. Positive clones were expanded, single-cell cloned, and confirmed by multiple assays.

Example 13

Generation of Fully Human Antibodies

Xenomouse™ IgG2κλ and IgG4 κλ mice were immunized with KLH-conjugated human hepcidin (SEQ ID NO: 9) using standard methods. 23,040 IgG2 supernatants and 11,520 IgG4 supernatants were screened at a single concentration against biotinylated human hepcidin anchored to a plate. From this screen 617 IgG2 and 1013 IgG4 supernatants were tested for binding to both human and mouse biotinylated hepcidin using an antibody capture ELISA in which the amount of antibody captured was limited to minimize the effect of concentration differences between supernatants. Top-ranking samples (70 IgG2 and 110 IgG4) were further characterized in a bridging ELISA which measures solution-phase hepcidin-antibody binding over a range of antibody concentrations. This assay provided a relative affinity ranking of antibody binding.

Supernatants from each of the IgG2 and IgG4 panels were designated as follows: 1C9 (SEQ ID NOs: 107-116), 3B3 (SEQ ID NOs: 117-126), 4E1 (SEQ ID NOs: 127-136), 7A3 (SEQ ID NOs: 137-146), 9D12 (SEQ ID NOs: 147-156), 12B9 (SEQ ID NOs: 157-166), 15E1 (SEQ ID NOs: 167-176), 18D8 (SEQ ID NOs: 310-319), 19C1 (SEQ ID NOs: 320-329), 19D12 (SEQ ID NOs: 290-299), 19H6 (SEQ ID NOs: 300-309), 23F11 (SEQ ID NOs: 177-186), and 26F11 (SEQ ID NOs:. 187-196).

The binding affinities of these antibodies to human hepcidin were determined by BIAcore, which were then confirmed by KinExA if the $K_D$ as estimated by BIAcore was below 100 pM. The $K_D$ for the lead antibodies were in the range of between 1 pM and more than 400 pM.

Relative species cross-reactivity and binding to Hepc20 (SEQ ID NO: 96) was determined by competition ELISA. Results suggest that the relative binding compared to human hepcidin was: 2-fold lower for cynomolgus hepcidin (SEQ ID NO: 6), 500- to >1000-fold lower for mouse hepcidin (SEQ ID NO: 80), and 150- to >1500-fold lower for canine hepcidin (SEQ ID NO: 92).

Example 14

Binding Analysis of Antibodies to Human and Mouse Hepcidin

Solution equilibrium binding analysis was performed using BIAcore to study the interaction of R9, Ab43, 2.7 and 2.41 antibodies with recombinant mouse hepcidin (SEQ ID NO: 80) and human hepcidin (SEQ ID NO: 9).

Preparation of BIAcore chip surfaces: Immobilization of proteins to a BIAcore was performed according to manufacturer's instructions at a flow rate 10 μL/min of running buffer (DPBS: Dulbecco's Phosphate Buffer Saline1X, GIBCO 14190, with 0.005% Biacore surfactant P-20). The carboxylated matrix of the sensor chip was first activated with a 100 μL injection of 1:1 mixture of EDC (75 mg/mL N-ethyl-N-(dimethylamine-propyl)carbodiimide in water, from BIAcore) and NHS (11.5 mg/mL N-hydroxysuccinimide in water, from Biacore). 180 μL of recombinant human hepcidin or recombinant murine hepcidin (~20 μg/ml in 10 mM Na-acetate pH4.0) was injected to immobilize onto the sensor chip at 30 μL/min. The excess reactive groups of the sensor chip were deactivated with an injection of 100 μL of ethanolamine (1.0M, from Biacore).

Equilibrium binding analysis of antibody/hepcidin interactions on immobilized hepcidin surface: Fixed concentrations of antibody were incubated with various concentrations of hepcidin at room temperature for several hours before run through the immobilized hepcidin surface. After each sample injection, the surfaces were regenerated by injecting 30 μL 10 nM glycine, pH1.5. The binding signal obtained is proportional to the free antibody in solution at equilibrium. The equilibrium dissociation constant ($K_D$) was calculated from nonlinear regression analysis of the competition curves using a one or dual-curve one-site homogeneous binding model (KinExA™ software, Sapidyne Instruments Inc., Boise Id.). Table 3 summarizes the results of R9, Ab43, 2.7 and 2.41 binding to recombinant mouse and human hepcidin.

TABLE 3

| Antibody | human hepcidin | 95% CI | mouse hepcidin | 95% CI |
|---|---|---|---|---|
| R9   | 21 nM   | 13-28 nM   | 20 nM  | 13-27 nM |
| Ab43 | 560 pM  | 400-700 pM | 14 nM  | 12-16 nM |
| 2.7  | 110 pM  | 80-150 pM  | 40 nM  | 27-44 nM |
| 2.41 | 50 pM   | 20-90 pM   | 30 nM  | 24-38 nM |

Example 15

Binding of Anti-Human Hepcidin Antibodies to Recombinant Cyno Hepcidin

The following example describes KinExA and BIAcore binding analysis for various antibodies to recombinant cyno hepcidin (rcyno).

A) KinExA solution equilibrium binding analysis for mAb 2.7 and 2.41 binding to rcynoHepc. Reacti-Gel 6× beads (Pierce, Rockford, Ill.) were pre-coated with rcyno hepcidin (SEQ ID NO: 6) and blocked with BSA according to manufacturer's instructions. Fixed concentrations of antibodies 2.7 and 2.41 were incubated with various concentrations of rcyno hepcidin at room temperature for 8 hours before being run through the rcyno Hepcidin-coated beads. The amount of the bead-bound antibody was quantified by fluorescently (Cy5)-labeled goat anti-murine-IgG (H+L) antibody (Jackson Immuno Research, West Grove, Pa.). The binding signal is proportional to the concentration of free antibody at equilibrium. Dissociation equilibrium constant ($K_D$) was obtained from nonlinear regression of the competition curves using a dual-curve one-site homogeneous binding model (KinExA™ Pro software). The results are set forth in Table 4.

TABLE 4

| antibody | $K_D$ (to rcynohepc) | 95% CI |
|---|---|---|
| 2.7  | ~16 pM | 11~23 pM |
| 2.41 | ~9 pM  | 6~14 pM  |

B) BIAcore solution equilibrium binding analysis for mAb R9 and Ab43 binding to rcynoHepc. Antibody surface immobilization: antibodies R9 and Ab43 were immobilized on a CM5 chip. The immobilization was performed at a flow rate 10 uL/min of running buffer (DPBS: Dulbecco's Phosphate Buffer Saline1, GIBCO 14190, with 0.005% BIAcore surfactant P-20) according to manufacturer's instructions. The carboxylated matrix of the sensor chip was first activated with a 100 ul injection of 1:1 mixture of EDC (75 mg/mL N-ethyl-N-(dimethylamine-propyl)carbodiimide in water, from BIAcore) and NHS (11.5 mg/mL N-hydroxysuccinimide in water, from BIAcore). 180 ul of antibodies (~20 ug/ml in 10 mM Na-acetate pH4.0) was injected to immobilize onto the sensor chip at 30 uL/min. The excess reactive groups of the sensor chip were deactivated with an injection of 100 uL of ethanolamine (1.0M, from BIAcore).

BIAcore analysis: Fixed concentrations of rcynoHepc were incubated with various concentrations of mAb R9 and Ab43 at room temperature for several hours before run through the immobilized antibody surfaces. The binding signal obtained is proportional to the free rcynoHepc in solution at equilibrium. The equilibrium dissociation constant ($K_D$) was calculated from nonlinear regression analysis of the competition curves using a one-curve one-site homogeneous binding model (KinEx™ software, Sapidyne Instruments Inc., Boise Id.). Both R9 and Ab43 demonstrated significant binding affinity to rcyno hepcidin. The results are set forth in Table 5.

TABLE 5

| antibody | $K_D$ (to rcynohepc) | 95% CI |
|---|---|---|
| R9 | ~10 nM  | 9~12 nM   |
| 43 | ~100 pM | 60~160 pM |

Example 16

Characterization of Hepcidin-Specific Monoclonal Antibody Binding Activity in an Enzyme-Linked Immunosorbent Assay (ELISA)

96-well E.I.A./R.I.A. flat bottom plates (Costar 359) were coated with biotin-conjugated recombinant human or biotin-conjugated murine hepcidin at 100 to 1000 ng/ml in 0.1M Sodium Acetate (pH5.5) at 4° C. overnight. The plates were blocked with PBS containing 2% BSA and 0.2% goat serum (GIBCO) at room temperature for 1 hour. After washing the plates, 50 ul of hybridoma conditioned medium was added to each well and incubated on a shaker at RT for 2 hours. The plates were washed three times with washing solution (0.05% Tween-20 in PBS) and incubated with 50 ul/well of horseradish peroxidase conjugated goat anti-rat IgG (Chemicon) at RT for 30 min. After washing the plates three times, 50 ul/well of TMB substrate (KPL) was added and allowed to incubate at RT for 5-10 min. The reaction was stopped with the addition of 50 ul of 0.5N H2SO4 and the plate read at 450 nm in a micro-plate reader. Anti-sera of immunized rats were used as positive control antibodies and media alone as background controls.

Rat monoclonal antibody R9 was identified to be specific to both human and murine hepcidin. The hybridoma cell line was sorted through a cell sorter (Becton Dickinson, FACS-Diva) at one cell per well for subcloning.

Example 17

Anti-Hepcidin Antibodies Recognize Different Structural Epitopes

The epitope specificity of anti-human hepcidin antibodies was evaluated by assessing ability of the antibodies to bind to mature human hepcidin (SEQ ID NO: 9) after pre-complex formation with different hepcidin variants.

Recombinant hepcidin was immobilized on a CM5 chip according to manufacturer's instructions at a flow rate 10 μL/min of running buffer (DPBS: Dulbecco's Phosphate Buffer Saline1X, GIBCO 14190, with 0.005% BIAcore surfactant P-20). The carboxylated matrix of the sensor chip was first activated with a 100 μL injection of 1:1 mixture of EDC (75 mg/mL N-ethyl-N-(dimethylamine-propyl)carbodiimide in water, from Biacore) and NHS (11.5 mg/mL N-hydroxysuccinimide in water, from Biacore). 180 μL of rhHepc (~20 μg/ml in 10 mM Na-acetate pH4.0) was injected to immobilize onto the sensor chip at 30 μL/min. The excess reactive groups of the sensor chip were deactivated with an injection of 100 μL of ethanolamine (1.0M, from Biacore).

Forms of hepcidin used for the pre-complex were: correctly folded hepcidin as a positive control, the C1-C8, C3-C6 hepcidin variant (see Example 9), hepcidin 20 (N-terminally truncated, see Example 9) and linear hepcidin (Example 9). 1 nM solutions of antibody (2.41, 2.7, 43, and R9) were preincubated with 10 nM of each antigen at room temperature for several hours before run through the immobilized hepcidin surface. The binding signal obtained was proportional to the concentration of free antibody in solution at equilibrium. The results are set forth in Table 6.

TABLE 6

| | Binding to Hepcidin Surface | | | |
|---|---|---|---|---|
| Antibody | No competition | Folded Hepcidin | C1-C8 C3-C6 | Hepc20 | Linear Hepcidin |
| R9 | 100% | 79% | 63% | 88% | 100% |
| Ab43 | 100% | 11% | 25% | 100% | 100% |
| 2.7 | 100% | 2% | 3% | 3% | 100% |
| 2.41 | 100% | 0% | 1% | 1% | 99% |

Interpretation of the data in Table 6 to give a representation of the ability of different anti-hepcidin antibodies to bind to different epitopes is set forth in Table 7.

TABLE 7

| | Binding to Solution Epitopes | | | |
|---|---|---|---|---|
| Antibody | Folded Hepcidin | C1-C8 C3-C6 | Hepc20 | Linear Hepcidin |
| R9 | + | + | + | − |
| Ab43 | ++++ | +++ | − | − |
| 2.7 | ++++ | ++++ | +++ | − |
| 2.41 | ++++ | ++++ | +++ | − |

Binding ranges from ++++ (0% antibody binding to the hepcidin surface and therefore 100% inhibition by hepcidin in solution), to − (100% antibody binding to the hepcidin surface and therefore no inhibition by hepcidin in solution). These data indicate that all antibodies require a folded peptide for antigenicity. Some antibodies require the five amino acids at the N-terminus of the molecule (e.g. Ab43 and to a lesser extent, R9). For some antibodies (e.g. R9), elimination of the C2-C4 and C5-C7 disulfide bonds greatly reduced antibody recognition of the hepcidin molecule.

Example 18

Figure 8:
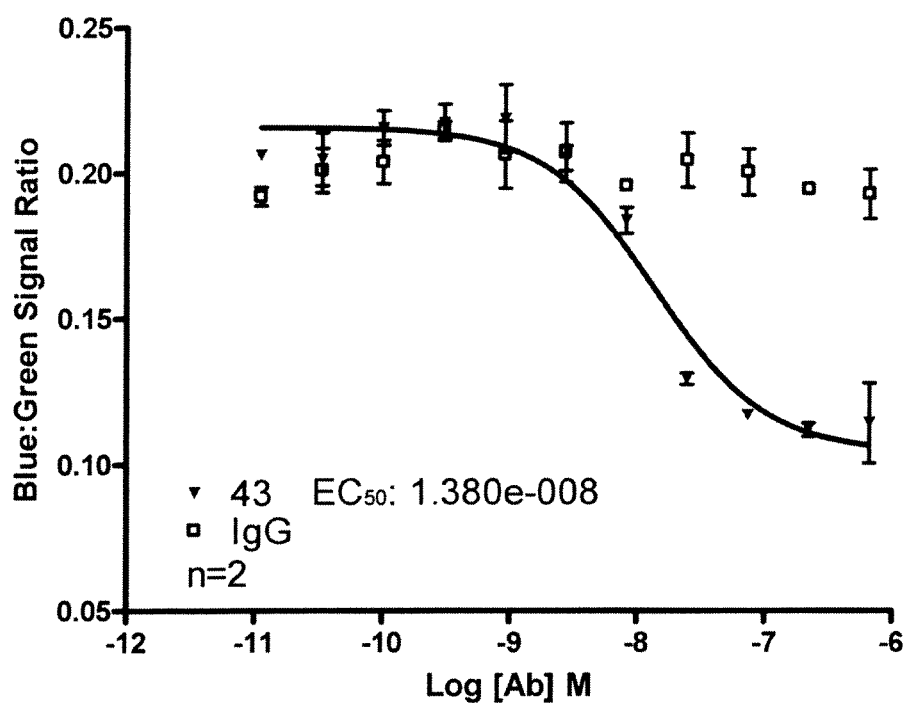
FIG. 8 shows murine anti-hepcidin antibody Ab 43's functional ability to drive down intracellular iron concentrations in a beta-lactamase iron-response assay.
Figure 9:
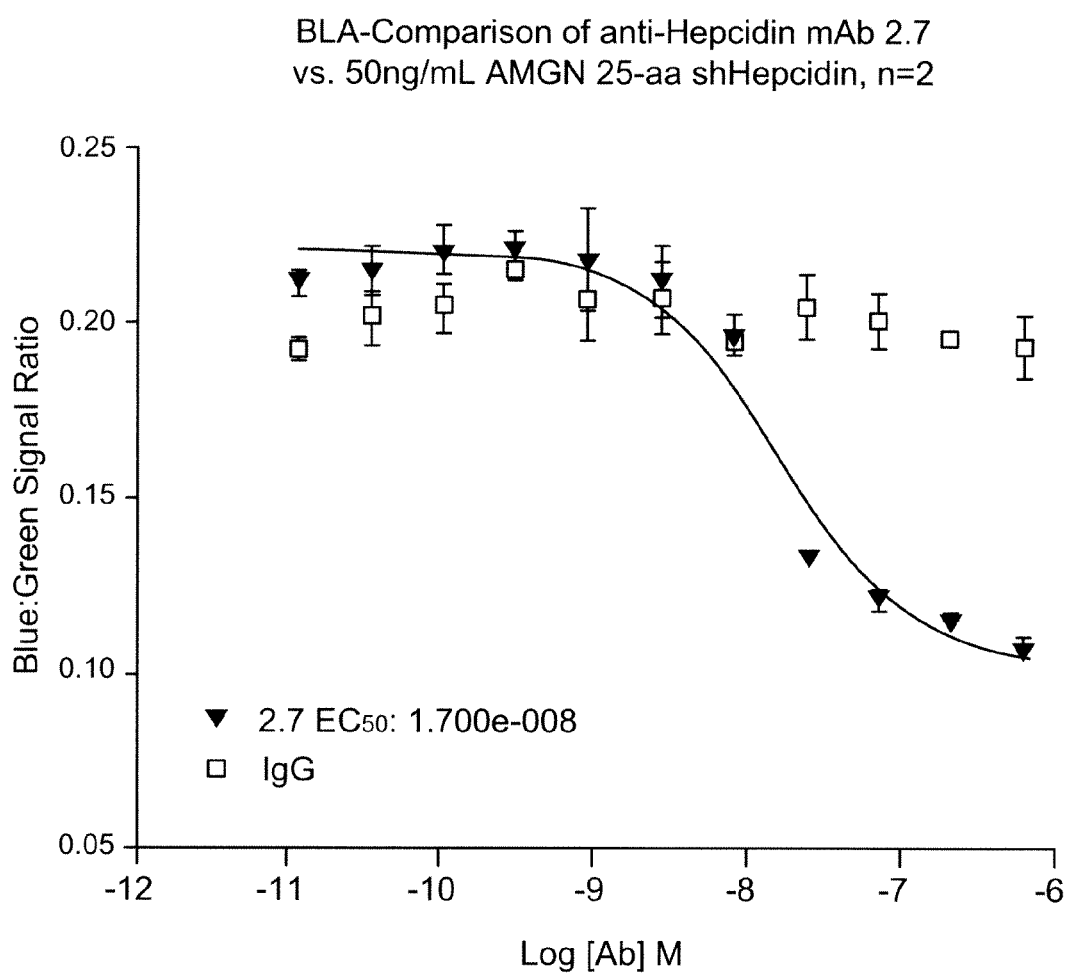
FIG. 9 shows murine anti-hepcidin antibody 2.7's functional ability to drive down intracellular iron concentrations in a beta-lactamase iron-response assay.
Figure 10:
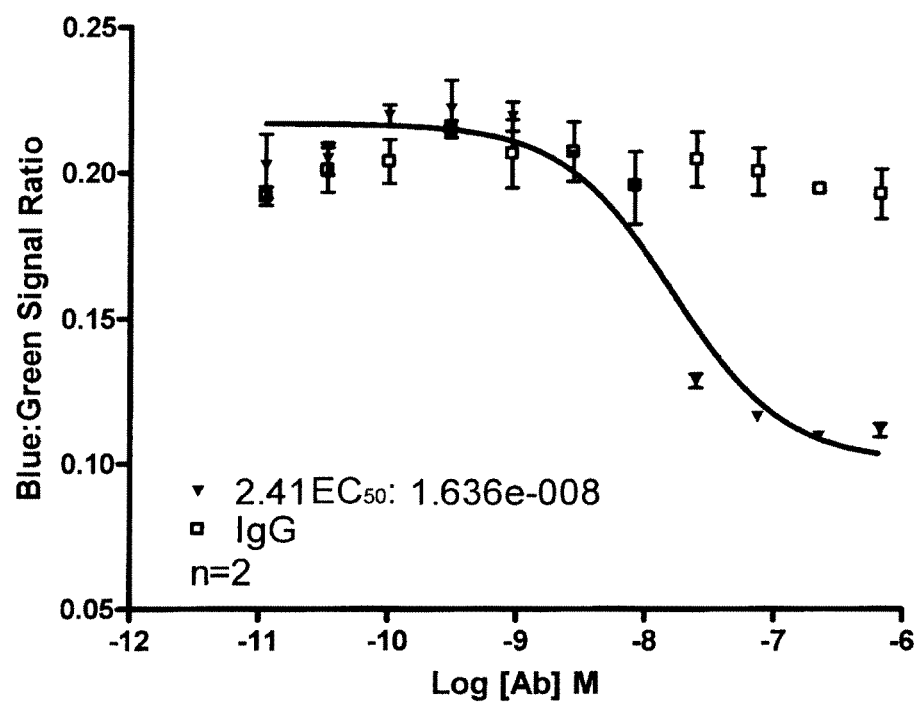
FIG. 10 shows murine anti-hepcidin antibody 2.41's functional ability to drive down intracellular iron concentrations in a beta-lactamase iron-response assay.

In vitro Hepcidin Activity in an Iron-Responsive β-Lactamase Assay can be Neutralized by Anti-Hepcidin Antibodies Hepcidin causes ferroportin to be internalized and removed from the cell surface, thus inhibiting release of iron and raising intracellular iron concentrations. The effect of anti-human hepcidin antibodies on this hepcidin-mediated iron sequestration was evaluated in vitro. A 293 cell line containing a doxycycline-inducible ferroportin (Fpn) expression construct as well as a beta-lactamase (BLA) expression construct containing one copy of the 5' iron response element (IRE) from ferritin having the following nucleotide sequence (tcggccccgcctcctgccaccgcagat-tggccgctagccctccccgagcgccct-gcctccgagggccggcgcaccataaaagaa gccgccctagccacgtcccctcg-cagttcggcggtcccgcgggtctgtctcttgcttcaacagtgtttggacggaacaga-tccgggga ctctcttccagcctccgaccgccctc-cgatttcctctccgcttgcaacctccgg-gaccatcttctcggccatctcctgcttctgggacctgc cagcaccgtttttgtggt-tagctccttcttgccaacc) (SEQ ID NO: 103) that regulate mRNA translation was constructed. These 293/Fpn/BLA cells, taken from a 70-80% confluent culture, were plated at 2.8×10⁵ cells/mL in DMEM (Invitrogen Cat#11965) 5% FBS (Invitrogen Cat#10099-141) PSQ (Invitrogen Cat#10378-016), 90 uL/well (25,000 cells/well) in BioCoat Poly-D Lysine coated plates (Becton-Dickinson Cat#35-6640) and incubated at 37 C with 5% CO$_2$. At the end of the same day, a solution of assay medium (DMEM 5% FBS PSQ) with 100 ug/mL doxycycline was made, 10 uL/well of it added to the plate, and the plate incubated overnight or for at least 20 hours. The next day, media was removed from the wells and replaced with premade mixes of DMEM 5% FBS PSQ, 2.5 ug/mL ferric citrate, 50 ng/mL synthetic human hepcidin and serial dilutions of the antibodies (2.7, 2.41, and Ab43, which were generated as described in Examples 8 and 9 below), all prepared in a 96-well polypropylene deep-well block plate immediately before addition to the assay plate. Mixtures were added at 100 uL/well and incubated overnight at 37 C, 5% CO2 in a cell culture incubator. Plates were then removed from the incubator and equilibrated to room temperature for 10 minutes before adding 20 uL/well of the prepared Invitrogen GeneBlazer CCF4 A/M development reagent (Invitrogen Kit#K1085) and incubating for 90 minutes in the dark. Development reagent was also added to 16 wells of a control assay plate without cells containing 100 uL assay medium (DMEM 5% FBS PSQ) and incubated for the same time. Blue & Green fluorescence signals were then read on an Envision Multilabel Reader (Perkin-Elmer Inc.) by exciting at 409 nm and reading emissions at 447 nm (blue) and 520 nm (green). The results are depicted in FIGS. 8-10. It was determined that mAB 43, 2.7 and 2.41 decreased intracellular concentration of iron at an $EC_{50}$ of $1.380\times10^{-8}$, $1.700\times10^{-8}$, and $1.636\times10^{-8}$, respectively.

Example 19

Anti-Hepcidin Antibodies Neutralize Human Hepcidin in Mice

Figure 11A:
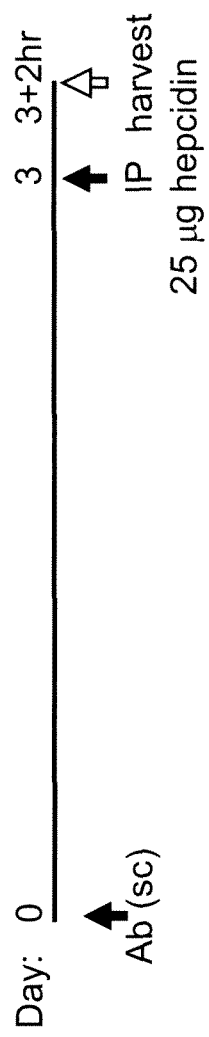
FIG. 11 demonstrates that an anti-hepcidin antibody neutralizes human hepcidin injected into mice.
Figure 11B:
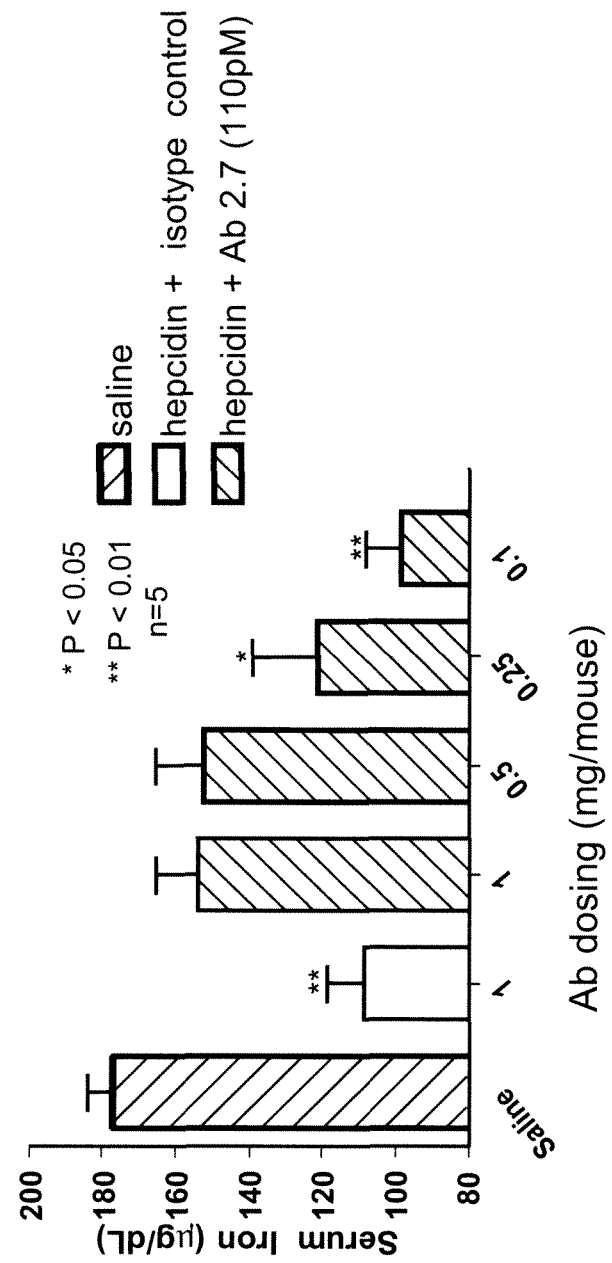

Activity of anti-human hepcidin antibodies was evaluated in vivo in mice that were administered human hepcidin in an amount sufficient to generate a hypoferremic response. On day 0, female C57BL/6 mice were injected subcutaneously with a murine monoclonal antibody (Ab2.7) directed against human hepcidin. Control mice received murine IgG1 as an isotypic control. At day 3, the mice received a single intraperitoneal injection of 25 μg E. coli-derived recombinant human Hepcidin (rhHepc). Serum iron levels were analyzed two hours later. Control animals treated with saline had normal serum iron levels, while animals treated with hepcidin and an isotype control antibody showed hypoferremia. Results are set forth in FIG. 11. Both 1mg and 0.5 mg of mAb2.7 provided statistically significant protection from the hypoferremic response. Although a reduction in hypoferremia was observed at the 0.25 mg dose of Ab 2.7, the lower doses (0.25 and 0.1 mg) were defined as non-neutralizing doses. Statistics represent ANOVA with a Dunnett's post-hoc test comparing all groups against the saline control.

Example 20

Figure 12B:
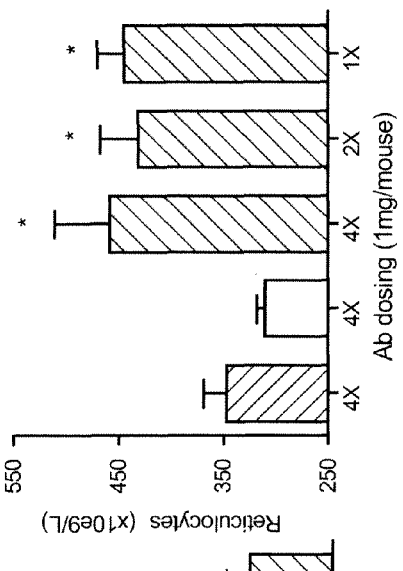
FIG. 12 demonstrates that antibody neutralization of human hepcidin virally expressed mice restores normal early red cell characteristics.
Figure 12C:
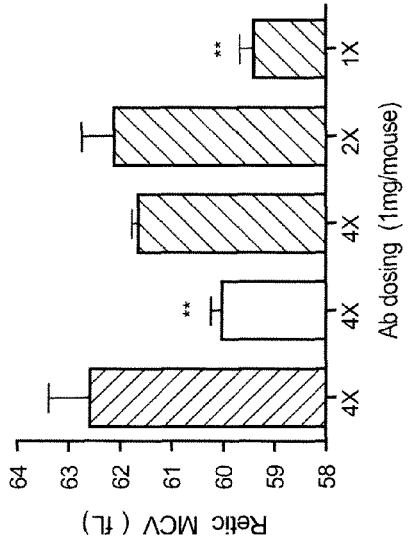
Figure 12D:
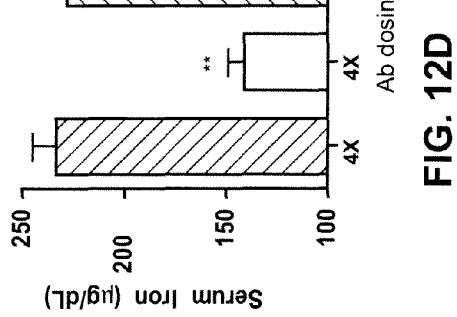
Figure 12E:
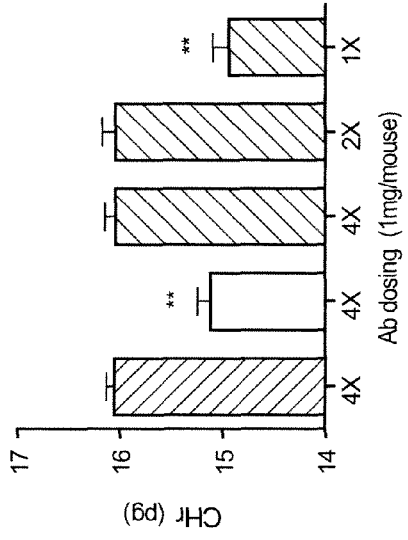

Antibody Neutralization of AAV-Delivered Hepcidin Restores Normal Early Red Blood Cell Characteristics AAV-mediated human hepcidin expression in mice produces a microcytic, hypochromic anemia consistent with iron deprivation. The activity of anti-human hepcidin antibodies was evaluated in vivo in these mice overexpressing human hepcidin. Male C57Bl/6 mice were injected with AAV ($1.5\times10^{12}$ particles/mouse, I.V.) containing expression cassettes for either human hepcidin or beta-galactosidase (β-gal) as a negative control. The mice were left for two weeks to allow constitutive production of huHepc before being treated with 1 mg/mouse of Ab 2.7 or isotype control (muIgG1) at various dosing frequencies (1×, 2× and 4× per week) as shown in FIG. 12A. Blood was drawn on the fifth day for serum iron levels and determination of early red blood cell (reticulocyte) characteristics (reticulocyte count, reticulocyte hemoglobin content (CHr), and reticulocyte mean cell volume (Retic. MCV))

Results are set forth in FIGS. 12B-12E. Serum iron levels were restored to normal in mice receiving 4× dosing of Ab2.7 but not isotype control. All mice receiving Ab2.7 show increased reticulocyte production. The reticulocyte hemoglobin content (CHr) is normal in mice given the 4× and 2× dosing of Ab 2.7, but hypochromicity is still seen in groups with 1× dosing, or the isotype control group. Treatment with Ab2.7 at the 4× and 2× dose restores normal volume to reticulocytes (Retic. MCV) but microcytosis is still present in the 1× and isotype control groups. Statistical comparisons to β-gal injected animals with isotype control treatment were determined to look for restoration of normal red cell characteristics (ANOVA with Dunnett's post-hoc test).

Example 21

Viral Hepcidin Over-Expression Results in Hypo-Responsiveness to Erythropoietin

The following Example investigated the role of hepcidin and hepcidin activity antagonists in erythropoietin hypo-responsive mice.

Figure 13B:
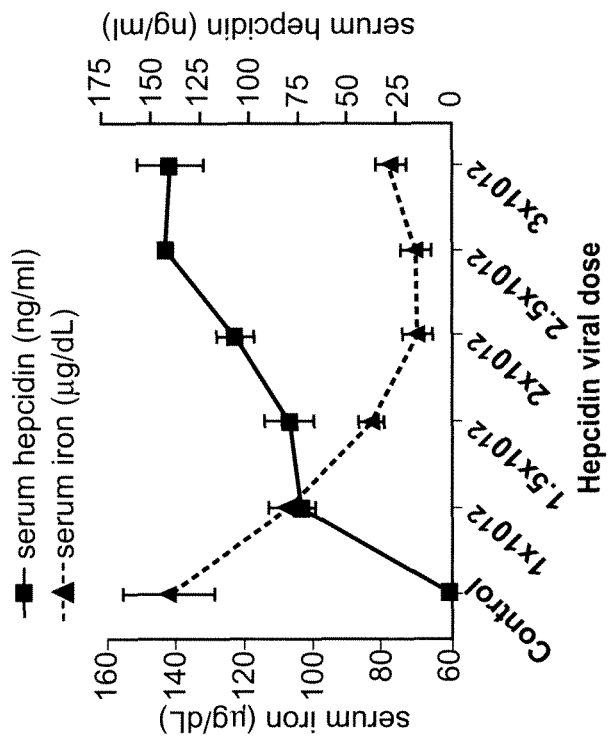
FIG. 13B shows a titration of adenovirus-associated virus (AAV)-mediated hepcidin expression and resulting serum iron concentrations.

Titration of AAV-mediated human hepcidin expression in mice causes an increase in serum hepcidin levels and dose-dependent hypoferremia, as shown in FIG. 13B. Doses of AAV-human hepcidin were selected that gave an erythropoietin resistant phenotype and expressed levels of hepcidin in a similar range to that detected in cancer patient samples in previous studies (as described in co-pending co-owned U.S. patent application Ser. No. 11/880,313 and International Patent Application No. PCT/US2007/016477, the disclosures of which are incorporated herein by reference in their entirety). Male C57BL/6 mice were injected with AAV expressing human hepcidin or GFP as an expression control (n=4 per group). The mice were injected through the tail vein (human hepcidin, from $1\times10^{12}$ to $3\times10^{12}$ particles/mouse; GFP $3\times10^{12}$ particles/mouse). Protein expression was allowed to develop for two weeks prior to harvest. At two weeks, serum was collected from the mice and iron and hepcidin levels were determined. Results are reported in FIG. 13B.

Figure 13A:
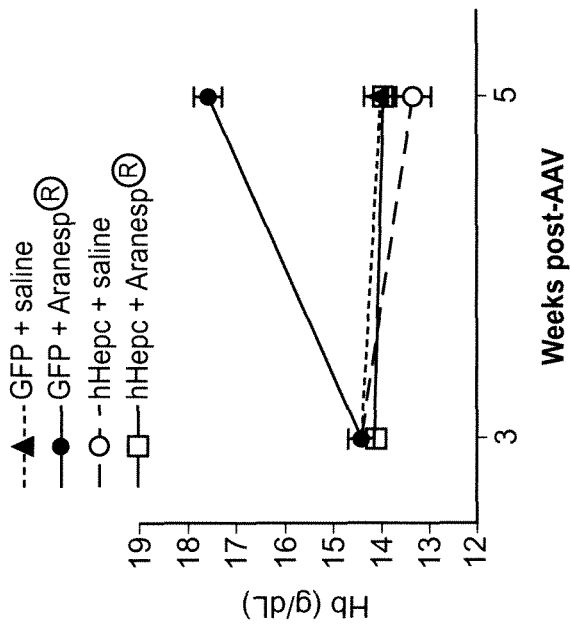
FIG. 13A shows that viral overexpression of hepcidin causes hypo-responsiveness to erythropoietin.

In order to evaluate hepcidin's effect on erythropoietin resistance, male C57BL/6 mice were injected with AAV ($3\times10^{12}$ particles/mouse, hepatic portal vein delivery) containing expression cassettes for either human hepcidin or GFP as a negative control (n=5 per group). The mice were left for three weeks to allow constitutive production of human hepcidin, and then bled to determine baseline hemoglobin (Hb) levels. The mice were treated with darbepoetin alfa (100 μg/kg/mouse) or saline as a negative control at four weeks. At five weeks, hemoglobin levels were again measured. Results are shown in FIG. 13A. Mice over-expressing human hepcidin are resistant to high doses of darbepoetin alfa. Resistance to darbepoetin alfa demonstrates that elevated hepcidin levels are sufficient to cause hypo-responsiveness to erythropoetin.

Example 22

Figure 15A:
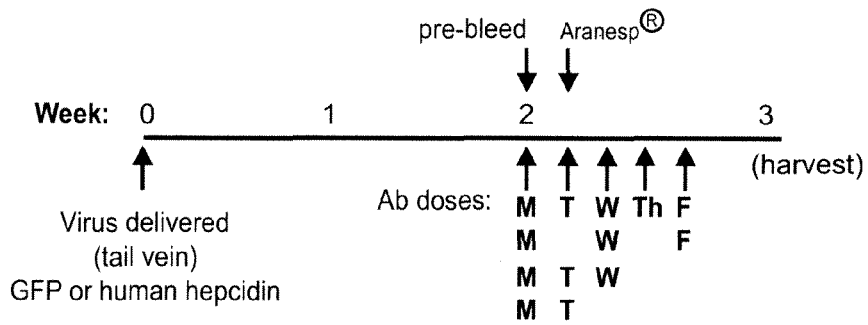
FIG. 15A shows a schematic of the experimental procedure of Example 22.

Combination Therapy with Hepcidin Activity Antagonist and an Erythropoiesis Stimulator in a Viral Hepcidin Over-Expression Model Treating mice that possessed an erythropoetin resistant phenotype with an anti-hepcidin antibody restored responsiveness to treatment with darbepoetin alfa. Male C57BL/6 mice were injected with AAV ($5\times10^{12}$ particles/mouse, I.V.) containing genes coding for either human hepcidin or GFP as an expression control (n=5 per group). After allowing two weeks to establish constitutive protein expression, mice were bled to determine baseline hemoglobin (Hb) levels, then treated with Ab 2.7 (1 mg/mouse) or isotype control at various dose frequencies. On the day after the first dose, they were treated with darbepoetin alfa (100 μg/kg, subcutaneous). A schematic of the dosing schedule appears in FIG. 15A.

Figure 15B:
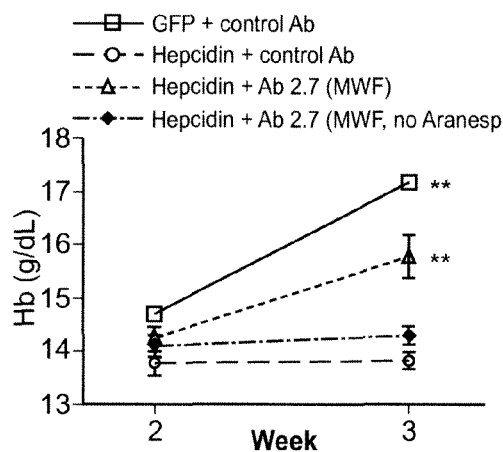
FIGS. 15B-E demonstrate that an anti-hepcidin antibody restores responsiveness to erythropoietin in mice virally over-expressing hepcidin.
Figure 15C:
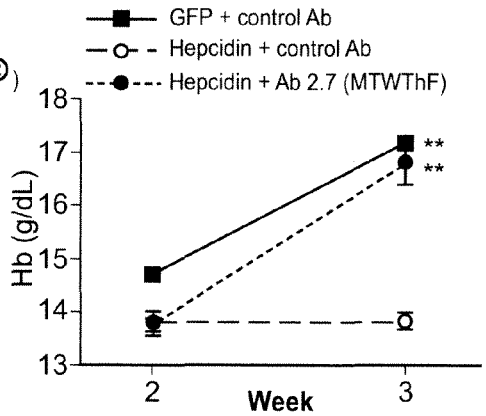
Figure 15D:
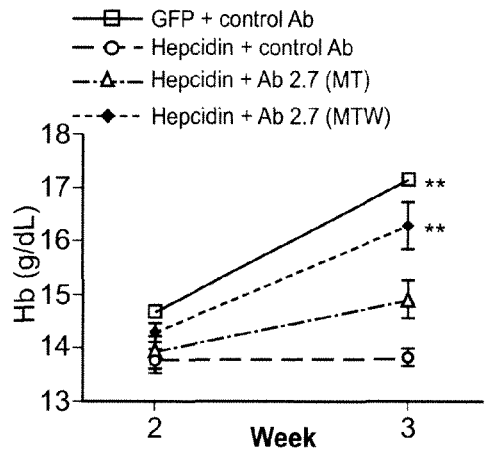
Figure 15E:
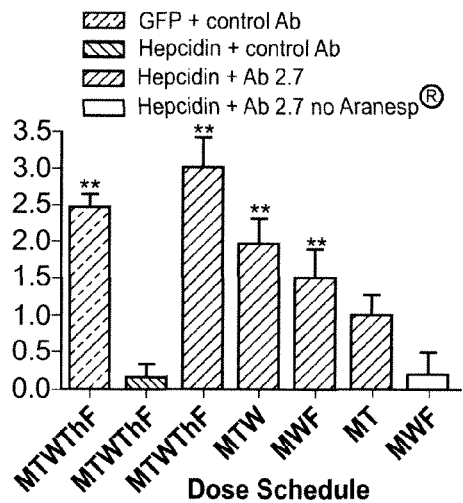

Neutralization of hepcidin restores responsiveness to darbepoetin alfa. Monday-Wednesday-Friday dosing of the antibody led to a partial response to darbepoietin alfa treatment as measured by an increase in Hb levels; a cohort with the same antibody dosing without darbepoietin alfa treatment showed no rise in Hb levels. (See FIG. 15B.) A maximal response to darbepoietin alfa was achieved in mice receiving daily (Monday through Friday) dosing of Ab 2.7. (See FIG. 15C.) Two and three doses of antibody in combination with darbepoietin alfa treatment led to a partial response, as measured by Hb levels. (See FIG. 15D.) Antibody dose and proximity of antibody dose to darbepoietin alfa treatment affected overall Hb response to anti-hepcidin antibody treatment, as shown in FIG. 15E (results varying from the control where p<0.01 by ANOVA with Dunnett's post-hoc test are noted with double asterisks). Thus, antibody-mediated neutralization of hepcidin was shown to be an effective treatment for anemia caused by elevated hepcidin levels.

Example 23

Design and Synthesis of siRNAs for Murine Hepcidin 1

Screening of murine Hepcidin 1 siRNAs in vitro: CHO-mHepcidin stable cells (Helen Kim) were seeded into 96-well plates at 30,000 cells/well. The following day, cells were transfected by removing the culture medium and adding 100 ul of transfection complex. The transfection complex was made as follows: 1 μl of 100 μM siRNA was added to 125 μl Opti-MEM (Invitrogen #31985) in Tube A. In Tube B, 15 μl of TransIT-TKO transfection reagent (Mirus #MIR-2154) was added to 125 μl Opti-MEM. Both tubes were incubated at room temperature for 12 min. Contents of the 2 tubes were mixed and incubated at room temperature for 15 minutes, then added to the cells. At 18 hr post-transfection, medium was removed and cells were lysed using 100 μl of 1 × QuantiGene Lysis Mixture (Panomics #QG 0502). Lysates were analyzed for mHepcidin and mCyclophilin A mRNA levels using branched DNA assays (QuantiGene Assay Kit, Panomics #QG0003). See Table 8 for siRNA sequences and % mRNA knockdown in CHO-mHepcidin cells.

Conversion of siRNAs #6 and #10 to pENTR-U6-shRNA expression constructs:

pENTR-U6-shRNA expression constructs were generated by 2-stage overlap PCR. Step 1 generates 2 overlapping sequences through a 5'-PCR reaction and a 3'-PCR reaction. The 5'-PCR reaction produces a sequence containing the attB1 recombination site, hU6 promoter, the siRNA sense sequence, a loop and the siRNA antisense sequence. Reaction was as follows in 10 μl total volume: 1× PCR Supermix (Invitrogen #10572-014), 1 μM attB-111-U6 forward primer (5'-GGGGACAAGTTTGTACAAAAAAGC AGGCTTA-GATCTGAATTCAATTTACGCGTGGGATCCAAGGTC-3', SEQ ID NO: 105), 0.1 μM REV-U6-shRNA primer (unique for #6: 5'-CTTTTCTCATGAAAAAGGCTG-CAGCTCTGTAGCGGTGTTTCGTCC-3' (SEQ ID NO: 63), and #10: 5'-TACATCTCATGAATGTAGTCTGTC TCATCTGTCGGTGTTTCGTCC-3' (SEQ ID NO: 67) ),and 0.5 ng (1 μl ) pSuppressor template plasmid (IMGENEX #IMG-700). The 3'-PCR reaction produces a sequence containing the shRNA sense, loop, and antisense sequence, a PolIII terminator and the attB2 recombination site. Reaction was as follows in 10 μl total volume: 1× PCR Supermix (Invitrogen #10572-014), 1 μM AttB-202 reverse primer (GGGGACCACTTTGTACAA GAAAGCTGGGTAAAAA, SEQ ID NO: 106), 0.1 μM FW-U6-shRNA primer (unique for #6: 5'-CTTTT TCATGAGAAAAGGCTGCAGCTCTG-TAGCTTTTTACCCAGC-3' (SEQ ID NO: 63), and #10: 5'-TACATTCATGAGATGTAGTCTGTCT-CATCTGTCTTTTTACCCAGC-3' (SEQ ID NO: 67)). PCR conditions for both reactions were as follows: 1 cycle of 3 min 95° C., 30 cycles of 95° C. 45 s, 52° C. 45 s, 72° C. 45 s and 1 cycle of 5 min 72° C. Step 2 of the PCR combines the 5' and 3' PCR products from step 1 for an annealing/fill-in reaction to generate the full length sequence: attB1-hU6 promoter-sense-loop-antisense-terminator-attB2. The reaction was as follows in 20 μl total volume: PCR products from step 1: 5' and 3' PCR reactions were mixed and run in the thermal cycler with the following conditions: 95° C. 2 min, 52° C. 2 min, 72° C. 2 min (5 cycles) plus 72° C. 10 min.

The PCR products were recombined by Gateway BP recombination into pDONR221 to generate pENTR constructs as follows: 7.5 ng (1 μl ) pDONR221 (Invitrogen #12536-017), 1 μl 5×BP reaction buffer (Invitrogen #52891), 1 μl BP clonase (Invitrogen #11789-013), and 2.5 μl of overlap PCR product were mixed together and incubated 2 hours at room temperature. 1 μl Proteinase K (Invitrogen #52895) was then added and incubated at 37° C. for 10 min. The entire 6 μl recombination reaction was transformed into One Shot Top 10 Chemically Competent cells (Invitrogen #C4040-03) and plated on LB-kanamycin plates. Colonies were selected & amplified. Plasmid DNA was confirmed by DNA sequencing of the U6-shRNA region using M13FW and M13REV sequencing primers.

TABLE 8

| siRNA Number | siRNA Sequence (Sense, 5'-3') | % mRNA knockdown by siRNA in CHO-mHepcidin cells | % mRNA knockdown by AAV-shRNA in HEK293 cells | SEQ ID NO: |
|---|---|---|---|---|
| 1 | UGU AAA UGC UGU AAC AAU U | 95 | | 58 |
| 2 | GCU GUA AAU GCU GUA ACA A | 95 | | 59 |
| 3 | GUG UGG UAU CUG UUG CAA A | 96 | | 60 |
| 4 | GCA GAC AUU GCG AUA CCA A | 90 | | 61 |
| 5 | AUA CCA AUG CAG AAG AGA A | 94 | | 62 |
| 6 | CUA CAG AGC UGC AGC CUU U | 95 | 69 | 63 |
| 7 | GAA GAG AGA CAC CAA CUU C | 88 | | 64 |
| 8 | ACU UCC CCA UCU GCA UCU U | 27 | | 65 |
| 9 | CUG AGC AGC ACC ACC UAU C | 86 | | 66 |
| 10 | ACA GAU GAG ACA GAC UAC A | 96 | 81 | 67 |
| 11 | CAA UGC AGA AGA GAA GGA A | 86 | | 68 |
| 12 | AAU UCC CAG UGU GGU AUC U | 65 | | 69 |

Example 24

Combination Therapy with Hepcidin Expression Inhibitor and Erythropoiesis Stimulator in a Mouse Model of Inflammatory Anemia Combination therapy with a hepcidin expression inhibitor and an erythropoiesis stimulator was evaluated in a murine inflammatory anemia model as follows.

A polynucleotide hepcidin expression inhibitor which causes suppression of murine hepcidin was prepared as follows. siRNAs demonstrated to have specific activity against hepcidin in vitro (siRNA 6 CUACAGAGCUGCAGCCUUU (SEQ ID NO: 70); siRNA 10 ACAGAUGAGACAGAC-UACA (SEQ ID NO: 71) were converted to shRNAs in an AAV expression system as described in Example 23.

Mice were injected in the portal vein with AAV virus containing either a negative control shRNA (anti-luciferase, $2\times10^{12}$ particles/mouse) or specific anti-hepcidin shRNA (shRNA 6, $5\times10^{11}$ particles/mouse=low dose; $2\times10^{12}$ particles/mouse=medium dose; and shRNA10, $2\times10^{12}$ particles/mouse=high dose). Inflammation was induced in these mice by treatment with *Brucella abortus* (BA) ($5\times10^8$ particles/mouse, given 7 days before harvest). Control mice with no inflammation induction and no shRNA treatment were also evaluated to determine the average hepcidin levels in untreated animals.

Mouse hepcidin levels were determined using MALDI-TOF mass spectrometry. MSIA-tips (affinity pipettes with immobilized anti-mouse hepcidin antibody R9) were used to extract hepcidin from mouse serum. The extracted hepcidin was eluted onto a MALDI target for time of flight mass spectrometric detection. Human hepcidin was used as an internal standard for quantitation.

Serum hepcidin and serum hemoglobin levels were determined 25 days after shRNA injection. Mice treated with anti-hepcidin shRNA showed suppression of hepcidin levels to non-inflammatory levels. See FIG. 14A. Hepcidin mRNA levels were consistent with those of serum hepcidin.

Figure 14B:
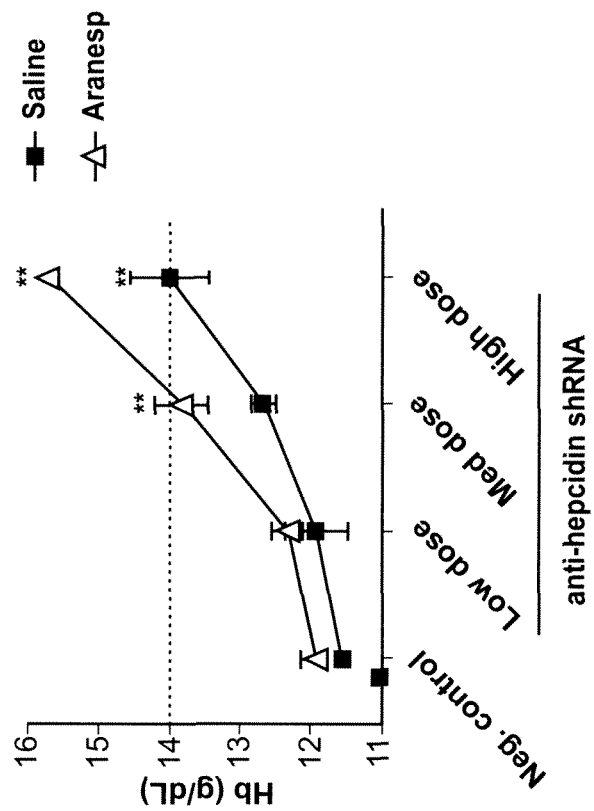
FIG. 14 shows that suppressing hepcidin restores responsiveness to Aranesp® (darbepoetin alfa) in an inflammatory anemia model.
Figure 14A:
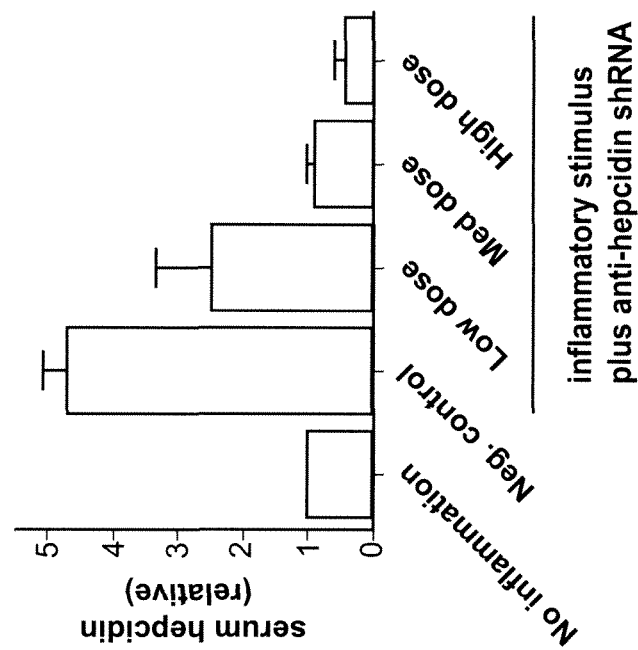

Mice in parallel groups were injected with virus as described above (either negative control or hepcidin-specific shRNA) and 18 days later treated with *Brucella abortus* to induce inflammatory anemia. On day 19, animals were injected with 100 µg/kg of Aranesp to stimulate an erythropoietic response and hemoglobin (Hb) levels determined a week later (same harvest timepoint as above). FIG. 14B shows that control animals without inflammatory treatment responded normally to Aranesp with a Hb rise of 3-4 g/dL, whereas animals treated with BA had a blunted response to Aranesp. In contrast, mice with BA treatment that received hepcidin expression inhibitor showed a response to Aranesp. Thus, treatment with a hepcidin expression inhibitor to suppress hepcidin to pre-inflammatory levels in combination with Aranesp treatment resulted in normal hemoglobin levels. See FIG. 14B. These results show that treatment with a hepcidin expression inhibitor restores responsiveness to Aranesp.

Example 25

Combination Therapy with an Anti-Hepicin Antibody and Erythropoiesis Stimulator in a Mouse Model of Inflammatory Anemia Combination therapy with a hepcidin activity antagonist and an erythropoiesis stimulator was also evaluated in a murine inflammatory anemia model as follows.

Mice were generated such that murine hepcidin 1 was knocked out and replaced with human hepcidin. Female mice, both homozygous for human hepcidin expression and wild-type littermate controls, were injected with *Brucella abortus* ($2\times10^8$ particles/mouse, I.P.) on day 0 and then bled on day 6 to assess hemoglobin levels. The mice were then treated with either Antibody 2.7 or an isotype control antibody (1 mg/mouse/day) on days 6 through 9. Darbepoetin alfa was administered (100 µg/kg/mouse) on day 7, and Hb levels evaluated on day 13. A schematic of the protocol is shown in FIG. 16A.

Wild-type control mice which still possessed the mouse hepcidin 1 gene did not respond to darbepoietin alfa either with or without Ab 2.7. (See FIG. 16B.) Human knock-in mice treated with Antibody 2.7 exhibited a restored responsiveness to darbepoietin alfa treatment, as shown by the maintenance of stable hemoglobin levels. (See FIG. 16C).

These results demonstrate that hepcidin activity antagonists can be used to neutralize hepcidin under conditions of hepcidin excess and restore responsiveness to erythropoietic agents in hepcidin-mediated anemias such as the anemia of inflammation.

Example 26

Measurement of Hepcidin Level in Patients

The level of hepcidin in human patients was measured as previously described in co-pending co-owned U.S. patent application Ser. No. 11/880,313 and International Patent Application No. PCT/US2007/016477, the disclosures of which are incorporated herein by reference in their entirety. The method is reproduced below.

Samples from patients suffering from anemia of cancer (obtained from ProteoGenex) or volunteers (control) were collected. 100 µL of each sample, serum blanks and calibration standards consisting of seven non-zero concentrations in duplicates (10, 25, 50, 100, 250, 500, 1000 ng/mL) were extracted by SPE using an Oasis HLB mElution 96-well plate (Waters, Milford, Mass.). Washing solvent was 30% methanol/water with a pH of about 10 adjusted with ammonium hydroxide. Elution solvent was 90% methanol/water solution with a pH of about 5 adjusted with acetic acid. The SPE plate was activated with 500 µL methanol and conditioned with 500 µL water, then 100 µL serum sample and 200 µL internal standard were loaded onto the elution plate, washed with 350 µL water and 350 µL washing solvent. Elution was done using 100 µL elution solvent and diluted with 100 µL water. The resulting 200 µL eluate was analyzed by LC-MS/MS.

20 µl of each extracted sample was injected onto a Polaris C18A, 5 µm HPLC column (2.1×50 mm, Varian). The LC flow rate was set to 300 µl/min. The HPLC mobile phase A was 5:95 methanol/water, and mobile phase B was 95:5 methanol/water, both containing 0.1% formic acid. The gradient conditions were set as follows: 0-0.1 min, isocratic 2% B/98% A; 2% B to 95% B at 0.1-4.5 min; 95% B at 4.5-4.9 min; 95% B to 2% B at 4.9-5.0 min; 5.0-6.0 min, isocratic 2% B.

A Sciex API4000 triple quadrupole mass spectrometer from Applied Biosystems (Foster City, Calif.) with Turbo ESI source was used for hepcidin detection in MRM mode with ion transition of m/z 930.60 to m/z 110.15. Quantification was achieved by comparing the ratio of the LC peak areas of the hepcidin and the internal standard to the ratios obtained from a series of standards where the amounts of hepcidin and internal standard were known.

Figure 18:
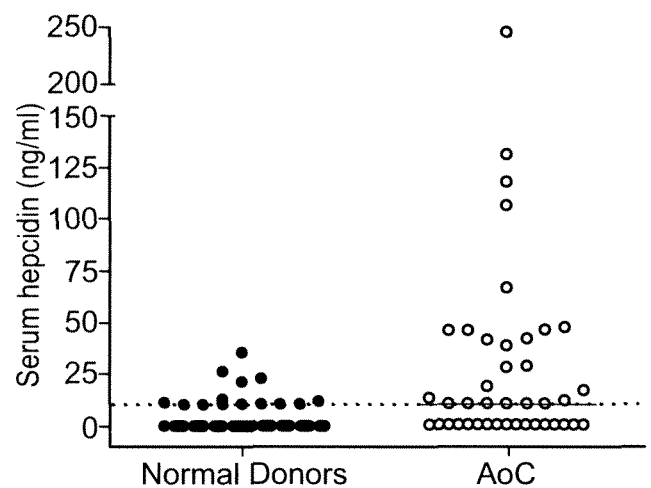
FIG. 18 demonstrates that hepcidin levels are elevated in anemia of cancer patients (AoC) and not in normal patients.

This experiment allowed for the determination of the serum levels of hepcidin in a control population presumed to contain a large number of healthy individuals as well as the serum level of hepcidin from patients suffering anemia of cancers (AoC). The results are shown in FIG. 18.

Figure 19:
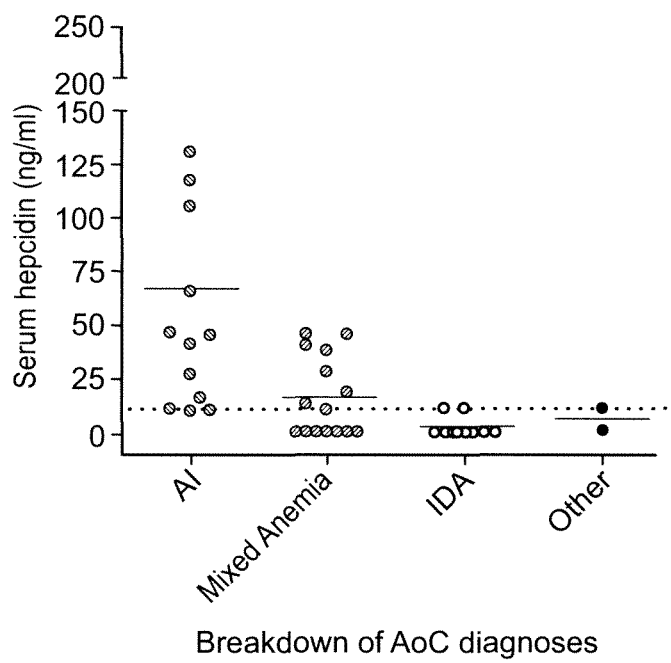
FIG. 19 demonstrates that hepcidin levels correlate with diagnosis of inflammatory anemia and not iron deficiency anemia.

Each patient's sample was then analyzed for other iron index concentrations to determine whether a patient had inflammation or iron deficiency anemia (FIG. 19). The parameters were measured as follows: serum iron, UIBC, ferritin, and CRP were measured on an Olympus AU400 clinical laboratory analyzer using standard procedures; sTfR was measured using a standard ELISA method (R&D systems).

Example 27

The Commercially Available DRG Prohepcidin ELISA does not Detect Mature Hepcidin The following Example demonstrates that a commercially-available prohepcidin ELISA kit (DRG Intl. Inc., Germany) is not capable of detecting mature hepcidin in a sample.

Figure 20B:
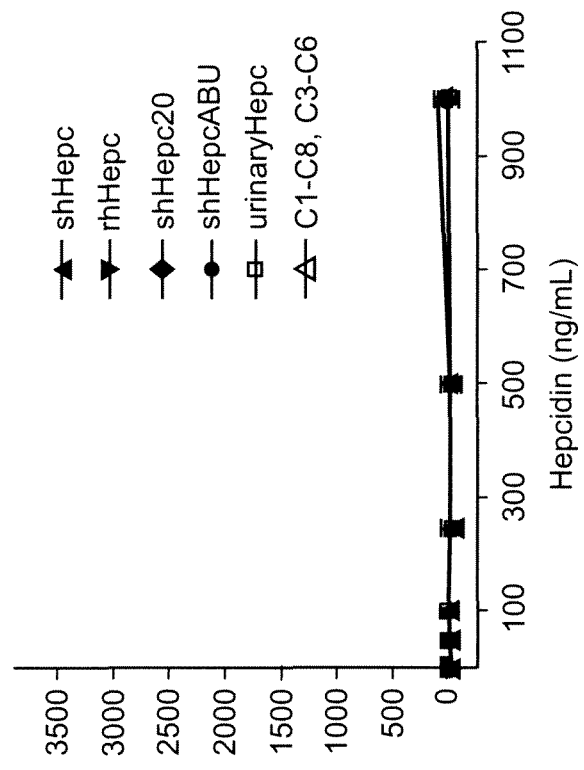
FIG. 20 shows that the commercially available DRG pro-hepcidin ELISA is unable to detect mature hepcidin.
Figure 20A:
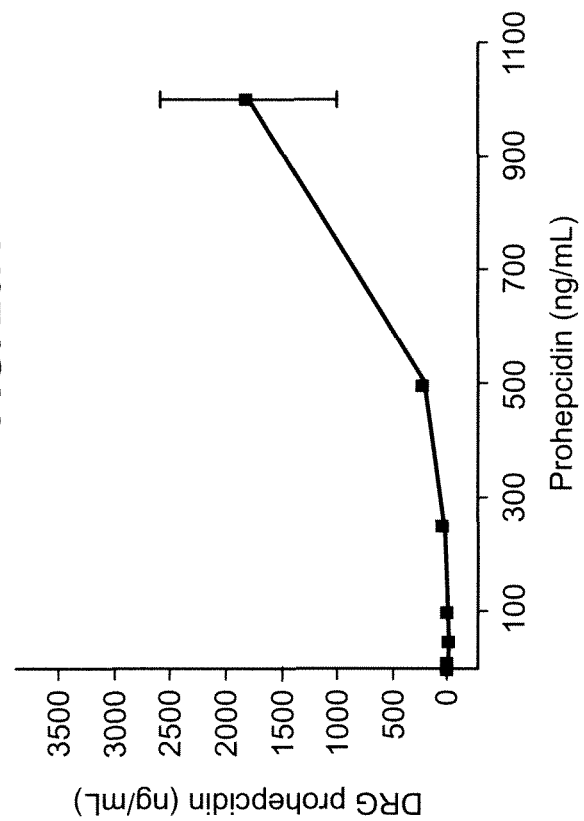

Multiple preparations of synthetic and recombinant hepcidin, including hepcidin produced synthetically (as described in Example 3), recombinantly (as described in Example 2), and isolated from urine (as described in Example 1), were produced in order to evaluate the reactivity of each preparation of hepcidin as compared to recombinant prohepcidin. Each of the hepcidin samples demonstrated biological activity in vitro and in vivo. The commercially-available prohepcidin ELISA kit (DRG Intl. Inc., Germany) detected recombinant prohepcidin (FIG. 20A) but not the multiple preparations of mature hepcidin (FIG. 20B). Additional forms of hepcidin, including shHepc (synthetically produced, folded human hepcidin), rhHepc (material expressed recombinantly in *E. coli* as propeptide then folded and cleaved;), shHepc20 (a variant of hepcidin lacking the five amino acids at the N-terminus), shHepc ABU (a linear version of hepcidin with cysteine residues substituted for 5-amino butyric acid (ABU) to eliminate disulfide bond formation), urinary hepcidin (purified from sepsis patient urine) and C1-C8, C3-C6 (a form of the molecule missing two disulfide connections due to ABU substitutions at C2, C4, C5 and C7) were also tested using the DRG prohepcidin ELISA kit. Similar to the results observed for mature hepcidin, these forms of hepcidin were not detected by the DRG prohepcidin ELISA.

The above data confirm that the commercially-available DRG prohepcidin ELISA kit is unable to detect mature hepcidin.

Example 28

Hepcidin, but not DRG Prohepcidin is Associated with Inflammation in Anemia of Cancer (AoC) Patients Attempts have been made to use the DRG prohepcidin ELISA kit to correlate hepcidin with inflammatory status. (See, e.g., Hsu et al., Blood Purification, 24:311-16, 2006; Kemna et al., Blood, 106:1864-66, 2005; Ouz et al., Anadolu Kardiyoloji Dergisi, 6:239-42, 2006; Taes et al., Clinical Chemistry & Laboratory Medicine, 42:387-89, 2004; Theurl et al., Blood, 107:4142-48, 2006.) This example shows that prohepcidin levels measured using the DRG prohepcidin ELISA kit, however, do not correlate with the mature hepcidin levels of the patients, nor do prohepcidin levels correlate with the inflammatory status of patients.

Figure 21:
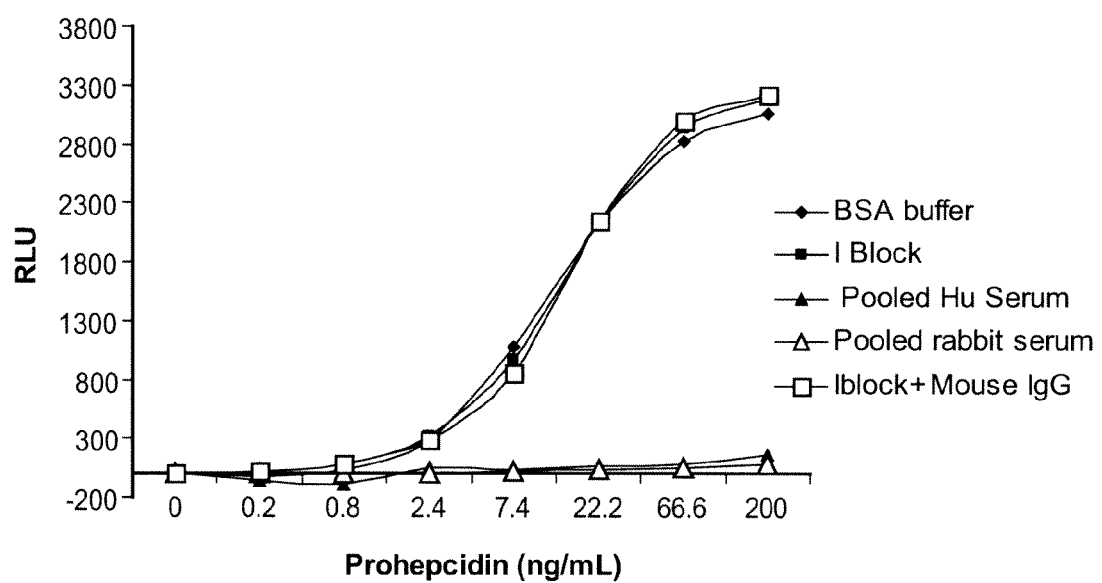
FIG. 21 shows prohepcidin concentration measured by a sandwich immunoassay, demonstrating that prohepcidin is not detectable in serum.

In order to reliably assess prohepcidin concentrations, a prohepcidin standard was measured after incubation for 60 minutes at 25° C. in a range of different buffers or sera. Prohepcidin concentration was determined by a sandwich immunoassay using Ab2.7 for capture (Ab2.7 detects an epitope in mature hepcidin) and biotinylated rabbit anti-prohepcidin polyclonal antibody (detects an epitope in the pro-region) for detection. The results, shown in FIG. 21, demonstrate that prohepcidin was not detectable in serum, suggesting it is rapidly degraded.

Figure 22:
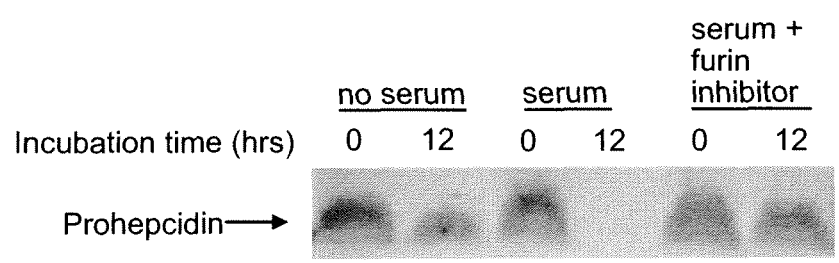
FIG. 22 shows a prohepcidin western blot, indicating that prohepcidin is degraded in serum unless protected by the presence of furin inhibitors
Figure 23:
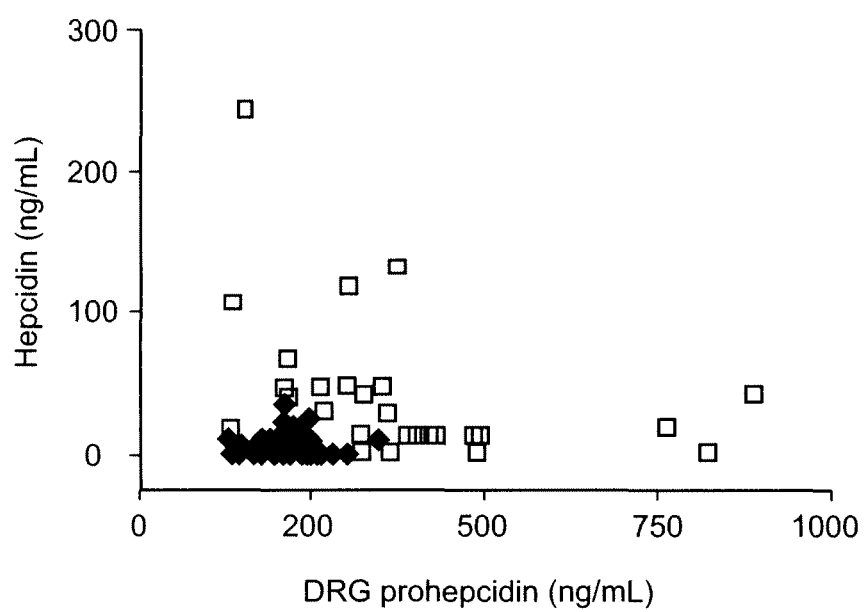
FIG. 23 shows that hepcidin and prohepcidin levels (as measured by the commercially available DRG prohepcidin ELISA) do not correlate in patient samples.

Western blotting experiments confirmed that prohepcidin is degraded in serum unless furin inhibitors are added (FIG. 22). Prohepcidin (2 mg) was incubated for 12 hrs at 37° C. or added immediately before the gel run to medium alone or to medium containing 10% fetal bovine serum with or without a furin inhibitor. Non-reduced samples were separated using a NuPage 4-12% Bis-Tris gel, blotted onto a nitrocellulose membrane and detected using a rabbit anti-hepcidin polyclonal antiserum followed by an anti-rabbit HRP-conjugated secondary antibody.

Given the unstable nature of prohepcidin in serum, the elevated levels of prohepcidin detected in patient samples using the DRG prohepcidin ELISA kit likely reflect is either the cleaved N-terminal portion of prohepcidin or another protein. In order to determine whether serum prohepcidin levels correlated with serum hepcidin levels, hepcidin and prohepcidin levels were measured in the serum of control donors and anemia of cancer (AoC) patients. Hepcidin concentrations were determined using a mass spectrometry-based quantitation method described in co-pending co-owned U.S. patent application Ser. No. 11/880,313 and International Patent Application No. PCT/US2007/016477, the disclosures of which are incorporated herein by reference in their entirety. No significant relationship was found between hepcidin levels measured by the mass spectrometry-based quantitation method and prohepcidin levels measured by the DRG prohepcidin ELISA kit in AoC patients ($r=0.1014$; NS) or control donors ($r=-0.1128$; NS). (FIG. 19.) Hence, elevated prohepcidin levels as measured by the DRG prohepcidin ELISA kit cannot be used as a surrogate for hepcidin levels.

To determine if hepcidin or prohepcidin levels as measured by the DRG prohepcidin ELISA kit were elevated in patients with inflammation, both indices were compared to C-reactive protein (CRP) levels in the patient sera. CRP is a well-established marker of inflammation. A strong relationship was observed between CRP and hepcidin levels in the anemia of cancer patients (FIG. 24A), but no relationship was observed between CRP and DRG prohepcidin (FIG. 24B) in those patients. Normal donors showed no significant relationship between CRP and either hepcidin or DRG prohepcidin, but levels of CRP were not markedly elevated in these donors, making relationships difficult to detect. Hepcidin, but not prohepcidin, shows a relationship with CRP in anemia of cancer patients, and can therefore be used as a marker of inflammation.

Distinguishing the anemia of inflammation (AI) from iron deficiency anemia (IDA) and mixed anemia (components of both AI and IDA) is complicated since most of the commonly used lab parameters are influenced by acute phase responses. A ratio utilizing soluble transferrin receptor (sTfR) and ferritin (Ft) values has been described in the literature as a means to provide a more accurate diagnosis. See Punnonen et al., Blood, 89:1052-57, 1997. Anemia of inflammation is characterized by a low sTfR/log Ft quotient (values less than one), while a high ratio is indicative of IDA. Hence, the sTfR/log Ft ratio may serve as an accurate predictor of the three conditions when combined with an inflammatory marker to aid diagnosis of mixed anemia from absolute IDA.

Figures 25A, 25B:
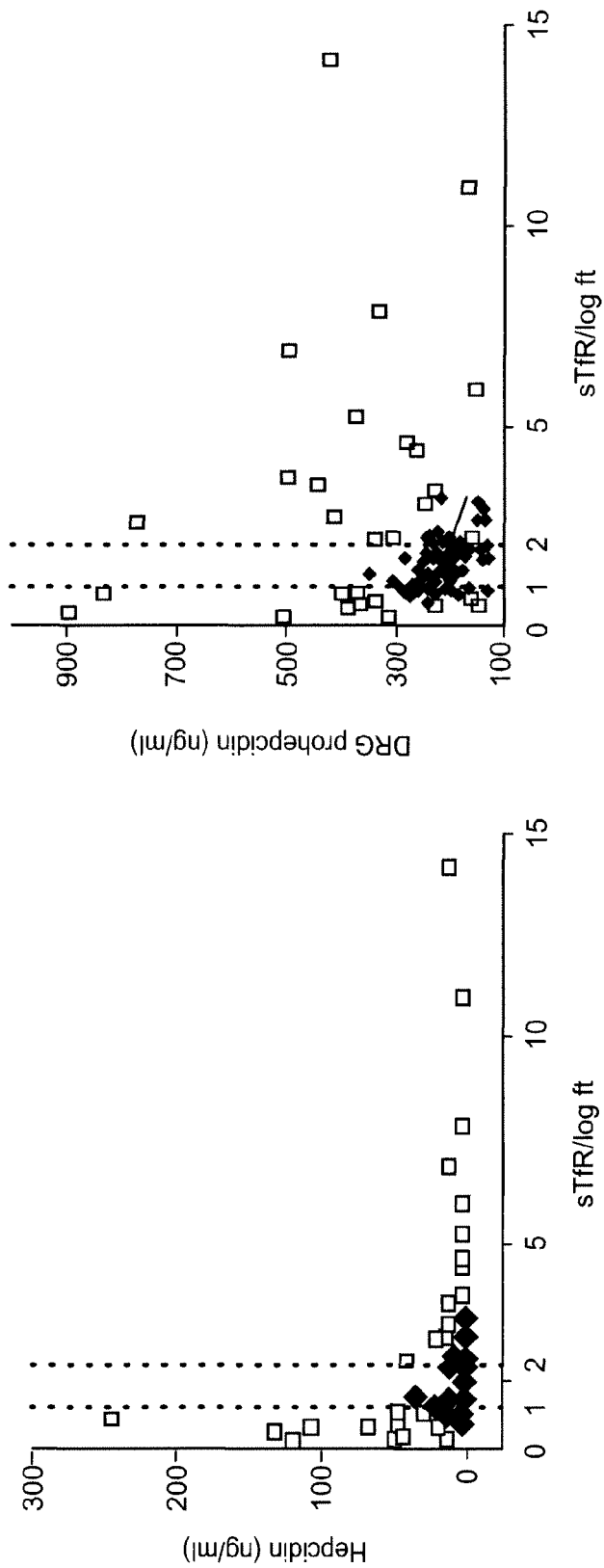
FIGS. 25A-B show that hepcidin levels aid in diagnosis of anemia of inflammation (A), and prohepcidin levels do not (B).

Both hepcidin and prohepcidin as measured by the DRG prohepcidin ELISA kit were tested for their ability to aid in this diagnosis. Hepcidin levels are elevated in AI as determined by sTfR/log Ft. Hepcidin levels are strongly related to sTfR/log Ft levels in AoC patients (r=−0.6407; P<0.0001). Thus, hepcidin levels are strongly related to sTfR/log Ft levels in AoC patients showing a clear relationship and aiding patient diagnosis (FIG. 25A). No such relationship was seen with DRG prohepcidin (FIG. 25B).

Figure 17A:
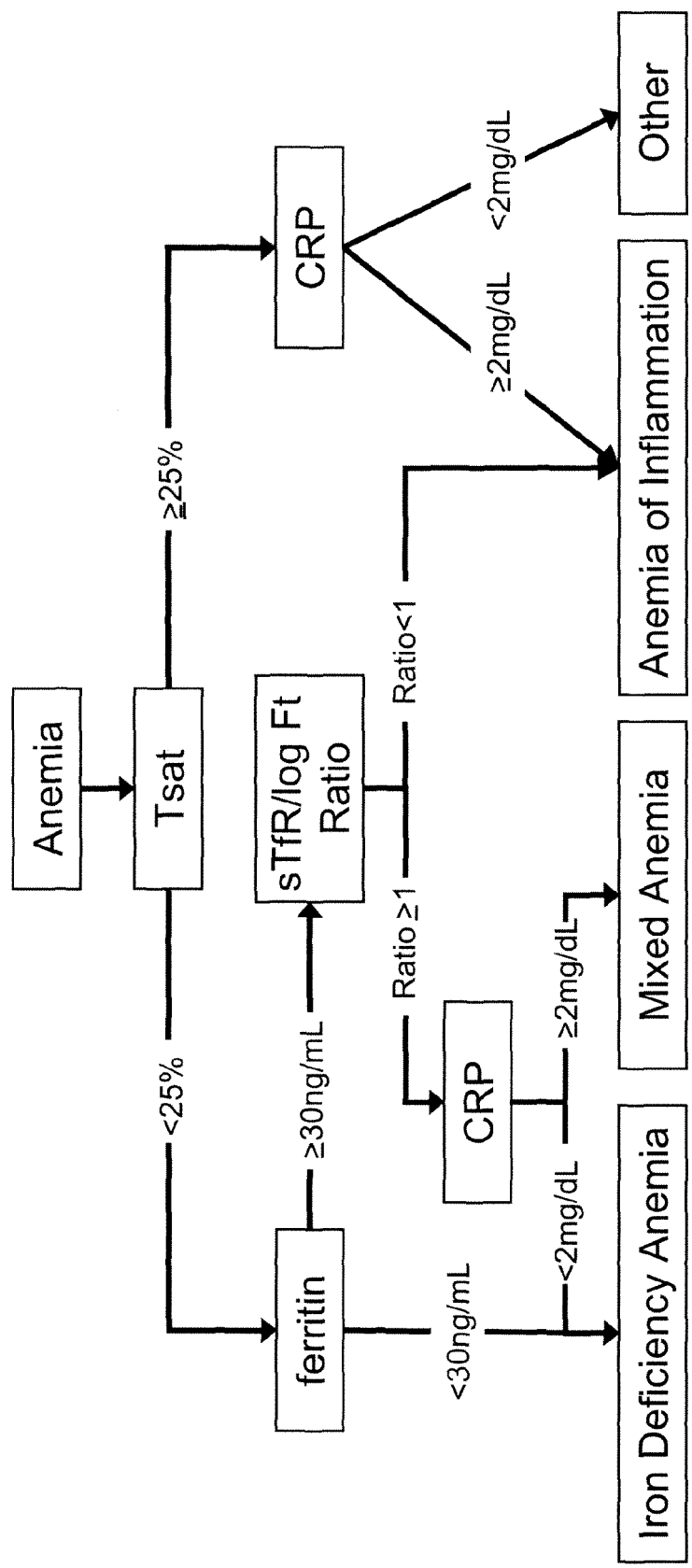
FIG. 17A shows a decision tree of iron indices and disease states for assessment of a patient, in the absence of hepcidin measurement
Figure 17B:
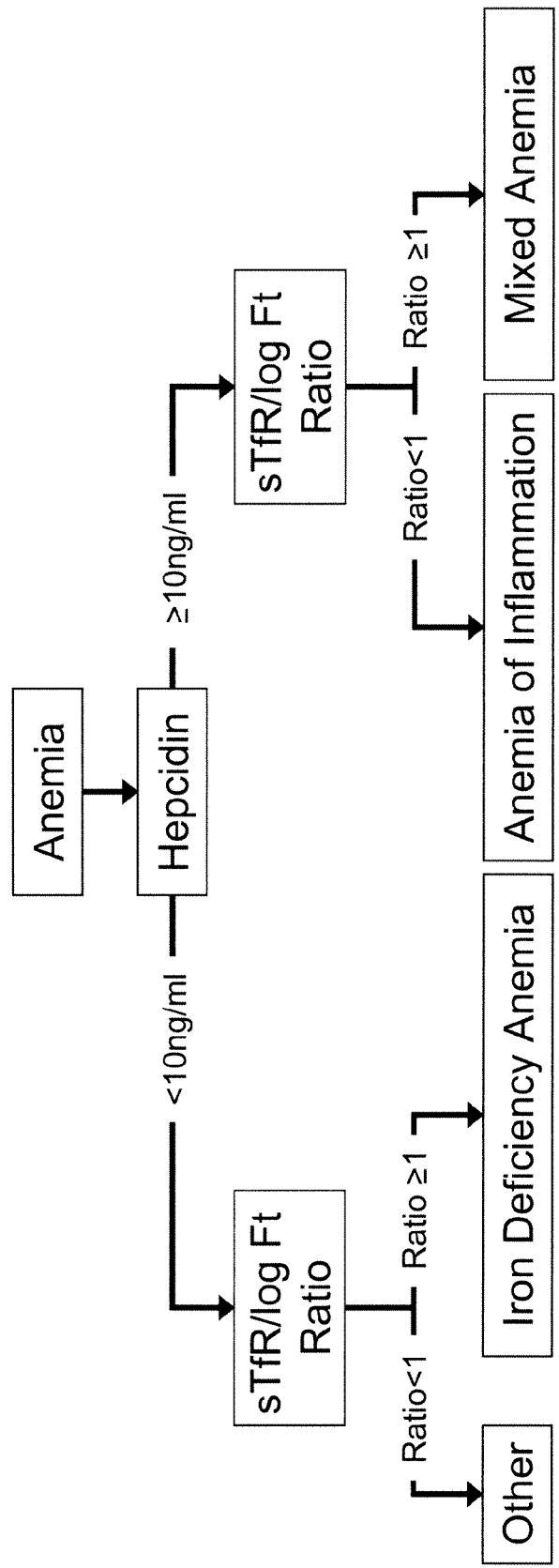
FIG. 17B shows a theoretical decision tree for assessment of a patient using measurement of hepcidin levels.

Using a decision tree combining CRP as a marker of inflammation and sTfR/logFt, anemia of cancer patients could be sub-divided into those with AI, with mixed anemia, with IDA and with an anemia of unknown origin, designated 'other' (FIG. 17A). Patients with elevated hepcidin levels were all observed to have either AI or a mixed anemia. (FIG. 26). Patients with low or absent hepcidin levels were observed to have either IDA or anemia of unknown origin. Hepcidin levels, as measured by the mass spectrometry-based method quantitation method described in co-pending co-owned U.S. patent application Ser. No. 11/880,313 and International Patent Application No. PCT/US2007/016477, the disclosures of which are incorporated herein by reference in their entirety, and discussed in detail above, can be used to diagnose inflammatory anemia.

Example 29

Polyclonal Antibodies in a Sandwich ELISA for Hepcidin

Because polyclonal antibodies represent a complex mixture of different antibodies against the immunogen, they represent one way of detecting all possible epitopes present in a protein. To determine if a monoclonal antibody sandwich ELISA against hepcidin was possible, preliminary experiments were conducted using polyclonal antibodies raised against KLH-conjugated mature human hepcidin.

Figure 27:
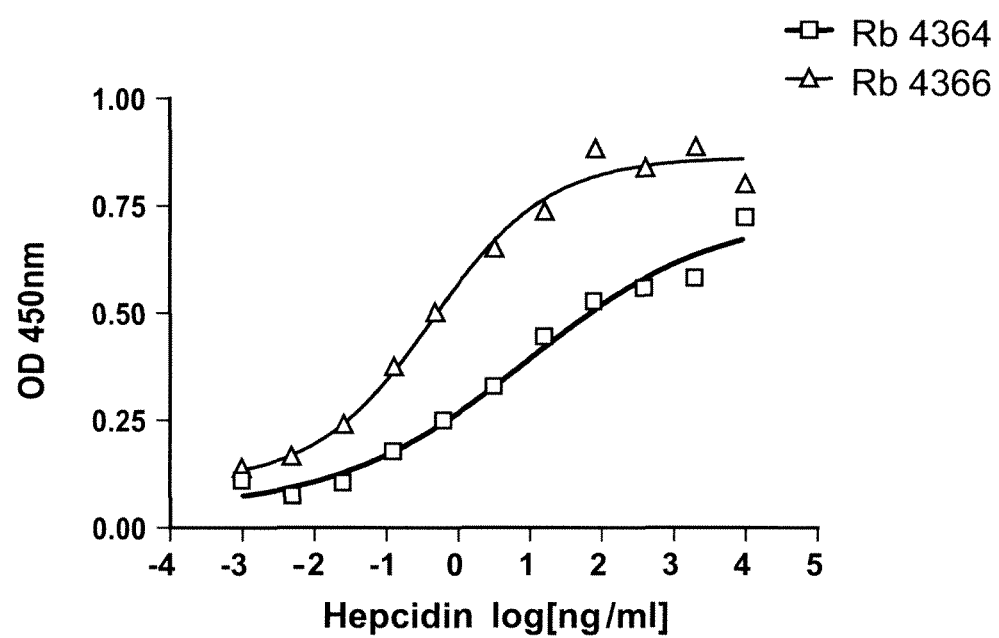
FIG. 27 demonstrates that polyclonal antibodies raised against mature hepcidin can be used to construct a sandwich ELISA.

IgG from polyclonal rabbit antisera were coated onto a microtiter plate, mature hepcidin was diluted and added to the plate and biotinylated IgG from the same source was used to detect bound hepcidin. All antibodies were used at concentrations of 10 μg/ml. As seen in FIG. 27, this experiment was able to detect bound hepcidin, suggesting that it might be possible to measure hepcidin in a sandwich format. The sensitivity of this assay was low, however, indicating that the ability of two antibodies to bind simultaneously to hepcidin may represent a rare event.

Example 30

Monoclonal Antibodies in a Sandwich Immunoassay for Hepcidin

The following Example describes a sandwich immunoassay to determine hepcidin levels in a sample.

Figure 28:
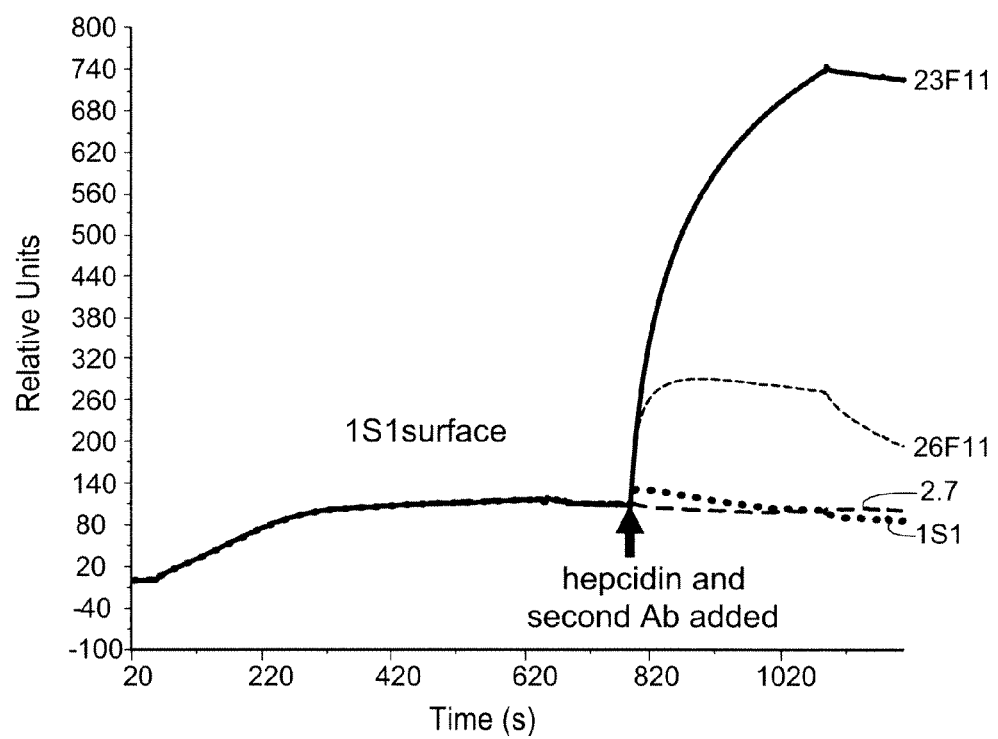
FIG. 28 shows a Biacore experiment demonstrating that two monoclonal antibodies can bind to hepcidin at once.

Using Biacore analysis, a surface coated with antibody 1S1 was tested for the concurrent binding of hepcidin and another antibody (FIG. 28). Immobilization of anti-Hepc antibody 1S1 to the sensor chip surface was performed according to manufacturer's instructions using a continuous flow of 0.005% P-20/PBS buffer. Briefly, carboxyl groups on the sensor chip surfaces were activated by injecting 60 μL of a mixture containing 0.2 M N-ethyl-N'-(dimethylaminopropyl)carbodiimide (EDC) and 0.05 M N-hydroxysuccinimide (NHS). This was followed by injecting 1S1 diluted in 10 mM acetate, pH 4.0 at concentrations between 20 μg/mL. Excess reactive groups on the surfaces were deactivated by injecting 60 μL of 1 M ethanolamine. Final immobilized levels were 5,000-6,000 resonance units (RU) for the Ab 1S1 surface. A blank, mock-coupled reference surface was also prepared on the sensor chip. 20 nM E. coli-derived human hepcidin was injected over and bound to the 1S1 antibody surface. Then 50 nM antibody 2.7, 23 F11, 26F11, and 1S1 were injected over the hepcidin 1 S1 surface. After the antibody injection, the surfaces were regenerated by injecting 30 μL 10 mM HCl pH 2.0.

There was a high selectivity of binding in the form of complexes. The murine antibody 2.7, which was used in the competitive assay above, was not able to form a sandwich pair with 1S1, and 26F11 showed markedly lower ability to bind to hepcidin concurrently with 1S1 than did 23F11.

Example 31

Figure 29:
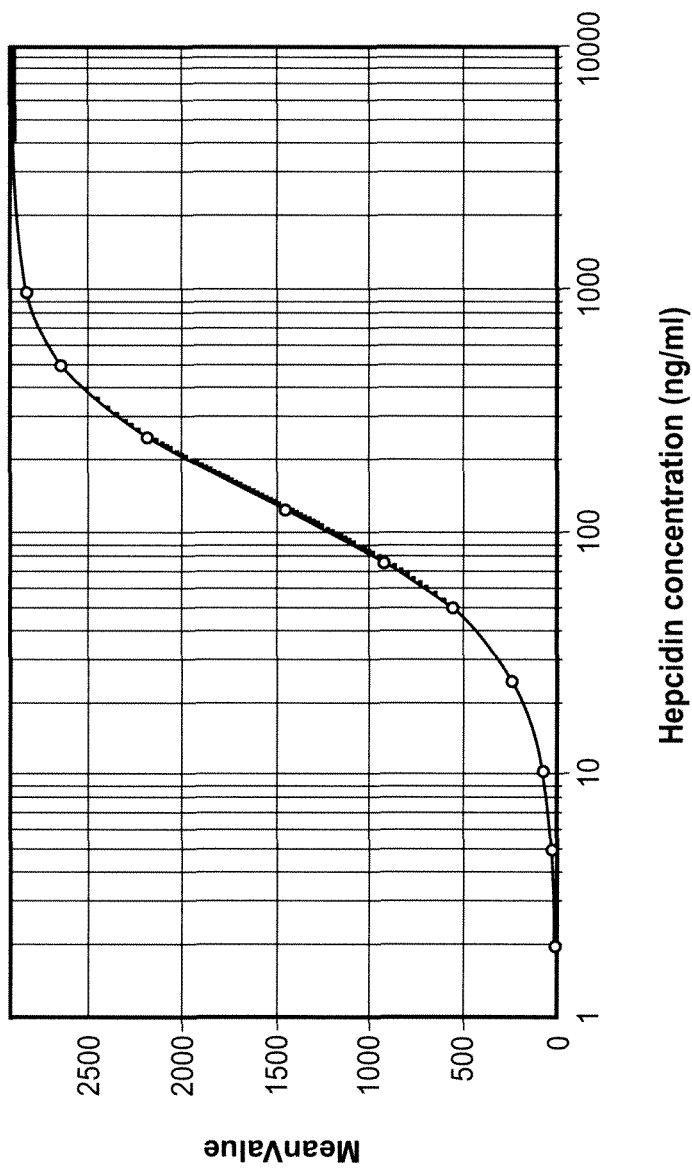
FIG. 29 demonstrates that a sandwich ELISA can be constructed with monoclonal antibodies raised against mature hepcidin.

Monoclonal Antibodies Raised Against Mature Hepcidin can be Used to Construct a Sandwich ELISA Following the Biacore result obtained in Example 30, 1100 antibodies which had previously been demonstrated to have reactivity with hepcidin were screened for the ability to "pair" with 12S1. Only 11 antibodies, or approximately 1%, were identified that were suitable. It therefore appears that the ability to form "pairs" that are usable in developing sandwich assays for hepcidin are rare. When 1S1 and 23F11 were assembled into a sandwich ELISA format, the sensitivity of the immunoassay for detecting hepcidin levels was improved by 50-fold. As shown in FIG. 29, the assay proved capable of measuring levels of hepcidin in normal sera after a 50-fold pre-dilution step. The axis represents the hepcidin levels pre-dilution.

Example 32

Competitive Binding Assay

The following Example describes a competitive binding assay to determine hepcidin levels. In one protocol, unlabeled hepcidin present in serum competes with biotinylated hepcidin for binding to an anti-hepcidin antibody (e.g., Antibody 2.7).

Figure 30:
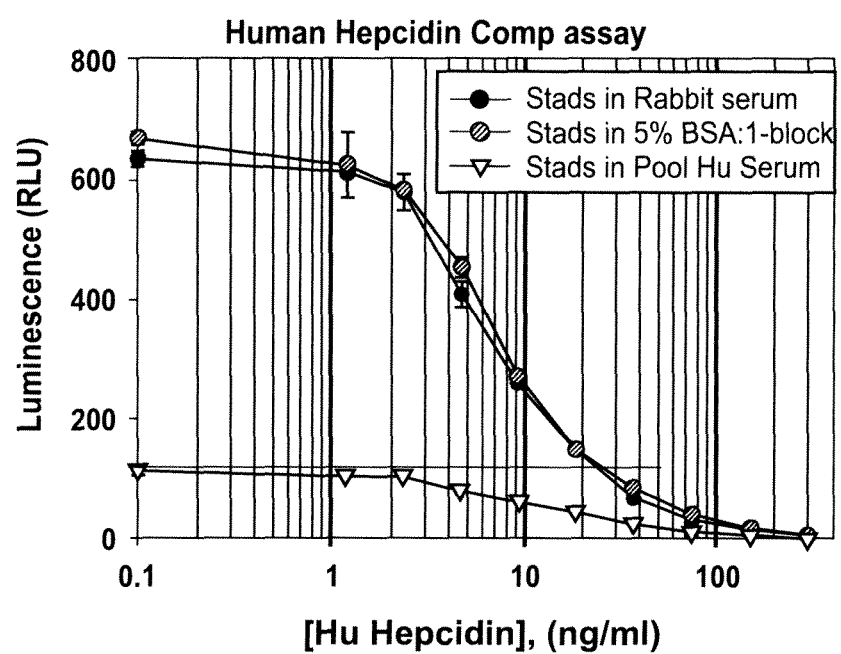
FIG. 30 shows the concentration of hepcidin present in buffer, rabbit serum and pooled human serum as determined by a competitive binding assay.

Hepcidin levels were determined using hepcidin standards of varying concentrations (from 1.4-300 ng/ml) spiked into buffer (5% BSA:I-block), rabbit serum, or pooled human serum. Hepcidin was added to equal volumes of 40 ng/mL of Ab2.7 and incubated for 120 minutes. 25 μl/well of mixed solution was added to Black half area plates coated with 1-2 μg/mL GxM capture antibody. 25 μL/well of biotinylated hepcidin was added at 0.25 nM. The plate was covered with plate film sealer and incubated at room temperature (25° C.) on a plate shaker at around ≤200 RPM for around 60 minutes. The plate was washed and then 50 μL/well of Poly horseradish peroxidase amplification reagent at 1:2000 was added. The plate was allowed to sit for 30 minutes and was then washed with a plate washer using PBS or KPL buffer 6 times. The plate was patted dry and a luminescent substrate (Femto or Pico) was quickly added. The plate was read with luminometer (ex: Lmax 340) for 1 second using Femto or Pico Substrate. Results indicated that hepcidin was measurable at a concentration range of 1-100 ng/ml in both the the rabbit serum and buffer. (FIG. 30).

Figure 31:
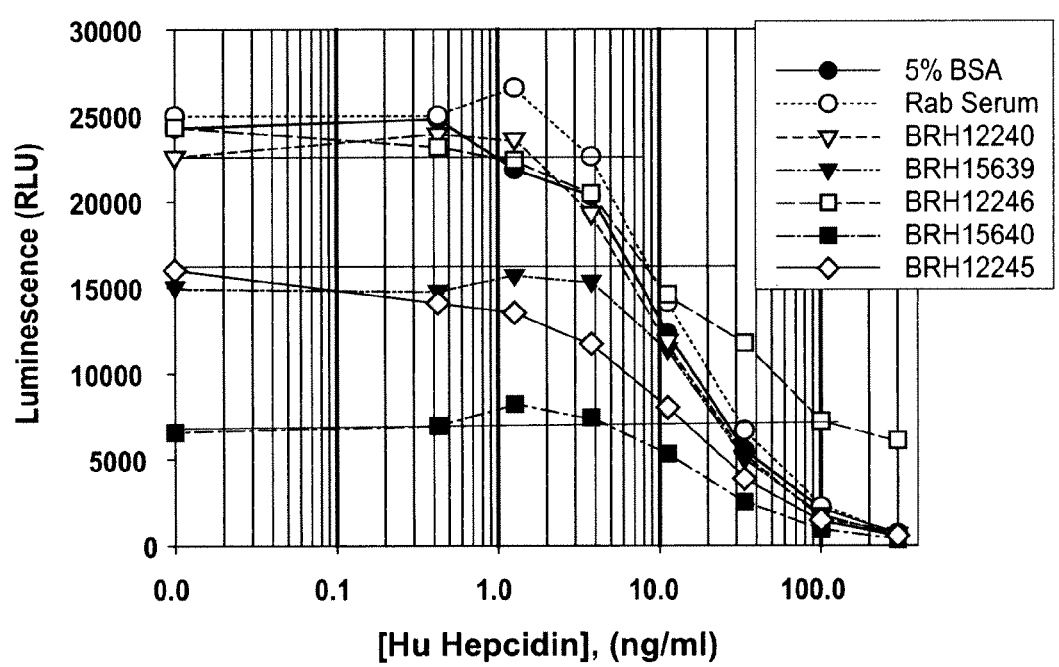
FIG. 31 demonstrates the measurement of hepcidin in human sera.

Pooled human serum appeared to have an existing hepcidin level of greater than 20 ng/ml. It was determined that the levels of hepcidin varied substantially in human sera, over the range of 1-30 ng/ml for various randomly selected sera (FIG. 31).

Figure 32:
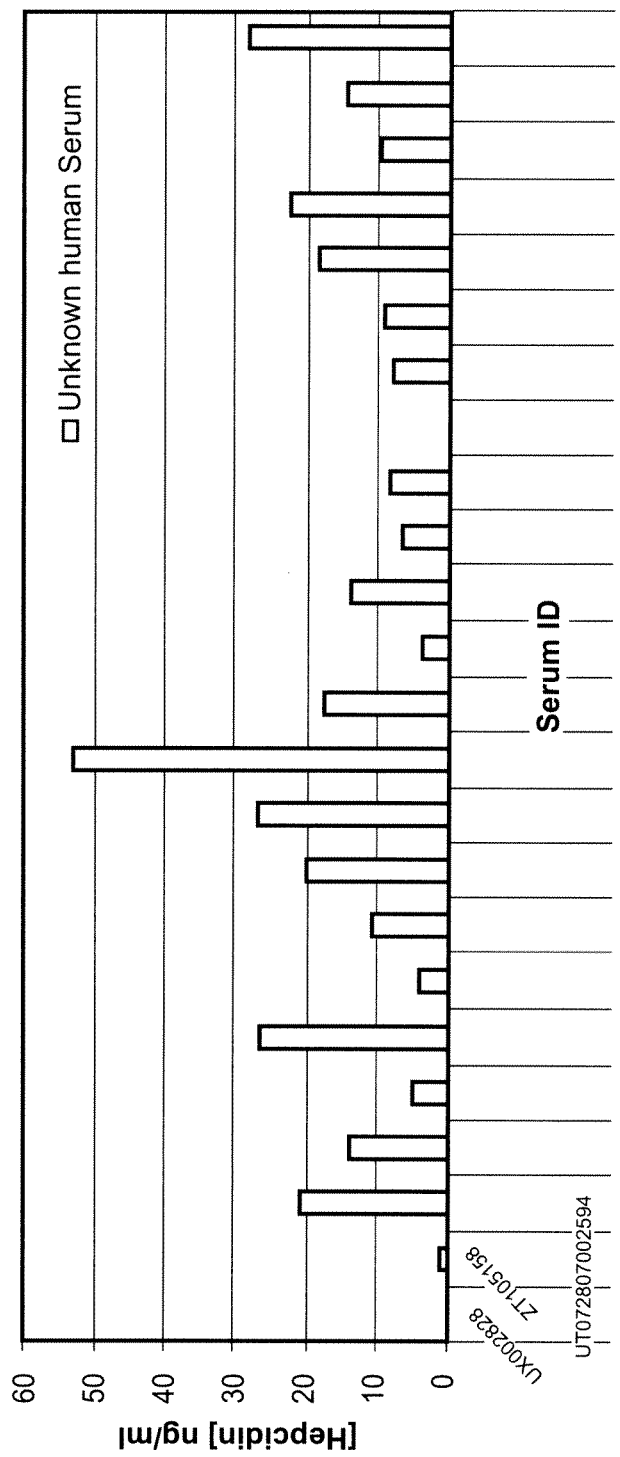
FIG. 32 demonstrates the concentration of hepcidin present in normal human sera using a competitive binding assay.
Figure 34A:
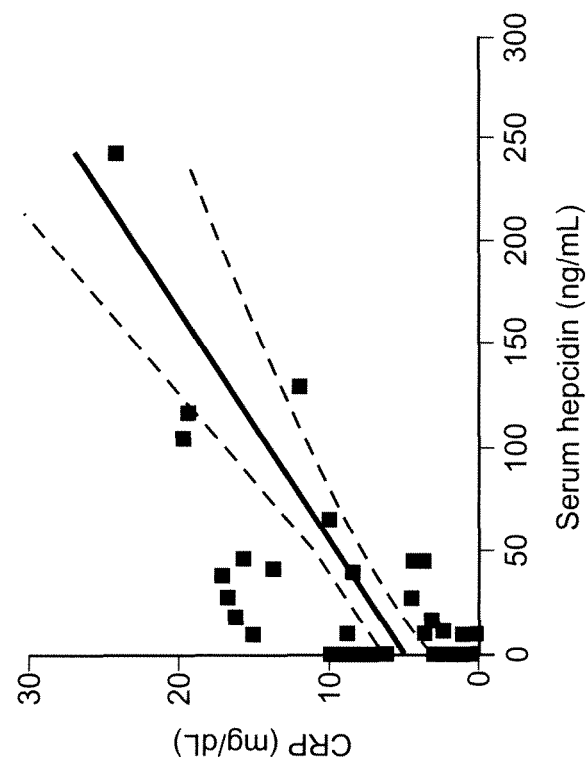
FIG. 34 demonstrates that AoC patients with elevated hepcidin levels also have elevated C-reactive protein (CRP levels).
Figure 34B:
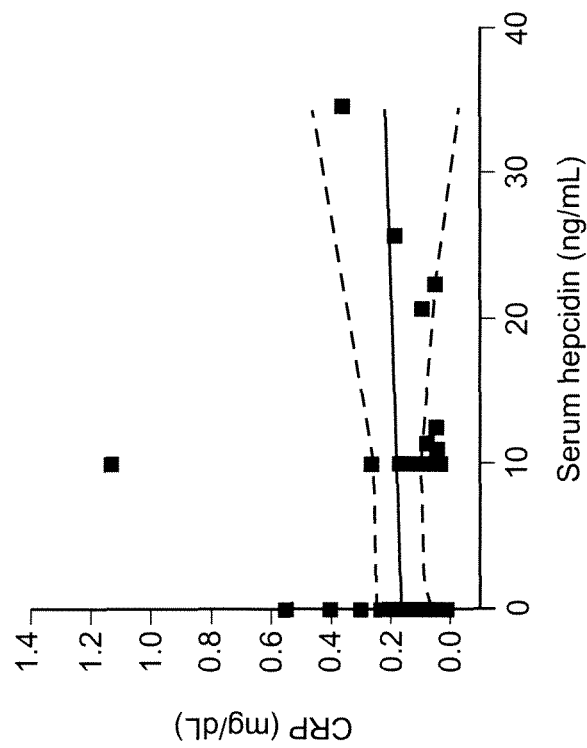

Using hepcidin standards in rabbit serum determined above, 24 random sera from normal human subjects was tested. The hepcidin levels varied from undetectable to over 50 ng/ml. See FIG. 32. These values were at variance with the results from the levels of hepcidin measured through the mass spectrometry-based quantitation method described in co-pending co-owned U.S. patent application Ser. No. 11/880,313 and International Patent Application No. PCT/US2007/016477, the disclosures of which are incorporated herein by reference in their entirety, which generally gave much lower values.

Example 33

Comparative Results of Various Methods of Obtaining Hepcidin Contentration in a Biological Sample The levels of hepcidin obtained by various techniques including mass spectrometry (Example 25), competitive ELISA (Example 32) and a sandwich ELISA (Examples 30-31) were compared. Results are set forth in FIG. 33.

For the sake of completeness of disclosure, all patent documents and literature articles cited herein are expressly incorporated in this specification by reference in their entireties.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. An isolated monoclonal antibody which specifically binds to human hepcidin, wherein said human hepcidin consists of the amino acid sequence set forth in SEQ ID NO: 9 and has a conformation comprising four disulfide-bond loops formed between residues 7 and 23, 10 and 13, 11 and 19, and 14 to 22 as located in SEQ ID NO: 9 and the isolated monoclonal antibody inhibits the iron-regulating activity of hepcidin.

2. The isolated monoclonal antibody of claim 1 that binds to human hepcidin of SEQ ID NO: 9 and increases circulating iron concentration or Tsat.

3. An isolated monoclonal antibody that competes with another antibody for binding to hepcidin (SEQ ID NO: 9) by at least about 75% said monoclonal antibody comprising the amino acid sequences having SEQ ID NOs: 164, 165, 166, 225, 226 and 227 or the monoclonal antibody comprising SEQ ID NO: 224 or the monoclonal antibody comprising SEQ ID NO: 229.

4. An isolated monoclonal antibody, wherein the antibody comprises the amino acid sequence of SEQ ID NO: 225, the amino acid sequence of SEQ ID NO: 226, the amino acid sequence of SEQ ID NO: 227, the amino acid sequence SEQ ID NO: 164, the amino acid sequence SEQ ID NO: 165 and the amino acid sequence SEQ ID NO: 166.

5. An isolated monoclonal antibody that competes with an antibody for binding to hepcidin (SEQ ID NO: 9) by at least about 75% said monoclonal antibody comprising the amino acid sequence of SEQ ID NO: 224 or SEQ ID NO:229.

6. An isolated monoclonal antibody comprising the amino acid sequence of SEQ ID NO: 229 or SEQ ID NO:224.

7. An isolated monoclonal antibody comprising the amino acid sequence of SEQ ID NO: 160 or SEQ ID NO:255.

8. An isolated monoclonal antibody comprising the amino acid sequence of SEQ ID NO: 255 and SEQ ID NO:229.

9. An isolated monoclonal antibody comprising the amino acid sequence of SEQ ID NO: 160 and SEQ ID NO:224.

10. The isolated monoclonal antibody of any one of claims 1, 2, 3, 4, 5, 6, 7, 8 or 9 wherein said antibody is selected from the group consisting of a chimerized antibody, a humanized antibody, a fully human antibody, a single chain Fv fragment, a (Fab')$_2$ fragment, a domain antibody (dAb), a diabody, and a maxibody.

11. The isolated monoclonal antibody of any one of claims 1, 2, 3, 4, 5, 6, 7, 8 or 9, wherein the antibody is a human antibody.

12. The isolated monoclonal antibody of any one of claims 1, 2, 3, 4, 5, 6, 7, 8 or 9, that binds both human hepcidin (SEQ ID NO: 9) and cynomologous monkey hepcidin (SEQ ID NO: 6).

13. The isolated monoclonal antibody of any one of claims 1, 2, 3, 4, 5, 6, 7, 8 or 9 that binds both human hepcidin (SEQ ID NO: 9) and murine hepcidin (SEQ ID NO: 80).

14. A composition comprising the antibody of any one of claims 1, 2, 3, 4, 5, 6, 7, 8 or 9 and pharmaceutically acceptable carrier, diluent or excipient.

15. A vial or prefilled syringe comprising the composition of claim 14.

* * * * *

UNITED STATES PATENT AND TRADEMARK OFFICE
CERTIFICATE OF CORRECTION

PATENT NO. : 8,629,250 B2
APPLICATION NO. : 12/022515
DATED : January 14, 2014
INVENTOR(S) : Sasu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 947 days.

Signed and Sealed this
Second Day of June, 2015

Michelle K. Lee
*Director of the United States Patent and Trademark Office*